(12) United States Patent
Eguchi et al.

(10) Patent No.: US 10,894,829 B2
(45) Date of Patent: *Jan. 19, 2021

(54) HUMANIZED ANTIBODY FOR TREATING OR PREVENTING COGNITIVE DISORDERS, PROCESS FOR PRODUCING THE SAME, AND AGENT FOR TREATING OR PREVENTING COGNITIVE DISORDERS USING THE SAME

(71) Applicants: TEIJIN PHARMA LIMITED, Tokyo (JP); MERCK SHARP & DOHME CORP., Rahway, NJ (US)

(72) Inventors: Hiroshi Eguchi, Tokyo (JP); Takashi Murakami, Tokyo (JP); Naoko Namiki, Tokyo (JP); Akira Tanokura, Tokyo (JP); Jeanne E. Baker, Redwood City, CA (US); Sophie Parmentier Batteur, Haverford, PA (US); Angela Marie Jablonski, North Wales, PA (US); Daniel Stephen Malashock, San Jose, CA (US); Carl Mieczkowski, Mountain View, CA (US); Gopalan (Raghu) Raghunathan, Santa Clara, CA (US)

(73) Assignees: TEIJIN PHARMA LIMITED, Tokyo (JP); MERCK SHARP & DOHME CORP., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/746,725

(22) Filed: Jan. 17, 2020

(65) Prior Publication Data
US 2020/0223916 A1   Jul. 16, 2020

Related U.S. Application Data

(63) Continuation of application No. 15/906,773, filed on Feb. 27, 2018, now Pat. No. 10,556,950.

(30) Foreign Application Priority Data

Feb. 27, 2017   (JP) .................................. 2017-035594

(51) Int. Cl.
*C07K 16/28*       (2006.01)
*C07K 16/18*       (2006.01)
(Continued)

(52) U.S. Cl.
CPC .............. *C07K 16/28* (2013.01); *A61P 25/16* (2018.01); *A61P 25/28* (2018.01); *C07K 16/065* (2013.01);
(Continued)

(58) Field of Classification Search
None
See application file for complete search history.

(56) References Cited

U.S. PATENT DOCUMENTS

2012/0087861 A1   4/2012  Nitsch et al.
2015/0183854 A1   7/2015  Hiroshi et al.

FOREIGN PATENT DOCUMENTS

WO    WO 2010115843 A2    10/2010
WO    WO 2010115843 A3    10/2010
(Continued)

OTHER PUBLICATIONS

International Search Report and Written Opinion dated Jun. 7, 2018 of International Patent Application No. PCT/IB2018/000249 (published as WO 2018154390) (11 pages).

*Primary Examiner* — Adam Weidner
(74) *Attorney, Agent, or Firm* — Jones Day

(57) ABSTRACT

The invention provides methods for using and compositions of humanized antibodies that bind tau protein that is phosphorylated at the serine at position 413.

17 Claims, 33 Drawing Sheets

Specification includes a Sequence Listing.

(51) Int. Cl.
*A61P 25/16* (2006.01)
*A61P 25/28* (2006.01)
*C07K 16/06* (2006.01)
*C07K 16/40* (2006.01)
*C07K 16/44* (2006.01)

(52) U.S. Cl.
CPC .............. C07K 16/18 (2013.01); C07K 16/40 (2013.01); C07K 16/44 (2013.01); *C07K 2317/24* (2013.01); *C07K 2317/56* (2013.01); *C07K 2317/92* (2013.01); *C07K 2317/94* (2013.01)

(56) References Cited

FOREIGN PATENT DOCUMENTS

| WO | WO 2010142423 A2 | 12/2010 |
|---|---|---|
| WO | WO 2010142423 A3 | 12/2010 |
| WO | WO 2012045882 A2 | 4/2012 |
| WO | WO 2012045882 A3 | 4/2012 |
| WO | WO 2013096380 A2 | 6/2013 |
| WO | WO 2013096380 A3 | 6/2013 |
| WO | WO 2014028777 A2 | 2/2014 |
| WO | WO 2014100600 A2 | 6/2014 |
| WO | WO 2014100600 A3 | 6/2014 |
| WO | WO 2015200806 A2 | 12/2015 |
| WO | WO 2015200806 A3 | 12/2015 |
| WO | WO 2016112078 A2 | 7/2016 |
| WO | WO 2016112078 A3 | 7/2016 |
| WO | WO 2017005732 A1 | 1/2017 |
| WO | WO 2017005734 A1 | 1/2017 |
| WO | WO 2017009308 A2 | 1/2017 |
| WO | WO 2017009308 A3 | 1/2017 |

FIG. 1A

Tau isoform

```
                    10         20         30         40         50         60
                    |          |          |          |          |          |
3R0N (Seq. ID:6)    MAEPRQEFEVMEDHAGTYGLGDRKDQGGYTMHQDQEGDTDAGLK------------------  44
3R1N (Seq. ID:5)    MAEPRQEFEVMEDHAGTYGLGDRKDQGGYTMHQDQEGDTDAGLKESPLQTPTEDGSEEPG  80
3R2N (Seq. ID:4)    MAEPRQEFEVMEDHAGTYGLGDRKDQGGYTMHQDQEGDTDAGLKESPLQTPTEDGSEEPG  80
4R0N (Seq. ID:3)    MAEPRQEFEVMEDHAGTYGLGDRKDQGGYTMHQDQEGDTDAGLK------------------  44
4R1N (Seq. ID:2)    MAEPRQEFEVMEDHAGTYGLGDRKDQGGYTMHQDQEGDTDAGLKESPLQTPTEDGSEEPG  80
4R2N (Seq. ID:1)    MAEPRQEFEVMEDHAGTYGLGDRKDQGGYTMHQDQEGDTDAGLKESPLQTPTEDGSEEPG  80
                    ************************************************
Prim. cons.         MAEPRQEFEVMEDHAGTYGLGDRKDQGGYTMHQDQEGDTDAGLKESPLQTPTEDGSEEPG 70         80         90         100        110        120
                    |          |          |          |          |          |
3R0N (Seq. ID:6)    ---------------------------------------AKKAGIGDTPSLEDEAAG   62
3R1N (Seq. ID:5)    SETSDAKSTPTAE---------------------------AKKAGIGDTPSLEDEAAG   91
3R2N (Seq. ID:4)    SETSDAKSTPTAEDVTAPLVDEGAPGKQAAAQPHTEIPEGTTAEEAGIGDTPSLEDEAAG  120
4R0N (Seq. ID:3)    ---------------------------------------AKKAGIGDTPSLEDEAAG   62
4R1N (Seq. ID:2)    SETSDAKSTPTAE---------------------------AKKAGIGDTPSLEDEAAG   91
4R2N (Seq. ID:1)    SETSDAKSTPTAEDVTAPLVDEGAPGKQAAAQPHTEIPEGTTAEEAGIGDTPSLEDEAAG  120
                                                            ******************
Prim. cons.         SETSDAKSTPTAEDVTAPLVDEGAPGKQAAAQPHTEIPEGTTAEEAGIGDTPSLEDEAAG 130        140        150        160        170        180
                    |          |          |          |          |          |
3R0N (Seq. ID:6)    HVTQARMVSKSKDGTGSDDKKAKGADGKTKIATPRGAAPPGQKGQANATRIPAKTPPAPK  122
3R1N (Seq. ID:5)    HVTQARMVSKSKDGTGSDDKKAKGADGKTKIATPRGAAPPGQKGQANATRIPAKTPPAPK  151
3R2N (Seq. ID:4)    HVTQARMVSKSKDGTGSDDKKAKGADGKTKIATPRGAAPPGQKGQANATRIPAKTPPAPK  180
4R0N (Seq. ID:3)    HVTQARMVSKSKDGTGSDDKKAKGADGKTKIATPRGAAPPGQKGQANATRIPAKTPPAPK  122
4R1N (Seq. ID:2)    HVTQARMVSKSKDGTGSDDKKAKGADGKTKIATPRGAAPPGQKGQANATRIPAKTPPAPK  151
4R2N (Seq. ID:1)    HVTQARMVSKSKDGTGSDDKKAKGADGKTKIATPRGAAPPGQKGQANATRIPAKTPPAPK  180
                    ************************************************************
Prim. cons.         HVTQARMVSKSKDGTGSDDKKAKGADGKTKIATPRGAAPPGQKGQANATRIPAKTPPAPK 190        200        210        220        230        240
                    |          |          |          |          |          |
3R0N (Seq. ID:6)    TPPSSGEPPKSGDRSGYSSPGSPGTPGSRSRTPSLPTPPTREPKKVAVVRTPPKSPSSAK  182
3R1N (Seq. ID:5)    TPPSSGEPPKSGDRSGYSSPGSPGTPGSRSRTPSLPTPPTREPKKVAVVRTPPKSPSSAK  211
3R2N (Seq. ID:4)    TPPSSGEPPKSGDRSGYSSPGSPGTPGSRSRTPSLPTPPTREPKKVAVVRTPPKSPSSAK  240
4R0N (Seq. ID:3)    TPPSSGEPPKSGDRSGYSSPGSPGTPGSRSRTPSLPTPPTREPKKVAVVRTPPKSPSSAK  182
4R1N (Seq. ID:2)    TPPSSGEPPKSGDRSGYSSPGSPGTPGSRSRTPSLPTPPTREPKKVAVVRTPPKSPSSAK  211
4R2N (Seq. ID:1)    TPPSSGEPPKSGDRSGYSSPGSPGTPGSRSRTPSLPTPPTREPKKVAVVRTPPKSPSSAK  240
                    ************************************************************
Prim. cons.         TPPSSGEPPKSGDRSGYSSPGSPGTPGSRSRTPSLPTPPTREPKKVAVVRTPPKSPSSAK
```

FIG. 1B

```
                   250       260       270       280       290       300
                    |         |         |         |         |         |
3R0N (Seq. ID:6)   SRLQTAPVPMPDLKNVKSKIGSTENLKHQPGGGK--------------------------- 238
3R1N (Seq. ID:5)   SRLQTAPVPMPDLKNVKSKIGSTENLKHQPGGGK--------------------------- 245
3R2N (Seq. ID:4)   SRLQTAPVPMPDLKNVKSKIGSTENLKHQPGGGK--------------------------- 274
4R0N (Seq. ID:3)   SRLQTAPVPMPDLKNVKSKIGSTENLKHQPGGGKVQIINKKLDLSNVQSKCGSKDNIKHV 242
4R1N (Seq. ID:2)   SRLQTAPVPMPDLKNVKSKIGSTENLKHQPGGGKVQIINKKLDLSNVQSKCGSKDNIKHV 271
4R2N (Seq. ID:1)   SRLQTAPVPMPDLKNVKSKIGSTENLKHQPGGGKVQIINKKLDLSNVQSKCGSKDNIKHV 300
                   **********************************
Prim. cons.        SRLQTAPVPMPDLKNVKSKIGSTENLKHQPGGGKVQIINKKLDLSNVQSKCGSKDNIKHV 310       320       330       340       350       360
                    |         |         |         |         |         |
3R0N (Seq. ID:6)   ------VQIVYKPVDLSKVTSKCGSLGNIHHKPGGGQVEVKSEKLDFKDRVQSKIGSLDNI 271
3R1N (Seq. ID:5)   ------VQIVYKPVDLSKVTSKCGSLGNIHHKPGGGQVEVKSEKLDFKDRVQSKIGSLDNI 300
3R2N (Seq. ID:4)   ------VQIVYKPVDLSKVTSKCGSLGNIHHKPGGGQVEVKSEKLDFKDRVQSKIGSLDNI 329
4R0N (Seq. ID:3)   PGGGSVQIVYKPVDLSKVTSKCGSLGNIHHKPGGGQVEVKSEKLDFKDRVQSKIGSLDNI 302
4R1N (Seq. ID:2)   PGGGSVQIVYKPVDLSKVTSKCGSLGNIHHKPGGGQVEVKSEKLDFKDRVQSKIGSLDNI 331
4R2N (Seq. ID:1)   PGGGSVQIVYKPVDLSKVTSKCGSLGNIHHKPGGGQVEVKSEKLDFKDRVQSKIGSLDNI 360
                         ******************************************************
Prim. cons.        PGGGSVQIVYKPVDLSKVTSKCGSLGNIHHKPGGGQVEVKSEKLDFKDRVQSKIGSLDNI 370       380       390       400       410       420
                    |         |         |         |         |         |
3R0N (Seq. ID:6)   THVPGGGNKKIETHKLTFRENAKAKTDHGAEIVYKSPVVSGDTSPRHLSNVSSTGSIDMV 331
3R1N (Seq. ID:5)   THVPGGGNKKIETHKLTFRENAKAKTDHGAEIVYKSPVVSGDTSPRHLSNVSSTGSIDMV 360
3R2N (Seq. ID:4)   THVPGGGNKKIETHKLTFRENAKAKTDHGAEIVYKSPVVSGDTSPRHLSNVSSTGSIDMV 389
4R0N (Seq. ID:3)   THVPGGGNKKIETHKLTFRENAKAKTDHGAEIVYKSPVVSGDTSPRHLSNVSSTGSIDMV 362
4R1N (Seq. ID:2)   THVPGGGNKKIETHKLTFRENAKAKTDHGAEIVYKSPVVSGDTSPRHLSNVSSTGSIDMV 391
4R2N (Seq. ID:1)   THVPGGGNKKIETHKLTFRENAKAKTDHGAEIVYKSPVVSGDTSPRHLSNVSSTGSIDMV 420
                   ***********************************************************
Prim. cons.        THVPGGGNKKIETHKLTFRENAKAKTDHGAEIVYKSPVVSGDTSPRHLSNVSSTGSIDMV 430       440
                    |         |
3R0N (Seq. ID:6)   DSPQLATLADEVSASLAKQGL 352
3R1N (Seq. ID:5)   DSPQLATLADEVSASLAKQGL 381
3R2N (Seq. ID:4)   DSPQLATLADEVSASLAKQGL 410
4R0N (Seq. ID:3)   DSPQLATLADEVSASLAKQGL 383
4R1N (Seq. ID:2)   DSPQLATLADEVSASLAKQGL 412
4R2N (Seq. ID:1)   DSPQLATLADEVSASLAKQGL 441
                   *********************
Prim. cons.        DSPQLATLADEVSASLAKQGL
```

FIG. 2A

```
                                          CDR-L1                              CDR-L2
L15 (Seq. ID:32)   DIVMTQSPLSLPVTLGEPASISCRSSQSIVHSNGNTYLEWYQQKPGQSPRLLIYTVSNRF
L36 (Seq. ID:34)   DIVMTQSPLSLPVTLGDPASISCRSSQSIVHSNGNTYLEWYQQKPGQSPQLLIYTVSNRF
L46 (Seq. ID:36)   DIVMTQSPLSLPVTLGEPASISCRSSQSIVHSNGNTYLEWYLQKPGQSPQLLIYTVSNRF
L47 (Seq. ID:38)   DIVMTQSPLSLPVTLGDPASISCRSSQSIVHSNGNTYLEWYQQKPGQSPQRLIYTVSNRF
L48 (Seq. ID:40)   DIVMTQSPLSLPVTLGDPASISCRSSQNIVHSNGNTYLEWYQQKPGQSPQLLIYTVSNRF
L50 (Seq. ID:42)   DIVMTQSPLSLPVTLGDPASISCRSSQNIVHSNGNTYLEWYQQKPGQSPRLLIYTVSNRF
                   ****************:********.,************ ******:*********
                   |         |         |         |         |         |
                   10        20        30        40        50        60

CDR-L3
L15 (Seq. ID:32)   SGVPDRFSGSGSGTDFTLKISRVEAEDLGVYYCFQGSHLPLTFGGGTKVEIK
L36 (Seq. ID:34)   SGVPDRFSGSGSGTDFTLKISRVEAEDLGVYYCFQGSHLPLTFGGGTKVEIK
L46 (Seq. ID:36)   SGVPDRFSGSGSGTDFTLKISRVEAEDLGVYYCFQGSHLPLTFGGGTKVEIK
L47 (Seq. ID:38)   SGVPDRFSGSGSGTDFTLKISRVEAEDLGVYYCFQGSHLPLTFGGGTKVEIK
L48 (Seq. ID:40)   SGVPDRFSGSGSGTDFTLKISRVEAEDLGVYYCFQGSHLPLTFGGGTKVEIK
L50 (Seq. ID:42)   SGVPDRFSGSGSGTDFTLKISRVEAEDLGVYYCFQGSHLPLTFGGGTKVEIK
                   ***************************************************
                   |         |         |         |         |
                   70        80        90        100       110
```

FIG. 2B

```
                                                    CDR-H1              CDR-H2
H11 (Seq. ID:18)  EVQLVESGGGLVQPGGSLRLSCAASGFTFSSFALNWVRQAPGKGLEWVGHIRSKTNNYAT
H12 (Seq. ID:20)  EVQLVESGGGLVQPGGSLRLSCAASGFAFNSFALNWVRQAPGKGLEWVGHIRSKTNNYAT
H47 (Seq. ID:22)  EVQLVESGGGLVQPGGSLRLSCAASGFAFNSFALNWVRQAPGKGLEWVGHIRSKTNNYAT
H61 (Seq. ID:24)  EVQLVESGGGLVQPGGSLRLSCAASGFTFNSFALNWVRQAPGKGLEWVVHIRSKTNNYAT
H62 (Seq. ID:26)  EVQLVESGGGLVQPGGSLRLSCAASGFAFNSFALNWVRQAPGKGLEWVVHIRSKTNNYAT
H64 (Seq. ID:28)  EVQLVESGGGLVQPGGSLRLSCAASGFTFNSFALNWVRQAPGKGLEWVVHIRSKTNNYAT
H65 (Seq. ID:30)  EVQLVESGGGLVQPGGSLRLSCAASGFAFNSFALNWVRQAPGKGLEWVVHIRSKTNNYAT
                  *************************:*.******************* **********
                          |         |         |         |         |         |
                         10        20        30        40        50        60

CDR-H2                                    CDR-H3
H11 (Seq. ID:18)  FYAASVKDRFTVSRDDSQNTAYLQMNSLKTEDTATYYCVRRGPRDSWFGYWGQGTLVTVS
H12 (Seq. ID:20)  FYADSVKDRFTVSRDDSKNTAYLQMNSLKTEDTATYYCVRRGPRDSWFGYWGQGTLVTVS
H47 (Seq. ID:22)  FYAASVKDRFTVSRDDSQNTAYLQMNSLKTEDTATYYCVRRGPRDSWFGYWGQGTLVTVS
H61 (Seq. ID:24)  FYADSVKDRFTVSRDDSKNTAYLQMNSLKTEDTATYYCVRRGPRDSWFGYWGQGTLVTVS
H62 (Seq. ID:26)  FYADSVKDRFTVSRDDSKNTAYLQMNSLKTEDTATYYCVRRGPRDSWFGYWGQGTLVTVS
H64 (Seq. ID:28)  FYAASVKDRFTVSRDDSQNTAYLQMNSLKTEDTATYYCVRRGPRDSWFGYWGQGTLVTVS
H65 (Seq. ID:30)  FYAASVKDRFTVSRDDSQNTAYLQMNSLKTEDTATYYCVRRGPRDSWFGYWGQGTLVTVS
                  *** *************:**********************************
                          |         |         |         |         |         |
                         70        80        90       100       110       120

H11 (Seq. ID:18)  S
H12 (Seq. ID:20)  S
H47 (Seq. ID:22)  S
H61 (Seq. ID:24)  S
H62 (Seq. ID:26)  S
H64 (Seq. ID:28)  S
H65 (Seq. ID:30)  S
                  *
```

FIG. 7A

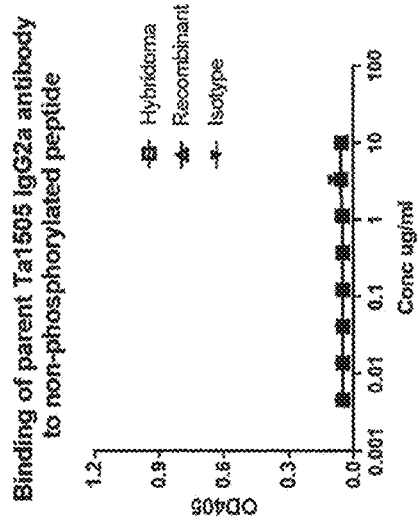
FIG. 8B
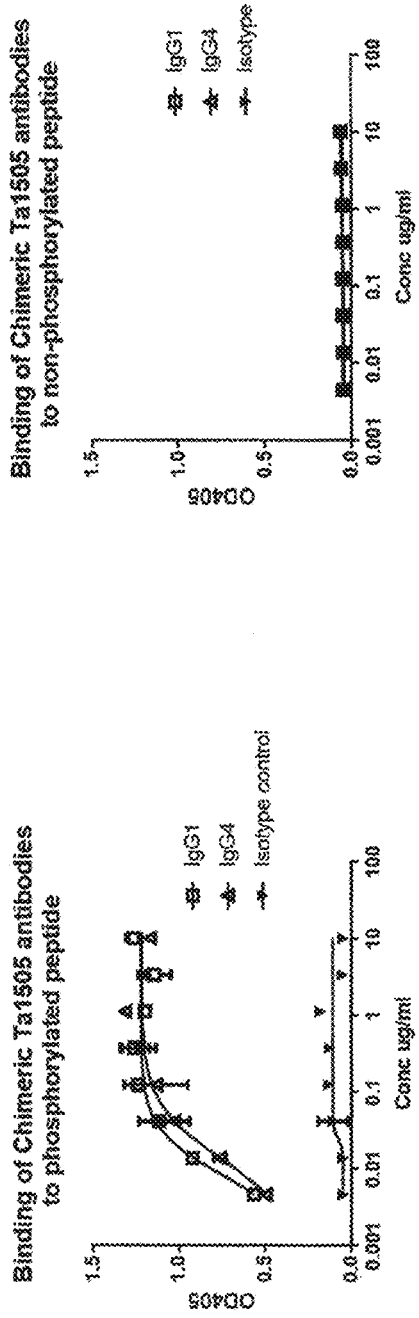
FIG. 8D
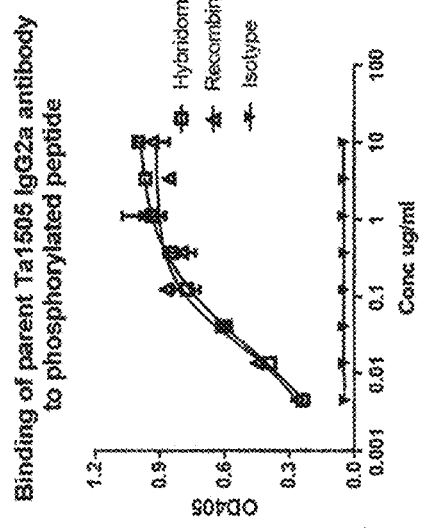
FIG. 8A
FIG. 8C

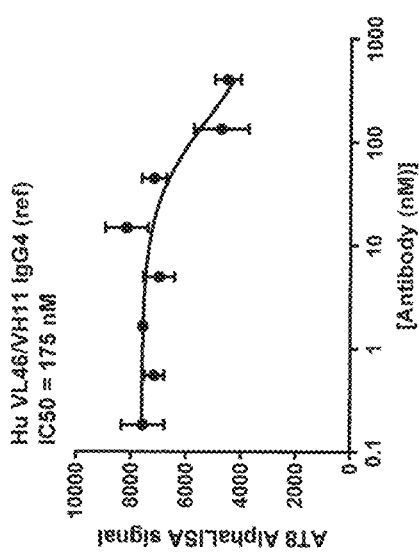
FIG. 10A
FIG. 10B
FIG. 10C
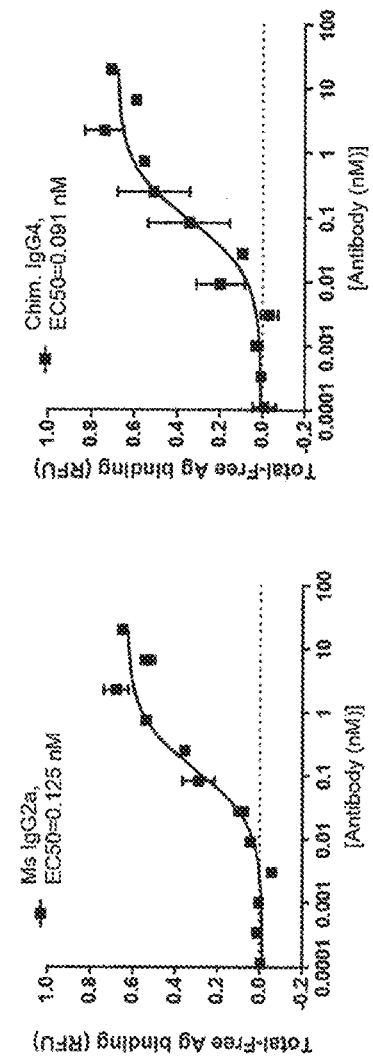
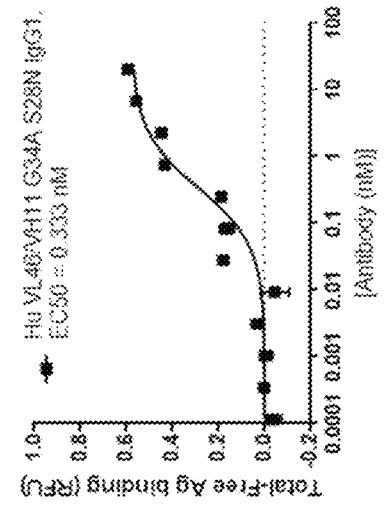
FIG. 10D
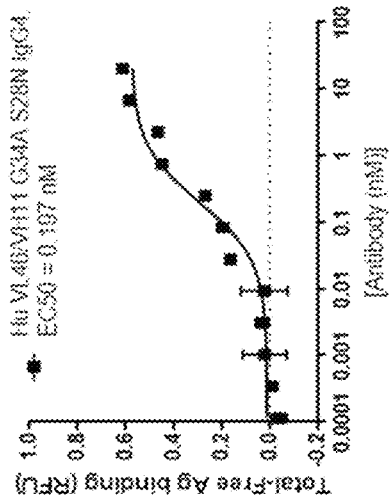
FIG. 10E

FIG. 11A

>Ta1505-VL00-Mouse SEQ ID NO:84
DILMTQTPLSLPVSLGDQASISCRSSQNIVHSNGNTYLEWYLQKPGQSPKVLIYTVSNRFSGVPDRFSGSGSGTDFTLKISRVEAEDLGVYYCFQGSHLPLTFGGGTKLELK vlCDR1 RSSQNIVHSNGNTYLE SEQ ID NO:81 vlCDR2 TVSNRFS SEQ ID NO:82 vlCDR3 FQGSHLPLT SEQ ID NO:83

>Ta1505-VL46 SEQ ID NO:103
DIVMTQSPLSLPVTLGEPASISCRSSQSIVHSNGNTYLEWYLQKPGQSPQLLIYTVSNRFSGVPDRFSGSGSGTDFTLKISRVEAEDLGVYYCFQGSHLPLTFGGGTKVEIK vlCDR1 RSSQSIVHSNGNTYLE SEQ ID NO:91 vlCDR2 TVSNRFS SEQ ID NO:82 vlCDR3 FQGSHLPLT SEQ ID NO:83

>Ta1505-VL47 SEQ ID NO:104
DIVMTQSPLSLPVTLGDPASISCRSSQSIVHSNGNTYLEWYQQKPGQSPQRLIYTVSNRFSGVPDRFSGSGSGTDFTLKISRVEAEDLGVYYCFQGSHLPLTFGGGTKVEIK vlCDR1 RSSQSIVHSNGNTYLE SEQ ID NO:92 vlCDR2 TVSNRFS SEQ ID NO:82 vlCDR3 FQGSHLPLT SEQ ID NO:83

FIG. 11B

>Ta1505-VL46_G34A SEQ ID NO:105
DIVMTQSPLSLPVTLGEPASISCRSSQSIVHSNANTYLEWYLQKPGQSPQLLIYTVSNRFSGVPDRFSGSGSGTDFTLKISRVEAEDLGVYYCFQGSHLPLTFGGGTKVEIK vlCDR1 RSSQSIVHSNANTYLE SEQ ID NO:93 vlCDR2 TVSNRFS   SEQ ID NO:82 vlCDR3 FQGSHLPLT SEQ ID NO:83

>Ta1505-VL46_G34S SEQ ID NO:106
DIVMTQSPLSLPVTLGEPASISCRSSQSIVHSNSNTYLEWYLQKPGQSPQLLIYTVSNRFSGVPDRFSGSGSGTDFTLKISRVEAEDLGVYYCFQGSHLPLTFGGGTKVEIK vlCDR1 RSSQSIVHSNSNTYLE SEQ ID NO:94 vlCDR2 TVSNRFS   SEQ ID NO:82 vlCDR3 FQGSHLPLT SEQ ID NO:83

>Ta1505-VL46_G34T SEQ ID NO:107
DIVMTQSPLSLPVTLGEPASISCRSSQSIVHSNTNTYLEWYLQKPGQSPQLLIYTVSNRFSGVPDRFSGSGSGTDFTLKISRVEAEDLGVYYCFQGSHLPLTFGGGTKVEIK vlCDR1 RSSQSIVHSNTNTYLE SEQ ID NO:95 vlCDR2 TVSNRFS   SEQ ID NO:82 vlCDR3 FQGSHLPLT SEQ ID NO:83

>Ta1505-VL46_N33Q SEQ ID NO:108
DIVMTQSPLSLPVTLGEPASISCRSSQSIVHSQGNTYLEWYLQKPGQSPQLLIYTVSNRFSGVPDRFSGSGSGTDFTLKISRVEAEDLGVYYCFQGSHLPLTFGGGTKVEIK vlCDR1 RSSQSIVHSQGNTYLE SEQ ID NO:96 vlCDR2 TVSNRFS   SEQ ID NO:82

FIG. 11C vlCDR3 FQGSHLPLT SEQ ID NO:83

>Ta1505-VL46_N33Q_G34A SEQ ID NO:109
DIVMTQSPLSLPVTLGEPASISCRSSQSIVHSQANTYLEWYLQKPGQSPQLLIYTVSNRFSGVPDRFSGSGSGTDFTLKISRVEAEDLGVYYCFQGSHLPLTFGGGTKVEIK vlCDR1 RSSQSIVHSQANTYLE SEQ ID NO:97
vlCDR2 TVSNRFS SEQ ID NO:82
vlCDR3 FQGSHLPLT SEQ ID NO:83

>Ta1505-VL46_N33D SEQ ID NO:110
DIVMTQSPLSLPVTLGEPASISCRSSQSIVHSDGNTYLEWYLQKPGQSPQLLIYTVSNRFSGVPDRFSGSGSGTDFTLKISRVEAEDLGVYYCFQGSHLPLTFGGGTKVEIK vlCDR1 RSSQSIVHSDGNTYLE SEQ ID NO:98
vlCDR2 TVSNRFS SEQ ID NO:82
vlCDR3 FQGSHLPLT SEQ ID NO:83

>Ta1505-VL46_N33S SEQ ID NO:111
DIVMTQSPLSLPVTLGEPASISCRSSQSIVHSSGNTYLEWYLQKPGQSPQLLIYTVSNRFSGVPDRFSGSGSGTDFTLKISRVEAEDLGVYYCFQGSHLPLTFGGGTKVEIK vlCDR1 RSSQSIVHSSGNTYLE SEQ ID NO:99
vlCDR2 TVSNRFS SEQ ID NO:82
vlCDR3 FQGSHLPLT SEQ ID NO:83

>Ta1505-VL46_N33T SEQ ID NO:112
DIVMTQSPLSLPVTLGEPASISCRSSQSIVHSTGNTYLEWYLQKPGQSPQLLIYTVSNRFSGVPDRFSGSGSGTDFTLKISRVEAEDLGVYYCFQGSHLPLTFGGGTKVEIK

FIG. 11D vlCDR1 RSSQSIVHSTGNTYLE SEQ ID NO:100
vlCDR2 TVSNRFS SEQ ID NO:82
vlCDR3 FQGSHLPLT SEQ ID NO:83

>Ta1505-VL46_S28N SEQ ID NO:113
DIVMTQSPLSLPVTLGEPASISCRSSQNIVHSNGNTYLEWYLQKPGQSPQLLIYTVSNRFSGVPDRFSGSGSGTDFTLKISRVEAEDLGVYYCFQGSHLPLTFGGGTKVEIK vlCDR1 RSSQNIVHSNGNTYLE SEQ ID NO:101
vlCDR2 TVSNRFS SEQ ID NO:82
vlCDR3 FQGSHLPLT SEQ ID NO:83

*Ta1505-VL46_G34A_S28N SEQ ID NO:114
DIVMTQSPLSLPVTLGEPASISCRSSQNIVHSNANTYLEWYLQKPGQSPQLLIYTVSNRFSGVPDRFSGSGSGTDFTLKISRVEAEDLGVYYCFQGSHLPLTFGGGTKVEIK vlCDR1 RSSQNIVHSNANTYLE SEQ ID NO:102
vlCDR2 TVSNRFS SEQ ID NO:82
vlCDR3 FQGSHLPLT SEQ ID NO:83

>Ta1505-VH00-Mouse SEQ ID NO:89
EVQLVESGGGLVQPKGSLKLSCAASGFAFNSFALNWVRQAPGKSLEWVVHIRSKTNNYATFYADSVKDRFTVSRDDSQSMVVLQMNNLKTEDTGIYYCVRRGPRDS
WFGYWGQGTLVTVSA vlCDR1 SFALN SEQ ID NO:86
vlCDR2 HIRSKTNNYATFYADSVKD SEQ ID NO:87
vlCDR3 RGPRDSWFGY SEQ ID NO:88

FIG. 11E

>Ta1505-VH11 SEQ ID NO:116
EVQLVESGGGLVQPGGSLRLSCAASGFTFSSFALNWVRQAPGKGLEWVGHIRSKTNNYATFYAASVKDRFTVSRDDSQNTAYLQMNSLKTEDTATYYCVRRGPRDS
WFGYWGQGTLVTVSS vhCDR1 SFALN SEQ ID NO:86 vhCDR2 HIRSKTNNYATFYAASVKD SEQ ID NO:115 vhCDR3 RGPRDSWFGY SEQ ID NO:88

>Ta1505-VH65 SEQ ID NO:117
EVQLVESGGGLVQPGGSLRLSCAASGFAFNSFALNWVRQAPGKGLEWVVHIRSKTNNYATFYAASVKDRFTVSRDDSQNTAYLQMNSLKTEDTATYYCVRRGPRDSW
FGYWGQGTLVTVSS vhCDR1 SFALN SEQ ID NO:86 vhCDR2 HIRSKTNNYATFYAASVKD SEQ ID NO:115 vhCDR3 RGPRDSWFGY SEQ ID NO:88

FIG. 12A

>Human_IgG1_P01857 SEQ ID NO:135

ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPC
PAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKA
KGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK

>Human_IgG1_P01857_L234A_L235A SEQ ID NO:136

ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPC
PAPEaaGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKA
KGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK

>Human_IgG1_P01857_L234A_L235A_D265S SEQ ID NO:137

ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPC
PAPEaaGGPSVFLFPPKPKDTLMISRTPEVTCVVVsVSHEDPEVKFNWYVDGVEVHNAKTKPREEQYNSTYRVVSVLTVLHQDWLNGKEYKCKVSNKALPAPIEKTISKA
KGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK

>Human_IgG1_YTE_P01857_(M252Y_S254T_T256E) SEQ ID NO:138

ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPC
PAPELLGGPSVFLFPPKPKDTLyitRePeVTCVVVDVSHEDPEVKFNWYVDGVEVHNAKTKPREEQYNSTYRVVSVLTVLHQDWLNGKEYKCKVSNKALPAPIEKTISKAK
GQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK >Human_IgG1_N297A_P01857 SEQ ID NO:139

FIG. 12B

ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPC
PAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKA
KGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK

>Human_IgG1_N297Q_P01857 SEQ ID NO:140

ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPC
PAPELLGGPSVFLFPPKPKDTLMISRTPEVTCVVVDVSHEDPEVKFNWYVDGVEVHNAKTKPREEQYQSTYRVVSVLTVLHQDWLNGKEYKCKVSNKALPAPIEKTISKA
KGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK

>P01859_Human_IgG2 SEQ ID NO:141

ASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKCCVECPPCPA
PPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKG
QPREPQVYTLPPSREEMTKNQVSLTCLVKGFYPSDISVEWESNGQPENNYKTTPPMLDSDGSFFLYSKLTVDKSRWQQGNVFSCSVMHEALHNHYTQKSLSLSPGK

>P01861_Human_IgG4 SEQ ID NO:142

ASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPSCPAP
EFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKG
QPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK

>Human_IgG4_S228P_P01861 SEQ ID NO:143

ASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAP
EFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKG
QPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK

FIG. 12C

Human kappa light constant domain SEQ ID NO:79

RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC

Human lambda light constant domain SEQ ID NO:80

GQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS

FIG. 13A

H11 HC IgG1: SEQ ID NO:144

EVQLVESGGGLVQPGGSLRLSCAASGFTFSSFALNWVRQAPGKGLEWVGHIRSKTNNYATFYAASVKDRFTVSRDDSQNTAYLQMNSLKTEDTATYYCVRRGPRDSWFGYWGQGTLVTVSS/ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK

H11 Human_IgG1_L234A_L235A SEQ ID NO:145

EVQLVESGGGLVQPGGSLRLSCAASGFTFSSFALNWVRQAPGKGLEWVGHIRSKTNNYATFYAASVKDRFTVSRDDSQNTAYLQMNSLKTEDTATYYCVRRGPRDSWFGYWGQGTLVTVSS/ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEaaGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK

H11 Human_IgG1_L234A_L235A_D265S SEQ ID NO:146

EVQLVESGGGLVQPGGSLRLSCAASGFTFSSFALNWVRQAPGKGLEWVGHIRSKTNNYATFYAASVKDRFTVSRDDSQNTAYLQMNSLKTEDTATYYCVRRGPRDSWFGYWGQGTLVTVSS/ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEaaGGPSVFLFPPKPKDTLMISRTPEVTCVVVSVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK

H11 Human_IgG1_YTE_(M252Y_S254T_T256E) SEQ ID NO:147

FIG. 13B

EVQLVESGGGLVQPGGSLRLSCAASGFTFSSFALNWVRQAPGKGLEWVGHIRSKTNNYATFYAASVKDRFTVSRDDSQNTAYLQMNSLKTEDTATYYCVRRGPRDS
WFGYWGQGTLVTVSS/STKGPSVFPLAPSSKSTSGGTAALGCLVKDYFPEPVTVSWNSGALTSGVHTFPAVLQSSGLYSLSSVVTVPSSSLGTQTYICNVNHKPSNTKVD
KKVEPKSCDKTHTCPPCPAPELLGGPSVFLFPPKPKDTLyitRePEVTCVVVDVSHEDPEVKFNWYVDGVEVHNAKTKPREEQYNSTYRVVSVLTVLHQDWLNGKEYKCK
VSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEAL
HNHYTQKSLSLSPGK H11 Human_IgG1_N297A SEQ ID NO:148

EVQLVESGGGLVQPGGSLRLSCAASGFTFSSFALNWVRQAPGKGLEWVGHIRSKTNNYATFYAASVKDRFTVSRDDSQNTAYLQMNSLKTEDTATYYCVRRGPRDS
WFGYWGQGTLVTVSS/ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKV
DKKVEPKSCDKTHTCPPCPAPELLGGPSVFLFPPKPKDTLMISRTPEVTCVVVDVSHEDPEVKFNWYVDGVEVHNAKTKPREEQYASTYRVVSVLTVLHQDWLNGKEYK
CKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHE
ALHNHYTQKSLSLSPGK

H11 Human_IgG1_N297Q_ SEQ ID NO:149

EVQLVESGGGLVQPGGSLRLSCAASGFTFSSFALNWVRQAPGKGLEWVGHIRSKTNNYATFYAASVKDRFTVSRDDSQNTAYLQMNSLKTEDTATYYCVRRGPRDS
WFGYWGQGTLVTVSS/STKGPSVFPLAPSSKSTSGGTAALGCLVKDYFPEPVTVSWNSGALTSGVHTFPAVLQSSGLYSLSSVVTVPSSSLGTQTYICNVNHKPSNTKVD
KKVEPKSCDKTHTCPPCPAPELLGGPSVFLFPPKPKDTLMISRTPEVTCVVVDVSHEDPEVQFNWYVDGVEVHNAKTKPREEQyqSTYRVVSVLTVLHQDWLNGKEYC
KVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEA
LHNHYTQKSLSLSPGK

H11 Human_IgG2 SEQ ID NO:150

EVQLVESGGGLVQPGGSLRLSCAASGFTFSSFALNWVRQAPGKGLEWVGHIRSKTNNYATFYAASVKDRFTVSRDDSQNTAYLQMNSLKTEDTATYYCVRRGPRDS
WFGYWGQGTLVTVSS/ASTKGPSVFPLAPCSRSTSESTAALGCLVKDYFPEPVTVSWNSGALTSGVHTFPAVLQSSGLYSLSSVVTVPSSNFGTQTYTCNVDHKPSNTKV
DKTVERKCCVECPPCPAPPVAGPSVFLFPPKPKDTLMISRTPEVTCVVVDVSHEDPEVQFNWYVDGVEVHNAKTKPREEQFNSTFRVVSVLTVLHQDWLNGKEYKCKV
SNKGLPAPIEKTISKTKGQPREPQVYTLPPSREEMTKNQVSLTCLVKGFYPSDISVEWESNGQPENNYKTTPPMLDSDGSFFLYSKLTVDKSRWQQGNVFSCSVMHEAL
HNHYTQKSLSLSPGK

FIG. 13C

H11 Human_IgG4 SEQ ID NO:151

EVQLVESGGGLVQPGGSLRLSCAASGFTTSSFALNWVRQAPGKGLEWVGHIRSKTNNYATFYAASVKDRFTVSRDDSQNTAYLQMNSLKTEDTATYYCVRRGPRDS
WFGYWGQGTLVTVSS/STKGPSVFPLAPCSRSTSESTAALGCLVKDYFPEPVTVSWNSGALTSGVHTFPAVLQSSGLYSLSSVVTVPSSSLGTKTYTCNVDHKPSNTKVDK
RVESKYGPPCPSCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVS
NKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALH
NHYTQKSLSLSLGK

H11 Human_IgG4_S228P SEQ ID NO:152

EVQLVESGGGLVQPGGSLRLSCAASGFTTSSFALNWVRQAPGKGLEWVGHIRSKTNNYATFYAASVKDRFTVSRDDSQNTAYLQMNSLKTEDTATYYCVRRGPRDS
WFGYWGQGTLVTVSS/STKGPSVFPLAPCSRSTSESTAALGCLVKDYFPEPVTVSWNSGALTSGVHTFPAVLQSSGLYSLSSVVTVPSSSLGTKTYTCNVDHKPSNTKV
DKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCK
VSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEAL
HNHYTQKSLSLSLGK

H65 Human_IgG1 SEQ ID NO:153

EVQLVESGGGLVQPGGSLRLSCAASGFAFNSFALNWVRQAPGKGLEWVVHIRSKTNNYATFYAASVKDRFTVSRDDSQNTAYLQMNSLKTEDTATYYCVRRGPRDSW
FGYWGQGTLVTVSS/STKGPSVFPLAPSSKSTSGGTAALGCLVKDYFPEPVTVSWNSHEDPEVKFNWYVDGVEVHNAKTKPREEQYNSTYRVVSVLTVLHQDWLNGKEYKCKV
VEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKV
SNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALH
NHYTQKSLSLSPGK

H65 Human_IgG1_P01857_L234A_L235A SEQ ID NO:154

EVQLVESGGGLVQPGGSLRLSCAASGFAFNSFALNWVRQAPGKGLEWVVHIRSKTNNYATFYAASVKDRFTVSRDDSQNTAYLQMNSLKTEDTATYYCVRRGPRDSW
FGYWGQGTLVTVSS/ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDK
KVEPKSCDKTHTCPPCPAPEaaGGPSVFLFPPKPKDTLMISRTPEVTCVVVDVSHEDPEVKFNWYVDGVEVHNAKTKPREEQYNSTYRVVSVLTVLHQDWLNGKEYKCK

FIG. 13D

VSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEAL
HNHYTQKSLSLSPGK

H65 Human_IgG1_L234A_L235A_D265S SEQ ID NO:155

EVQLVESGGGLVQPGGSLRLSCAASGFAFNSFALNWVRQAPGKGLEWVVHIRSKTNNYATFYAASVKDRFTVSRDDSQNTAYLQMNSLKTEDTATYYCVRRGPRDSW
FGYWGQGTLVTVSS/ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDK
KVEPKSCDKTHTCPPCPAPEaaGGPSVFLFPPKPKDTLMISRTPEVTCVVVSVSHEDPEVKFNWYVDGVEVHNAKTKPREEQYNSTYRVVSVLTVLHQDWLNGKEYKCK
VSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEAL
HNHYTQKSLSLSPGK

H65 Human_IgG1_YTE_(M252Y_S254T_T256E) SEQ ID NO:156

EVQLVESGGGLVQPGGSLRLSCAASGFAFNSFALNWVRQAPGKGLEWVVHIRSKTNNYATFYAASVKDRFTVSRDDSQNTAYLQMNSLKTEDTATYYCVRRGPRDSW
FGYWGQGTLVTVSS/ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDK
KVEPKSCDKTHTCPPCPAPELLGGPSVFLFPPKPKDTLyItRePEVTCVVVDVSHEDPEVKFNWYVDGVEVHNAKTKPREEQYNSTYRVVSVLTVLHQDWLNGKEYKCKV
SNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALH
NHYTQKSLSLSPGK

H65 human_IgG1_N297A SEQ ID NO:157

EVQLVESGGGLVQPGGSLRLSCAASGFAFNSFALNWVRQAPGKGLEWVVHIRSKTNNYATFYAASVKDRFTVSRDDSQNTAYLQMNSLKTEDTATYYCVRRGPRDSW
FGYWGQGTLVTVSS/ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDK
KVEPKSCDKTHTCPPCPAPELLGGPSVFLFPPKPKDTLMISRTPEVTCVVVDGVEVHNAKTKPREEQYASTYRVVSVLTVLHQDWLNGKEYKCK
VSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEAL
HNHYTQKSLSLSPGK

H65 Human_IgG1_N297Q_ SEQ ID NO:158

FIG. 13E

EVQLVESGGGLVQPGGSLRLSCAASGFAFNSFALNWVRQAPGKGLEWVVHIRSKTNNYATFYAASVKDRFTVSRDDSQNTAYLQMNSLKTEDTATYYCVRRGPRDSW
FGYWGQGTLVTVSS/ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDK
KVEPKSCDKTHTCPPCPAPELLGGPSVFLFPPKPKDTLMISRTPEVTCVVVDVSHEDPEVKFNWYVDGVEVHNAKTKPREEQYqSTYRVVSVLTVLHQDWLNGKEYKCK
VSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEAL
HNHYTQKSLSLSPGK

H65 Human_IgG2 SEQ ID NO:159

EVQLVESGGGLVQPGGSLRLSCAASGFAFNSFALNWVRQAPGKGLEWVVHIRSKTNNYATFYAASVKDRFTVSRDDSQNTAYLQMNSLKTEDTATYYCVRRGPRDSW
FGYWGQGTLVTVSS/ASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDK
TVERKCCVECPPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSN
KGLPAPIEKTISKTKGQPREPQVYTLPPSREEMTKNQVSLTCLVKGFYPSDISVEWESNGQPENNYKTTPPMLDSDGSFFLYSKLTVDKSRWQQGNVFSCSVMHEALHN
HYTQKSLSLSPGK

H65_Human_IgG4 SEQ ID NO:160

EVQLVESGGGLVQPGGSLRLSCAASGFAFNSFALNWVRQAPGKGLEWVVHIRSKTNNYATFYAASVKDRFTVSRDDSQNTAYLQMNSLKTEDTATYYCVRRGPRDSW
FGYWGQGTLVTVSS/ASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDK
RVESKYGPPCPSCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVS
NKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALH
NHYTQKSLSLSLGK

H65_Human_IgG4_S228P_P01861 SEQ ID NO:161

EVQLVESGGGLVQPGGSLRLSCAASGFAFNSFALNWVRQAPGKGLEWVVHIRSKTNNYATFYAASVKDRFTVSRDDSQNTAYLQMNSLKTEDTATYYCVRRGPRDSW
FGYWGQGTLVTVSS/ASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDK
RVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVS
NKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALH
NHYTQKSLSLSLGK

FIG. 14A

VL46_kappa SEQ ID NO:162
DIVMTQSPLSLPVTLGEPASISCRSSQSIVHSNGNTYLEWYLQKPGQSPQLLIYTVSNRFSGVPDRFSGSGSGTDFTLKISRVEAEDLGVYYCFQGSHLPLTFGGGTKVEIK
/RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC VL46_lambda SEQ ID NO:163
DIVMTQSPLSLPVTLGEPASISCRSSQSIVHSNGNTYLEWYLQKPGQSPQLLIYTVSNRFSGVPDRFSGSGSGTDFTLKISRVEAEDLGVYYCFQGSHLPLTFGGGTKVEIK
/ GQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS VL47 kappa SEQ ID NO:164
DIVMTQSPLSLPVTLGDPASISCRSSQSIVHSNGNTYLEWYQQKPGQSPQRLIYTVSNRFSGVPDRFSGSGSGTDFTLKISRVEAEDLGVYYCFQGSHLPLTFGGGTKVEI
K/ RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC VL47 lambda SEQ ID NO:165
DIVMTQSPLSLPVTLGDPASISCRSSQSIVHSNGNTYLEWYQQKPGQSPQRLIYTVSNRFSGVPDRFSGSGSGTDFTLKISRVEAEDLGVYYCFQGSHLPLTFGGGTKVEI
K/ GQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS VL46_G34A kappa SEQ ID NO:166
DIVMTQSPLSLPVTLGEPASISCRSSQSIVHSNANTYLEWYLQKPGQSPQLLIYTVSNRFSGVPDRFSGSGSGTDFTLKISRVEAEDLGVYYCFQGSHLPLTFGGGTKVEIK
/RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC VL46_G34A lambda SEQ ID NO:167
DIVMTQSPLSLPVTLGEPASISCRSSQSIVHSNANTYLEWYLQKPGQSPQLLIYTVSNRFSGVPDRFSGSGSGTDFTLKISRVEAEDLGVYYCFQGSHLPLTFGGGTKVEIK
/ GQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS VL46_G34S kappa SEQ ID NO:168
DIVMTQSPLSLPVTLGEPASISCRSSQSIVHSNSNTYLEWYLQKPGQSPQLLIYTVSNRFSGVPDRFSGSGSGTDFTLKISRVEAEDLGVYYCFQGSHLPLTFGGGTKVEIK
/RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC

FIG. 14B

VL46_G34S lambda SEQ ID NO:169
DIVMTQSPLSLPVTLGEPASISCRSSQSIVHSNSNTNTYLEWYLQKPGQSPQLLIYTVSNRFSGVPDRFSGSGSGTDFTLKISRVEAEDLGVYYCFQGSHLPLTFGGGTKVEIK/
GQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS VL46_G34T kappa SEQ ID NO:170
DIVMTQSPLSLPVTLGEPASISCRSSQSIVHSNTNTYLEWYLQKPGQSPQLLIYTVSNRFSGVPDRFSGSGSGTDFTLKISRVEAEDLGVYYCFQGSHLPLTFGGGTKVEIK/
RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC VL46_G34T lambda SEQ ID NO:171
DIVMTQSPLSLPVTLGEPASISCRSSQSIVHSNTNTYLEWYLQKPGQSPQLLIYTVSNRFSGVPDRFSGSGSGTDFTLKISRVEAEDLGVYYCFQGSHLPLTFGGGTKVEIK/
GQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS VL46_N33Q kappa SEQ ID NO:172
DIVMTQSPLSLPVTLGEPASISCRSSQSIVHSQGNTYLEWYLQKPGQSPQLLIYTVSNRFSGVPDRFSGSGSGTDFTLKISRVEAEDLGVYYCFQGSHLPLTFGGGTKVEIK/
RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC VL46_N33Q lambda SEQ ID NO:173
DIVMTQSPLSLPVTLGEPASISCRSSQSIVHSQGNTYLEWYLQKPGQSPQLLIYTVSNRFSGVPDRFSGSGSGTDFTLKISRVEAEDLGVYYCFQGSHLPLTFGGGTKVEIK/
GQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS VL46_N33Q_G34A kappa SEQ ID NO:174
DIVMTQSPLSLPVTLGEPASISCRSSQSIVHSQANTYLEWYLQKPGQSPQLLIYTVSNRFSGVPDRFSGSGSGTDFTLKISRVEAEDLGVYYCFQGSHLPLTFGGGTKVEIK/
RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC VL46_N33Q_G34A lambda SEQ ID NO:175
DIVMTQSPLSLPVTLGEPASISCRSSQSIVHSQANTYLEWYLQKPGQSPQLLIYTVSNRFSGVPDRFSGSGSGTDFTLKISRVEAEDLGVYYCFQGSHLPLTFGGGTKVEIK/
GQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS

FIG. 14C

VL46_N33D kappa SEQ ID NO:176
DIVMTQSPLSLPVTLGEPASISCRSSQSIVHSDGNTYLEWYLQKPGQSPQLLIYTVSNRFSGVPDRFSGSGSGTDFTLKISRVEAEDLGVYYCFQGSHLPLTFGGGTKVEIK
/ RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC VL46_N33D lambda SEQ ID NO:177
DIVMTQSPLSLPVTLGEPASISCRSSQSIVHSDGNTYLEWYLQKPGQSPQLLIYTVSNRFSGVPDRFSGSGSGTDFTLKISRVEAEDLGVYYCFQGSHLPLTFGGGTKVEIK
/ GQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS VL46_N33S kappa SEQ ID NO:178
DIVMTQSPLSLPVTLGEPASISCRSSQSIVHSSGNTYLEWYLQKPGQSPQLLIYTVSNRFSGVPDRFSGSGSGTDFTLKISRVEAEDLGVYYCFQGSHLPLTFGGGTKVEIK
/ RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC VL46_N33S lambda SEQ ID NO:179
DIVMTQSPLSLPVTLGEPASISCRSSQSIVHSSGNTYLEWYLQKPGQSPQLLIYTVSNRFSGVPDRFSGSGSGTDFTLKISRVEAEDLGVYYCFQGSHLPLTFGGGTKVEIK
/ GQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS VL46_N33T kappa SEQ ID NO:180
DIVMTQSPLSLPVTLGEPASISCRSSQSIVHSTGNTYLEWYLQKPGQSPQLLIYTVSNRFSGVPDRFSGSGSGTDFTLKISRVEAEDLGVYYCFQGSHLPLTFGGGTKVEIK
/ RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC VL46_N33T lambda SEQ ID NO:181
DIVMTQSPLSLPVTLGEPASISCRSSQSIVHSTGNTYLEWYLQKPGQSPQLLIYTVSNRFSGVPDRFSGSGSGTDFTLKISRVEAEDLGVYYCFQGSHLPLTFGGGTKVEIK
/ GQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS VL46_S28N kappa SEQ ID NO:182
DIVMTQSPLSLPVTLGEPASISCRSSQNIVHSNGNTYLEWYLQKPGQSPQLLIYTVSNRFSGVPDRFSGSGSGTDFTLKISRVEAEDLGVYYCFQGSHLPLTFGGGTKVEIK
/ RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC

FIG. 14D

VL46_S28N lambda SEQ ID NO:183
DIVMTQSPLSLPVTLGEPASISCRSSQNIVHSNGNTYLEWYLQKPGQSPQLLIYTVSNRFSGVPDRFSGSGSGTDFTLKISRVEAEDLGVYYCFQGSHLPLTFGGGTKVEIK
/ GQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS

*VL46_G34A_S28N kappa SEQ ID NO:184
DIVMTQSPLSLPVTLGEPASISCRSSQNIVHSNANTYLEWYLQKPGQSPQLLIYTVSNRFSGVPDRFSGSGSGTDFTLKISRVEAEDLGVYYCFQGSHLPLTFGGGTKVEIK
/ RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC VL46_G34A_S28N lambda SEQ ID NO:185
DIVMTQSPLSLPVTLGEPASISCRSSQNIVHSNANTYLEWYLQKPGQSPQLLIYTVSNRFSGVPDRFSGSGSGTDFTLKISRVEAEDLGVYYCFQGSHLPLTFGGGTKVEIK
/ GQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS

FIG. 15

| Variable light domain/variable heavy domain | VH11 | VH65 |
|---|---|---|
| VL46-kappa | A, B, C, D, E, F, G, H, I, J | A, B, C, D, E, F, G, H, I, J |
| VL46-lambda | A, B, C, D, E, F, G, H, I, J | A, B, C, D, E, F, G, H, I, J |
| VL47-kappa | A, B, C, D, E, F, G, H, I, J | A, B, C, D, E, F, G, H, I, J |
| VL47-lambda | A, B, C, D, E, F, G, H, I, J | A, B, C, D, E, F, G, H, I, J |
| VL46_G34A-kappa | A, B, C, D, E, F, G, H, I, J | A, B, C, D, E, F, G, H, I, J |
| VL46-G34A-lambda | A, B, C, D, E, F, G, H, I, J | A, B, C, D, E, F, G, H, I, J |
| VL46_G34S-kappa | A, B, C, D, E, F, G, H, I, J | A, B, C, D, E, F, G, H, I, J |
| VL46_G34S-lambda | A, B, C, D, E, F, G, H, I, J | A, B, C, D, E, F, G, H, I, J |
| VL46_G34T-kappa | A, B, C, D, E, F, G, H, I, J | A, B, C, D, E, F, G, H, I, J |
| VL46-G34T-lambda | A, B, C, D, E, F, G, H, I, J | A, B, C, D, E, F, G, H, I, J |
| VL46_N33Q-kappa | A, B, C, D, E, F, G, H, I, J | A, B, C, D, E, F, G, H, I, J |
| VL46-N33Q-lambda | A, B, C, D, E, F, G, H, I, J | A, B, C, D, E, F, G, H, I, J |
| VL46_N33Q_G34A-kappa | A, B, C, D, E, F, G, H, I, J | A, B, C, D, E, F, G, H, I, J |
| VL46-N33Q-G34A-lambda | A, B, C, D, E, F, G, H, I, J | A, B, C, D, E, F, G, H, I, J |
| VL46_N33D-kappa | A, B, C, D, E, F, G, H, I, J | A, B, C, D, E, F, G, H, I, J |
| VL46_N33D-lambda | A, B, C, D, E, F, G, H, I, J | A, B, C, D, E, F, G, H, I, J |
| VL46_N33S-kappa | A, B, C, D, E, F, G, H, I, J | A, B, C, D, E, F, G, H, I, J |
| VL46_N33S-lambda | A, B, C, D, E, F, G, H, I, J | A, B, C, D, E, F, G, H, I, J |
| VL46_N33T-kappa | A, B, C, D, E, F, G, H, I, J | A, B, C, D, E, F, G, H, I, J |
| VL46_N33T-lambda | A, B, C, D, E, F, G, H, I, J | A, B, C, D, E, F, G, H, I, J |
| VL46_S28N-kappa | A, B, C, D, E, F, G, H, I, J | A, B, C, D, E, F, G, H, I, J |
| VL46-S28N-lambda | A, B, C, D, E, F, G, H, I, J | A, B, C, D, E, F, G, H, I, J |
| VL46_G34A_S28N-kappa | A, B, C, D, E, F, G, H, I, J | A, B, C, D, E, F, G, H, I, J |
| VL46_G34A_S28N-lambda | A, B, C, D, E, F, G, H, I, J | A, B, C, D, E, F, G, H, I, J |

SEQUENCE LISTING

```
<160> NUMBER OF SEQ ID NOS: 185

<210> SEQ ID NO 1
<211> LENGTH: 441
<212> TYPE: PRT
<213> ORGANISM: Artificial Sequence
<220> FEATURE:
<223> OTHER INFORMATION: [4R2N Tau] [amino acid]

<400> SEQUENCE: 1
```

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu

```
            35                  40                  45
Gln Thr Pro Thr Glu Asp Gly Ser Glu Pro Gly Ser Glu Thr Ser
 50                  55                  60

Asp Ala Lys Ser Thr Pro Thr Ala Glu Asp Val Thr Ala Pro Leu Val
 65                  70                  75                  80

Asp Glu Gly Ala Pro Gly Lys Gln Ala Ala Gln Pro His Thr Glu
                 85                  90                  95

Ile Pro Glu Gly Thr Thr Ala Glu Glu Ala Gly Ile Gly Asp Thr Pro
                100                 105                 110

Ser Leu Glu Asp Glu Ala Ala Gly His Val Thr Gln Ala Arg Met Val
            115                 120                 125

Ser Lys Ser Lys Asp Gly Thr Gly Ser Asp Asp Lys Lys Ala Lys Gly
        130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
        435                 440

<210> SEQ ID NO 2
```

```
<211> LENGTH: 412
<212> TYPE: PRT
<213> ORGANISM: Artificial Sequence
<220> FEATURE:
<223> OTHER INFORMATION: [4R1N Tau] [amino acid]

<400> SEQUENCE: 2

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
50                  55                  60

Asp Ala Lys Ser Thr Pro Thr Ala Glu Ala Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys
            100                 105                 110

Ala Lys Gly Ala Asp Gly Lys Thr Lys Ile Ala Thr Pro Arg Gly Ala
        115                 120                 125

Ala Pro Pro Gly Gln Lys Gly Gln Ala Asn Ala Thr Arg Ile Pro Ala
    130                 135                 140

Lys Thr Pro Pro Ala Pro Lys Thr Pro Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
            180                 185                 190

Glu Pro Lys Lys Val Ala Val Val Arg Thr Pro Pro Lys Ser Pro Ser
        195                 200                 205

Ser Ala Lys Ser Arg Leu Gln Thr Ala Pro Val Pro Met Pro Asp Leu
    210                 215                 220

Lys Asn Val Lys Ser Lys Ile Gly Ser Thr Glu Asn Leu Lys His Gln
225                 230                 235                 240

Pro Gly Gly Gly Lys Val Gln Ile Ile Asn Lys Lys Leu Asp Leu Ser
                245                 250                 255

Asn Val Gln Ser Lys Cys Gly Ser Lys Asp Asn Ile Lys His Val Pro
            260                 265                 270

Gly Gly Gly Ser Val Gln Ile Val Tyr Lys Pro Val Asp Leu Ser Lys
        275                 280                 285

Val Thr Ser Lys Cys Gly Ser Leu Gly Asn Ile His His Lys Pro Gly
    290                 295                 300

Gly Gly Gln Val Glu Val Lys Ser Glu Lys Leu Asp Phe Lys Asp Arg
305                 310                 315                 320

Val Gln Ser Lys Ile Gly Ser Leu Asp Asn Ile Thr His Val Pro Gly
                325                 330                 335

Gly Gly Asn Lys Lys Ile Glu Thr His Lys Leu Thr Phe Arg Glu Asn
            340                 345                 350

Ala Lys Ala Lys Thr Asp His Gly Ala Glu Ile Val Tyr Lys Ser Pro
        355                 360                 365

Val Val Ser Gly Asp Thr Ser Pro Arg His Leu Ser Asn Val Ser Ser
    370                 375                 380
```

```
Thr Gly Ser Ile Asp Met Val Asp Ser Pro Gln Leu Ala Thr Leu Ala
385                 390                 395                 400

Asp Glu Val Ser Ala Ser Leu Ala Lys Gln Gly Leu
            405                 410
```

<210> SEQ ID NO 3
<211> LENGTH: 383
<212> TYPE: PRT
<213> ORGANISM: Artificial Sequence
<220> FEATURE:
<223> OTHER INFORMATION: [4R0N Tau] [amino acid]

<400> SEQUENCE: 3

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Ile Asn Lys Lys Leu
    210                 215                 220

Asp Leu Ser Asn Val Gln Ser Lys Cys Gly Ser Lys Asp Asn Ile Lys
225                 230                 235                 240

His Val Pro Gly Gly Gly Ser Val Gln Ile Val Tyr Lys Pro Val Asp
                245                 250                 255

Leu Ser Lys Val Thr Ser Lys Cys Gly Ser Leu Gly Asn Ile His His
            260                 265                 270

Lys Pro Gly Gly Gly Gln Val Glu Val Lys Ser Glu Lys Leu Asp Phe
        275                 280                 285

Lys Asp Arg Val Gln Ser Lys Ile Gly Ser Leu Asp Asn Ile Thr His
    290                 295                 300

Val Pro Gly Gly Gly Asn Lys Lys Ile Glu Thr His Lys Leu Thr Phe
305                 310                 315                 320

Arg Glu Asn Ala Lys Ala Lys Thr Asp His Gly Ala Glu Ile Val Tyr
                325                 330                 335
```

-continued

Lys Ser Pro Val Val Ser Gly Asp Thr Ser Pro Arg His Leu Ser Asn
                340                 345                 350

Val Ser Ser Thr Gly Ser Ile Asp Met Val Asp Ser Pro Gln Leu Ala
                355                 360                 365

Thr Leu Ala Asp Glu Val Ser Ala Ser Leu Ala Lys Gln Gly Leu
            370                 375                 380

<210> SEQ ID NO 4
<211> LENGTH: 410
<212> TYPE: PRT
<213> ORGANISM: Artificial Sequence
<220> FEATURE:
<223> OTHER INFORMATION: [3R2N Tau] [amino acid]

<400> SEQUENCE: 4

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Val Tyr Lys Pro Val Asp Leu Ser Lys Val Thr
        275                 280                 285

Ser Lys Cys Gly Ser Leu Gly Asn Ile His His Lys Pro Gly Gly Gly
    290                 295                 300

Gln Val Glu Val Lys Ser Glu Lys Leu Asp Phe Lys Asp Arg Val Gln
305                 310                 315                 320

```
Ser Lys Ile Gly Ser Leu Asp Asn Ile Thr His Val Pro Gly Gly Gly
            325                 330                 335

Asn Lys Lys Ile Glu Thr His Lys Leu Thr Phe Arg Glu Asn Ala Lys
        340                 345                 350

Ala Lys Thr Asp His Gly Ala Glu Ile Val Tyr Lys Ser Pro Val Val
        355                 360                 365

Ser Gly Asp Thr Ser Pro Arg His Leu Ser Asn Val Ser Ser Thr Gly
        370                 375                 380

Ser Ile Asp Met Val Asp Ser Pro Gln Leu Ala Thr Leu Ala Asp Glu
385                 390                 395                 400

Val Ser Ala Ser Leu Ala Lys Gln Gly Leu
                405                 410

<210> SEQ ID NO 5
<211> LENGTH: 381
<212> TYPE: PRT
<213> ORGANISM: Artificial Sequence
<220> FEATURE:
<223> OTHER INFORMATION: [3R1N Tau] [amino acid]

<400> SEQUENCE: 5

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Ala Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys
            100                 105                 110

Ala Lys Gly Ala Asp Gly Lys Thr Lys Ile Ala Thr Pro Arg Gly Ala
        115                 120                 125

Ala Pro Pro Gly Gln Lys Gly Gln Ala Asn Ala Thr Arg Ile Pro Ala
    130                 135                 140

Lys Thr Pro Pro Ala Pro Lys Thr Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Thr Arg
            180                 185                 190

Glu Pro Lys Lys Val Ala Val Val Arg Thr Pro Pro Lys Ser Pro Ser
        195                 200                 205

Ser Ala Lys Ser Arg Leu Gln Thr Ala Pro Val Pro Met Pro Asp Leu
    210                 215                 220

Lys Asn Val Lys Ser Lys Ile Gly Ser Thr Glu Asn Leu Lys His Gln
225                 230                 235                 240

Pro Gly Gly Gly Lys Val Gln Ile Val Tyr Lys Pro Val Asp Leu Ser
                245                 250                 255

Lys Val Thr Ser Lys Cys Gly Ser Leu Gly Asn Ile His His Lys Pro
            260                 265                 270
```

```
Gly Gly Gly Gln Val Glu Val Lys Ser Glu Lys Leu Asp Phe Lys Asp
            275                 280                 285

Arg Val Gln Ser Lys Ile Gly Ser Leu Asp Asn Ile Thr His Val Pro
290                 295                 300

Gly Gly Gly Asn Lys Lys Ile Glu Thr His Lys Leu Thr Phe Arg Glu
305                 310                 315                 320

Asn Ala Lys Ala Lys Thr Asp His Gly Ala Glu Ile Val Tyr Lys Ser
                325                 330                 335

Pro Val Val Ser Gly Asp Thr Ser Pro Arg His Leu Ser Asn Val Ser
                340                 345                 350

Ser Thr Gly Ser Ile Asp Met Val Asp Ser Pro Gln Leu Ala Thr Leu
            355                 360                 365

Ala Asp Glu Val Ser Ala Ser Leu Ala Lys Gln Gly Leu
            370                 375                 380

<210> SEQ ID NO 6
<211> LENGTH: 352
<212> TYPE: PRT
<213> ORGANISM: Artificial Sequence
<220> FEATURE:
<223> OTHER INFORMATION: [3R0N Tau] [amino acid]

<400> SEQUENCE: 6

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Val Tyr Lys Pro Val
210                 215                 220

Asp Leu Ser Lys Val Thr Ser Lys Cys Gly Ser Leu Gly Asn Ile His
225                 230                 235                 240

His Lys Pro Gly Gly Gly Gln Val Glu Val Lys Ser Glu Lys Leu Asp
                245                 250                 255
```

```
Phe Lys Asp Arg Val Gln Ser Lys Ile Gly Ser Leu Asp Asn Ile Thr
            260                 265                 270

His Val Pro Gly Gly Asn Lys Ile Glu Thr His Lys Leu Thr
            275                 280                 285

Phe Arg Glu Asn Ala Lys Ala Lys Thr Asp His Gly Ala Glu Ile Val
            290                 295                 300

Tyr Lys Ser Pro Val Val Ser Gly Asp Thr Ser Pro Arg His Leu Ser
305                 310                 315                 320

Asn Val Ser Ser Thr Gly Ser Ile Asp Met Val Asp Ser Pro Gln Leu
                325                 330                 335

Ala Thr Leu Ala Asp Glu Val Ser Ala Ser Leu Ala Lys Gln Gly Leu
            340                 345                 350

<210> SEQ ID NO 7
<211> LENGTH: 17
<212> TYPE: PRT
<213> ORGANISM: Artificial Sequence
<220> FEATURE:
<223> OTHER INFORMATION: [pS412/pS413] [amino acid]
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (9)..(9)
<223> OTHER INFORMATION: PHOSPHORYLATION

<400> SEQUENCE: 7

Pro Arg His Leu Ser Asn Val Ser Ser Thr Gly Ser Ile Asp Met Val
1               5                   10                  15

Asp

<210> SEQ ID NO 8
<211> LENGTH: 17
<212> TYPE: PRT
<213> ORGANISM: Artificial Sequence
<220> FEATURE:
<223> OTHER INFORMATION: [pS413] [amino acid]
<220> FEATURE:
<221> NAME/KEY: MOD_RES
<222> LOCATION: (9)..(9)
<223> OTHER INFORMATION: PHOSPHORYLATION

<400> SEQUENCE: 8

Pro Arg His Leu Ser Asn Val Ser Ser Thr Gly Ser Ile Asp Met Val
1               5                   10                  15

Asp

<210> SEQ ID NO 9
<211> LENGTH: 17
<212> TYPE: PRT
<213> ORGANISM: Artificial Sequence
<220> FEATURE:
<223> OTHER INFORMATION: [pS409/pS412/pS413] [amino acid]
<220> FEATURE:
<221> NAME/KEY: MOD_RES
<222> LOCATION: (5)..(5)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (9)..(9)
```

```
<223> OTHER INFORMATION: PHOSPHORYLATION

<400> SEQUENCE: 9

Pro Arg His Leu Ser Asn Val Ser Ser Thr Gly Ser Ile Asp Met Val
1               5                   10                  15
Asp

<210> SEQ ID NO 10
<211> LENGTH: 5
<212> TYPE: PRT
<213> ORGANISM: Artificial Sequence
<220> FEATURE:
<223> OTHER INFORMATION: [CDR-H1: 1M] [amino acid]

<400> SEQUENCE: 10

Ser Phe Ala Leu Asn
1               5

<210> SEQ ID NO 11
<211> LENGTH: 19
<212> TYPE: PRT
<213> ORGANISM: Artificial Sequence
<220> FEATURE:
<223> OTHER INFORMATION: [CDR-H2: 2M] [amino acid]

<400> SEQUENCE: 11

His Ile Arg Ser Lys Thr Asn Asn Tyr Ala Thr Phe Tyr Ala Asp Ser
1               5                   10                  15
Val Lys Asp

<210> SEQ ID NO 12
<211> LENGTH: 19
<212> TYPE: PRT
<213> ORGANISM: Artificial Sequence
<220> FEATURE:
<223> OTHER INFORMATION: [CDR-H2: 2H1] [amino acid]

<400> SEQUENCE: 12

His Ile Arg Ser Lys Thr Asn Asn Tyr Ala Thr Phe Tyr Ala Ala Ser
1               5                   10                  15
Val Lys Asp

<210> SEQ ID NO 13
<211> LENGTH: 10
<212> TYPE: PRT
<213> ORGANISM: Artificial Sequence
<220> FEATURE:
<223> OTHER INFORMATION: [CDR-H3: 3M] [amino acid]

<400> SEQUENCE: 13

Arg Gly Pro Arg Asp Ser Trp Phe Gly Tyr
1               5                   10

<210> SEQ ID NO 14
<211> LENGTH: 16
<212> TYPE: PRT
<213> ORGANISM: Artificial Sequence
<220> FEATURE:
<223> OTHER INFORMATION: [CDR-L1: 4L1] [amino acid]

<400> SEQUENCE: 14

Arg Ser Ser Gln Ser Ile Val His Ser Asn Gly Asn Thr Tyr Leu Glu
1               5                   10                  15
```

```
<210> SEQ ID NO 15
<211> LENGTH: 16
<212> TYPE: PRT
<213> ORGANISM: Artificial Sequence
<220> FEATURE:
<223> OTHER INFORMATION: [CDR-L1: 4M] [amino acid]

<400> SEQUENCE: 15

Arg Ser Ser Gln Asn Ile Val His Ser Asn Gly Asn Thr Tyr Leu Glu
1               5                   10                  15

<210> SEQ ID NO 16
<211> LENGTH: 7
<212> TYPE: PRT
<213> ORGANISM: Artificial Sequence
<220> FEATURE:
<223> OTHER INFORMATION: [CDR-L2: 5M] [amino acid]

<400> SEQUENCE: 16

Thr Val Ser Asn Arg Phe Ser
1               5

<210> SEQ ID NO 17
<211> LENGTH: 9
<212> TYPE: PRT
<213> ORGANISM: Artificial Sequence
<220> FEATURE:
<223> OTHER INFORMATION: [CDR-L3: 6M] [amino acid]

<400> SEQUENCE: 17

Phe Gln Gly Ser His Leu Pro Leu Thr
1               5

<210> SEQ ID NO 18
<211> LENGTH: 121
<212> TYPE: PRT
<213> ORGANISM: Artificial Sequence
<220> FEATURE:
<223> OTHER INFORMATION: [VH11] [amino acid]

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
                20                  25                  30

Ala Leu Asn Trp Val Arg Gln Ala Pro Gly Lys Gly Leu Glu Trp Val
            35                  40                  45

Gly His Ile Arg Ser Lys Thr Asn Asn Tyr Ala Thr Phe Tyr Ala Ala
        50                  55                  60

Ser Val Lys Asp Arg Phe Thr Val Ser Arg Asp Asp Ser Gln Asn Thr
65                  70                  75                  80

Ala Tyr Leu Gln Met Asn Ser Leu Lys Thr Glu Asp Thr Ala Thr Tyr
                85                  90                  95

Tyr Cys Val Arg Arg Gly Pro Arg Asp Ser Trp Phe Tyr Trp Gly
                100                 105                 110

Gln Gly Thr Leu Val Thr Val Ser Ser
        115                 120

<210> SEQ ID NO 19
<211> LENGTH: 363
<212> TYPE: DNA
<213> ORGANISM: Artificial Sequence
<220> FEATURE:
<223> OTHER INFORMATION: [VH11] [DNA]
```

<400> SEQUENCE: 19

```
gaggtgcagc tggtggagtc cggaggagga ctggtgcagc caggaggctc cctgcgcctg    60
agctgcgccg cttctggctt cacattttcc agctttgccc tgaactgggt gaggcaggct   120
cctggcaagg gactggagtg gtgggccat atccggagca agaccaacaa ttacgctaca   180
ttctatgccg cttctgtgaa ggacaggttc accgtgtcca gggacgatag ccagaacaca   240
gcctacctgc agatgaactc cctgaagacc gaggacaccg ctacatacta ttgcgtgagg   300
cggggcccta gggattcctg gttcggctat tggggccagg gtaccctggt gacagtgtct   360
tcc                                                                  363
```

<210> SEQ ID NO 20
<211> LENGTH: 121
<212> TYPE: PRT
<213> ORGANISM: Artificial Sequence
<220> FEATURE:
<223> OTHER INFORMATION: [VH12] [amino acid]

<400> SEQUENCE: 20

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Asn Ser Phe
            20                  25                  30

Ala Leu Asn Trp Val Arg Gln Ala Pro Gly Lys Gly Leu Glu Trp Val
        35                  40                  45

Gly His Ile Arg Ser Lys Thr Asn Asn Tyr Ala Thr Phe Tyr Ala Asp
    50                  55                  60

Ser Val Lys Asp Arg Phe Thr Val Ser Arg Asp Asp Ser Lys Asn Thr
65                  70                  75                  80

Ala Tyr Leu Gln Met Asn Ser Leu Lys Thr Glu Asp Thr Ala Thr Tyr
                85                  90                  95

Tyr Cys Val Arg Arg Gly Pro Arg Asp Ser Trp Phe Gly Tyr Trp Gly
            100                 105                 110

Gln Gly Thr Leu Val Thr Val Ser Ser
        115                 120
```

<210> SEQ ID NO 21
<211> LENGTH: 363
<212> TYPE: DNA
<213> ORGANISM: Artificial Sequence
<220> FEATURE:
<223> OTHER INFORMATION: [VH12] [DNA]

<400> SEQUENCE: 21

```
gaggtgcagc tggtggagtc cggaggagga ctggtgcagc caggaggctc cctgcgcctg    60
agctgcgccg cttctggctt cgcttttaat agctttgccc tgaactgggt gaggcaggct   120
cctggcaagg gactggagtg gtgggccat atccggagca agaccaacaa ttacgctaca   180
ttctatgccg actctgtgaa ggataggttc accgtgtcca gggacgatag caagaacaca   240
gcctacctgc agatgaactc cctgaagacc gaggacaccg ctacatacta ttgcgtgagg   300
cggggcccta gggattcctg gttcggctat tggggccagg gtaccctggt gacagtgtct   360
tcc                                                                  363
```

<210> SEQ ID NO 22
<211> LENGTH: 121
<212> TYPE: PRT

<213> ORGANISM: Artificial Sequence
<220> FEATURE:
<223> OTHER INFORMATION: [VH47] [amino acid]

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Asn Ser Phe
            20                  25                  30

Ala Leu Asn Trp Val Arg Gln Ala Pro Gly Lys Gly Leu Glu Trp Val
        35                  40                  45

Gly His Ile Arg Ser Lys Thr Asn Asn Tyr Ala Thr Phe Tyr Ala Ala
    50                  55                  60

Ser Val Lys Asp Arg Phe Thr Val Ser Arg Asp Asp Ser Gln Asn Thr
65                  70                  75                  80

Ala Tyr Leu Gln Met Asn Ser Leu Lys Thr Glu Asp Thr Ala Thr Tyr
                85                  90                  95

Tyr Cys Val Arg Arg Gly Pro Arg Asp Ser Trp Phe Gly Tyr Trp Gly
            100                 105                 110

Gln Gly Thr Leu Val Thr Val Ser Ser
        115                 120

<210> SEQ ID NO 23
<211> LENGTH: 363
<212> TYPE: DNA
<213> ORGANISM: Artificial Sequence
<220> FEATURE:
<223> OTHER INFORMATION: [VH47] [DNA]

<400> SEQUENCE: 23

```
gaggtgcagc tggtggagtc cggaggagga ctggtgcagc caggaggctc cctgcgcctg      60
agctgcgccg cttctggctt cgcttttaat agctttgccc tgaactgggt gaggcaggct     120
cctggcaagg gactggagtg ggtgggccat atccggagca agaccaacaa ttacgctaca     180
ttctatgccg cttctgtgaa ggacaggttc accgtgtcca gggacgatag ccagaacaca     240
gcctacctgc agatgaactc cctgaagacc gaggacaccg ctacatacta ttgcgtgagg     300
cggggcccta gggattcctg gttcggctat tggggccagg taccctggt gacagtgtct     360 tcc                                                                   363
```

<210> SEQ ID NO 24
<211> LENGTH: 121
<212> TYPE: PRT
<213> ORGANISM: Artificial Sequence
<220> FEATURE:
<223> OTHER INFORMATION: [VH61] [amino acid]

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Ser Phe
            20                  25                  30

Ala Leu Asn Trp Val Arg Gln Ala Pro Gly Lys Gly Leu Glu Trp Val
        35                  40                  45

Val His Ile Arg Ser Lys Thr Asn Asn Tyr Ala Thr Phe Tyr Ala Asp
    50                  55                  60

Ser Val Lys Asp Arg Phe Thr Val Ser Arg Asp Asp Ser Lys Asn Thr
65                  70                  75                  80

Ala Tyr Leu Gln Met Asn Ser Leu Lys Thr Glu Asp Thr Ala Thr Tyr
            85                  90                  95

Tyr Cys Val Arg Arg Gly Pro Arg Asp Ser Trp Phe Gly Tyr Trp Gly
            100                 105                 110

Gln Gly Thr Leu Val Thr Val Ser Ser
        115                 120

<210> SEQ ID NO 25
<211> LENGTH: 363
<212> TYPE: DNA
<213> ORGANISM: Artificial Sequence
<220> FEATURE:
<223> OTHER INFORMATION: [VH61] [DNA]

<400> SEQUENCE: 25
gaggtgcagc tggtggagtc cggaggagga ctggtgcagc caggaggctc cctgcgcctg      60
agctgcgccg cttctggctt cacatttaat agctttgccc tgaactgggt gaggcaggct     120
cctggcaagg gactggagtg ggtggtgcat atccggagca agaccaacaa ttacgctaca     180
ttctatgccg actctgtgaa ggataggttc accgtgtcca gggacgatag caagaacaca     240
gcctacctgc agatgaactc cctgaagacc gaggacaccg ctacatacta ttgcgtgagg     300
cggggcccta gggattcctg gttcggctat tggggccagg gtaccctggt gacagtgtct     360
tcc                                                                   363

<210> SEQ ID NO 26
<211> LENGTH: 121
<212> TYPE: PRT
<213> ORGANISM: Artificial Sequence
<220> FEATURE:
<223> OTHER INFORMATION: [VH62] [amino acid]

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Asn Ser Phe
            20                  25                  30

Ala Leu Asn Trp Val Arg Gln Ala Pro Gly Lys Gly Leu Glu Trp Val
        35                  40                  45

Val His Ile Arg Ser Lys Thr Asn Asn Tyr Ala Thr Phe Tyr Ala Asp
    50                  55                  60

Ser Val Lys Asp Arg Phe Thr Val Ser Arg Asp Asp Ser Lys Asn Thr
65                  70                  75                  80

Ala Tyr Leu Gln Met Asn Ser Leu Lys Thr Glu Asp Thr Ala Thr Tyr
            85                  90                  95

Tyr Cys Val Arg Arg Gly Pro Arg Asp Ser Trp Phe Gly Tyr Trp Gly
            100                 105                 110

Gln Gly Thr Leu Val Thr Val Ser Ser
        115                 120

<210> SEQ ID NO 27
<211> LENGTH: 363
<212> TYPE: DNA
<213> ORGANISM: Artificial Sequence
<220> FEATURE:
<223> OTHER INFORMATION: [VH62] [DNA]

<400> SEQUENCE: 27
gaggtgcagc tggtggagtc cggaggagga ctggtgcagc caggaggctc cctgcgcctg      60

```
agctgcgccg cttctggctt cgcttttaat agctttgccc tgaactgggt gaggcaggct    120
cctggcaagg gactggagtg ggtggtgcat atccggagca agaccaacaa ttacgctaca    180
ttctatgccg actctgtgaa ggataggttc accgtgtcca gggacgatag caagaacaca    240
gcctacctgc agatgaactc cctgaagacc gaggacaccg ctacatacta ttgcgtgagg    300
cggggcccta gggattcctg gttcggctat tggggccagg gtaccctggt gacagtgtct    360
tcc                                                                  363
```

<210> SEQ ID NO 28
<211> LENGTH: 121
<212> TYPE: PRT
<213> ORGANISM: Artificial Sequence
<220> FEATURE:
<223> OTHER INFORMATION: [VH64] [amino acid]

<400> SEQUENCE: 28

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Ser Phe
            20                  25                  30

Ala Leu Asn Trp Val Arg Gln Ala Pro Gly Lys Gly Leu Glu Trp Val
        35                  40                  45

Val His Ile Arg Ser Lys Thr Asn Asn Tyr Ala Thr Phe Tyr Ala Ala
    50                  55                  60

Ser Val Lys Asp Arg Phe Thr Val Ser Arg Asp Asp Ser Gln Asn Thr
65                  70                  75                  80

Ala Tyr Leu Gln Met Asn Ser Leu Lys Thr Glu Asp Thr Ala Thr Tyr
                85                  90                  95

Tyr Cys Val Arg Arg Gly Pro Arg Asp Ser Trp Phe Gly Tyr Trp Gly
            100                 105                 110

Gln Gly Thr Leu Val Thr Val Ser Ser
        115                 120
```

<210> SEQ ID NO 29
<211> LENGTH: 363
<212> TYPE: DNA
<213> ORGANISM: Artificial Sequence
<220> FEATURE:
<223> OTHER INFORMATION: [VH64] [DNA]

<400> SEQUENCE: 29

```
gaggtgcagc tggtggagtc cggaggagga ctggtgcagc caggaggctc cctgcgcctg    60
agctgcgccg cttctggctt cacatttaat agctttgccc tgaactgggt gaggcaggct    120
cctggcaagg gactggagtg ggtggtgcat atccggagca agaccaacaa ttacgctaca    180
ttctatgccg cttctgtgaa ggacaggttc accgtgtcca gggacgatag ccagaacaca    240
gcctacctgc agatgaactc cctgaagacc gaggacaccg ctacatacta ttgcgtgagg    300
cggggcccta gggattcctg gttcggctat tggggccagg gtaccctggt gacagtgtct    360
tcc                                                                  363
```

<210> SEQ ID NO 30
<211> LENGTH: 121
<212> TYPE: PRT
<213> ORGANISM: Artificial Sequence
<220> FEATURE:
<223> OTHER INFORMATION: [VH65] [amino acid]

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Asn Ser Phe
            20                  25                  30

Ala Leu Asn Trp Val Arg Gln Ala Pro Gly Lys Gly Leu Glu Trp Val
        35                  40                  45

Val His Ile Arg Ser Lys Thr Asn Asn Tyr Ala Thr Phe Tyr Ala Ala
50                  55                  60

Ser Val Lys Asp Arg Phe Thr Val Ser Arg Asp Asp Ser Gln Asn Thr
65                  70                  75                  80

Ala Tyr Leu Gln Met Asn Ser Leu Lys Thr Glu Asp Thr Ala Thr Tyr
                85                  90                  95

Tyr Cys Val Arg Arg Gly Pro Arg Asp Ser Trp Phe Gly Tyr Trp Gly
            100                 105                 110

Gln Gly Thr Leu Val Thr Val Ser Ser
        115                 120

<210> SEQ ID NO 31
<211> LENGTH: 363
<212> TYPE: DNA
<213> ORGANISM: Artificial Sequence
<220> FEATURE:
<223> OTHER INFORMATION: [VH65] [DNA]

<400> SEQUENCE: 31
gaggtgcagc tggtggagtc cggaggagga ctggtgcagc caggaggctc cctgcgcctg      60
agctgcgccg cttctggctt cgcttttaat agctttgccc tgaactgggt gaggcaggct     120
cctggcaagg gactggagtg ggtggtgcat atccggagca agaccaacaa ttacgctaca     180
ttctatgccg cttctgtgaa ggacaggttc accgtgtcca gggacgatag ccagaacaca     240
gcctacctgc agatgaactc cctgaagacc gaggacaccg ctacatacta ttgcgtgagg     300
cggggcccta gggattcctg gttcggctat tggggccagg gtaccctggt gacagtgtct     360
tcc                                                                   363

<210> SEQ ID NO 32
<211> LENGTH: 112
<212> TYPE: PRT
<213> ORGANISM: Artificial Sequence
<220> FEATURE:
<223> OTHER INFORMATION: [VL15] [amino acid]

<400> SEQUENCE: 32

Asp Ile Val Met Thr Gln Ser Pro Leu Ser Leu Pro Val Thr Leu Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Gln Gln Lys Pro Gly Gln Ser
        35                  40                  45

Pro Arg Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Leu Pro Leu Thr Phe Gly Gly Gly Thr Lys Val Glu Ile Lys
            100                 105                 110

<210> SEQ ID NO 33
<211> LENGTH: 336
<212> TYPE: DNA
<213> ORGANISM: Artificial Sequence
<220> FEATURE:
<223> OTHER INFORMATION: [VL15] [DNA]

<400> SEQUENCE: 33

```
gacatcgtga tgacccagag cccctgagc ctgcctgtga cactgggaga gccagcctct    60
atcagctgcc ggagcagcca gagcatcgtg cactccaacg gcaataccta cctggagtgg   120
tatcagcaga agccaggaca gagccccgg ctgctgatct acacagtgtc taaccggttc    180
agcggcgtgc ctgacagatt ttccggctct ggcagcggca ccgatttcac actgaagatc   240
tcccgggtgg aggcagagga tctgggcgtg tactattgtt tccagggctc tcacctgcca   300
ctgacctttg gcggcggtac caaggtggag atcaag                             336
```

<210> SEQ ID NO 34
<211> LENGTH: 112
<212> TYPE: PRT
<213> ORGANISM: Artificial Sequence
<220> FEATURE:
<223> OTHER INFORMATION: [VL36] [amino acid]

<400> SEQUENCE: 34

```
Asp Ile Val Met Thr Gln Ser Pro Leu Ser Leu Pro Val Thr Leu Gly
 1               5                  10                  15
Asp Pro Ala Ser Ile Ser Cys Arg Ser Ser Gln Ser Ile Val His Ser
            20                  25                  30
Asn Gly Asn Thr Tyr Leu Glu Trp Tyr Gln Gln Lys Pro Gly Gln Ser
        35                  40                  45
Pro Gln Leu Leu Ile Tyr Thr Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Leu Gly Val Tyr Tyr Cys Phe Gln Gly
                85                  90                  95
Ser His Leu Pro Leu Thr Phe Gly Gly Gly Thr Lys Val Glu Ile Lys
            100                 105                 110
```

<210> SEQ ID NO 35
<211> LENGTH: 336
<212> TYPE: DNA
<213> ORGANISM: Artificial Sequence
<220> FEATURE:
<223> OTHER INFORMATION: [VL36] [DNA]

<400> SEQUENCE: 35

```
gatatcgtga tgacacagtc tccactgtcc ctgccagtga ccctgggaga tccagcttcc    60
atcagctgcc gctccagcca gagcatcgtg cattctaacg gcaataccta cctggagtgg   120
tatcagcaga agcctggcca gtccccacag ctgctgatct acacagtgtc caacaggttc   180
agcggcgtgc ccgaccggtt ttctggctcc ggcagcggca ccgatttcac actgaagatc   240
tctagggtgg aggccgagga cctgggcgtg tactattgct tccagggctc ccacctgcca   300
ctgacctttg gcggcggtac caaggtggag atcaag                             336
```

<210> SEQ ID NO 36
<211> LENGTH: 112

```
<212> TYPE: PRT
<213> ORGANISM: Artificial Sequence
<220> FEATURE:
<223> OTHER INFORMATION: [VL46] [amino acid]

<400> SEQUENCE: 36

Asp Ile Val Met Thr Gln Ser Pro Leu Ser Leu Pro Val Thr Leu Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Leu Pro Leu Thr Phe Gly Gly Gly Thr Lys Val Glu Ile Lys
            100                 105                 110

<210> SEQ ID NO 37
<211> LENGTH: 336
<212> TYPE: DNA
<213> ORGANISM: Artificial Sequence
<220> FEATURE:
<223> OTHER INFORMATION: [VL46] [DNA]

<400> SEQUENCE: 37
gatatcgtga tgacacagtc tccactgtcc ctgccagtga ccctgggaga accagcttcc      60
atcagctgcc gctccagcca gagcatcgtg cattctaacg gcaataccta cctggagtgg     120
tatctgcaga agcctggcca gtccccacag ctgctgatct acacagtgtc caacaggttc     180
agcggcgtgc ccgaccggtt ttctggctcc ggcagcggca ccgatttcac actgaagatc     240
tctagggtgg aggccgagga cctgggcgtg tactattgct tccagggctc ccacctgcca     300
ctgacctttg gcggcggtac caaggtggag atcaag                               336

<210> SEQ ID NO 38
<211> LENGTH: 112
<212> TYPE: PRT
<213> ORGANISM: Artificial Sequence
<220> FEATURE:
<223> OTHER INFORMATION: [VL47] [amino acid]

<400> SEQUENCE: 38

Asp Ile Val Met Thr Gln Ser Pro Leu Ser Leu Pro Val Thr Leu Gly
1               5                   10                  15

Asp Pro Ala Ser Ile Ser Cys Arg Ser Ser Gln Ser Ile Val His Ser
            20                  25                  30

Asn Gly Asn Thr Tyr Leu Glu Trp Tyr Gln Gln Lys Pro Gly Gln Ser
        35                  40                  45

Pro Gln Arg Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Leu Pro Leu Thr Phe Gly Gly Gly Thr Lys Val Glu Ile Lys
```

<210> SEQ ID NO 39
<211> LENGTH: 336
<212> TYPE: DNA
<213> ORGANISM: Artificial Sequence
<220> FEATURE:
<223> OTHER INFORMATION: [VL47] [DNA]

<400> SEQUENCE: 39

```
gatatcgtga tgacacagtc tccactgtcc ctgccagtga ccctgggaga tccagcttcc    60
atcagctgcc gctccagcca gagcatcgtg cattctaacg gcaataccta cctggagtgg   120
tatcagcaga agcctggcca gtccccacag cggctgatct acacagtgtc caacaggttc   180
agcggcgtgc ccgaccggtt ttctggctcc ggcagcggca ccgatttcac actgaagatc   240
tctagggtgg aggccgagga cctgggcgtg tactattgct ccagggctc ccacctgcca   300
ctgacctttg gcggcggtac caaggtggag atcaag                              336
```

<210> SEQ ID NO 40
<211> LENGTH: 112
<212> TYPE: PRT
<213> ORGANISM: Artificial Sequence
<220> FEATURE:
<223> OTHER INFORMATION: [VL48] [amino acid]

<400> SEQUENCE: 40

```
Asp Ile Val Met Thr Gln Ser Pro Leu Ser Leu Pro Val Thr Leu Gly
1               5                   10                  15
Asp Pro Ala Ser Ile Ser Cys Arg Ser Ser Gln Asn Ile Val His Ser
            20                  25                  30
Asn Gly Asn Thr Tyr Leu Glu Trp Tyr Gln Gln Lys Pro Gly Gln Ser
        35                  40                  45
Pro Gln Leu Leu Ile Tyr Thr Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Leu Gly Val Tyr Tyr Cys Phe Gln Gly
                85                  90                  95
Ser His Leu Pro Leu Thr Phe Gly Gly Gly Thr Lys Val Glu Ile Lys
            100                 105                 110
```

<210> SEQ ID NO 41
<211> LENGTH: 336
<212> TYPE: DNA
<213> ORGANISM: Artificial Sequence
<220> FEATURE:
<223> OTHER INFORMATION: [VL48] [DNA]

<400> SEQUENCE: 41

```
gatatcgtga tgacacagtc tccactgtcc ctgccagtga ccctgggaga tccagcttcc    60
atcagctgcc gctccagcca gaacatcgtg cattctaacg gcaataccta cctggagtgg   120
tatcagcaga agcctggcca gtccccacag ctgctgatct acacagtgtc caacaggttc   180
agcggcgtgc ccgaccggtt ttctggctcc ggcagcggca ccgatttcac actgaagatc   240
tctagggtgg aggccgagga cctgggcgtg tactattgct tccagggctc ccacctgcca   300
ctgacctttg gcggcggtac caaggtggag atcaag                              336
```

<210> SEQ ID NO 42

<211> LENGTH: 112
<212> TYPE: PRT
<213> ORGANISM: Artificial Sequence
<220> FEATURE:
<223> OTHER INFORMATION: [VL50] [amino acid]

<400> SEQUENCE: 42

Asp Ile Val Met Thr Gln Ser Pro Leu Ser Leu Pro Val Thr Leu Gly
1               5                   10                  15
Asp Pro Ala Ser Ile Ser Cys Arg Ser Ser Gln Asn Ile Val His Ser
            20                  25                  30
Asn Gly Asn Thr Tyr Leu Glu Trp Tyr Gln Gln Lys Pro Gly Gln Ser
        35                  40                  45
Pro Arg Leu Leu Ile Tyr Thr Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Leu Gly Val Tyr Tyr Cys Phe Gln Gly
                85                  90                  95
Ser His Leu Pro Leu Thr Phe Gly Gly Gly Thr Lys Val Glu Ile Lys
            100                 105                 110

<210> SEQ ID NO 43
<211> LENGTH: 336
<212> TYPE: DNA
<213> ORGANISM: Artificial Sequence
<220> FEATURE:
<223> OTHER INFORMATION: [VL50] [DNA]

<400> SEQUENCE: 43
gatatcgtga tgacacagtc tccactgtcc ctgccagtga ccctgggaga tccagcttcc      60
atcagctgcc gctccagcca gaacatcgtg cattctaacg gcaataccta cctggagtgg     120
tatcagcaga agcctggcca gtccccaagg ctgctgatct acacagtgtc caacaggttc     180
agcggcgtgc ccgaccggtt ttctggctcc ggcagcggca ccgatttcac actgaagatc     240
tctagggtgg aggccgagga cctgggcgtg tactattgct tccagggctc ccacctgcca     300
ctgacctttg gcggcggtac caaggtggag atcaag                               336

<210> SEQ ID NO 44
<211> LENGTH: 238
<212> TYPE: PRT
<213> ORGANISM: Artificial Sequence
<220> FEATURE:
<223> OTHER INFORMATION: [Ta1505: Light chain] [amino acid]

<400> SEQUENCE: 44

Met Lys Leu Pro Val Arg Leu Leu Val Leu Met Phe Trp Ile Pro Gly
1               5                   10                  15
Ser Ser Ser Asp Ile Leu Met Thr Gln Thr Pro Leu Ser Leu Pro Val
            20                  25                  30
Ser Leu Gly Asp Gln Ala Ser Ile Ser Cys Arg Ser Ser Gln Asn Ile
        35                  40                  45
Val His Ser Asn Gly Asn Thr Tyr Leu Glu Trp Tyr Leu Gln Lys Pro
    50                  55                  60
Gly Gln Ser Pro Lys Val Leu Ile Tyr Thr Val Ser Asn Arg Phe Ser
65                  70                  75                  80
Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser His Leu Pro Leu Thr Phe Gly Gly Gly Thr Lys Leu
        115                 120                 125

Glu Leu Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235

<210> SEQ ID NO 45
<211> LENGTH: 717
<212> TYPE: DNA
<213> ORGANISM: Artificial Sequence
<220> FEATURE:
<223> OTHER INFORMATION: [Ta1505: Light chain] [DNA]

<400> SEQUENCE: 45
atgaagttgc ctgttaggct gttggtgctg atgttctgga ttcctgggtc cagcagtgat      60
attttgatga cccaaactcc actctccctg cctgtcagtc ttggagatca agcctccatc     120
tcttgcagat ctagtcagaa cattgttcat agtaatggaa acacctattt agaatggtac     180
ctgcagaagc caggccagtc tccaaaggtc ctgatataca gtttccaa ccgattttct       240 ggggtccccg acaggttcag tggcagtgga tcaggacag atttcacact caagatcagc     300
agagtggagg ctgaggatct ggagttttat tactgctttc agggttcaca tcttccgctc     360
acgttcggtg gtgggaccaa gctggagctg aaacggctg atgctgcacc aactgtatcc     420
atcttcccac catccagtga gcagttaaca tctggaggtg cctcagtcgt gtgcttcttg     480
aacaacttct accccaaaga catcaatgtc aagtggaaga ttgatggcag tgaacgacaa     540
aatggcgtcc tgaacagttg gactgatcag gacagcaaag acagcaccta cagcatgagc     600
agcaccctca cgttgaccaa ggacgagtat gaacgacata acagctatac ctgtgaggcc     660
actcacaaga catcaacttc acccattgtc aagagcttca caggaatga gtgttag        717

<210> SEQ ID NO 46
<211> LENGTH: 474
<212> TYPE: PRT
<213> ORGANISM: Artificial Sequence
<220> FEATURE:
<223> OTHER INFORMATION: [Ta1505: Heavy chain] [amino acid]

<400> SEQUENCE: 46

Met Thr Leu Asn Arg Leu Leu Gly Leu Lys Trp Val Phe Phe Val Val
1               5                   10                  15

Phe Tyr Gln Gly Val His Cys Glu Val Gln Leu Val Glu Ser Gly Gly
            20                  25                  30

Gly Leu Val Gln Pro Lys Gly Ser Leu Lys Leu Ser Cys Ala Ala Ser
        35                  40                  45

```
Gly Phe Ala Phe Asn Ser Phe Ala Leu Asn Trp Val Arg Gln Ala Pro
 50                  55                  60

Gly Lys Ser Leu Glu Trp Val Val His Ile Arg Ser Lys Thr Asn Asn
 65                  70                  75                  80

Tyr Ala Thr Phe Tyr Ala Asp Ser Val Lys Asp Arg Phe Thr Val Ser
                 85                  90                  95

Arg Asp Asp Ser Gln Ser Met Val Tyr Leu Gln Met Asn Asn Leu Lys
                100                 105                 110

Thr Glu Asp Thr Gly Ile Tyr Tyr Cys Val Arg Arg Gly Pro Arg Asp
                115                 120                 125

Ser Trp Phe Gly Tyr Trp Gly Gln Gly Thr Leu Val Thr Val Ser Ala
    130                 135                 140

Ala Lys Thr Thr Ala Pro Ser Val Tyr Pro Leu Ala Pro Val Cys Gly
145                 150                 155                 160

Asp Thr Thr Gly Ser Ser Val Thr Leu Gly Cys Leu Val Lys Gly Tyr
                165                 170                 175

Phe Pro Glu Pro Val Thr Leu Thr Trp Asn Ser Gly Ser Leu Ser Ser
                180                 185                 190

Gly Val His Thr Phe Pro Ala Val Leu Gln Ser Asp Leu Tyr Thr Leu
        195                 200                 205

Ser Ser Ser Val Thr Val Thr Ser Ser Thr Trp Pro Ser Gln Ser Ile
210                 215                 220

Thr Cys Asn Val Ala His Pro Ala Ser Ser Thr Lys Val Asp Lys Lys
225                 230                 235                 240

Ile Glu Pro Arg Gly Pro Thr Ile Lys Pro Cys Pro Pro Cys Lys Cys
                245                 250                 255

Pro Ala Pro Asn Leu Leu Gly Gly Pro Ser Val Phe Ile Phe Pro Pro
                260                 265                 270

Lys Ile Lys Asp Val Leu Met Ile Ser Leu Ser Pro Ile Val Thr Cys
                275                 280                 285

Val Val Val Asp Val Ser Glu Asp Asp Pro Asp Val Gln Ile Ser Trp
    290                 295                 300

Phe Val Asn Asn Val Glu Val His Thr Ala Gln Thr Gln Thr His Arg
305                 310                 315                 320

Glu Asp Tyr Asn Ser Thr Leu Arg Val Val Ser Ala Leu Pro Ile Gln
                325                 330                 335

His Gln Asp Trp Met Ser Gly Lys Glu Phe Lys Cys Lys Val Asn Asn
                340                 345                 350

Lys Asp Leu Pro Ala Pro Ile Glu Arg Thr Ile Ser Lys Pro Lys Gly
            355                 360                 365

Ser Val Arg Ala Pro Gln Val Tyr Val Leu Pro Pro Pro Glu Glu Glu
    370                 375                 380

Met Thr Lys Lys Gln Val Thr Leu Thr Cys Met Val Thr Asp Phe Met
385                 390                 395                 400

Pro Glu Asp Ile Tyr Val Glu Trp Thr Asn Asn Gly Lys Thr Glu Leu
                405                 410                 415

Asn Tyr Lys Asn Thr Glu Pro Val Leu Asp Ser Asp Gly Ser Tyr Phe
                420                 425                 430

Met Tyr Ser Lys Leu Arg Val Glu Lys Lys Asn Trp Val Glu Arg Asn
        435                 440                 445

Ser Tyr Ser Cys Ser Val Val His Glu Gly Leu His Asn His His Thr
450                 455                 460
```

Thr Lys Ser Phe Ser Arg Thr Pro Gly Lys
465                 470

<210> SEQ ID NO 47
<211> LENGTH: 1425
<212> TYPE: DNA
<213> ORGANISM: Artificial Sequence
<220> FEATURE:
<223> OTHER INFORMATION: [Ta1505: Heavy chain] [DNA]

<400> SEQUENCE: 47

| | | | | | |
|---|---|---|---|---|---|
| atgacattga | acaggctgtt | ggggctgaag | tgggttttct | tgttgttttt | ttatcaaggt | 60 |
| gtgcattgtg | aggtgcagct | tgttgagtct | ggtggaggat | tggtgcagcc | taaagggtca | 120 |
| ttgaaactct | catgtgcagc | ctctggattc | gccttcaatt | ccttcgccct | gaactgggtc | 180 |
| cgccaggctc | caggaaagtc | tttggagtgg | gttgttcaca | taagaagtaa | aactaataat | 240 |
| tatgcaacgt | tttatgccga | ttcagtgaaa | gacagattca | ccgtctccag | agatgattca | 300 |
| caaagcatgg | tctatctgca | aatgaacaac | ttgaaaactg | aagacacagg | catatattac | 360 |
| tgtgtgagac | ggggaccacg | agattcctgg | tttggttact | ggggccaagg | gactctggtc | 420 |
| actgtctctg | cagccaaaac | aacagcccca | tcggtctatc | cactggcccc | tgtgtgtgga | 480 |
| gatacaactg | gctcctcggt | gactctagga | tgcctggtca | agggttattt | ccctgagcca | 540 |
| gtgaccttga | cctggaactc | tggatccctg | tccagtggtg | tgcacacctt | cccagctgtc | 600 |
| ctgcagtctg | acctctacac | cctcagcagc | tcagtgactg | taacctcgag | cacctggccc | 660 |
| agccagtcca | tcacctgcaa | tgtggcccac | ccggcaagca | gcaccaaggt | ggacaagaaa | 720 |
| attgagccca | gagggcccac | aatcaagccc | tgtcctccat | gcaaatgccc | agcacctaac | 780 |
| ctcttgggtg | gaccatccgt | cttcatcttc | cctccaaaga | tcaaggatgt | actcatgatc | 840 |
| tccctgagcc | ccatagtcac | atgtgtggtg | gtggatgtga | gcgaggatga | cccagatgtc | 900 |
| cagatcagct | ggtttgtgaa | caacgtggaa | gtacacacag | ctcagacaca | aacccataga | 960 |
| gaggattaca | acagtactct | ccgggtggtc | agtgccctcc | ccatccagca | ccaggactgg | 1020 |
| atgagtggca | aggagttcaa | atgcaaggtc | aacaacaaag | acctcccagc | gcccatcgag | 1080 |
| agaaccatct | caaacccaa | agggtcagta | agagctccac | aggtatatgt | cttgcctcca | 1140 |
| ccagaagaag | agatgactaa | gaaacaggtc | actctgacct | gcatggtcac | agacttcatg | 1200 |
| cctgaagaca | tttacgtgga | gtggaccaac | aacgggaaaa | cagagctaaa | ctacaagaac | 1260 |
| actgaaccag | tcctggactc | tgatggttct | tacttcatgt | acagcaagct | gagagtggaa | 1320 |
| aagaagaact | gggtggaaag | aaatagctac | tcctgttcag | tggtccacga | gggtctgcac | 1380 |
| aatcaccaca | cgactaagag | cttctcccgg | actccgggta | aatga | | 1425 |

<210> SEQ ID NO 48
<211> LENGTH: 219
<212> TYPE: PRT
<213> ORGANISM: Artificial Sequence
<220> FEATURE:
<223> OTHER INFORMATION: [Chimeric: Light chain] [amino acid]

<400> SEQUENCE: 48

Asp Ile Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asn Gly Asn Thr Tyr Leu Glu Trp Tyr Leu Gln Lys Pro Gly Gln Ser
        35                  40                  45

Pro Lys Val Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Leu Pro Leu Thr Phe Gly Gly Gly Thr Lys Leu Glu Leu Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215

<210> SEQ ID NO 49
<211> LENGTH: 660
<212> TYPE: DNA
<213> ORGANISM: Artificial Sequence
<220> FEATURE:
<223> OTHER INFORMATION: [Chimeric: Light chain] [DNA]

<400> SEQUENCE: 49
gatatcctga tgacccagac accactgtct ctgcccgtgt ccctgggcga ccaggcttcc        60
atcagctgcc gctccagcca gaacatcgtg cattccaacg gcaataccta cctggagtgg       120
tatctgcaga agcctggcca gagcccaaag gtgctgatct acacagtgag caataggttc       180
tctggcgtgc ccgaccggtt ttctggctcc ggcagcggca ccgatttcac actgaagatc       240
tctagggtgg aggccgagga tctgggcgtg tactattgct tccagggctc cacctgcca       300
ctgaccttg gcggcggcac aaagctggag ctgaagagga ccgtggctgc tcctagcgtg       360
ttcatctttc cccttctga cgagcagctg aagtccggca gcctccgt ggtgtgcctg         420
ctgaacaact tctacccaag agaggccaag gtgcagtgga aggtggataa cgctctgcag       480
tctggcaatt cccaggagag cgtgaccgag caggactcta aggattccac atatagcctg       540
tcttccaccc tgacactgag caaggccgac tacgagaagc acaaggtgta tgcttgcgag       600
gtgacccatc agggcctgag ctctcccgtg acaaagtctt ttaaccgcgg cgagtgttga       660

<210> SEQ ID NO 50
<211> LENGTH: 450
<212> TYPE: PRT
<213> ORGANISM: Artificial Sequence
<220> FEATURE:
<223> OTHER INFORMATION: [Chimeric: Heavy chain] [amino acid]

<400> SEQUENCE: 50

Glu Val Gln Leu Val Glu Ser Gly Gly Gly Leu Val Gln Pro Lys Gly
1               5                   10                  15

-continued

```
Ser Leu Lys Leu Ser Cys Ala Ala Ser Gly Phe Ala Phe Asn Ser Phe
             20                  25                  30
Ala Leu Asn Trp Val Arg Gln Ala Pro Gly Lys Ser Leu Glu Trp Val
         35                  40                  45
Val His Ile Arg Ser Lys Thr Asn Asn Tyr Ala Thr Phe Tyr Ala Asp
     50                  55                  60
Ser Val Lys Asp Arg Phe Thr Val Ser Arg Asp Asp Ser Gln Ser Met
65                  70                  75                  80
Val Tyr Leu Gln Met Asn Asn Leu Lys Thr Glu Asp Thr Gly Ile Tyr
                 85                  90                  95
Tyr Cys Val Arg Arg Gly Pro Arg Asp Ser Trp Phe Gly Tyr Trp Gly
            100                 105                 110
Gln Gly Thr Leu Val Thr Val Ser Ala Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Lys Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
```

Pro Gly
    450

<210> SEQ ID NO 51
<211> LENGTH: 1353
<212> TYPE: DNA
<213> ORGANISM: Artificial Sequence
<220> FEATURE:
<223> OTHER INFORMATION: [Chimeric: Heavy chain] [DNA]

<400> SEQUENCE: 51

| | |
|---|---|
| gaagtccagc tggtcgagtc cggggggggc ctggtgcagc caagggctc cctgaagctg | 60 |
| agctgcgccg cttctggctt cgcctttaac agcttcgctc tgaattgggt gaggcaggcc | 120 |
| cctggcaagt ctctggagtg gtggtgcac atccggtcca agaccaacaa ttacgccaca | 180 |
| ttctatgctg acagcgtgaa ggataggttc accgtgtcca gggacgattc ccagagcatg | 240 |
| gtgtacctgc agatgaacaa tctgaagacc gaggacacag gcatctacta ttgcgtgagg | 300 |
| cggggcccta gagattcttg gttcggctat tggggacagg gcaccctggt gacagtgtcc | 360 |
| gccgcctcca ccaagggacc atccgtgttt ccactggctc cctccagcaa gtctacctcc | 420 |
| ggaggcacag ccgctctggg atgtctggtg aaggactact cccagagcc cgtgacagtg | 480 |
| tcttggaact ccggcgccct gacctccgga gtgcatacat tccagctgt gctgcagtct | 540 |
| tccggcctgt acagcctgag ctctgtggtg accgtgccct ccagctctct gggcacccag | 600 |
| acatatatct gcaacgtgaa tcacaagcca tccaatacaa aggtggacaa gaaggtggag | 660 |
| cccaagagct gtgataagac ccatacatgc ccccccttgtc ctgctccaga gctgctggga | 720 |
| ggaccatccg tgttcctgtt ccacccaag cctaaggaca ccctgatgat ctctcgcacc | 780 |
| cccgaggtga catgcgtggt ggtggacgtg tcccacgagg accccgaggt gaagtttaac | 840 |
| tggtacgtgg atggcgtgga ggtgcataat gctaagacca gccaaggga ggagcagtac | 900 |
| aactccacct atcgggtggt gagcgtgctg acagtgctgc accaggactg gctgaacggc | 960 |
| aaggagtata gtgcaaggt gagcaataag gccctgcccg ctcctatcga aagaccatc | 1020 |
| tctaaggcca agggccagcc tagagagcca caggtgtaca cactgcctcc aagccgcgac | 1080 |
| gagctgacca gaaccaggt gtctctgaca tgtctggtga agggcttcta ccttccgat | 1140 |
| atcgctgtgg agtgggagag caatggccag ccagagaaca attacaagac cacccccct | 1200 |
| gtgctggaca gcgatggctc tttctttctg tattctaagc tgaccgtgga taagtccagg | 1260 |
| tggcagcagg gcaacgtgtt ctcctgttct gtgatgcacg aagccctgca caatcattac | 1320 |
| acccagaaga gcctgagcct gtcacctggt tga | 1353 |

<210> SEQ ID NO 52
<211> LENGTH: 107
<212> TYPE: PRT
<213> ORGANISM: Artificial Sequence
<220> FEATURE:
<223> OTHER INFORMATION: [Human Ig kappa: CL] [amino acid]

<400> SEQUENCE: 52

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

```
Ser Gly Asn Ser Gln Glu Ser Val Thr Glu Gln Asp Ser Lys Asp Ser
         50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
                100                 105

<210> SEQ ID NO 53
<211> LENGTH: 321
<212> TYPE: DNA
<213> ORGANISM: Artificial Sequence
<220> FEATURE:
<223> OTHER INFORMATION: [Human Ig kappa: CL] [DNA]

<400> SEQUENCE: 53
cggaccgtgg ccgctccttc cgtgttcatc tttcccccta gcgacgagca gctgaagtct    60
ggcacagcta gcgtcgtgtg cctgctgaac aacttctacc ccgcgaggc caaggtgcag   120 tggaaggtgg acaatgccct gcagagcggc aacagccagg aaagcgtgac cgagcaggac   180
agcaaggact ccacctacag cctgagcagc accctgacac tgagcaaggc cgactacgag   240
aagcacaagg tgtacgcctg cgaagtgacc caccagggcc tgtctagccc cgtgaccaag   300
agcttcaacc ggggcgagtg c                                              321

<210> SEQ ID NO 54
<211> LENGTH: 329
<212> TYPE: PRT
<213> ORGANISM: Artificial Sequence
<220> FEATURE:
<223> OTHER INFORMATION: [Human Ig gamma1: CH] [amino acid]

<400> SEQUENCE: 54

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
             115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
```

```
                    180                 185                 190
His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 55
<211> LENGTH: 987
<212> TYPE: DNA
<213> ORGANISM: Artificial Sequence
<220> FEATURE:
<223> OTHER INFORMATION: [Human Ig gamma1: CH] [DNA]

<400> SEQUENCE: 55

```
gctagcacca agggcccatc cgtgtttcca ctggctccca gctctaagag cacctctgga    60
ggcacagccg ctctgggatg tctggtgaag gattacttcc cagagccgtg acagtgtct   120
tggaactccg gcgccctgac ctccggagtg cacacatttc cagctgtgct gcagtccagc   180
ggcctgtaca gcctgtcttc cgtggtgacc gtgcccagct cttccctggg cacccagaca   240
tatatctgca acgtgaatca caagccatcc aatacaaagg tggacaagaa ggtggagccc   300
aagagctgtg ataagaccca tacatgcccc ccttgtcctg ctccagagct gctgggagga   360
ccaagcgtgt tcctgtttcc acccaagcct aaggacaccc tgatgatctc tcggaccccc   420
gaggtgacat gcgtggtggt ggacgtgtcc cacgaggacc ccgaggtgaa gtttaactgg   480
tacgtggatg gcgtggaggt gcataatgct aagaccaagc caagggagga gcagtacaat   540
tccacctatc gggtggtgag cgtgctgaca gtgctgcacc aggactggct gaacggcaag   600
gagtataagt gcaaggtgag caataaggcc ctgcccgctc ctatcgagaa gaccatctct   660
aaggccaagg gccagcctag agagccacag gtgtacacac tgcctccatc ccgcgacgag   720
ctgaccaaga accaggtgag cctgacatgt ctggtgaagg gcttctatcc tagcgatatc   780
gctgtggagt gggagtctaa tggccagcca gagaacaatt acaagaccac ccccctgtg   840
ctggacagcg atggctcttt ctttctgtat tctaagctga ccgtggataa gtccaggtgg   900
cagcagggca acgtgttttc ctgtagcgtg atgcatgagg ctctgcacaa tcattacaca   960
cagaagtctc tgtccctgag ccctggc                                       987
```

<210> SEQ ID NO 56
<211> LENGTH: 22
<212> TYPE: PRT
<213> ORGANISM: Artificial Sequence
<220> FEATURE:

```
<223> OTHER INFORMATION: [Human Ig kappa: signal peptide] [amino acid]

<400> SEQUENCE: 56

Met Asp Met Arg Val Pro Ala Gln Leu Leu Gly Leu Leu Leu Leu Trp
1               5                   10                  15

Leu Ser Gly Ala Arg Cys
            20

<210> SEQ ID NO 57
<211> LENGTH: 66
<212> TYPE: DNA
<213> ORGANISM: Artificial Sequence
<220> FEATURE:
<223> OTHER INFORMATION: [Human Ig kappa: signal peptide] [DNA]

<400> SEQUENCE: 57
atggacatga gggtccctgc tcagctcctg gggctcctgc tgctctggct ctcaggtgcc    60
agatgt                                                              66

<210> SEQ ID NO 58
<211> LENGTH: 19
<212> TYPE: PRT
<213> ORGANISM: Artificial Sequence
<220> FEATURE:
<223> OTHER INFORMATION: [Human Ig gamma1: signal peptide] [amino acid]

<400> SEQUENCE: 58

Met Glu Leu Gly Leu Ser Trp Ile Phe Leu Leu Ala Ile Leu Lys Gly
1               5                   10                  15

Val Gln Cys

<210> SEQ ID NO 59
<211> LENGTH: 57
<212> TYPE: DNA
<213> ORGANISM: Artificial Sequence
<220> FEATURE:
<223> OTHER INFORMATION: [Human Ig gamma1: signal peptide] [DNA]

<400> SEQUENCE: 59
atggagttgg gactgagctg gattttcctt ttggctattt taaaaggtgt ccagtgt       57

<210> SEQ ID NO 60
<211> LENGTH: 17
<212> TYPE: PRT
<213> ORGANISM: Artificial Sequence
<220> FEATURE:
<223> OTHER INFORMATION: [S413, Non P] [amino acid]

<400> SEQUENCE: 60

Pro Arg His Leu Ser Asn Val Ser Ser Thr Gly Ser Ile Asp Met Val
1               5                   10                  15

Asp

<210> SEQ ID NO 61
<211> LENGTH: 9
<212> TYPE: PRT
<213> ORGANISM: Artificial Sequence
<220> FEATURE:
<223> OTHER INFORMATION: [pS46] [amino acid]
<220> FEATURE:
<221> NAME/KEY: MOD_RES
<222> LOCATION: (5)..(5)
<223> OTHER INFORMATION: PHOSPHORYLATION

<400> SEQUENCE: 61
```

```
Gly Leu Lys Glu Ser Pro Leu Gln Thr
1               5
```

```
<210> SEQ ID NO 62
<211> LENGTH: 11
<212> TYPE: PRT
<213> ORGANISM: Artificial Sequence
<220> FEATURE:
<223> OTHER INFORMATION: [pS199] [amino acid]
<220> FEATURE:
<221> NAME/KEY: MOD_RES
<222> LOCATION: (5)..(5)
<223> OTHER INFORMATION: PHOSPHORYLATION

<400> SEQUENCE: 62

Ser Gly Tyr Ser Ser Pro Gly Ser Pro Gly Cys
1               5                   10
```

```
<210> SEQ ID NO 63
<211> LENGTH: 10
<212> TYPE: PRT
<213> ORGANISM: Artificial Sequence
<220> FEATURE:
<223> OTHER INFORMATION: [pS202] [amino acid]
<220> FEATURE:
<221> NAME/KEY: MOD_RES
<222> LOCATION: (5)..(5)
<223> OTHER INFORMATION: PHOSPHORYLATION

<400> SEQUENCE: 63

Ser Ser Pro Gly Ser Pro Gly Thr Pro Cys
1               5                   10
```

```
<210> SEQ ID NO 64
<211> LENGTH: 26
<212> TYPE: PRT
<213> ORGANISM: Artificial Sequence
<220> FEATURE:
<223> OTHER INFORMATION: [pT212/pS214] [amino acid]
<220> FEATURE:
<221> NAME/KEY: MOD_RES
<222> LOCATION: (14)..(14)
<223> OTHER INFORMATION: PHOSPHORYLATION
<220> FEATURE:
<221> NAME/KEY: MOD_RES
<222> LOCATION: (16)..(16)
<223> OTHER INFORMATION: PHOSPHORYLATION

<400> SEQUENCE: 64

Gly Cys Gly Ser Pro Gly Thr Pro Gly Ser Arg Ser Arg Thr Pro Ser
1               5                   10                  15

Leu Pro Thr Pro Pro Thr Arg Glu Pro Lys
            20                  25
```

```
<210> SEQ ID NO 65
<211> LENGTH: 25
<212> TYPE: PRT
<213> ORGANISM: Artificial Sequence
<220> FEATURE:
<223> OTHER INFORMATION: [pT217] [amino acid]
<220> FEATURE:
<221> NAME/KEY: MOD_RES
<222> LOCATION: (13)..(13)
<223> OTHER INFORMATION: PHOSPHORYLATION

<400> SEQUENCE: 65

Gly Cys Gly Ser Arg Ser Arg Thr Pro Ser Leu Pro Thr Pro Pro Thr
1               5                   10                  15
```

Arg Glu Pro Lys Lys Val Ala Val Val
            20                  25

<210> SEQ ID NO 66
<211> LENGTH: 13
<212> TYPE: PRT
<213> ORGANISM: Artificial Sequence
<220> FEATURE:
<223> OTHER INFORMATION: [pT231] [amino acid]
<220> FEATURE:
<221> NAME/KEY: MOD_RES
<222> LOCATION: (7)..(7)
<223> OTHER INFORMATION: PHOSPHORYLATION

<400> SEQUENCE: 66

Lys Val Ala Val Val Arg Thr Pro Pro Lys Ser Pro Ser
1               5                   10

<210> SEQ ID NO 67
<211> LENGTH: 32
<212> TYPE: PRT
<213> ORGANISM: Artificial Sequence
<220> FEATURE:
<223> OTHER INFORMATION: [pS396/pS400/pS404] [amino acid]
<220> FEATURE:
<221> NAME/KEY: MOD_RES
<222> LOCATION: (20)..(20)
<223> OTHER INFORMATION: PHOSPHORYLATION
<220> FEATURE:
<221> NAME/KEY: MOD_RES
<222> LOCATION: (24)..(24)
<223> OTHER INFORMATION: PHOSPHORYLATION
<220> FEATURE:
<221> NAME/KEY: MOD_RES
<222> LOCATION: (28)..(28)
<223> OTHER INFORMATION: PHOSPHORYLATION

<400> SEQUENCE: 67

Gly Cys Arg Glu Asn Ala Lys Ala Lys Thr Asp His Gly Ala Glu Ile
1               5                   10                  15
Val Tyr Lys Ser Pro Val Val Ser Gly Asp Thr Ser Pro Arg His Leu
            20                  25                  30

<210> SEQ ID NO 68
<211> LENGTH: 8
<212> TYPE: PRT
<213> ORGANISM: Artificial Sequence
<220> FEATURE:
<223> OTHER INFORMATION: [pS412] [amino acid]
<220> FEATURE:
<221> NAME/KEY: MOD_RES
<222> LOCATION: (3)..(3)
<223> OTHER INFORMATION: PHOSPHORYLATION

<400> SEQUENCE: 68

Asn Val Ser Ser Thr Gly Ser Cys
1               5

<210> SEQ ID NO 69
<211> LENGTH: 17
<212> TYPE: PRT
<213> ORGANISM: Artificial Sequence
<220> FEATURE:
<223> OTHER INFORMATION: [S413] [amino acid]

<400> SEQUENCE: 69

Pro Arg His Leu Ser Asn Val Ser Ser Thr Gly Ser Ile Asp Met Val
1               5                   10                  15
Asp

<210> SEQ ID NO 70
<211> LENGTH: 447
<212> TYPE: PRT
<213> ORGANISM: Artificial Sequence
<220> FEATURE:
<223> OTHER INFORMATION: [4R2N Tau-His6] [amino acid]

<400> SEQUENCE: 70

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365
```

```
Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Thr Gly Ser
                405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu His His His His His His
            435                 440                 445
```

```
<210> SEQ ID NO 71
<211> LENGTH: 1344
<212> TYPE: DNA
<213> ORGANISM: Artificial Sequence
<220> FEATURE:
<223> OTHER INFORMATION: [4R2N Tau-His6] [DNA]

<400> SEQUENCE: 71
atggctgagc ccgccagga gttcgaagtg atggaagatc acgctgggac gtacgggttg        60
ggggacagga aagatcaggg gggctacacc atgaccaag accaagaggg tgacacggac       120
gctggcctga agaatctcc cctgcagacc cccactgagg acggatctga ggaaccgggc       180
tctgaaacct ctgatgctaa gagcactcca acagcggaag atgtgacagc acccttagtg       240
gatgagggag ctcccggcaa gcaggctgcc gcgcagcccc acacggagat cccagaagga       300
accacagctg aagaagcagg cattggagac accccagcc tggaagacga agctgctggt       360
cacgtgaccc aagctcgcat ggtcagtaaa agcaaagacg ggactggaag cgatgacaaa       420
aaagccaagg gggctgatgg taaaacgaag atcgccacac gcggggagc agcccctcca       480
ggccagaagg gccaggccaa cgccaccagg attccagcaa aaaccccgcc cgctccaaag       540
acacccccca gctctggtga acctccaaaa tcagggatc gcagcggcta cagcagcccc       600
ggctccccag gcactcccgg cagccgctcc cgcaccccgt cccttccaac cccacccacc       660
cgggagccca gaaggtggc agtggtccgt actccaccca gtcgccgtc ttccgccaag       720
agccgcctgc agacagcccc cgtgcccatg ccagacctga gaatgtcaa gtccaagatc       780
ggctccactg agaacctgaa gcaccagccg ggaggcggga aggtgcagat aattaataag       840
aagctggatc ttagcaacgt ccagtccaag tgtggctcaa aggataatat caaacacgtc       900
ccgggaggcg gcagtgtgca aatagtctac aaaccagttg acctgagcaa ggtgacctcc       960
aagtgtggct cattaggcaa catccatcat aaaccaggag gtggccaggt ggaagtaaaa      1020
tctgagaagc ttgacttcaa ggacagagtc cagtcgaaga ttgggtccct ggacaatatc      1080
acccacgtcc ctggcggagg aaataaaaag attgaaaccc acaagctgac cttccgcgag      1140
aacgccaaag ccaagacaga ccacggggcg gagatcgtgt acaagtcgcc agtggtgtct      1200
ggggacacgt ctccacggca tctcagcaat gtctcctcca ccggcagcat cgacatggta      1260
gactcgcccc agctcgccac gctagctgac gaggtgtctg cctccctggc caagcagggt      1320
ttgcatcacc accaccacca ctga                                             1344
```

```
<210> SEQ ID NO 72
<211> LENGTH: 433
<212> TYPE: PRT
<213> ORGANISM: Artificial Sequence
<220> FEATURE:
<223> OTHER INFORMATION: [GSK3 beta] [amino acid]
```

<400> SEQUENCE: 72

Met Ser Gly Arg Pro Arg Thr Thr Ser Phe Ala Glu Ser Cys Lys Pro
1               5                   10                  15

Val Gln Gln Pro Ser Ala Phe Gly Ser Met Lys Val Ser Arg Asp Lys
            20                  25                  30

Asp Gly Ser Lys Val Thr Thr Val Ala Thr Pro Gly Gln Gly Pro
        35                  40                  45

Asp Arg Pro Gln Glu Val Ser Tyr Thr Asp Thr Lys Val Ile Gly Asn
    50                  55                  60

Gly Ser Phe Gly Val Val Tyr Gln Ala Lys Leu Cys Asp Ser Gly Glu
65                  70                  75                  80

Leu Val Ala Ile Lys Lys Val Leu Gln Asp Lys Arg Phe Lys Asn Arg
                85                  90                  95

Glu Leu Gln Ile Met Arg Lys Leu Asp His Cys Asn Ile Val Arg Leu
            100                 105                 110

Arg Tyr Phe Phe Tyr Ser Ser Gly Glu Lys Lys Asp Glu Val Tyr Leu
        115                 120                 125

Asn Leu Val Leu Asp Tyr Val Pro Glu Thr Val Tyr Arg Val Ala Arg
130                 135                 140

His Tyr Ser Arg Ala Lys Gln Thr Leu Pro Val Ile Tyr Val Lys Leu
145                 150                 155                 160

Tyr Met Tyr Gln Leu Phe Arg Ser Leu Ala Tyr Ile His Ser Phe Gly
                165                 170                 175

Ile Cys His Arg Asp Ile Lys Pro Gln Asn Leu Leu Leu Asp Pro Asp
            180                 185                 190

Thr Ala Val Leu Lys Leu Cys Asp Phe Gly Ser Ala Lys Gln Leu Val
        195                 200                 205

Arg Gly Glu Pro Asn Val Ser Tyr Ile Cys Ser Arg Tyr Tyr Arg Ala
210                 215                 220

Pro Glu Leu Ile Phe Gly Ala Thr Asp Tyr Thr Ser Ser Ile Asp Val
225                 230                 235                 240

Trp Ser Ala Gly Cys Val Leu Ala Glu Leu Leu Leu Gly Gln Pro Ile
                245                 250                 255

Phe Pro Gly Asp Ser Gly Val Asp Gln Leu Val Glu Ile Ile Lys Val
            260                 265                 270

Leu Gly Thr Pro Thr Arg Glu Gln Ile Arg Glu Met Asn Pro Asn Tyr
        275                 280                 285

Thr Glu Phe Lys Phe Pro Gln Ile Lys Ala His Pro Trp Thr Lys Asp
    290                 295                 300

Ser Ser Gly Thr Gly His Phe Thr Ser Gly Val Arg Val Phe Arg Pro
305                 310                 315                 320

Arg Thr Pro Pro Glu Ala Ile Ala Leu Cys Ser Arg Leu Leu Glu Tyr
                325                 330                 335

Thr Pro Thr Ala Arg Leu Thr Pro Leu Glu Ala Cys Ala His Ser Phe
            340                 345                 350

Phe Asp Glu Leu Arg Asp Pro Asn Val Lys Leu Pro Asn Gly Arg Asp
        355                 360                 365

Thr Pro Ala Leu Phe Asn Phe Thr Thr Gln Glu Leu Ser Ser Asn Pro
    370                 375                 380

Pro Leu Ala Thr Ile Leu Ile Pro Pro His Ala Arg Ile Gln Ala Ala
385                 390                 395                 400

Ala Ser Thr Pro Thr Asn Ala Thr Ala Ala Ser Asp Ala Asn Thr Gly

```
                405                 410                 415
Asp Arg Gly Gln Thr Asn Asn Ala Ala Ser Ala Ser Ala Ser Asn Ser
            420                 425                 430

Thr
```

<210> SEQ ID NO 73
<211> LENGTH: 1302
<212> TYPE: DNA
<213> ORGANISM: Artificial Sequence
<220> FEATURE:
<223> OTHER INFORMATION: [GSK3 beta] [DNA]

<400> SEQUENCE: 73

```
atgtcagggc ggcccagaac cacctccttt gcggagagct gcaagccggt gcagcagcct    60
tcagcttttg gcagcatgaa agttagcaga gacaaggacg gcagcaaggt gacaacagtg   120
gtggcaactc ctgggcaggg tccagacagg ccacaagaag tcagctatac agacactaaa   180
gtgattggaa atggatcatt tggtgtggta tatcaagcca aactttgtga ttcaggagaa   240
ctggtcgcca tcaagaaagt attgcaggac aagagattta agaatcgaga gctccagatc   300
atgagaaagc tagatcactg taacatagtc gattgcgtt atttcttcta ctccagtggt   360
gagaagaaag atgaggtcta tcttaatctg gtgctggact atgttccgga aacagtatac   420
agagttgcca gacactatag tcgagccaaa cagacgctcc ctgtgattta tgtcaagttg   480
tatatgtatc agctgttccg aagtttagcc tatatccatt cctttggaat ctgccatcgg   540
gatattaaac gcagaacct cttgttggat cctgatactg ctgtattaaa actctgtgac   600
tttggaagtg caaagcagct ggtccgagga gaacccaatg tttcgtatat ctgttctcgg   660
tactataggg caccagagtt gatctttgga gccactgatt atacctctag tatagatgta   720
tggtctgctg gctgtgtgtt ggctgagctg ttactaggac aaccaatatt tccaggggat   780
agtggtgtgg atcagttggt agaaataatc aaggtcctgg aactccaac aagggagcaa   840
atcagagaaa tgaacccaaa ctacacagaa tttaaattcc ctcaaattaa ggcacatcct   900
tggactaagg attcgtcagg aacaggacat ttcacctcag gagtgcgggt cttccgaccc   960
cgaactccac cggaggcaat tgcactgtgt agccgtctgc tggagtatac accaactgcc  1020
cgactaacac cactggaagc ttgtgcacat tcatttttg atgaattacg ggacccaaat  1080
gtcaaactac aaatgggcg agacacacct gcactcttca acttcaccac tcaagaactg  1140
tcaagtaatc cacctctggc taccatcctt attcctcctc atgctcggat tcaagcagct  1200
gcttcaaccc ccacaaatgc cacagcagcg tcagatgcta atactggaga ccgtggacag  1260
accaataatg ctgcttctgc atcagcttcc aactccacct ga                     1302
```

<210> SEQ ID NO 74
<211> LENGTH: 403
<212> TYPE: PRT
<213> ORGANISM: Artificial Sequence
<220> FEATURE:
<223> OTHER INFORMATION: [His6-Tau 4R0N] [amino acid]

<400> SEQUENCE: 74

```
Met Gly Ser Ser His His His His His His Ser Ser Gly Leu Val Pro
1               5                   10                  15

Arg Gly Ser His Met Ala Glu Pro Arg Gln Glu Phe Glu Val Met Glu
            20                  25                  30

Asp His Ala Gly Thr Tyr Gly Leu Gly Asp Arg Lys Asp Gln Gly Gly
        35                  40                  45
```

Tyr Thr Met His Gln Asp Gln Glu Gly Asp Thr Asp Ala Gly Leu Lys
50                  55                  60

Ala Glu Glu Ala Gly Ile Gly Asp Thr Pro Ser Leu Glu Asp Glu Ala
65                  70                  75                  80

Ala Gly His Val Thr Gln Ala Arg Met Val Ser Lys Ser Lys Asp Gly
                85                  90                  95

Thr Gly Ser Asp Asp Lys Lys Ala Lys Gly Ala Asp Gly Lys Thr Lys
                100                 105                 110

Ile Ala Thr Pro Arg Gly Ala Ala Pro Pro Gly Gln Lys Gly Gln Ala
            115                 120                 125

Asn Ala Thr Arg Ile Pro Ala Lys Thr Pro Ala Pro Lys Thr Pro
130                 135                 140

Pro Ser Ser Gly Glu Pro Pro Lys Ser Gly Asp Arg Ser Gly Tyr Ser
145                 150                 155                 160

Ser Pro Gly Ser Pro Gly Thr Pro Gly Ser Arg Ser Arg Thr Pro Ser
                165                 170                 175

Leu Pro Thr Pro Pro Thr Arg Glu Pro Lys Lys Val Ala Val Val Arg
            180                 185                 190

Thr Pro Pro Lys Ser Pro Ser Ser Ala Lys Ser Arg Leu Gln Thr Ala
            195                 200                 205

Pro Val Pro Met Pro Asp Leu Lys Asn Val Lys Ser Lys Ile Gly Ser
210                 215                 220

Thr Glu Asn Leu Lys His Gln Pro Gly Gly Gly Lys Val Gln Ile Ile
225                 230                 235                 240

Asn Lys Lys Leu Asp Leu Ser Asn Val Gln Ser Lys Cys Gly Ser Lys
                245                 250                 255

Asp Asn Ile Lys His Val Pro Gly Gly Gly Ser Val Gln Ile Val Tyr
            260                 265                 270

Lys Pro Val Asp Leu Ser Lys Val Thr Ser Lys Cys Gly Ser Leu Gly
            275                 280                 285

Asn Ile His His Lys Pro Gly Gly Gly Gln Val Glu Val Lys Ser Glu
290                 295                 300

Lys Leu Asp Phe Lys Asp Arg Val Gln Ser Lys Ile Gly Ser Leu Asp
305                 310                 315                 320

Asn Ile Thr His Val Pro Gly Gly Gly Asn Lys Lys Ile Glu Thr His
                325                 330                 335

Lys Leu Thr Phe Arg Glu Asn Ala Lys Ala Lys Thr Asp His Gly Ala
            340                 345                 350

Glu Ile Val Tyr Lys Ser Pro Val Val Ser Gly Asp Thr Ser Pro Arg
            355                 360                 365

His Leu Ser Asn Val Ser Ser Thr Gly Ser Ile Asp Met Val Asp Ser
370                 375                 380

Pro Gln Leu Ala Thr Leu Ala Asp Glu Val Ser Ala Ser Leu Ala Lys
385                 390                 395                 400

Gln Gly Leu

<210> SEQ ID NO 75
<211> LENGTH: 22
<212> TYPE: PRT
<213> ORGANISM: Artificial Sequence
<220> FEATURE:
<223> OTHER INFORMATION: [1xP] [amino acid]
<220> FEATURE:
<221> NAME/KEY: MOD_RES
<222> LOCATION: (11)..(11)

<223> OTHER INFORMATION: PHOSPHORYLATION

<400> SEQUENCE: 75

Thr Ser Pro Arg His Leu Ser Asn Val Ser Ser Thr Gly Ser Ile Asp
1               5                   10                  15

Met Val Asp Ser Pro Cys
            20

<210> SEQ ID NO 76
<211> LENGTH: 22
<212> TYPE: PRT
<213> ORGANISM: Artificial Sequence
<220> FEATURE:
<223> OTHER INFORMATION: [3xP] [amino acid]
<220> FEATURE:
<221> NAME/KEY: MOD_RES
<222> LOCATION: (7)..(7)
<223> OTHER INFORMATION: PHOSPHORYLATION
<220> FEATURE:
<221> NAME/KEY: MOD_RES
<222> LOCATION: (10)..(10)
<223> OTHER INFORMATION: PHOSPHORYLATION
<220> FEATURE:
<221> NAME/KEY: MOD_RES
<222> LOCATION: (11)..(11)
<223> OTHER INFORMATION: PHOSPHORYLATION

<400> SEQUENCE: 76

Thr Ser Pro Arg His Leu Ser Asn Val Ser Ser Thr Gly Ser Ile Asp
1               5                   10                  15

Met Val Asp Ser Pro Cys
            20

<210> SEQ ID NO 77
<211> LENGTH: 22
<212> TYPE: PRT
<213> ORGANISM: Artificial Sequence
<220> FEATURE:
<223> OTHER INFORMATION: [Non P] [amino acid]

<400> SEQUENCE: 77

Thr Ser Pro Arg His Leu Ser Asn Val Ser Ser Thr Gly Ser Ile Asp
1               5                   10                  15

Met Val Asp Ser Pro Cys
            20

<210> SEQ ID NO 78
<211> LENGTH: 57
<212> TYPE: PRT
<213> ORGANISM: Artificial Sequence
<220> FEATURE:
<223> OTHER INFORMATION: 4x phosphorylated peptide

<400> SEQUENCE: 78

Gly Ala Glu Ile Val Tyr Lys Pro Ser Pro Val Val Ser Gly Asp Thr
1               5                   10                  15

Pro Ser Pro Arg His Leu Ser Asn Val Ser Pro Ser Thr Gly Ser Ile
            20                  25                  30

Asp Met Val Asp Pro Ser Pro Gln Leu Ala Thr Leu Ala Asp Glu Val
            35                  40                  45

Ser Ala Ser Leu Ala Lys Gln Gly Leu
        50                  55

<210> SEQ ID NO 79
<211> LENGTH: 107

<212> TYPE: PRT
<213> ORGANISM: Artificial Sequence
<220> FEATURE:
<223> OTHER INFORMATION: Human kappa light constant domain

<400> SEQUENCE: 79

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 80
<211> LENGTH: 106
<212> TYPE: PRT
<213> ORGANISM: Artificial Sequence
<220> FEATURE:
<223> OTHER INFORMATION: Human lambda light constant domain

<400> SEQUENCE: 80

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 81
<211> LENGTH: 16
<212> TYPE: PRT
<213> ORGANISM: Artificial Sequence
<220> FEATURE:
<223> OTHER INFORMATION: Ta1505-VL00-Mouse, VL-CDR1

<400> SEQUENCE: 81

Arg Ser Ser Gln Asn Ile Val His Ser Asn Gly Asn Thr Tyr Leu Glu
1               5                   10                  15

<210> SEQ ID NO 82
<211> LENGTH: 7
<212> TYPE: PRT
<213> ORGANISM: Artificial Sequence
<220> FEATURE:
<223> OTHER INFORMATION: Ta1505-VL00-Mouse, VL-CDR2

<400> SEQUENCE: 82

Thr Val Ser Asn Arg Phe Ser
1               5

<210> SEQ ID NO 83
<211> LENGTH: 9
<212> TYPE: PRT
<213> ORGANISM: Artificial Sequence
<220> FEATURE:
<223> OTHER INFORMATION: Ta1505-VL00-Mouse, VL-CDR3

<400> SEQUENCE: 83

Phe Gln Gly Ser His Leu Pro Leu Thr
1               5

<210> SEQ ID NO 84
<211> LENGTH: 112
<212> TYPE: PRT
<213> ORGANISM: Artificial Sequence
<220> FEATURE:
<223> OTHER INFORMATION: Ta1505-VL00-Mouse, VL

<400> SEQUENCE: 84

Asp Ile Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asn Gly Asn Thr Tyr Leu Glu Trp Tyr Leu Gln Lys Pro Gly Gln Ser
        35                  40                  45

Pro Lys Val Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Leu Pro Leu Thr Phe Gly Gly Gly Thr Lys Leu Glu Leu Lys
            100                 105                 110

<210> SEQ ID NO 85
<211> LENGTH: 219
<212> TYPE: PRT
<213> ORGANISM: Artificial Sequence
<220> FEATURE:
<223> OTHER INFORMATION: Ta1505-VL00-Mouse, light chain

<400> SEQUENCE: 85

Asp Ile Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asn Gly Asn Thr Tyr Leu Glu Trp Tyr Leu Gln Lys Pro Gly Gln Ser
        35                  40                  45

Pro Lys Val Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Leu Pro Leu Thr Phe Gly Gly Gly Thr Lys Leu Glu Leu Lys

```
                100             105             110
Arg Ala Asp Ala Ala Pro Thr Val Ser Ile Phe Pro Pro Ser Ser Glu
            115                 120                 125

Gln Leu Thr Ser Gly Gly Ala Ser Val Val Cys Phe Leu Asn Asn Phe
        130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 86
<211> LENGTH: 5
<212> TYPE: PRT
<213> ORGANISM: Artificial Sequence
<220> FEATURE:
<223> OTHER INFORMATION: Ta1505-VL00-Mouse, VH-CDR1

<400> SEQUENCE: 86

Ser Phe Ala Leu Asn
1               5

<210> SEQ ID NO 87
<211> LENGTH: 19
<212> TYPE: PRT
<213> ORGANISM: Artificial Sequence
<220> FEATURE:
<223> OTHER INFORMATION: Ta1505-VL00-Mouse, VH-CDR2

<400> SEQUENCE: 87

His Ile Arg Ser Lys Thr Asn Asn Tyr Ala Thr Phe Tyr Ala Asp Ser
1               5                   10                  15

Val Lys Asp

<210> SEQ ID NO 88
<211> LENGTH: 10
<212> TYPE: PRT
<213> ORGANISM: Artificial Sequence
<220> FEATURE:
<223> OTHER INFORMATION: Ta1505-VL00-Mouse, VH-CDR3

<400> SEQUENCE: 88

Arg Gly Pro Arg Asp Ser Trp Phe Gly Tyr
1               5                   10

<210> SEQ ID NO 89
<211> LENGTH: 121
<212> TYPE: PRT
<213> ORGANISM: Artificial Sequence
<220> FEATURE:
<223> OTHER INFORMATION: Ta1505-VL00-Mouse, VH

<400> SEQUENCE: 89

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Ala Phe Asn Ser Phe
            20                  25                  30
```

```
Ala Leu Asn Trp Val Arg Gln Ala Pro Gly Lys Ser Leu Glu Trp Val
            35                  40                  45

Val His Ile Arg Ser Lys Thr Asn Asn Tyr Ala Thr Phe Tyr Ala Asp
 50                  55                  60

Ser Val Lys Asp Arg Phe Thr Val Ser Arg Asp Asp Ser Gln Ser Met
 65                  70                  75                  80

Val Tyr Leu Gln Met Asn Asn Leu Lys Thr Glu Asp Thr Gly Ile Tyr
                 85                  90                  95

Tyr Cys Val Arg Arg Gly Pro Arg Asp Ser Trp Phe Gly Tyr Trp Gly
                100                 105                 110

Gln Gly Thr Leu Val Thr Val Ser Ala
            115                 120

<210> SEQ ID NO 90
<211> LENGTH: 451
<212> TYPE: PRT
<213> ORGANISM: Artificial Sequence
<220> FEATURE:
<223> OTHER INFORMATION: Ta1505-VL00-Mouse, heavy chain

<400> SEQUENCE: 90

Glu Val Gln Leu Val Glu Ser Gly Gly Gly Leu Val Gln Pro Lys Gly
 1               5                  10                  15

Ser Leu Lys Leu Ser Cys Ala Ala Ser Gly Phe Ala Phe Asn Ser Phe
             20                  25                  30

Ala Leu Asn Trp Val Arg Gln Ala Pro Gly Lys Ser Leu Glu Trp Val
            35                  40                  45

Val His Ile Arg Ser Lys Thr Asn Asn Tyr Ala Thr Phe Tyr Ala Asp
 50                  55                  60

Ser Val Lys Asp Arg Phe Thr Val Ser Arg Asp Asp Ser Gln Ser Met
 65                  70                  75                  80

Val Tyr Leu Gln Met Asn Asn Leu Lys Thr Glu Asp Thr Gly Ile Tyr
                 85                  90                  95

Tyr Cys Val Arg Arg Gly Pro Arg Asp Ser Trp Phe Gly Tyr Trp Gly
                100                 105                 110

Gln Gly Thr Leu Val Thr Val Ser Ala Ala Lys Thr Thr Ala Pro Ser
            115                 120                 125

Val Tyr Pro Leu Ala Pro Val Cys Gly Asp Thr Thr Gly Ser Ser Val
        130                 135                 140

Thr Leu Gly Cys Leu Val Lys Gly Tyr Phe Pro Glu Pro Val Thr Leu
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Thr
            180                 185                 190

Ser Ser Thr Trp Pro Ser Gln Ser Ile Thr Cys Asn Val Ala His Pro
        195                 200                 205

Ala Ser Ser Thr Lys Val Asp Lys Lys Ile Glu Pro Arg Gly Pro Thr
    210                 215                 220

Ile Lys Pro Cys Pro Pro Cys Lys Cys Pro Ala Pro Asn Leu Leu Gly
225                 230                 235                 240

Gly Pro Ser Val Phe Ile Phe Pro Pro Lys Ile Lys Asp Val Leu Met
                245                 250                 255

Ile Ser Leu Ser Pro Ile Val Thr Cys Val Val Val Asp Val Ser Glu
            260                 265                 270
```

```
Asp Asp Pro Asp Val Gln Ile Ser Trp Phe Val Asn Val Glu Val
        275                 280                 285

His Thr Ala Gln Thr Gln Thr His Arg Glu Asp Tyr Asn Ser Thr Leu
    290                 295                 300

Arg Val Val Ser Ala Leu Pro Ile Gln His Gln Asp Trp Met Ser Gly
305                 310                 315                 320

Lys Glu Phe Lys Cys Lys Val Asn Asn Lys Asp Leu Pro Ala Pro Ile
                325                 330                 335

Glu Arg Thr Ile Ser Lys Pro Lys Gly Ser Val Arg Ala Pro Gln Val
                340                 345                 350

Tyr Val Leu Pro Pro Glu Glu Met Thr Lys Lys Gln Val Thr
            355                 360                 365

Leu Thr Cys Met Val Thr Asp Phe Met Pro Glu Asp Ile Tyr Val Glu
    370                 375                 380

Trp Thr Asn Asn Gly Lys Thr Glu Leu Asn Tyr Lys Asn Thr Glu Pro
385                 390                 395                 400

Val Leu Asp Ser Asp Gly Ser Tyr Phe Met Tyr Ser Lys Leu Arg Val
                405                 410                 415

Glu Lys Lys Asn Trp Val Glu Arg Asn Ser Tyr Ser Cys Ser Val Val
                420                 425                 430

His Glu Gly Leu His Asn His His Thr Thr Lys Ser Phe Ser Arg Thr
            435                 440                 445

Pro Gly Lys
    450

<210> SEQ ID NO 91
<211> LENGTH: 16
<212> TYPE: PRT
<213> ORGANISM: Artificial Sequence
<220> FEATURE:
<223> OTHER INFORMATION: Ta1505-VL46, VL-CDR1

<400> SEQUENCE: 91

Arg Ser Ser Gln Ser Ile Val His Ser Asn Gly Asn Thr Tyr Leu Glu
1               5                   10                  15

<210> SEQ ID NO 92
<211> LENGTH: 16
<212> TYPE: PRT
<213> ORGANISM: Artificial Sequence
<220> FEATURE:
<223> OTHER INFORMATION: Ta1505-VL47, VL-CDR1

<400> SEQUENCE: 92

Arg Ser Ser Gln Ser Ile Val His Ser Asn Gly Asn Thr Tyr Leu Glu
1               5                   10                  15

<210> SEQ ID NO 93
<211> LENGTH: 16
<212> TYPE: PRT
<213> ORGANISM: Artificial Sequence
<220> FEATURE:
<223> OTHER INFORMATION: Ta1505-VL46_G34A, VL-CDR1

<400> SEQUENCE: 93

Arg Ser Ser Gln Ser Ile Val His Ser Asn Ala Asn Thr Tyr Leu Glu
1               5                   10                  15

<210> SEQ ID NO 94
<211> LENGTH: 16
```

<212> TYPE: PRT
<213> ORGANISM: Artificial Sequence
<220> FEATURE:
<223> OTHER INFORMATION: Ta1505-VL46_G34S, VL-CDR1

<400> SEQUENCE: 94

Arg Ser Ser Gln Ser Ile Val His Ser Asn Ser Asn Thr Tyr Leu Glu
1               5                   10                  15

<210> SEQ ID NO 95
<211> LENGTH: 16
<212> TYPE: PRT
<213> ORGANISM: Artificial Sequence
<220> FEATURE:
<223> OTHER INFORMATION: Ta1505-VL46_G34T, VL-CDR1

<400> SEQUENCE: 95

Arg Ser Ser Gln Ser Ile Val His Ser Asn Thr Asn Thr Tyr Leu Glu
1               5                   10                  15

<210> SEQ ID NO 96
<211> LENGTH: 16
<212> TYPE: PRT
<213> ORGANISM: Artificial Sequence
<220> FEATURE:
<223> OTHER INFORMATION: Ta1505-VL46_N33Q, VL-CDR1

<400> SEQUENCE: 96

Arg Ser Ser Gln Ser Ile Val His Ser Gln Gly Asn Thr Tyr Leu Glu
1               5                   10                  15

<210> SEQ ID NO 97
<211> LENGTH: 16
<212> TYPE: PRT
<213> ORGANISM: Artificial Sequence
<220> FEATURE:
<223> OTHER INFORMATION: Ta1505-VL46_N33Q_G34A, VL-CDR1

<400> SEQUENCE: 97

Arg Ser Ser Gln Ser Ile Val His Ser Gln Ala Asn Thr Tyr Leu Glu
1               5                   10                  15

<210> SEQ ID NO 98
<211> LENGTH: 16
<212> TYPE: PRT
<213> ORGANISM: Artificial Sequence
<220> FEATURE:
<223> OTHER INFORMATION: Ta1505-VL46_N33D, VL-CDR1

<400> SEQUENCE: 98

Arg Ser Ser Gln Ser Ile Val His Ser Asp Gly Asn Thr Tyr Leu Glu
1               5                   10                  15

<210> SEQ ID NO 99
<211> LENGTH: 16
<212> TYPE: PRT
<213> ORGANISM: Artificial Sequence
<220> FEATURE:
<223> OTHER INFORMATION: Ta1505-VL46_N33S, VL-CDR1

<400> SEQUENCE: 99

Arg Ser Ser Gln Ser Ile Val His Ser Ser Gly Asn Thr Tyr Leu Glu
1               5                   10                  15

<210> SEQ ID NO 100
<211> LENGTH: 16
<212> TYPE: PRT

<213> ORGANISM: Artificial Sequence
<220> FEATURE:
<223> OTHER INFORMATION: Ta1505-VL46_N33T, VL-CDR1

<400> SEQUENCE: 100

Arg Ser Ser Gln Ser Ile Val His Ser Thr Gly Asn Thr Tyr Leu Glu
1               5                   10                  15

<210> SEQ ID NO 101
<211> LENGTH: 16
<212> TYPE: PRT
<213> ORGANISM: Artificial Sequence
<220> FEATURE:
<223> OTHER INFORMATION: Ta1505-VL46_S28N, VL-CDR1

<400> SEQUENCE: 101

Arg Ser Ser Gln Asn Ile Val His Ser Asn Gly Asn Thr Tyr Leu Glu
1               5                   10                  15

<210> SEQ ID NO 102
<211> LENGTH: 16
<212> TYPE: PRT
<213> ORGANISM: Artificial Sequence
<220> FEATURE:
<223> OTHER INFORMATION: Ta1505-VL46_G34A_S28N, VL-CDR1

<400> SEQUENCE: 102

Arg Ser Ser Gln Asn Ile Val His Ser Asn Ala Asn Thr Tyr Leu Glu
1               5                   10                  15

<210> SEQ ID NO 103
<211> LENGTH: 112
<212> TYPE: PRT
<213> ORGANISM: Artificial Sequence
<220> FEATURE:
<223> OTHER INFORMATION: Ta1505-VL46, VL

<400> SEQUENCE: 103

Asp Ile Val Met Thr Gln Ser Pro Leu Ser Leu Pro Val Thr Leu Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Leu Pro Leu Thr Phe Gly Gly Gly Thr Lys Val Glu Ile Lys
            100                 105                 110

<210> SEQ ID NO 104
<211> LENGTH: 112
<212> TYPE: PRT
<213> ORGANISM: Artificial Sequence
<220> FEATURE:
<223> OTHER INFORMATION: Ta1505-VL47, VL

<400> SEQUENCE: 104

Asp Ile Val Met Thr Gln Ser Pro Leu Ser Leu Pro Val Thr Leu Gly
1               5                   10                  15

```
Asp Pro Ala Ser Ile Ser Cys Arg Ser Ser Gln Ser Ile Val His Ser
            20                  25                  30

Asn Gly Asn Thr Tyr Leu Glu Trp Tyr Gln Leu Lys Pro Gly Gln Ser
        35                  40                  45

Pro Gln Arg Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Leu Pro Leu Thr Phe Gly Gly Gly Thr Lys Val Glu Ile Lys
                100                 105                 110
```

<210> SEQ ID NO 105
<211> LENGTH: 112
<212> TYPE: PRT
<213> ORGANISM: Artificial Sequence
<220> FEATURE:
<223> OTHER INFORMATION: Ta1505-VL46_G34A, VL

<400> SEQUENCE: 105

```
Asp Ile Val Met Thr Gln Ser Pro Leu Ser Leu Pro Val Thr Leu Gly
1               5                   10                  15

Glu Pro Ala Ser Ile Ser Cys Arg Ser Ser Gln Ser Ile Val His Ser
            20                  25                  30

Asn Ala Asn Thr Tyr Leu Glu Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Leu Pro Leu Thr Phe Gly Gly Gly Thr Lys Val Glu Ile Lys
                100                 105                 110
```

<210> SEQ ID NO 106
<211> LENGTH: 112
<212> TYPE: PRT
<213> ORGANISM: Artificial Sequence
<220> FEATURE:
<223> OTHER INFORMATION: Ta1505-VL46_G34S, VL

<400> SEQUENCE: 106

```
Asp Ile Val Met Thr Gln Ser Pro Leu Ser Leu Pro Val Thr Leu Gly
1               5                   10                  15

Glu Pro Ala Ser Ile Ser Cys Arg Ser Ser Gln Ser Ile Val His Ser
            20                  25                  30

Asn Ser Asn Thr Tyr Leu Glu Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Leu Pro Leu Thr Phe Gly Gly Gly Thr Lys Val Glu Ile Lys
                100                 105                 110
```

<210> SEQ ID NO 107
<211> LENGTH: 112
<212> TYPE: PRT
<213> ORGANISM: Artificial Sequence
<220> FEATURE:
<223> OTHER INFORMATION: Ta1505-VL46_G34T, VL

<400> SEQUENCE: 107

```
Asp Ile Val Met Thr Gln Ser Pro Leu Ser Leu Pro Val Thr Leu Gly
1               5                   10                  15

Glu Pro Ala Ser Ile Ser Cys Arg Ser Ser Gln Ser Ile Val His Ser
            20                  25                  30

Asn Thr Asn Thr Tyr Leu Glu Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Leu Pro Leu Thr Phe Gly Gly Gly Thr Lys Val Glu Ile Lys
            100                 105                 110
```

<210> SEQ ID NO 108
<211> LENGTH: 112
<212> TYPE: PRT
<213> ORGANISM: Artificial Sequence
<220> FEATURE:
<223> OTHER INFORMATION: Ta1505-VL46_N33Q, VL

<400> SEQUENCE: 108

```
Asp Ile Val Met Thr Gln Ser Pro Leu Ser Leu Pro Val Thr Leu Gly
1               5                   10                  15

Glu Pro Ala Ser Ile Ser Cys Arg Ser Ser Gln Ser Ile Val His Ser
            20                  25                  30

Gln Gly Asn Thr Tyr Leu Glu Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Leu Pro Leu Thr Phe Gly Gly Gly Thr Lys Val Glu Ile Lys
            100                 105                 110
```

<210> SEQ ID NO 109
<211> LENGTH: 112
<212> TYPE: PRT
<213> ORGANISM: Artificial Sequence
<220> FEATURE:
<223> OTHER INFORMATION: Ta1505-VL46_N33Q_G34A, VL

<400> SEQUENCE: 109

```
Asp Ile Val Met Thr Gln Ser Pro Leu Ser Leu Pro Val Thr Leu Gly
1               5                   10                  15

Glu Pro Ala Ser Ile Ser Cys Arg Ser Ser Gln Ser Ile Val His Ser
            20                  25                  30
```

```
Gln Ala Asn Thr Tyr Leu Glu Trp Tyr Leu Gln Lys Pro Gly Gln Ser
            35                  40                  45

Pro Gln Leu Leu Ile Tyr Thr Val Ser Asn Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                85                  90                  95

Ser His Leu Pro Leu Thr Phe Gly Gly Gly Thr Lys Val Glu Ile Lys
            100                 105                 110

<210> SEQ ID NO 110
<211> LENGTH: 112
<212> TYPE: PRT
<213> ORGANISM: Artificial Sequence
<220> FEATURE:
<223> OTHER INFORMATION: Ta1505-VL46_N33D, VL

<400> SEQUENCE: 110

Asp Ile Val Met Thr Gln Ser Pro Leu Ser Leu Pro Val Thr Leu Gly
 1               5                  10                  15

Glu Pro Ala Ser Ile Ser Cys Arg Ser Ser Gln Ser Ile Val His Ser
            20                  25                  30

Asp Gly Asn Thr Tyr Leu Glu Trp Tyr Leu Gln Lys Pro Gly Gln Ser
            35                  40                  45

Pro Gln Leu Leu Ile Tyr Thr Val Ser Asn Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                85                  90                  95

Ser His Leu Pro Leu Thr Phe Gly Gly Gly Thr Lys Val Glu Ile Lys
            100                 105                 110

<210> SEQ ID NO 111
<211> LENGTH: 112
<212> TYPE: PRT
<213> ORGANISM: Artificial Sequence
<220> FEATURE:
<223> OTHER INFORMATION: Ta1505-VL46_N33S, VL

<400> SEQUENCE: 111

Asp Ile Val Met Thr Gln Ser Pro Leu Ser Leu Pro Val Thr Leu Gly
 1               5                  10                  15

Glu Pro Ala Ser Ile Ser Cys Arg Ser Ser Gln Ser Ile Val His Ser
            20                  25                  30

Ser Gly Asn Thr Tyr Leu Glu Trp Tyr Leu Gln Lys Pro Gly Gln Ser
            35                  40                  45

Pro Gln Leu Leu Ile Tyr Thr Val Ser Asn Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                85                  90                  95

Ser His Leu Pro Leu Thr Phe Gly Gly Gly Thr Lys Val Glu Ile Lys
            100                 105                 110

<210> SEQ ID NO 112
```

<211> LENGTH: 112
<212> TYPE: PRT
<213> ORGANISM: Artificial Sequence
<220> FEATURE:
<223> OTHER INFORMATION: Ta1505-VL46_N33T, VL

<400> SEQUENCE: 112

Asp Ile Val Met Thr Gln Ser Pro Leu Ser Leu Pro Val Thr Leu Gly
1               5                   10                  15

Glu Pro Ala Ser Ile Ser Cys Arg Ser Ser Gln Ser Ile Val His Ser
            20                  25                  30

Thr Gly Asn Thr Tyr Leu Glu Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Leu Pro Leu Thr Phe Gly Gly Gly Thr Lys Val Glu Ile Lys
            100                 105                 110

<210> SEQ ID NO 113
<211> LENGTH: 112
<212> TYPE: PRT
<213> ORGANISM: Artificial Sequence
<220> FEATURE:
<223> OTHER INFORMATION: Ta1505-VL46_S28N, VL

<400> SEQUENCE: 113

Asp Ile Val Met Thr Gln Ser Pro Leu Ser Leu Pro Val Thr Leu Gly
1               5                   10                  15

Glu Pro Ala Ser Ile Ser Cys Arg Ser Ser Gln Asn Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Leu Pro Leu Thr Phe Gly Gly Gly Thr Lys Val Glu Ile Lys
            100                 105                 110

<210> SEQ ID NO 114
<211> LENGTH: 112
<212> TYPE: PRT
<213> ORGANISM: Artificial Sequence
<220> FEATURE:
<223> OTHER INFORMATION: Ta1505-VL46_G34A_S28N, VL

<400> SEQUENCE: 114

Asp Ile Val Met Thr Gln Ser Pro Leu Ser Leu Pro Val Thr Leu Gly
1               5                   10                  15

Glu Pro Ala Ser Ile Ser Cys Arg Ser Ser Gln Asn Ile Val His Ser
            20                  25                  30

Asn Ala Asn Thr Tyr Leu Glu Trp Tyr Leu Gln Lys Pro Gly Gln Ser
        35                  40                  45

```
Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Leu Pro Leu Thr Phe Gly Gly Gly Thr Lys Val Glu Ile Lys
            100                 105                 110
```

<210> SEQ ID NO 115
<211> LENGTH: 19
<212> TYPE: PRT
<213> ORGANISM: Artificial Sequence
<220> FEATURE:
<223> OTHER INFORMATION: Ta1505-VH11 or Ta1505-VH65, VH-CDR2

<400> SEQUENCE: 115

```
His Ile Arg Ser Lys Thr Asn Asn Tyr Ala Thr Phe Tyr Ala Ala Ser
1               5                   10                  15

Val Lys Asp
```

<210> SEQ ID NO 116
<211> LENGTH: 121
<212> TYPE: PRT
<213> ORGANISM: Artificial Sequence
<220> FEATURE:
<223> OTHER INFORMATION: Ta1505-VH11, VH

<400> SEQUENCE: 116

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Leu Asn Trp Val Arg Gln Ala Pro Gly Lys Gly Leu Glu Trp Val
        35                  40                  45

Gly His Ile Arg Ser Lys Thr Asn Asn Tyr Ala Thr Phe Tyr Ala Ala
    50                  55                  60

Ser Val Lys Asp Arg Phe Thr Val Ser Arg Asp Asp Ser Gln Asn Thr
65                  70                  75                  80

Ala Tyr Leu Gln Met Asn Ser Leu Lys Thr Glu Asp Thr Ala Thr Tyr
                85                  90                  95

Tyr Cys Val Arg Arg Gly Pro Arg Asp Ser Trp Phe Gly Tyr Trp Gly
            100                 105                 110

Gln Gly Thr Leu Val Thr Val Ser Ser
        115                 120
```

<210> SEQ ID NO 117
<211> LENGTH: 121
<212> TYPE: PRT
<213> ORGANISM: Artificial Sequence
<220> FEATURE:
<223> OTHER INFORMATION: Ta1505-VH65, VH

<400> SEQUENCE: 117

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Asn Ser Phe
            20                  25                  30

Ala Leu Asn Trp Val Arg Gln Ala Pro Gly Lys Gly Leu Glu Trp Val
        35                  40                  45
```

```
Val His Ile Arg Ser Lys Thr Asn Asn Tyr Ala Thr Phe Tyr Ala Ala
 50                  55                  60

Ser Val Lys Asp Arg Phe Thr Val Ser Arg Asp Asp Ser Gln Asn Thr
 65                  70                  75                  80

Ala Tyr Leu Gln Met Asn Ser Leu Lys Thr Glu Asp Thr Ala Thr Tyr
                 85                  90                  95

Tyr Cys Val Arg Arg Gly Pro Arg Asp Ser Trp Phe Gly Tyr Trp Gly
            100                 105                 110

Gln Gly Thr Leu Val Thr Val Ser Ser
            115                 120

<210> SEQ ID NO 118
<211> LENGTH: 330
<212> TYPE: PRT
<213> ORGANISM: Artificial Sequence
<220> FEATURE:
<223> OTHER INFORMATION: Human_IgG1_P01857, backbone

<400> SEQUENCE: 118

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 119
<211> LENGTH: 330
<212> TYPE: PRT
<213> ORGANISM: Artificial Sequence
<220> FEATURE:
<223> OTHER INFORMATION: Human_IgG1_P01857_L234A_L235A, backbone

<400> SEQUENCE: 119

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

```
Gln Lys Ser Leu Ser Leu Ser Pro Gly Lys
            325                 330

<210> SEQ ID NO 120
<211> LENGTH: 330
<212> TYPE: PRT
<213> ORGANISM: Artificial Sequence
<220> FEATURE:
<223> OTHER INFORMATION: Human_IgG1_P01857_ L234A_L235A_D265S, backbone

<400> SEQUENCE: 120

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Ser Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 121
```

<211> LENGTH: 330
<212> TYPE: PRT
<213> ORGANISM: Artificial Sequence
<220> FEATURE:
<223> OTHER INFORMATION: Human_IgG1_P01857_YTE, backbone

<400> SEQUENCE: 121

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Tyr Ile Thr Arg Glu Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 122
<211> LENGTH: 330
<212> TYPE: PRT
<213> ORGANISM: Artificial Sequence
<220> FEATURE:
<223> OTHER INFORMATION: Human_IgG1_P01857_N297A, backbone -continued

<400> SEQUENCE: 122

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 123
<211> LENGTH: 330
<212> TYPE: PRT
<213> ORGANISM: Artificial Sequence
<220> FEATURE:
<223> OTHER INFORMATION: Human_IgG1_P01857_N297Q, backbone

<400> SEQUENCE: 123

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

```
            20                  25                  30
Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gln Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 124
<211> LENGTH: 326
<212> TYPE: PRT
<213> ORGANISM: Artificial Sequence
<220> FEATURE:
<223> OTHER INFORMATION: Human_IgG2_P01859, backbone

<400> SEQUENCE: 124

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
```

```
                      50                  55                  60
Leu Ser Ser Val Val Thr Val Pro Ser Asn Phe Gly Thr Gln Thr
 65                  70                  75                  80

Tyr Thr Cys Asn Val Asp His Lys Pro Ser Asn Thr Lys Val Asp Lys
                    85                  90                  95

Thr Val Glu Arg Lys Cys Cys Val Glu Cys Pro Pro Cys Pro Ala Pro
                100                 105                 110

Pro Val Ala Gly Pro Ser Val Phe Leu Phe Pro Pro Lys Pro Lys Asp
                115                 120                 125

Thr Leu Met Ile Ser Arg Thr Pro Glu Val Thr Cys Val Val Val Asp
            130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
                180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
                260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 125
<211> LENGTH: 327
<212> TYPE: PRT
<213> ORGANISM: Artificial Sequence
<220> FEATURE:
<223> OTHER INFORMATION: Human_IgG4_P01861, backbone

<400> SEQUENCE: 125

Ala Ser Thr Lys Gly Pro Ser Val Phe Pro Leu Ala Pro Cys Ser Arg
  1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
```

```
                    85                  90                  95
Arg Val Glu Ser Lys Tyr Gly Pro Pro Cys Pro Ser Cys Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 126
<211> LENGTH: 327
<212> TYPE: PRT
<213> ORGANISM: Artificial Sequence
<220> FEATURE:
<223> OTHER INFORMATION: Human_IgG4_P01861_S228P, backbone

<400> SEQUENCE: 126

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
```

```
        115                 120                 125
Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
                195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Glu Gly Asn Val Phe Ser
                290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 127
<211> LENGTH: 219
<212> TYPE: PRT
<213> ORGANISM: Artificial Sequence
<220> FEATURE:
<223> OTHER INFORMATION: hu VL46 / VH11 G34A S28N IgG1 or hu VL46 / VH11
      G34A S28N IgG4-S228P, light chain

<400> SEQUENCE: 127

Asp Ile Val Met Thr Gln Ser Pro Leu Ser Leu Pro Val Thr Leu Gly
1               5                   10                  15

Glu Pro Ala Ser Ile Ser Cys Arg Ser Ser Gln Asn Ile Val His Ser
                20                  25                  30

Asn Ala Asn Thr Tyr Leu Glu Trp Tyr Leu Gln Lys Pro Gly Gln Ser
                35                  40                  45

Pro Gln Leu Leu Ile Tyr Thr Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Leu Pro Leu Thr Phe Gly Gly Gly Thr Lys Val Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
130                 135                 140
```

```
Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 128
<211> LENGTH: 451
<212> TYPE: PRT
<213> ORGANISM: Artificial Sequence
<220> FEATURE:
<223> OTHER INFORMATION: hu VL46 / VH11 G34A S28N IgG1, heavy chain

<400> SEQUENCE: 128

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Leu Asn Trp Val Arg Gln Ala Pro Gly Lys Gly Leu Glu Trp Val
        35                  40                  45

Gly His Ile Arg Ser Lys Thr Asn Asn Tyr Ala Thr Phe Tyr Ala Ala
    50                  55                  60

Ser Val Lys Asp Arg Phe Thr Val Ser Arg Asp Ser Gln Asn Thr
65                  70                  75                  80

Ala Tyr Leu Gln Met Asn Ser Leu Lys Thr Glu Asp Thr Ala Thr Tyr
                85                  90                  95

Tyr Cys Val Arg Arg Gly Pro Arg Asp Ser Trp Phe Gly Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285
```

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 129
<211> LENGTH: 448
<212> TYPE: PRT
<213> ORGANISM: Artificial Sequence
<220> FEATURE:
<223> OTHER INFORMATION: hu VL46 / VH11 G34A S28N IgG4-S228P, heavy
      chain

<400> SEQUENCE: 129

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Leu Asn Trp Val Arg Gln Ala Pro Gly Lys Gly Leu Glu Trp Val
        35                  40                  45

Gly His Ile Arg Ser Lys Thr Asn Asn Tyr Ala Thr Phe Tyr Ala Ala
    50                  55                  60

Ser Val Lys Asp Arg Phe Thr Val Ser Arg Asp Asp Ser Gln Asn Thr
65                  70                  75                  80

Ala Tyr Leu Gln Met Asn Ser Leu Lys Thr Glu Asp Thr Ala Thr Tyr
                85                  90                  95

Tyr Cys Val Arg Arg Gly Pro Arg Asp Ser Trp Phe Gly Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

```
Pro Ser Ser Ser Leu Gly Thr Lys Thr Tyr Thr Cys Asn Val Asp His
            195                 200                 205
Lys Pro Ser Asn Thr Lys Val Asp Lys Arg Val Glu Ser Lys Tyr Gly
    210                 215                 220
Pro Pro Cys Pro Pro Cys Pro Ala Pro Glu Phe Leu Gly Gly Pro Ser
225             230                 235                 240
Val Phe Leu Phe Pro Pro Lys Pro Lys Asp Thr Leu Met Ile Ser Arg
                245                 250                 255
Thr Pro Glu Val Thr Cys Val Val Asp Val Ser Gln Glu Asp Pro
            260                 265                 270
Glu Val Gln Phe Asn Trp Tyr Val Asp Gly Val Glu Val His Asn Ala
            275                 280                 285
Lys Thr Lys Pro Arg Glu Glu Gln Phe Asn Ser Thr Tyr Arg Val Val
    290                 295                 300
Ser Val Leu Thr Val Leu His Gln Asp Trp Leu Asn Gly Lys Glu Tyr
305             310                 315                 320
Lys Cys Lys Val Ser Asn Lys Gly Leu Pro Ser Ser Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Gln Glu Glu Met Thr Lys Asn Gln Val Ser Leu Thr Cys
            355                 360                 365
Leu Val Lys Gly Phe Tyr Pro Ser Asp Ile Ala Val Glu Trp Glu Ser
        370                 375                 380
Asn Gly Gln Pro Glu Asn Asn Tyr Lys Thr Thr Pro Pro Val Leu Asp
385             390                 395                 400
Ser Asp Gly Ser Phe Phe Leu Tyr Ser Arg Leu Thr Val Asp Lys Ser
                405                 410                 415
Arg Trp Gln Glu Gly Asn Val Phe Ser Cys Ser Val Met His Glu Ala
            420                 425                 430
Leu His Asn His Tyr Thr Gln Lys Ser Leu Ser Leu Ser Leu Gly Lys
            435                 440                 445

<210> SEQ ID NO 130
<211> LENGTH: 219
<212> TYPE: PRT
<213> ORGANISM: Artificial Sequence
<220> FEATURE:
<223> OTHER INFORMATION: Humanized variant light chain, L1

<400> SEQUENCE: 130

Asp Ile Val Met Thr Gln Ser Pro Leu Ser Leu Pro Val Thr Leu Gly
1               5                   10                  15
Gln Pro Ala Ser Ile Ser Cys Arg Ser Ser Gln Ser Ile Val His Ser
            20                  25                  30
Asn Gly Asn Thr Tyr Leu Glu Trp Tyr Gln Gln Lys Pro Gly Gln Ser
        35                  40                  45
Pro Arg Leu Leu Ile Tyr Thr Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Phe Gln Gly
                85                  90                  95
Ser His Leu Pro Leu Thr Phe Gly Gly Gly Thr Lys Val Glu Ile Lys
            100                 105                 110
```

```
Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 131
<211> LENGTH: 219
<212> TYPE: PRT
<213> ORGANISM: Artificial Sequence
<220> FEATURE:
<223> OTHER INFORMATION: Humanized variant light chain, L2

<400> SEQUENCE: 131

Asp Ile Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Ser His Ser
            20                  25                  30

Asn Gly Asn Thr Tyr Leu Glu Trp Tyr Gln Gln Lys Pro Gly Gln Ser
        35                  40                  45

Pro Arg Leu Leu Ile Tyr Thr Ala Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Leu Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 132
<211> LENGTH: 219
<212> TYPE: PRT
<213> ORGANISM: Artificial Sequence
```

```
<220> FEATURE:
<223> OTHER INFORMATION: Humanized variant light chain, L3

<400> SEQUENCE: 132

Asp Ile Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Ser His Ser
            20                  25                  30

Asn Gly Asn Thr Tyr Leu Glu Trp Tyr Gln Gln Lys Pro Gly Gln Ser
        35                  40                  45

Pro Arg Leu Leu Ile Tyr Thr Ala Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Leu Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 133
<211> LENGTH: 451
<212> TYPE: PRT
<213> ORGANISM: Artificial Sequence
<220> FEATURE:
<223> OTHER INFORMATION: Humanized variant heavy chain, H1

<400> SEQUENCE: 133

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Asn Ser Phe
            20                  25                  30

Ala Leu Asn Trp Val Arg Gln Ala Pro Gly Lys Gly Leu Glu Trp Val
        35                  40                  45

Gly His Ile Arg Ser Lys Thr Asn Asn Tyr Ala Thr Phe Tyr Ala Ala
    50                  55                  60

Ser Val Lys Gly Arg Phe Thr Val Ser Arg Asp Asp Ser Lys Asn Ser
65                  70                  75                  80

Val Tyr Leu Gln Met Asn Ser Leu Lys Thr Glu Asp Thr Ala Val Tyr
                85                  90                  95

Tyr Cys Val Arg Arg Gly Pro Arg Asp Ser Trp Phe Gly Tyr Trp Gly
            100                 105                 110

Gln Gly Thr Leu Val Thr Val Ser Ser Ala Ser Thr Lys Gly Pro Ser
```

```
                115                 120                 125
Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Val Glu Pro Lys Ser Cys
        210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
        435                 440                 445

Pro Gly Lys
    450

<210> SEQ ID NO 134
<211> LENGTH: 451
<212> TYPE: PRT
<213> ORGANISM: Artificial Sequence
<220> FEATURE:
<223> OTHER INFORMATION: Humanized variant heavy chain, H2

<400> SEQUENCE: 134

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
```

-continued

```
             20                  25                  30
Ala Leu Asn Trp Val Arg Gln Ala Pro Gly Lys Gly Leu Glu Trp Val
         35                  40                  45
Gly His Ile Arg Ser Lys Thr Asn Asn Tyr Ala Thr Phe Tyr Ala Ala
     50                  55                  60
Ser Val Lys Gly Arg Phe Thr Val Ser Arg Asp Ser Lys Asn Thr
 65                  70                  75                  80
Ala Tyr Leu Gln Met Asn Ser Leu Lys Thr Glu Asp Thr Ala Thr Tyr
                 85                  90                  95
Tyr Cys Val Arg Arg Gly Pro Arg Asp Ser Trp Phe Gly Tyr Trp Gly
                100                 105                 110
Gln Gly Thr Leu Val Thr Val Ser Ser Ala Ser Thr Lys Gly Pro Ser
             115                 120                 125
Val Phe Pro Leu Ala Pro Ser Ser Lys Ser Thr Ser Gly Gly Thr Ala
         130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
            195                 200                 205
Lys Pro Ser Asn Thr Lys Val Asp Lys Val Glu Pro Lys Ser Cys
        210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
```

```
Pro Gly Lys
    450

<210> SEQ ID NO 135
<211> LENGTH: 330
<212> TYPE: PRT
<213> ORGANISM: Artificial Sequence
<220> FEATURE:
<223> OTHER INFORMATION: Human IgG1 wt heavy constant domain

<400> SEQUENCE: 135

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 136
```

```
<211> LENGTH: 330
<212> TYPE: PRT
<213> ORGANISM: Artificial Sequence
<220> FEATURE:
<223> OTHER INFORMATION: Human_IgG1_P01857_L234A_L235A heavy constant
      domain

<400> SEQUENCE: 136

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 137
<211> LENGTH: 330
<212> TYPE: PRT
<213> ORGANISM: Artificial Sequence
<220> FEATURE:
<223> OTHER INFORMATION: Human_IgG1_ P01857_L234A_L235A_D265S heavy
``` constant domain

<400> SEQUENCE: 137

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Ser Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 138
<211> LENGTH: 330
<212> TYPE: PRT
<213> ORGANISM: Artificial Sequence
<220> FEATURE:
<223> OTHER INFORMATION: Human_IgG1_YTE heavy constant domain

<400> SEQUENCE: 138

Ala Ser Thr Lys Gly Pro Ser Val Phe Pro Leu Ala Pro Ser Ser Lys
1               5                   10                  15

```
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Tyr Ile Thr Arg Glu Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 139
<211> LENGTH: 330
<212> TYPE: PRT
<213> ORGANISM: Artificial Sequence
<220> FEATURE:
<223> OTHER INFORMATION: Human_IgG1_N297A heavy constant domain

<400> SEQUENCE: 139

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

```
Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 140
<211> LENGTH: 330
<212> TYPE: PRT
<213> ORGANISM: Artificial Sequence
<220> FEATURE:
<223> OTHER INFORMATION: Human_IgG1_N297Q heavy constant domain

<400> SEQUENCE: 140

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
 65                  70                  75                  80
```

```
Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gln Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 141
<211> LENGTH: 326
<212> TYPE: PRT
<213> ORGANISM: Artificial Sequence
<220> FEATURE:
<223> OTHER INFORMATION: Human heavy constant chain wild type IgG2

<400> SEQUENCE: 141

Ala Ser Thr Lys Gly Pro Ser Val Phe Pro Leu Ala Pro Cys Ser Arg
1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110
```

```
Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 142
<211> LENGTH: 327
<212> TYPE: PRT
<213> ORGANISM: Artificial Sequence
<220> FEATURE:
<223> OTHER INFORMATION: Human IgG4 wild type heavy constant chain

<400> SEQUENCE: 142

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140
```

```
Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 143
<211> LENGTH: 327
<212> TYPE: PRT
<213> ORGANISM: Artificial Sequence
<220> FEATURE:
<223> OTHER INFORMATION: Human IgG4 S228P heavy constant domain

<400> SEQUENCE: 143

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175
```

```
Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 144
<211> LENGTH: 451
<212> TYPE: PRT
<213> ORGANISM: Artificial Sequence
<220> FEATURE:
<223> OTHER INFORMATION: H11 HC IgG1

<400> SEQUENCE: 144

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Leu Asn Trp Val Arg Gln Ala Pro Gly Lys Gly Leu Glu Trp Val
        35                  40                  45

Gly His Ile Arg Ser Lys Thr Asn Asn Tyr Ala Thr Phe Tyr Ala Ala
    50                  55                  60

Ser Val Lys Asp Arg Phe Thr Val Ser Arg Asp Asp Ser Gln Asn Thr
65                  70                  75                  80

Ala Tyr Leu Gln Met Asn Ser Leu Lys Thr Glu Asp Thr Ala Thr Tyr
                85                  90                  95

Tyr Cys Val Arg Arg Gly Pro Arg Asp Ser Trp Phe Gly Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205
```

Lys Pro Ser Asn Thr Lys Val Asp Lys Lys Val Glu Pro Lys Ser Cys
            210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 145
<211> LENGTH: 451
<212> TYPE: PRT
<213> ORGANISM: Artificial Sequence
<220> FEATURE:
<223> OTHER INFORMATION: H11 Human_IgG1_L234A_L235A

<400> SEQUENCE: 145

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Leu Asn Trp Val Arg Gln Ala Pro Gly Lys Gly Leu Glu Trp Val
        35                  40                  45

Gly His Ile Arg Ser Lys Thr Asn Asn Tyr Ala Thr Phe Tyr Ala Ala
    50                  55                  60

Ser Val Lys Asp Arg Phe Thr Val Ser Arg Asp Asp Ser Gln Asn Thr
65                  70                  75                  80

Ala Tyr Leu Gln Met Asn Ser Leu Lys Thr Glu Asp Thr Ala Thr Tyr
                85                  90                  95

Tyr Cys Val Arg Arg Gly Pro Arg Asp Ser Trp Phe Gly Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 146
<211> LENGTH: 450
<212> TYPE: PRT
<213> ORGANISM: Artificial Sequence
<220> FEATURE:
<223> OTHER INFORMATION: H11 Human_IgG1_ L234A_L235A_D265S

<400> SEQUENCE: 146

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Phe Thr Phe Ser Ser Phe
            20                  25                  30

Ala Leu Asn Trp Val Arg Gln Ala Pro Gly Lys Gly Leu Glu Trp Val
        35                  40                  45

Gly His Ile Arg Ser Lys Thr Asn Asn Tyr Ala Thr Phe Tyr Ala Ala
    50                  55                  60

Ser Val Lys Asp Arg Phe Thr Val Ser Arg Asp Asp Ser Gln Asn Thr
65                  70                  75                  80

Ala Tyr Leu Gln Met Asn Ser Leu Lys Thr Glu Asp Thr Ala Thr Tyr
                85                  90                  95

Tyr Cys Val Arg Arg Gly Pro Arg Asp Ser Trp Phe Gly Tyr Trp Gly
            100                 105                 110

Gln Gly Thr Leu Val Thr Val Ser Ser Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
    195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Ser Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430
```

```
Glu Ala Leu His Asn His Tyr Thr Gln Lys Ser Leu Ser Leu Ser Pro
            435                 440                 445
Gly Lys
    450

<210> SEQ ID NO 147
<211> LENGTH: 450
<212> TYPE: PRT
<213> ORGANISM: Artificial Sequence
<220> FEATURE:
<223> OTHER INFORMATION: H11 Human_IgG1_YTE_(M252Y_S254T_T256E)

<400> SEQUENCE: 147

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Leu Asn Trp Val Arg Gln Ala Pro Gly Lys Gly Leu Glu Trp Val
            35                  40                  45

Gly His Ile Arg Ser Lys Thr Asn Asn Tyr Ala Thr Phe Tyr Ala Ala
        50                  55                  60

Ser Val Lys Asp Arg Phe Thr Val Ser Arg Asp Asp Ser Gln Asn Thr
65                  70                  75                  80

Ala Tyr Leu Gln Met Asn Ser Leu Lys Thr Glu Asp Thr Ala Thr Tyr
                85                  90                  95

Tyr Cys Val Arg Arg Gly Pro Arg Asp Ser Trp Phe Gly Tyr Trp Gly
            100                 105                 110

Gln Gly Thr Leu Val Thr Val Ser Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Tyr Ile
                245                 250                 255

Thr Arg Glu Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335
```

```
Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 148
<211> LENGTH: 451
<212> TYPE: PRT
<213> ORGANISM: Artificial Sequence
<220> FEATURE:
<223> OTHER INFORMATION: H11 Human_IgG1_N297A

<400> SEQUENCE: 148

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Leu Asn Trp Val Arg Gln Ala Pro Gly Lys Gly Leu Glu Trp Val
        35                  40                  45

Gly His Ile Arg Ser Lys Thr Asn Asn Tyr Ala Thr Phe Tyr Ala Ala
    50                  55                  60

Ser Val Lys Asp Arg Phe Thr Val Ser Arg Asp Asp Ser Gln Asn Thr
65                  70                  75                  80

Ala Tyr Leu Gln Met Asn Ser Leu Lys Thr Glu Asp Thr Ala Thr Tyr
                85                  90                  95

Tyr Cys Val Arg Arg Gly Pro Arg Asp Ser Trp Phe Gly Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240
```

-continued

```
Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 149
<211> LENGTH: 450
<212> TYPE: PRT
<213> ORGANISM: Artificial Sequence
<220> FEATURE:
<223> OTHER INFORMATION: H11 Human_IgG1_N297Q_

<400> SEQUENCE: 149

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Leu Asn Trp Val Arg Gln Ala Pro Gly Lys Gly Leu Glu Trp Val
        35                  40                  45

Gly His Ile Arg Ser Lys Thr Asn Asn Tyr Ala Thr Phe Tyr Ala Ala
    50                  55                  60

Ser Val Lys Asp Arg Phe Thr Val Ser Arg Asp Asp Ser Gln Asn Thr
65                  70                  75                  80

Ala Tyr Leu Gln Met Asn Ser Leu Lys Thr Glu Asp Thr Ala Thr Tyr
                85                  90                  95

Tyr Cys Val Arg Arg Gly Pro Arg Asp Ser Trp Phe Gly Tyr Trp Gly
            100                 105                 110

Gln Gly Thr Leu Val Thr Val Ser Ser Ser Lys Gly Pro Ser Val
        115                 120                 125

Phe Pro Leu Ala Pro Ser Ser Lys Ser Thr Ser Gly Gly Thr Ala Ala
    130                 135                 140
```

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Gln Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 150
<211> LENGTH: 447
<212> TYPE: PRT
<213> ORGANISM: Artificial Sequence
<220> FEATURE:
<223> OTHER INFORMATION: H11 Human_IgG2

<400> SEQUENCE: 150

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Leu Asn Trp Val Arg Gln Ala Pro Gly Lys Gly Leu Glu Trp Val
        35                  40                  45
```

```
Gly His Ile Arg Ser Lys Thr Asn Asn Tyr Ala Thr Phe Tyr Ala Ala
 50                  55                  60

Ser Val Lys Asp Arg Phe Thr Val Ser Arg Asp Asp Ser Gln Asn Thr
 65                  70                  75                  80

Ala Tyr Leu Gln Met Asn Ser Leu Lys Thr Glu Asp Thr Ala Thr Tyr
                 85                  90                  95

Tyr Cys Val Arg Arg Gly Pro Arg Asp Ser Trp Phe Gly Tyr Trp Gly
            100                 105                 110

Gln Gly Thr Leu Val Thr Val Ser Ala Ser Thr Lys Gly Pro Ser
        115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Asn Phe Gly Thr Gln Thr Tyr Thr Cys Asn Val Asp His
            195                 200                 205

Lys Pro Ser Asn Thr Lys Val Asp Lys Thr Val Glu Arg Lys Cys Cys
210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ser Val Glu Trp Glu Ser Asn
370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 151
<211> LENGTH: 447
<212> TYPE: PRT
```

<213> ORGANISM: Artificial Sequence
<220> FEATURE:
<223> OTHER INFORMATION: H11 Human_IgG4

<400> SEQUENCE: 151

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Leu Asn Trp Val Arg Gln Ala Pro Gly Lys Gly Leu Glu Trp Val
        35                  40                  45

Gly His Ile Arg Ser Lys Thr Asn Asn Tyr Ala Thr Phe Tyr Ala Ala
    50                  55                  60

Ser Val Lys Asp Arg Phe Thr Val Ser Arg Asp Asp Ser Gln Asn Thr
65                  70                  75                  80

Ala Tyr Leu Gln Met Asn Ser Leu Lys Thr Glu Asp Thr Ala Thr Tyr
                85                  90                  95

Tyr Cys Val Arg Arg Gly Pro Arg Asp Ser Trp Phe Gly Tyr Trp Gly
            100                 105                 110

Gln Gly Thr Leu Val Thr Val Ser Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Ser Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
```

```
                385                 390                 395                 400
Asp Gly Ser Phe Phe Leu Tyr Ser Arg Leu Thr Val Asp Lys Ser Arg
                    405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
                435                 440                 445

<210> SEQ ID NO 152
<211> LENGTH: 448
<212> TYPE: PRT
<213> ORGANISM: Artificial Sequence
<220> FEATURE:
<223> OTHER INFORMATION: H11 Human_IgG4_S228P

<400> SEQUENCE: 152

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Leu Asn Trp Val Arg Gln Ala Pro Gly Lys Gly Leu Glu Trp Val
        35                  40                  45

Gly His Ile Arg Ser Lys Thr Asn Asn Tyr Ala Thr Phe Tyr Ala Ala
    50                  55                  60

Ser Val Lys Asp Arg Phe Thr Val Ser Arg Asp Ser Gln Asn Thr
65                  70                  75                  80

Ala Tyr Leu Gln Met Asn Ser Leu Lys Thr Glu Asp Thr Ala Thr Tyr
                85                  90                  95

Tyr Cys Val Arg Arg Gly Pro Arg Asp Ser Trp Phe Gly Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
```

```
            305                 310                 315                 320
Lys Cys Lys Val Ser Asn Lys Gly Leu Pro Ser Ser Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
            405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
            435                 440                 445

<210> SEQ ID NO 153
<211> LENGTH: 450
<212> TYPE: PRT
<213> ORGANISM: Artificial Sequence
<220> FEATURE:
<223> OTHER INFORMATION: H65 Human_IgG1

<400> SEQUENCE: 153

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Asn Ser Phe
            20                  25                  30

Ala Leu Asn Trp Val Arg Gln Ala Pro Gly Lys Gly Leu Glu Trp Val
            35                  40                  45

Val His Ile Arg Ser Lys Thr Asn Asn Tyr Ala Thr Phe Tyr Ala Ala
        50                  55                  60

Ser Val Lys Asp Arg Phe Thr Val Ser Arg Asp Asp Ser Gln Asn Thr
65                  70                  75                  80

Ala Tyr Leu Gln Met Asn Ser Leu Lys Thr Glu Asp Thr Ala Thr Tyr
            85                  90                  95

Tyr Cys Val Arg Arg Gly Pro Arg Asp Ser Trp Phe Gly Tyr Trp Gly
            100                 105                 110

Gln Gly Thr Leu Val Thr Val Ser Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Leu Leu Gly Gly
```

```
              225                 230                 235                 240
Pro Ser Val Phe Leu Phe Pro Pro Lys Pro Lys Asp Thr Leu Met Ile
                    245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 154
<211> LENGTH: 451
<212> TYPE: PRT
<213> ORGANISM: Artificial Sequence
<220> FEATURE:
<223> OTHER INFORMATION: H65 Human_IgG1_P01857_L234A_L235A

<400> SEQUENCE: 154

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Asn Ser Phe
            20                  25                  30

Ala Leu Asn Trp Val Arg Gln Ala Pro Gly Lys Gly Leu Glu Trp Val
        35                  40                  45

Val His Ile Arg Ser Lys Thr Asn Asn Tyr Ala Thr Phe Tyr Ala Ala
    50                  55                  60

Ser Val Lys Asp Arg Phe Thr Val Ser Arg Asp Ser Gln Asn Thr
65                  70                  75                  80

Ala Tyr Leu Gln Met Asn Ser Leu Lys Thr Glu Asp Thr Ala Thr Tyr
                85                  90                  95

Tyr Cys Val Arg Arg Gly Pro Arg Asp Ser Trp Phe Gly Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
```

```
            130                 135                 140
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 155
<211> LENGTH: 451
<212> TYPE: PRT
<213> ORGANISM: Artificial Sequence
<220> FEATURE:
<223> OTHER INFORMATION: H65 Human_IgG1_L234A_L235A_D265S

<400> SEQUENCE: 155

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Asn Ser Phe
                20                  25                  30

Ala Leu Asn Trp Val Arg Gln Ala Pro Gly Lys Gly Leu Glu Trp Val
```

```
                35                  40                  45
Val His Ile Arg Ser Lys Thr Asn Asn Tyr Ala Thr Phe Tyr Ala Ala
 50                  55                  60

Ser Val Lys Asp Arg Phe Thr Val Ser Arg Asp Asp Ser Gln Asn Thr
 65                  70                  75                  80

Ala Tyr Leu Gln Met Asn Ser Leu Lys Thr Glu Asp Thr Ala Thr Tyr
                 85                  90                  95

Tyr Cys Val Arg Arg Gly Pro Arg Asp Ser Trp Phe Gly Tyr Trp Gly
                100                 105                 110

Gln Gly Thr Leu Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
                130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Ser Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
                290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
                370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
450
```

<210> SEQ ID NO 156
<211> LENGTH: 451
<212> TYPE: PRT
<213> ORGANISM: Artificial Sequence
<220> FEATURE:
<223> OTHER INFORMATION: H65 Human_IgG1_YTE _(M252Y_S254T_T256E)

<400> SEQUENCE: 156

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ala Phe Asn Ser Phe
            20                  25                  30

Ala Leu Asn Trp Val Arg Gln Ala Pro Gly Lys Gly Leu Glu Trp Val
        35                  40                  45

Val His Ile Arg Ser Lys Thr Asn Asn Tyr Ala Thr Phe Tyr Ala Ala
    50                  55                  60

Ser Val Lys Asp Arg Phe Thr Val Ser Arg Asp Asp Ser Gln Asn Thr
65                  70                  75                  80

Ala Tyr Leu Gln Met Asn Ser Leu Lys Thr Glu Asp Thr Ala Thr Tyr
                85                  90                  95

Tyr Cys Val Arg Arg Gly Pro Arg Asp Ser Trp Phe Gly Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Tyr
                245                 250                 255

Ile Thr Arg Glu Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365
```

-continued

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 157
<211> LENGTH: 451
<212> TYPE: PRT
<213> ORGANISM: Artificial Sequence
<220> FEATURE:
<223> OTHER INFORMATION: H65 human_IgG1_N297A

<400> SEQUENCE: 157

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Asn Ser Phe
            20                  25                  30

Ala Leu Asn Trp Val Arg Gln Ala Pro Gly Lys Gly Leu Glu Trp Val
        35                  40                  45

Val His Ile Arg Ser Lys Thr Asn Asn Tyr Ala Thr Phe Tyr Ala Ala
    50                  55                  60

Ser Val Lys Asp Arg Phe Thr Val Ser Arg Asp Asp Ser Gln Asn Thr
65                  70                  75                  80

Ala Tyr Leu Gln Met Asn Ser Leu Lys Thr Glu Asp Thr Ala Thr Tyr
                85                  90                  95

Tyr Cys Val Arg Arg Gly Pro Arg Asp Ser Trp Phe Gly Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

```
Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Ala Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 158
<211> LENGTH: 451
<212> TYPE: PRT
<213> ORGANISM: Artificial Sequence
<220> FEATURE:
<223> OTHER INFORMATION: H65 Human_IgG1_N297Q_

<400> SEQUENCE: 158

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Asn Ser Phe
            20                  25                  30

Ala Leu Asn Trp Val Arg Gln Ala Pro Gly Lys Gly Leu Glu Trp Val
        35                  40                  45

Val His Ile Arg Ser Lys Thr Asn Asn Tyr Ala Thr Phe Tyr Ala Ala
50                  55                  60

Ser Val Lys Asp Arg Phe Thr Val Ser Arg Asp Asp Ser Gln Asn Thr
65                  70                  75                  80

Ala Tyr Leu Gln Met Asn Ser Leu Lys Thr Glu Asp Thr Ala Thr Tyr
                85                  90                  95

Tyr Cys Val Arg Arg Gly Pro Arg Asp Ser Trp Phe Gly Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175
```

-continued

```
Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Gln Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 159
<211> LENGTH: 447
<212> TYPE: PRT
<213> ORGANISM: Artificial Sequence
<220> FEATURE:
<223> OTHER INFORMATION: H65 Human_IgG2

<400> SEQUENCE: 159

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Asn Ser Phe
            20                  25                  30

Ala Leu Asn Trp Val Arg Gln Ala Pro Gly Lys Gly Leu Glu Trp Val
        35                  40                  45

Val His Ile Arg Ser Lys Thr Asn Asn Tyr Ala Thr Phe Tyr Ala Ala
    50                  55                  60

Ser Val Lys Asp Arg Phe Thr Val Ser Arg Asp Asp Ser Gln Asn Thr
65                  70                  75                  80
```

Ala Tyr Leu Gln Met Asn Ser Leu Lys Thr Glu Asp Thr Ala Thr Tyr
                85                  90                  95

Tyr Cys Val Arg Arg Gly Pro Arg Asp Ser Trp Phe Gly Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ser Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 160
<211> LENGTH: 448
<212> TYPE: PRT
<213> ORGANISM: Artificial Sequence
<220> FEATURE:
<223> OTHER INFORMATION: H65 _Human_IgG4

<400> SEQUENCE: 160

-continued

```
Glu Val Gln Leu Val Glu Ser Gly Gly Leu Val Gln Pro Gly Gly
1               5                   10                  15

Ser Leu Arg Leu Ser Cys Ala Ala Ser Gly Phe Ala Phe Asn Ser Phe
            20                  25                  30

Ala Leu Asn Trp Val Arg Gln Ala Pro Gly Lys Gly Leu Glu Trp Val
            35                  40                  45

Val His Ile Arg Ser Lys Thr Asn Asn Tyr Ala Thr Phe Tyr Ala Ala
        50                  55                  60

Ser Val Lys Asp Arg Phe Thr Val Ser Arg Asp Asp Ser Gln Asn Thr
65                  70                  75                  80

Ala Tyr Leu Gln Met Asn Ser Leu Lys Thr Glu Asp Thr Ala Thr Tyr
                85                  90                  95

Tyr Cys Val Arg Arg Gly Pro Arg Asp Ser Trp Phe Gly Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
            195                 200                 205

Lys Pro Ser Asn Thr Lys Val Asp Lys Arg Val Glu Ser Lys Tyr Gly
        210                 215                 220

Pro Pro Cys Pro Ser Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser Gln Glu Asp Pro
            260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415
```

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
            435                 440                 445

<210> SEQ ID NO 161
<211> LENGTH: 448
<212> TYPE: PRT
<213> ORGANISM: Artificial Sequence
<220> FEATURE:
<223> OTHER INFORMATION: H65 Human_IgG4_S228P_P01861

<400> SEQUENCE: 161

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Asn Ser Phe
            20                  25                  30

Ala Leu Asn Trp Val Arg Gln Ala Pro Gly Lys Gly Leu Glu Trp Val
            35                  40                  45

Val His Ile Arg Ser Lys Thr Asn Asn Tyr Ala Thr Phe Tyr Ala Ala
        50                  55                  60

Ser Val Lys Asp Arg Phe Thr Val Ser Arg Asp Asp Ser Gln Asn Thr
65                  70                  75                  80

Ala Tyr Leu Gln Met Asn Ser Leu Lys Thr Glu Asp Thr Ala Thr Tyr
                85                  90                  95

Tyr Cys Val Arg Arg Gly Pro Arg Asp Ser Trp Phe Gly Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

```
Ile Ser Lys Ala Lys Gly Gln Pro Arg Glu Pro Gln Val Tyr Thr Leu
                340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 162
<211> LENGTH: 219
<212> TYPE: PRT
<213> ORGANISM: Artificial Sequence
<220> FEATURE:
<223> OTHER INFORMATION: VL46_kappa

<400> SEQUENCE: 162

Asp Ile Val Met Thr Gln Ser Pro Leu Ser Leu Pro Val Thr Leu Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Leu Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 163
<211> LENGTH: 218
<212> TYPE: PRT
<213> ORGANISM: Artificial Sequence
<220> FEATURE:
```

-continued

<223> OTHER INFORMATION: VL46_lambda

<400> SEQUENCE: 163

Asp Ile Val Met Thr Gln Ser Pro Leu Ser Leu Pro Val Thr Leu Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Leu Pro Leu Thr Phe Gly Gly Gly Thr Lys Val Glu Ile Lys
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Thr Glu Cys Ser
    210                 215

<210> SEQ ID NO 164
<211> LENGTH: 219
<212> TYPE: PRT
<213> ORGANISM: Artificial Sequence
<220> FEATURE:
<223> OTHER INFORMATION: VL47 kappa

<400> SEQUENCE: 164

Asp Ile Val Met Thr Gln Ser Pro Leu Ser Leu Pro Val Thr Leu Gly
1               5                   10                  15

Asp Pro Ala Ser Ile Ser Cys Arg Ser Ser Gln Ser Ile Val His Ser
            20                  25                  30

Asn Gly Asn Thr Tyr Leu Glu Trp Tyr Gln Gln Lys Pro Gly Gln Ser
        35                  40                  45

Pro Gln Arg Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Leu Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
            130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 165
<211> LENGTH: 218
<212> TYPE: PRT
<213> ORGANISM: Artificial Sequence
<220> FEATURE:
<223> OTHER INFORMATION: VL47 lambda

<400> SEQUENCE: 165

Asp Ile Val Met Thr Gln Ser Pro Leu Ser Leu Pro Val Thr Leu Gly
1               5                   10                  15

Asp Pro Ala Ser Ile Ser Cys Arg Ser Ser Gln Ser Ile Val His Ser
            20                  25                  30

Asn Gly Asn Thr Tyr Leu Glu Trp Tyr Gln Gln Lys Pro Gly Gln Ser
        35                  40                  45

Pro Gln Arg Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Leu Pro Leu Thr Phe Gly Gly Gly Thr Lys Val Glu Ile Lys
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Thr Glu Cys Ser
    210                 215

<210> SEQ ID NO 166
<211> LENGTH: 219
<212> TYPE: PRT
<213> ORGANISM: Artificial Sequence
<220> FEATURE:
<223> OTHER INFORMATION: VL46_G34A kappa

<400> SEQUENCE: 166

Asp Ile Val Met Thr Gln Ser Pro Leu Ser Leu Pro Val Thr Leu Gly
1               5                   10                  15

Glu Pro Ala Ser Ile Ser Cys Arg Ser Ser Gln Ser Ile Val His Ser
            20                  25                  30

Asn Ala Asn Thr Tyr Leu Glu Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Leu Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 167
<211> LENGTH: 218
<212> TYPE: PRT
<213> ORGANISM: Artificial Sequence
<220> FEATURE:
<223> OTHER INFORMATION: VL46_G34A lambda

<400> SEQUENCE: 167

Asp Ile Val Met Thr Gln Ser Pro Leu Ser Leu Pro Val Thr Leu Gly
1               5                   10                  15

Glu Pro Ala Ser Ile Ser Cys Arg Ser Ser Gln Ser Ile Val His Ser
            20                  25                  30

Asn Ala Asn Thr Tyr Leu Glu Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Leu Pro Leu Thr Phe Gly Gly Gly Thr Lys Val Glu Ile Lys
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
            165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
            195                 200                 205

Glu Lys Thr Val Ala Pro Thr Glu Cys Ser
210                 215

<210> SEQ ID NO 168
<211> LENGTH: 219
<212> TYPE: PRT
<213> ORGANISM: Artificial Sequence
<220> FEATURE:
<223> OTHER INFORMATION: VL46_G34S kappa

<400> SEQUENCE: 168

Asp Ile Val Met Thr Gln Ser Pro Leu Ser Leu Pro Val Thr Leu Gly
1               5                   10                  15

Glu Pro Ala Ser Ile Ser Cys Arg Ser Ser Gln Ser Ile Val His Ser
            20                  25                  30

Asn Ser Asn Thr Tyr Leu Glu Trp Tyr Leu Gln Lys Pro Gly Gln Ser
            35                  40                  45

Pro Gln Leu Leu Ile Tyr Thr Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
            85                  90                  95

Ser His Leu Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
210                 215

<210> SEQ ID NO 169
<211> LENGTH: 218
<212> TYPE: PRT
<213> ORGANISM: Artificial Sequence
<220> FEATURE:
<223> OTHER INFORMATION: VL46_G34S lambda

<400> SEQUENCE: 169

```
Asp Ile Val Met Thr Gln Ser Pro Leu Ser Leu Pro Val Thr Leu Gly
1               5                   10                  15

Glu Pro Ala Ser Ile Ser Cys Arg Ser Ser Gln Ser Ile Val His Ser
            20                  25                  30

Asn Ser Asn Thr Tyr Leu Glu Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Leu Pro Leu Thr Phe Gly Gly Gly Thr Lys Val Glu Ile Lys
            100                 105                 110

Gly Gln Pro Lys Ala Ala Pro Ser Val Thr Leu Phe Pro Pro Ser Ser
            115                 120                 125

Glu Glu Leu Gln Ala Asn Lys Ala Thr Leu Val Cys Leu Ile Ser Asp
130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
            195                 200                 205

Glu Lys Thr Val Ala Pro Thr Glu Cys Ser
            210                 215

<210> SEQ ID NO 170
<211> LENGTH: 219
<212> TYPE: PRT
<213> ORGANISM: Artificial Sequence
<220> FEATURE:
<223> OTHER INFORMATION: VL46_G34T kappa

<400> SEQUENCE: 170

Asp Ile Val Met Thr Gln Ser Pro Leu Ser Leu Pro Val Thr Leu Gly
1               5                   10                  15

Glu Pro Ala Ser Ile Ser Cys Arg Ser Ser Gln Ser Ile Val His Ser
            20                  25                  30

Asn Thr Asn Thr Tyr Leu Glu Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Leu Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140
```

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
        180                 185                 190

Lys His Lys Val Tyr Ala Cys Glu Val Thr His Gln Gly Leu Ser Ser
    195                 200                 205

Pro Val Thr Lys Ser Phe Asn Arg Gly Glu Cys
210                 215

<210> SEQ ID NO 171
<211> LENGTH: 218
<212> TYPE: PRT
<213> ORGANISM: Artificial Sequence
<220> FEATURE:
<223> OTHER INFORMATION: VL46_G34T lambda

<400> SEQUENCE: 171

Asp Ile Val Met Thr Gln Ser Pro Leu Ser Leu Pro Val Thr Leu Gly
1               5                   10                  15

Glu Pro Ala Ser Ile Ser Cys Arg Ser Ser Gln Ser Ile Val His Ser
            20                  25                  30

Asn Thr Asn Thr Tyr Leu Glu Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
            85                  90                  95

Ser His Leu Pro Leu Thr Phe Gly Gly Gly Thr Lys Val Glu Ile Lys
        100                 105                 110

Gly Gln Pro Lys Ala Ala Pro Ser Val Thr Leu Phe Pro Pro Ser Ser
    115                 120                 125

Glu Glu Leu Gln Ala Asn Lys Ala Thr Leu Val Cys Leu Ile Ser Asp
130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Pro Ser Lys Gln Ser Asn Asn Asn
            165                 170                 175

Lys Tyr Ala Ala Ser Ser Tyr Leu Ser Leu Thr Pro Glu Gln Trp Lys
        180                 185                 190

Ser His Arg Ser Tyr Ser Cys Gln Val Thr His Glu Gly Ser Thr Val
    195                 200                 205

Glu Lys Thr Val Ala Pro Thr Glu Cys Ser
210                 215

<210> SEQ ID NO 172
<211> LENGTH: 219
<212> TYPE: PRT
<213> ORGANISM: Artificial Sequence
<220> FEATURE:
<223> OTHER INFORMATION: VL46_N33Q kappa

<400> SEQUENCE: 172

Asp Ile Val Met Thr Gln Ser Pro Leu Ser Leu Pro Val Thr Leu Gly
1               5                   10                  15

Glu Pro Ala Ser Ile Ser Cys Arg Ser Ser Gln Ser Ile Val His Ser
            20                  25                  30

Gln Gly Asn Thr Tyr Leu Glu Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Leu Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 173
<211> LENGTH: 218
<212> TYPE: PRT
<213> ORGANISM: Artificial Sequence
<220> FEATURE:
<223> OTHER INFORMATION: VL46_N33Q lambda

<400> SEQUENCE: 173

Asp Ile Val Met Thr Gln Ser Pro Leu Ser Leu Pro Val Thr Leu Gly
1               5                   10                  15

Glu Pro Ala Ser Ile Ser Cys Arg Ser Ser Gln Ser Ile Val His Ser
            20                  25                  30

Gln Gly Asn Thr Tyr Leu Glu Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Leu Pro Leu Thr Phe Gly Gly Gly Thr Lys Val Glu Ile Lys
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Pro Ser Lys Gln Ser Asn Asn
              165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
            195                 200                 205

Glu Lys Thr Val Ala Pro Thr Glu Cys Ser
        210                 215

<210> SEQ ID NO 174
<211> LENGTH: 219
<212> TYPE: PRT
<213> ORGANISM: Artificial Sequence
<220> FEATURE:
<223> OTHER INFORMATION: VL46_N33Q_G34A kappa

<400> SEQUENCE: 174

Asp Ile Val Met Thr Gln Ser Pro Leu Ser Leu Pro Val Thr Leu Gly
1               5                   10                  15

Glu Pro Ala Ser Ile Ser Cys Arg Ser Ser Gln Ser Ile Val His Ser
            20                  25                  30

Gln Ala Asn Thr Tyr Leu Glu Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Leu Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 175
<211> LENGTH: 218
<212> TYPE: PRT
<213> ORGANISM: Artificial Sequence
<220> FEATURE:
<223> OTHER INFORMATION: VL46_N33Q_G34A lambda

<400> SEQUENCE: 175

Asp Ile Val Met Thr Gln Ser Pro Leu Ser Leu Pro Val Thr Leu Gly
1               5                   10                  15

Glu Pro Ala Ser Ile Ser Cys Arg Ser Ser Gln Ser Ile Val His Ser
            20                  25                  30

```
                    20                  25                  30
Gln Ala Asn Thr Tyr Leu Glu Trp Tyr Leu Gln Lys Pro Gly Gln Ser
                35                  40                  45

Pro Gln Leu Leu Ile Tyr Thr Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Leu Pro Leu Thr Phe Gly Gly Gly Thr Lys Val Glu Ile Lys
                100                 105                 110

Gly Gln Pro Lys Ala Ala Pro Ser Val Thr Leu Phe Pro Pro Ser Ser
                115                 120                 125

Glu Glu Leu Gln Ala Asn Lys Ala Thr Leu Val Cys Leu Ile Ser Asp
                130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Pro Ser Lys Gln Ser Asn Asn
                165                 170                 175

Lys Tyr Ala Ala Ser Ser Tyr Leu Ser Leu Thr Pro Glu Gln Trp Lys
                180                 185                 190

Ser His Arg Ser Tyr Ser Cys Gln Val Thr His Glu Gly Ser Thr Val
                195                 200                 205

Glu Lys Thr Val Ala Pro Thr Glu Cys Ser
                210                 215

<210> SEQ ID NO 176
<211> LENGTH: 219
<212> TYPE: PRT
<213> ORGANISM: Artificial Sequence
<220> FEATURE:
<223> OTHER INFORMATION: VL46_N33D kappa

<400> SEQUENCE: 176

Asp Ile Val Met Thr Gln Ser Pro Leu Ser Leu Pro Val Thr Leu Gly
 1               5                  10                  15

Glu Pro Ala Ser Ile Ser Cys Arg Ser Ser Gln Ser Ile Val His Ser
                20                  25                  30

Asp Gly Asn Thr Tyr Leu Glu Trp Tyr Leu Gln Lys Pro Gly Gln Ser
                35                  40                  45

Pro Gln Leu Leu Ile Tyr Thr Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Leu Pro Leu Thr Phe Gly Gly Gly Thr Lys Val Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
                130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
```

```
                    165                 170                 175
Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 177
<211> LENGTH: 218
<212> TYPE: PRT
<213> ORGANISM: Artificial Sequence
<220> FEATURE:
<223> OTHER INFORMATION: VL46_N33D lambda

<400> SEQUENCE: 177

```
Asp Ile Val Met Thr Gln Ser Pro Leu Ser Leu Pro Val Thr Leu Gly
1               5                   10                  15

Glu Pro Ala Ser Ile Ser Cys Arg Ser Ser Gln Ser Ile Val His Ser
            20                  25                  30

Asp Gly Asn Thr Tyr Leu Glu Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Leu Pro Leu Thr Phe Gly Gly Gly Thr Lys Val Glu Ile Lys
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Thr Glu Cys Ser
    210                 215
```

<210> SEQ ID NO 178
<211> LENGTH: 219
<212> TYPE: PRT
<213> ORGANISM: Artificial Sequence
<220> FEATURE:
<223> OTHER INFORMATION: VL46_N33S kappa

<400> SEQUENCE: 178

```
Asp Ile Val Met Thr Gln Ser Pro Leu Ser Leu Pro Val Thr Leu Gly
1               5                   10                  15

Glu Pro Ala Ser Ile Ser Cys Arg Ser Ser Gln Ser Ile Val His Ser
            20                  25                  30
```

Ser Gly Asn Thr Tyr Leu Glu Trp Tyr Leu Gln Lys Pro Gly Gln Ser
            35                  40                  45

Pro Gln Leu Leu Ile Tyr Thr Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Leu Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 179
<211> LENGTH: 218
<212> TYPE: PRT
<213> ORGANISM: Artificial Sequence
<220> FEATURE:
<223> OTHER INFORMATION: VL46_N33S lambda

<400> SEQUENCE: 179

Asp Ile Val Met Thr Gln Ser Pro Leu Ser Leu Pro Val Thr Leu Gly
1               5                   10                  15

Glu Pro Ala Ser Ile Ser Cys Arg Ser Ser Gln Ser Ile Val His Ser
            20                  25                  30

Ser Gly Asn Thr Tyr Leu Glu Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Leu Pro Leu Thr Phe Gly Gly Gly Thr Lys Val Glu Ile Lys
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

```
Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
            195                 200                 205

Glu Lys Thr Val Ala Pro Thr Glu Cys Ser
    210                 215

<210> SEQ ID NO 180
<211> LENGTH: 219
<212> TYPE: PRT
<213> ORGANISM: Artificial Sequence
<220> FEATURE:
<223> OTHER INFORMATION: VL46_N33T kappa

<400> SEQUENCE: 180

Asp Ile Val Met Thr Gln Ser Pro Leu Ser Leu Pro Val Thr Leu Gly
1               5                   10                  15

Glu Pro Ala Ser Ile Ser Cys Arg Ser Gln Ser Ile Val His Ser
            20                  25                  30

Thr Gly Asn Thr Tyr Leu Glu Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Leu Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 181
<211> LENGTH: 218
<212> TYPE: PRT
<213> ORGANISM: Artificial Sequence
<220> FEATURE:
<223> OTHER INFORMATION: VL46_N33T lambda

<400> SEQUENCE: 181

Asp Ile Val Met Thr Gln Ser Pro Leu Ser Leu Pro Val Thr Leu Gly
1               5                   10                  15

Glu Pro Ala Ser Ile Ser Cys Arg Ser Gln Ser Ile Val His Ser
            20                  25                  30

Thr Gly Asn Thr Tyr Leu Glu Trp Tyr Leu Gln Lys Pro Gly Gln Ser
        35                  40                  45
```

```
Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Leu Pro Leu Thr Phe Gly Gly Gly Thr Lys Val Glu Ile Lys
                100                 105                 110

Gly Gln Pro Lys Ala Ala Pro Ser Val Thr Leu Phe Pro Pro Ser Ser
            115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
                180                 185                 190

Ser His Arg Ser Tyr Ser Cys Gln Val Thr His Glu Gly Ser Thr Val
            195                 200                 205

Glu Lys Thr Val Ala Pro Thr Glu Cys Ser
    210                 215

<210> SEQ ID NO 182
<211> LENGTH: 219
<212> TYPE: PRT
<213> ORGANISM: Artificial Sequence
<220> FEATURE:
<223> OTHER INFORMATION: VL46_S28N kappa

<400> SEQUENCE: 182

Asp Ile Val Met Thr Gln Ser Pro Leu Ser Leu Pro Val Thr Leu Gly
1               5                   10                  15

Glu Pro Ala Ser Ile Ser Cys Arg Ser Ser Gln Asn Ile Val His Ser
                20                  25                  30

Asn Gly Asn Thr Tyr Leu Glu Trp Tyr Leu Gln Lys Pro Gly Gln Ser
            35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Leu Pro Leu Thr Phe Gly Gly Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190
```

```
Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215
```

<210> SEQ ID NO 183
<211> LENGTH: 218
<212> TYPE: PRT
<213> ORGANISM: Artificial Sequence
<220> FEATURE:
<223> OTHER INFORMATION: VL46_S28N lambda

<400> SEQUENCE: 183

```
Asp Ile Val Met Thr Gln Ser Pro Leu Ser Leu Pro Val Thr Leu Gly
1               5                   10                  15

Glu Pro Ala Ser Ile Ser Cys Arg Ser Ser Gln Asn Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Leu Pro Leu Thr Phe Gly Gly Gly Thr Lys Val Glu Ile Lys
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Thr Glu Cys Ser
    210                 215
```

<210> SEQ ID NO 184
<211> LENGTH: 219
<212> TYPE: PRT
<213> ORGANISM: Artificial Sequence
<220> FEATURE:
<223> OTHER INFORMATION: *VL46_G34A_S28N kappa

<400> SEQUENCE: 184

```
Asp Ile Val Met Thr Gln Ser Pro Leu Ser Leu Pro Val Thr Leu Gly
1               5                   10                  15

Glu Pro Ala Ser Ile Ser Cys Arg Ser Ser Gln Asn Ile Val His Ser
            20                  25                  30

Asn Ala Asn Thr Tyr Leu Glu Trp Tyr Leu Gln Lys Pro Gly Gln Ser
        35                  40                  45

Pro Gln Leu Leu Ile Tyr Thr Val Ser Asn Arg Phe Ser Gly Val Pro
```

```
                50             55             60
Asp Arg Phe Ser Gly Ser Gly Ser Gly Thr Asp Phe Thr Leu Lys Ile
 65              70             75             80

Ser Arg Val Glu Ala Glu Asp Leu Gly Val Tyr Tyr Cys Phe Gln Gly
                85             90                 95

Ser His Leu Pro Leu Thr Phe Gly Gly Gly Thr Lys Val Glu Ile Lys
               100            105                110

Arg Thr Val Ala Ala Pro Ser Val Phe Ile Phe Pro Pro Ser Asp Glu
               115            120            125

Gln Leu Lys Ser Gly Thr Ala Ser Val Val Cys Leu Leu Asn Asn Phe
       130            135             140

Tyr Pro Arg Glu Ala Lys Val Gln Trp Lys Val Asp Asn Ala Leu Gln
145            150             155             160

Ser Gly Asn Ser Gln Glu Ser Val Thr Glu Gln Asp Ser Lys Asp Ser
               165             170             175

Thr Tyr Ser Leu Ser Ser Thr Leu Thr Leu Ser Lys Ala Asp Tyr Glu
               180             185             190

Lys His Lys Val Tyr Ala Cys Glu Val Thr His Gln Gly Leu Ser Ser
       195             200             205

Pro Val Thr Lys Ser Phe Asn Arg Gly Glu Cys
       210             215

<210> SEQ ID NO 185
<211> LENGTH: 218
<212> TYPE: PRT
<213> ORGANISM: Artificial Sequence
<220> FEATURE:
<223> OTHER INFORMATION: VL46_G34A_S28N lambda

<400> SEQUENCE: 185

Asp Ile Val Met Thr Gln Ser Pro Leu Ser Leu Pro Val Thr Leu Gly
 1               5              10             15

Glu Pro Ala Ser Ile Ser Cys Arg Ser Ser Gln Asn Ile Val His Ser
               20              25             30

Asn Ala Asn Thr Tyr Leu Glu Trp Tyr Leu Gln Lys Pro Gly Gln Ser
       35              40             45

Pro Gln Leu Leu Ile Tyr Thr Val Ser Asn Arg Phe Ser Gly Val Pro
       50              55             60

Asp Arg Phe Ser Gly Ser Gly Ser Gly Thr Asp Phe Thr Leu Lys Ile
 65              70             75             80

Ser Arg Val Glu Ala Glu Asp Leu Gly Val Tyr Tyr Cys Phe Gln Gly
                85             90                 95

Ser His Leu Pro Leu Thr Phe Gly Gly Gly Thr Lys Val Glu Ile Lys
               100            105                110

Gly Gln Pro Lys Ala Ala Pro Ser Val Thr Leu Phe Pro Pro Ser Ser
       115             120            125

Glu Glu Leu Gln Ala Asn Lys Ala Thr Leu Val Cys Leu Ile Ser Asp
       130             135             140

Phe Tyr Pro Gly Ala Val Thr Val Ala Trp Lys Ala Asp Ser Ser Pro
145            150             155             160

Val Lys Ala Gly Val Glu Thr Thr Thr Pro Ser Lys Gln Ser Asn Asn
               165             170             175
```

```
Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Thr Glu Cys Ser
    210                 215
```

HUMANIZED ANTIBODY FOR TREATING OR PREVENTING COGNITIVE DISORDERS, PROCESS FOR PRODUCING THE SAME, AND AGENT FOR TREATING OR PREVENTING COGNITIVE DISORDERS USING THE SAME

I. CROSS REFERENCE TO RELATED APPLICATIONS

This application is a continuation of U.S. patent application Ser. No. 15/906,773, filed Feb. 27, 2018, now U.S. Pat. No. 10,556,950, which claims the benefit of Japanese Application No. 2017-035594, filed on Feb. 27, 2017, the disclosure of each of which is incorporated herein by reference in its entirety.

II. SEQUENCE LISTING

This application incorporates by reference in its entirety the Computer Readable Form (CRF) of a Sequence Listing in ASCII text format submitted via EFS-Web. The Sequence Listing text file submitted via EFS-Web, entitled 14463-026-999_SUB_SEQ_LISTING.txt, was created on Mar. 18, 2020, and is 317,785 bytes in size.

III. TECHNICAL FIELD

The present disclosure relates to a humanized antibody for use in the therapeutic or prophylactic treatment of cognitive disorders, a process of producing the humanized antibody, a therapeutic or prophylactic agent for cognitive disorders using the antibody, and methods for treatment or prevention of cognitive disorders using the therapeutic agents disclosed herein. More specifically, the present disclosure relates to a novel humanized anti-phosphorylated tau antibody having excellent effect of improving cognitive function, a process of producing the humanized antibody, a therapeutic or prophylactic agent for cognitive disorders containing the humanized antibody, and methods for treatment or prevention of cognitive disorders using the humanized anti-phosphorylated tau antibody.

IV. BACKGROUND OF THE INVENTION

A cognitive disorder, or dementia, is a condition where developed intelligence deteriorates due to some acquired cause, resulting in a hindrance to social adaptation. Cognitive disorders are classified as neurodegenerative diseases, vascular cognitive diseases, prion diseases, infectious diseases, metabolic/endocrine diseases, trauma and cerebral surgical diseases, and toxic diseases (see Toshifumi Kishimoto & Shigeki Takahashi (Edit.), "STEP Series Seishinka" (Japanese document), 2th Edition, Kaibashobo, 2008, pp.103-104). There were about 2.1 million dementia patients in Japan as of 2010, with a morbidity prevalence rate of about 8 to 10%, or even more than 10%, among the elderly over age 65, and this has been recognized as a serious problem in the worldwide aging society (Takashi Asada, "Igaku no Ayumi" (Japanese document), supplementary volume, "Cognitive disorders", Ishiyaku Publishing, 2011, pp.5-10). Data on underlying diseases of cognitive disorders indicate that the majority are neurodegenerative diseases such as Alzheimer's disease (AD) and frontotemporal lobar degeneration (FTLD), with about 35% being AD, about 15% being a combination of AD and cerebrovascular disease, and 5% being FTLD (Id.) Cognitive disorders associated with neurodegenerative diseases are characterized by insidious onset of memory impairment and/or personality changes which progresses over a period of at least six months or more. Neurodegenerative processes correlate highly with the degree of impairment of cognitive function, and a consistent characteristics involved therein is the presence of neurofibrillary tangles (NFT) (Alistair Burns et al. (Edit.), Dementia, 3rd Edition, 2005, CRC Press, pp.408-464).

The tau protein is a protein encoded by the MAPT gene, which is located on chromosome 17 (17q21) in the human genome. Tau protein is one of the microtubule-binding proteins abundantly expressed in the central nervous system. The tau has been found to be a major constituent protein in the paired helical filaments and straight filaments forming NFT in AD, one of the most prominent neurodegenerative diseases, and its intracellular accumulation has been demonstrated in a variety of neuropathological conditions.

Tau was first implicated in neurodegenerative diseases based on the relationship between mutations in the MAPT gene and accumulation of tau in chromosome 17-linked frontotemporal dementia with Parkinsonism (FTDP-17). More than 40 gene mutations in the MAPT gene have been reported in relation to FTDP-17 (Tetsuaki Arai, "Shinkei Naika" (Japanese document), Vol. 72, special number, (Suppl.6), 2010, pp.46-51). These gene mutations are suggested as altering the proportions of tau isoforms or altering the structure and changing the interaction between mutant tau and microtubules, thus contributing to development of pathology. However, unlike familial neurodegenerative diseases, mutations in MAPT are rarely observed in sporadic neurodegenerative diseases such as AD. In addition, tau accumulated in neurodegenerative diseases is characterized by being highly modified via phosphorylation. Moreover, in patients exhibiting mild cognitive impairment (MCI), a correlation is observed between the level of phosphorylated tau in the spinal fluid and the degree of pituitary atrophy, suggesting phosphorylated tau as a highly reliable biomarker for neurodegeneration in patients with tauopathy (Wendy Noble et al., Expert Opinion on Drug Discovery, 2011, Vol. 6, No. 8, pp.797-810). Based on these findings, attempts have been made to develop a treatment using inhibitors against kinases, which are enzymes involved in phosphorylation, and particularly against GSK-3 beta, for inhibiting excessive phosphorylation of tau (Id). However, there is a concern about possible side effects, since kinases such as GSK-3 beta are implicated not only in pathological conditions, but also in function controls in normal physiological processes. In fact, some of the sites where tau is phosphorylated by GSK-3 beta coincide with sites of tau phosphorylation seen in fetal and normal human brains (Burnes, et. al., supra) suggesting the possibility that this strategy may affect normal tau function.

Although it was believed that extracellular tau originates from leakage from degenerated nerve cells as a consequence of cell death, recent studies have suggested that following excessive intracellular phosphorylation, tau is processed and then actively secreted out of the cell. Phosphorylated tau secreted from the cell is thought to be dephosphorylated at certain phosphorylation sites and subsequently to act on muscarine receptors M1 and M3 of surrounding cells, thus resulting in various effects such as promoting intracellular tau phosphorylation and contributing to cell death (Miguel Diaz-Hernandes et al., Journal of Biological Chemistry, 2010, Vol. 285, No. 42, pp.32539-32548 and Venessa Plouffe et al., PLoS ONE, 2012, Vol. 7, p.36873). Experiments relating to immunotherapy for tauopathies using tau protein as the target have been reported, as attempts aimed at executing specific action against tau (see Noble, supra, Kishimoto, supra, Asada, supra and Burns, supra).

The major symptoms in human cognitive disorders are memory impairment and cognitive function impairmen, which is especially important given the role of cognitive function in memory-based judgment, communication and performance. Motor function, on the other hand, while being a symptom found in chromosome 17-linked frontotemporal dementia with Parkinsonism (FTDP-17) and terminal-stage Alzheimer's disease, is not necessarily a major symptom exhibited in cognitive disorders. Therefore, the main issue to be considered for treating cognitive disorders is improvement of cognitive functions. However, there is currently suitable animal models for testing tauopathy-associated cognitive function impairment that would allow identification of a therapeutic or prophylactic agent for treating cognitive disorders. In addition, no such agent exists that exhibits specific and superior effects against cognitive disorders.

In view of the therapeutic and prophylactic applications against cognitive disorders in human subjects, there is a demand for a humanized anti-phosphorylated tau antibody which not only has high binding affinity to phosphorylated tau, but also exhibits reduced antigenicity to the human body.

V. SUMMARY OF THE INVENTION

Against this background, among a large number of phosphorylated sites in the tau protein which can undergo abnormal phosphorylation in the conditions of Alzheimer's disease, the present inventors focused on the phosphorylated site of the serine residue at position 413 (Ser413), and succeeded in producing a polyclonal rabbit antibody and a monoclonal mouse antibody which are specific to the Ser413-phosphorylated tau. The present inventors also administered the monoclonal mouse antibodies to model mice of cognitive disorders which showed abnormal expression of phosphorylated tau proteins, and confirmed that improvement in cognitive functions was observed (WO2013/180238A).

In some embodiments, the present disclosure provides proteins, such as antibodies, that include an antigen binding portion that specifically binds to Tau protein that is phosphorylated at serine residue 413 (pS413-Tau). In some embodiments, the present disclosure provides nucleic acids encoding the proteins. In some embodiments, the present disclosure provides cells that include such nucleic acids encoding the proteins. In some embodiments, the present disclosure provides methods for treating a tauopathy (e.g., Alzheimer's disease) by administering the proteins, nucleic acids, or cells disclosed herein to a patient in need thereof.

Accordingly, in some aspects the invention provides a humanized antibody or a fragment or derivative thereof, which causes an antigen-antibody reaction with a tau protein or a tau peptide phosphorylated at least on an amino acid residue corresponding to Ser413 of SEQ ID NO: 1. In some cases, the humanized antibody or fragment or derivative thereof has an equilibrium dissociation constant of $1.86 \times 10^{-8}$M or less for the tau protein or tau peptide.

In further aspects, the humanized antibody or fragment or derivative thereof has an improved selective affinity with the phosphorylated tau protein (or tau peptide, e.g. SEQ ID NO:8) compared to a non-phosphorylated tau protein (or tau peptide, e.g. SEQ ID NO:69).

In an additional aspect, the humanized antibody or fragment or derivative thereof described herein has an improved ability to enter the brain when administered into the blood.

In a further aspect, the humanized antibody or fragment or derivative thereof comprises CDRs as follows: a CDR-H1 sequence, an amino acid sequence having 80% or more homology with sequence 1M; as a CDR-H2 sequence, an amino acid sequence having 84% or more homology with sequence 2M or 2H1; as a CDR-H3 sequence, an amino acid sequence having 80% or more homology with sequence 3M; as a CDR-L1 sequence, an amino acid sequence having 87% or more homology with sequence 4L1 or 4M; as a CDR-L2 sequence, an amino acid sequence having 85% or more homology with sequence 5M; and as a CDR-L3 sequence, an amino acid sequence having 77% or more homology with sequence 6M.

In an additional aspect, the humanized antibody or fragment or derivative thereof comprises CDRs as follows: as a CDR-H1 sequence, the amino acid sequence of sequence 1M; as a CDR-H2 sequence, the amino acid sequence of sequence 2H1 or an amino acid sequence differs from sequence 2H1 in that Ala at position 15 is substituted with Asp; as a CDR-H3 sequence, the amino acid sequence of sequence 3M; as a CDR-L1 sequence, the amino acid sequence of sequence 4L1 or an amino acid sequence that differs from sequence 4L1 in that Ser at position 5 is substituted with Asn; as a CDR-L2 sequence, the amino acid sequence of sequence 5M; and as a CDR-L3 sequence, the amino acid sequence of sequence 6M.

In a further aspect, the humanized antibody or fragment or derivative thereof has CDRs as follows: (1) as a CDR-H1 sequence, the amino acid sequence of 1M; as a CDR-H2 sequence, the amino acid sequence of 2H1; as a CDR-H3 sequence, the amino acid sequence of 3M; as a CDR-L1 sequence, the amino acid sequence of 4L1; as a CDR-L2 sequence, the amino acid sequence of 5M; and as a CDR-L3 sequence, the amino acid sequence of 6M, or (2) as a CDR-H1 sequence, the amino acid sequence of 1M; as a CDR-H2 sequence, the amino acid sequence of 2H1; as a CDR-H3 sequence, the amino acid sequence of 3M; as a CDR-L1 sequence, the amino acid sequence of 4M; as a CDR-L2 sequence, the amino acid sequence of 5M; and as a CDR-L3 sequence, the amino acid sequence of 6M, or (3) as a CDR-H1 sequence, the amino acid sequence of 1M; as a CDR-H2 sequence, the amino acid sequence of 2M; as a CDR-H3 sequence, the amino acid sequence of 3M; as a CDR-L1 sequence, the amino acid sequence of 4M; as a CDR-L2 sequence, the amino acid sequence of 5M; and as a CDR-L3 sequence, the amino acid sequence of 6M.

In additional aspects the humanized antibody or fragment or derivative thereof comprises: as a heavy chain variable region, an amino acid sequence having 90% or more homology with a sequence selected from sequences VH11, VH12, VH47, VH61, VH62, VH64, and VH65; and as a light chain variable region, an amino acid sequence having 90% or more homology with a sequence selected from sequences VL15, VL36, VL46, VL47, VL48, and VL50.

In a further aspect, the humanized antibody or fragment or derivative thereof comprises: as a heavy chain variable region, the amino acid sequence of sequence VH65 or an amino acid sequence which differs from sequence VH65 in comprising one or more substitutions selected from the group consisting of a substitution of Ala with Thr at position 28 (Kabat numbering: H28), a substitution of Asn with Ser at position 30 (Kabat numbering: H30), a substitution of Val with Gly at position 49 (Kabat numbering: H49), a substitution of Ala with Asp at position 64 (Kabat numbering: H61), and a substitution of Gln with Lys at position 78 (Kabat numbering: H75); and as a light chain variable region, the amino acid sequence of sequence VL47 or an amino acid sequence which differs from sequence VL47 in comprising one or more substitutions selected from the group consisting of a substitution of Asp with Glu at position 17 (Kabat numbering: L17), a substitution of Ser with Asn at position 28 (Kabat numbering: L27A), a substitution of Gln with Leu at position 42 (Kabat numbering: L37), a substitution of Gln with Arg at position 50 (Kabat numbering: L45), and a substitution of Arg with Leu at position 51 (Kabat numbering: L46).

In a further aspect, the humanized antibody or fragment or derivative thereof comprises any of the following sequence combinations: (a) sequence VH11 as a heavy chain variable region and sequence VL15 as a light chain variable region; (b) sequence VH11 as a heavy chain variable region and sequence VL36 as a light chain variable region; (c) sequence VH11 as a heavy chain variable region and sequence VL46 as a light chain variable region; (d) sequence VH11 as a heavy chain variable region and sequence VL47 as a light chain variable region; (e) sequence VH11 as a heavy chain variable region and sequence VL48 as a light chain variable region; (f) sequence VH11 as a heavy chain variable region and sequence VL50 as a light chain variable region; (g) sequence VH12 as a heavy chain variable region and sequence VL48 as a light chain variable region; (h) sequence VH47 as a heavy chain variable region and sequence VL48 as a light chain variable region; (i) sequence VH61 as a heavy chain variable region and sequence VL48 as a light chain variable region; (j) sequence VH62 as a heavy chain variable region and sequence VL48 as a light chain variable region; (k) sequence VH64 as a heavy chain variable region and sequence VL47 as a light chain variable region; (l) sequence VH64 as a heavy chain variable region and sequence VL48, and (m) sequence VH65 as a heavy chain variable region and sequence VL47.

In an additional aspect, the invention provides an agent for treating or preventing dementia, comprising the humanized antibody or fragment or derivative thereof as described herein.

In a further aspect, the invention provides methods and agents for treating or preventing dementia or a tauopathy, including Alzheimer's disease, corticobasal degeneration, progressive supranuclear palsy, Pick's disease, argyrophilic grain dementia (argyrophilic grain disease), multiple system tauopathy with presenile dementia (MSTD), frontotemporal dementia and parkinsonism linked to chromosome 17 (FTDP-17), dementia with neurofibrillary tangles, diffuse neurofibrillary tangle with calcification (DNTC), white matter tauopathy with globular glial inclusions (WMT-GGI) or frontotemporal lobar degeneration with tau pathology (FTLD-tau).

In an additional aspect, the invention provides pharmaceutical compositions comprising the humanized antibody or fragment or derivative thereof as described herein and a pharmaceutically acceptable carrier.

In a further aspect, the invention provides anti-pSer413 tau antibodies comprising: a) a heavy variable domain comprising a vhCDR1 comprising SEQ ID NO:86, a vhCDR2 comprising SEQ ID NO:115 and a vhCDR3 comprising SEQ ID NO:88; and b) a light variable domain comprising a set of vlCDRs selected from the group consisting of: i) a vlCDR1 comprising SEQ ID NO:102, a vlCDR2 comprising SEQ ID NO:82 and a vlCDR3 comprising SEQ ID NO:83; ii) a vlCDR1 comprising SEQ ID NO:91, a vlCDR2 comprising SEQ ID NO82: and a vlCDR3 comprising SEQ ID NO:83; iii) a vlCDR1 comprising SEQ ID NO:92, a vlCDR2 comprising SEQ ID NO:82 and a vlCDR3 comprising SEQ ID NO:83; iv) a vlCDR1 comprising SEQ ID NO:93, a vlCDR2 comprising SEQ ID NO82: and a vlCDR3 comprising SEQ ID NO:83; v) a vlCDR1 comprising SEQ ID NO:94, a vlCDR2 comprising SEQ ID NO:82 and a vlCDR3 comprising SEQ ID NO:83; vi) a vlCDR1 comprising SEQ ID NO:95, a vlCDR2 comprising SEQ ID NO:82 and a vlCDR3 comprising SEQ ID NO:83; vii) a vlCDR1 comprising SEQ ID NO:96, a vlCDR2 comprising SEQ ID NO:82 and a vlCDR3 comprising SEQ ID NO:83; viii) a vlCDR1 comprising SEQ ID NO:97, a vlCDR2 comprising SEQ ID NO:82 and a vlCDR3 comprising SEQ ID NO:83; ix) a vlCDR1 comprising SEQ ID NO:98, a vlCDR2 comprising SEQ ID NO:82 and a vlCDR3 comprising SEQ ID NO:83; x) a vlCDR1 comprising SEQ ID NO:99, a vlCDR2 comprising SEQ ID NO:82 and a vlCDR3 comprising SEQ ID NO:83; xi) a vlCDR1 comprising SEQ ID NO:100, a vlCDR2 comprising SEQ ID NO:82 and a vlCDR3 comprising SEQ ID NO:83; and xii) a vlCDR1 comprising SEQ ID NO:101, a vlCDR2 comprising SEQ ID NO:82 and a vlCDR3 comprising SEQ ID NO:83. In some cases, the antibody has a ratio of antibody binding to the phosphorylated peptide of SEQ ID NO:8 to antibody binding to the non-phosphorylated peptide of SEQ ID NO:69 of at least about 40.

In additional aspects, the invention provides anti-pSer413 tau antibodies comprising: a) a heavy variable domain selected from SEQ ID NO:116 and SEQ ID NO:117; and b) a light variable domain selected from SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113 and SEQ ID NO:114. In some cases, the antibody has a ratio of antibody binding to the phosphorylated peptide of SEQ ID NO:8 to antibody binding to the non-phosphorylated peptide of SEQ ID NO:69 of at least about 40.

In an additional aspect, the antibodies of the invention comprises a heavy constant domain selected from SEQ ID NO:135, SEQ ID NO:136, SEQ ID NO:137, SEQ ID NO:138, SEQ ID NO:139, SEQ ID NO:140, SEQ ID NO:141, SEQ ID NO:142 and SEQ ID NO:144.

In a further aspect, the antibodies of the invention comprise a light constant domain selected from SEQ ID NO:79 and SEQ ID NO:80.

In an additional aspect, the antibodies of the invention comprise a variable heavy domain selected from SEQ ID NO:116 and SEQ ID NO:117.

In a further aspect, the antibodies of invention comprise a variable light domain selected from SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113 and SEQ ID NO:114.

In an additional aspect, the antibodies comprise heavy and light chains selected from the pairs LC SEQ ID NO:184 and HC SEQ ID NO:144; LC SEQ ID NO:184 and HC SEQ ID NO:145; LC SEQ ID NO:184 and HC SEQ ID NO:146; LC SEQ ID NO:184 and HC SEQ ID NO:147; LC SEQ ID NO:184 and HC SEQ ID NO:148; LC SEQ ID NO:184 and HC SEQ ID NO:149; LC SEQ ID NO:184 and HC SEQ ID NO:150; LC SEQ ID NO:184 and HC SEQ ID NO:151; LC SEQ ID NO:184 and HC SEQ ID NO:152; LC SEQ ID NO:184 and HC SEQ ID NO:153; LC SEQ ID NO:184 and HC SEQ ID NO:154; LC SEQ ID NO:184 and HC SEQ ID NO:155; LC SEQ ID NO:184 and HC SEQ ID NO:156; LC SEQ ID NO:184 and HC SEQ ID NO:157; LC SEQ ID NO:184 and HC SEQ ID NO:158; LC SEQ ID NO:184 and HC SEQ ID NO:159; LC SEQ ID NO:184 and HC SEQ ID NO:160; LC SEQ ID NO:184 and HC SEQ ID NO:161; LC SEQ ID NO:185 and HC SEQ ID NO:144; LC SEQ ID NO:185 and HC SEQ ID NO:145; LC SEQ ID NO:185 and HC SEQ ID NO:146; LC SEQ ID NO:185 and HC SEQ ID NO:147; LC SEQ ID NO:185 and HC SEQ ID NO:148; LC SEQ ID NO:185 and HC SEQ ID NO:149; LC SEQ ID NO:185 and HC SEQ ID NO:150; LC SEQ ID NO:185 and HC SEQ ID NO:151; LC SEQ ID NO:185 and HC SEQ ID NO:152; LC SEQ ID NO:185 and HC SEQ ID NO:153; LC SEQ ID NO:185 and HC SEQ ID NO:154; LC SEQ ID NO:185 and HC SEQ ID NO:155; LC SEQ ID NO:185 and HC SEQ ID NO:156; LC SEQ ID NO:185 and HC SEQ ID NO:157; LC SEQ ID NO:185 and HC SEQ ID NO:158; LC SEQ ID NO:185 and HC SEQ ID NO:159; LC SEQ ID NO:185 and HC SEQ ID NO:160 and LC SEQ ID NO:185 and HC SEQ ID NO:161.

In a further aspect, the antibody of the invention has a light chain comprising or consisting of SEQ ID NO:184 and a heavy chain comprising or consisting of SEQ ID NO:144.

In an additional aspect, the antibody of the invention has a light chain comprising or consisting of SEQ ID NO:184 and a heavy chain comprising or consisting of SEQ ID NO:152.

In a further aspect, the invention provides nucleic acid compositions comprising: a) a first nucleic acid encoding a light chain selected from SEQ ID NO:162, SEQ ID NO:163, SEQ ID NO:164, SEQ ID NO:165, SEQ ID NO:166, SEQ ID NO:167, SEQ ID NO:168, SEQ ID NO:169, SEQ ID NO:170, SEQ ID NO:171, SEQ ID NO:172, SEQ ID NO:173, SEQ ID NO:174, SEQ ID NO:175, SEQ ID NO:176, SEQ ID NO:177, SEQ ID NO:178, SEQ ID NO:179, SEQ ID NO:180, SEQ ID NO:181, SEQ ID NO:182, SEQ ID NO:183, SEQ ID NO:184 and SEQ ID NO:185; and b) a second nucleic acid encoding a heavy chain selected from SEQ ID NO:144; SEQ ID NO:145; SEQ ID NO:146; SEQ ID NO:147; SEQ ID NO:148; SEQ ID NO:149; SEQ ID NO:150; SEQ ID NO:151; SEQ ID NO:152; SEQ ID NO:153; SEQ ID NO:154; SEQ ID NO:155; SEQ ID NO:156; SEQ ID NO:157; SEQ ID NO:158; SEQ ID NO:159; SEQ ID NO:160 and SEQ ID NO:161.

In an additional aspect, the invention provides expression vector compositions comprising a first and a second nucleic acid, wherein the first nucleic acid is contained in a first expression vector and the second nucleic acid is contained in a second expression vector.

In a further aspect, the invention provides an expression vector composition wherein the first nucleic acid and the second nucleic acid is contained in a single expression vector.

In an additional aspect, the invention provides host cells comprising the expression vector composition, and methods of making an anti-pSer413 tau antibody comprising culturing the host cell under conditions wherein said antibody is expressed and recovering said antibody.

In a further aspect, the invention provides methods of treating a tauopathy in a subject comprising administering the antibodies of the invention.

VI. BRIEF DESCRIPTION OF THE DRAWINGS

The invention may be best understood from the following detailed description when read in conjunction with the accompanying drawings. Included in the drawings are the following figures:

FIG. 1A and FIG. 1B collectively show an alignment of various human isoforms of Tau protein, prepared using ClustalW.

FIG. 2A shows an alignment of light chain variable region sequences, highlighting CDR-L1, CDR-L2, and CDR-L3 sequences, according to the Kabat numbering system, of several anti-pS413-Tau binding proteins, in accordance with some embodiments of the disclosure.

FIG. 2B shows an alignment of heavy chain variable region sequences, highlighting CDR-H1, CDR-H2, and CDR-H3 sequences, according to the Kabat numbering system, of several anti-pS413-Tau binding proteins, in accordance with some embodiments of the disclosure.

Figure 5A:
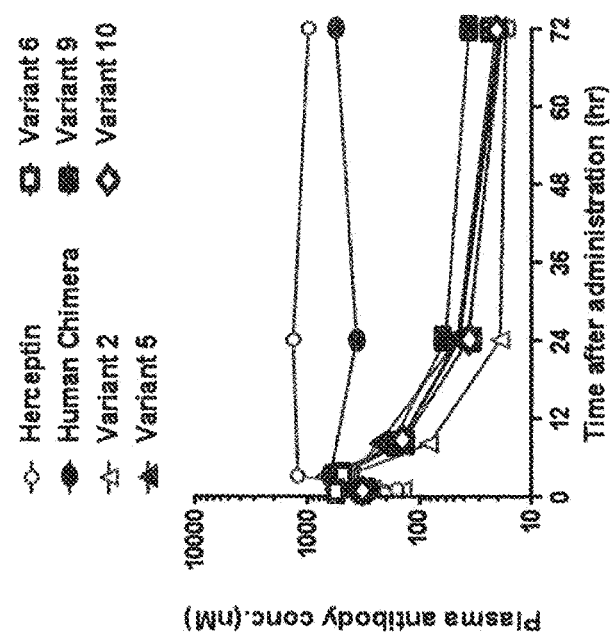
Figure 5B:
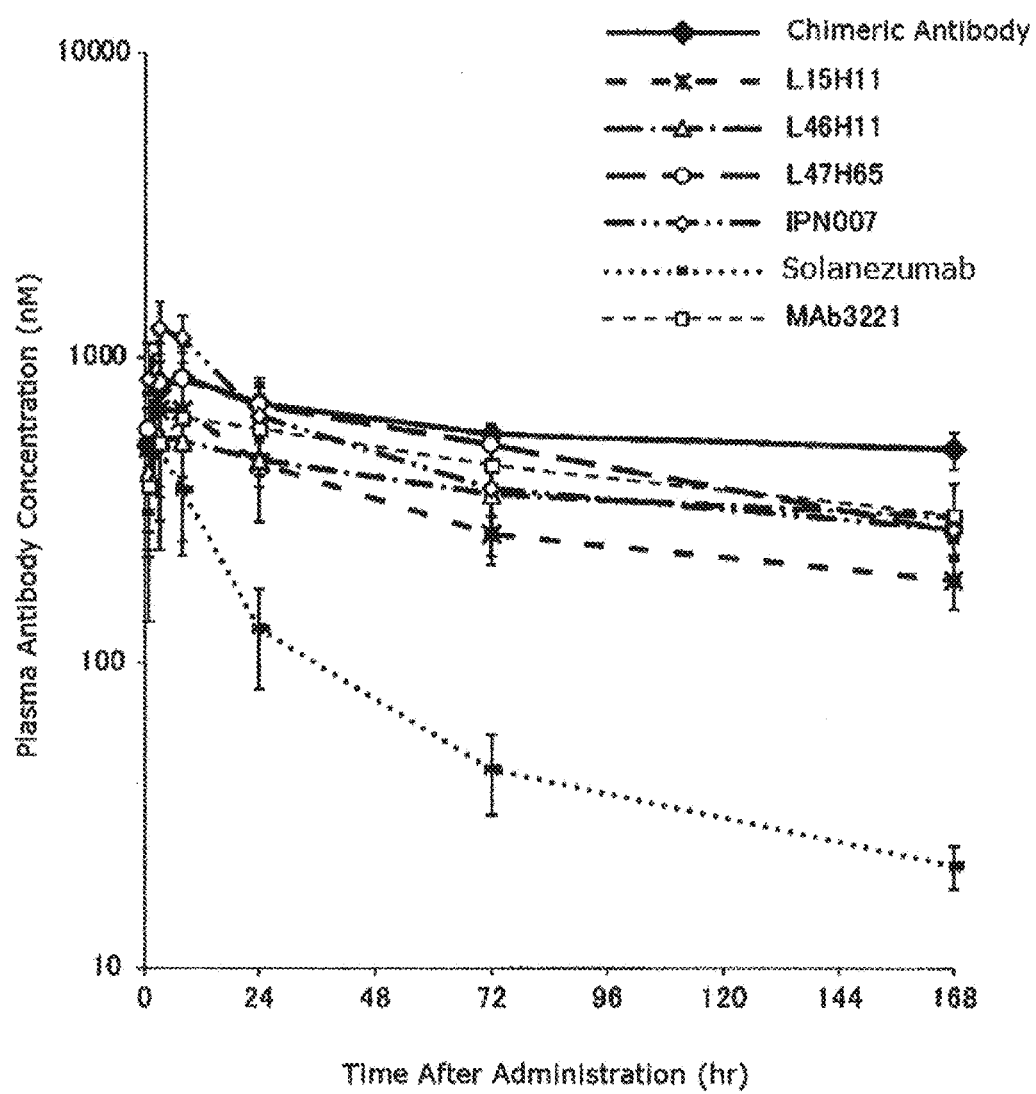

FIG. 5A and FIG. 5B show pharmacokinetics of humanized antibody variants in mouse plasma over time. FIG. 5A demonstrates that five initial humanized antibody variants 2, 5, 6, 9, and 10 exhibited rapid elimination from the mouse plasma. FIG. 5B demonstrates that three later developed humanized antibody variants L15H11, L46H11, and L47H65 exhibited pharmacokinetics profiles comparable to the chimeric antibody.

Figure 6A:
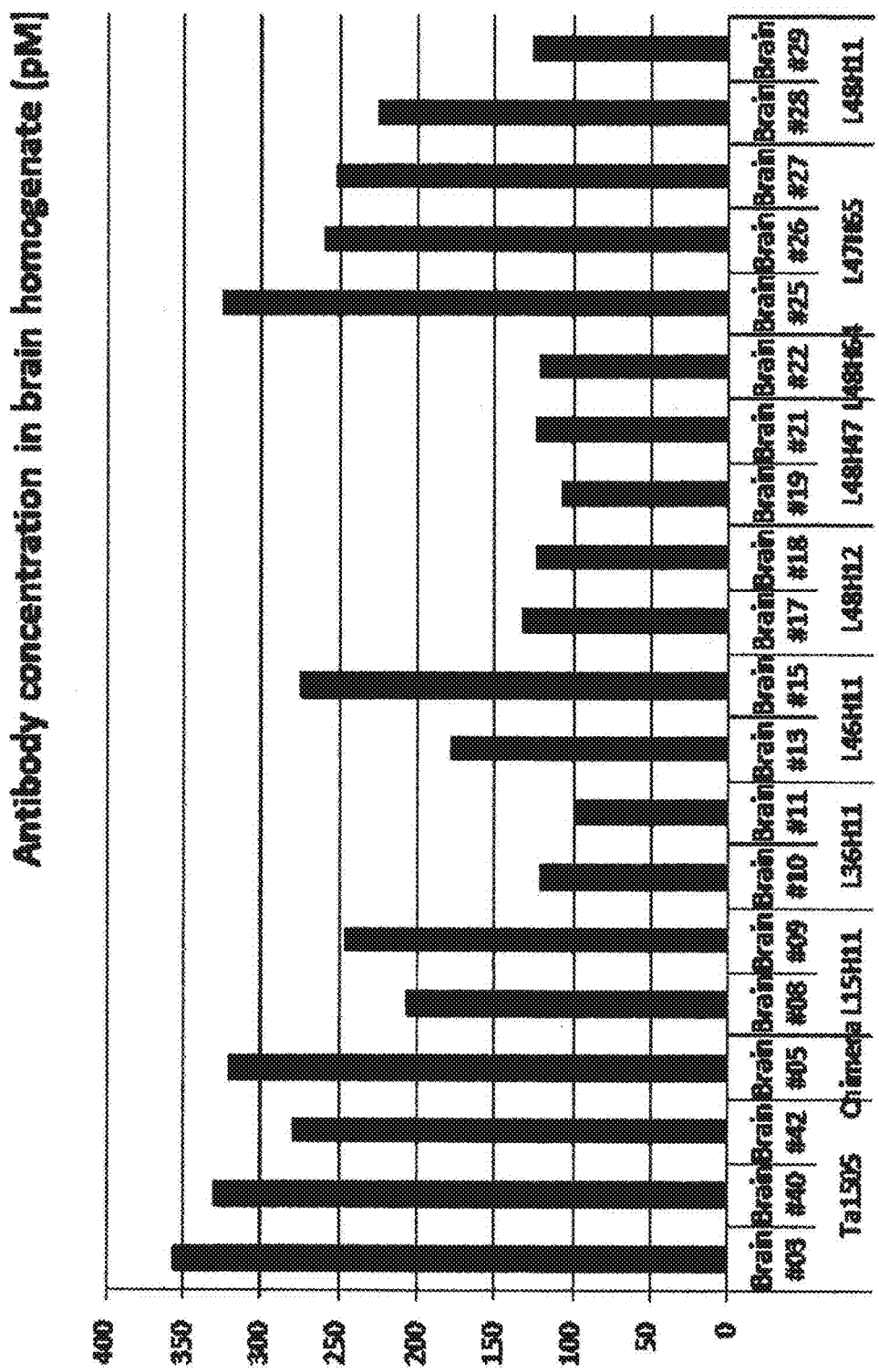
Figure 6B:
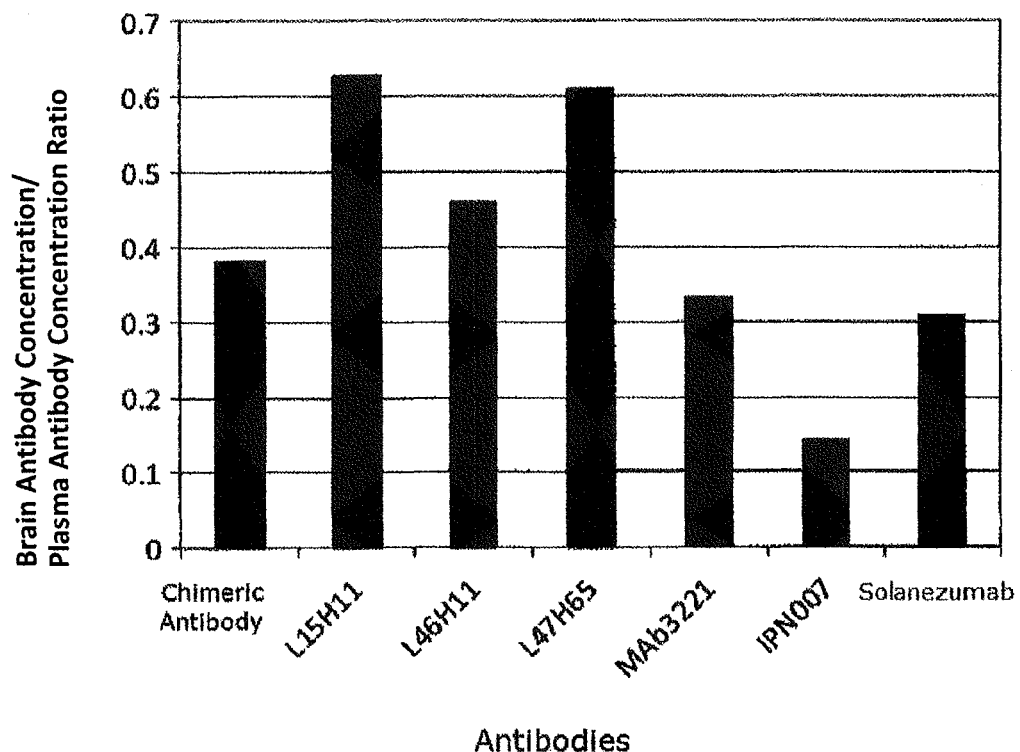

FIG. 6A and FIG. 6B show different humanized antibody variants have different intracerebral migration. FIG. 6A shows concentration of various humanized antibodies in brain homogenate. FIG. 6B shows the ratio of the level of representative humanized antibodies in the brain to the level of the corresponding antibodies in the plasma.

Figure 7A:
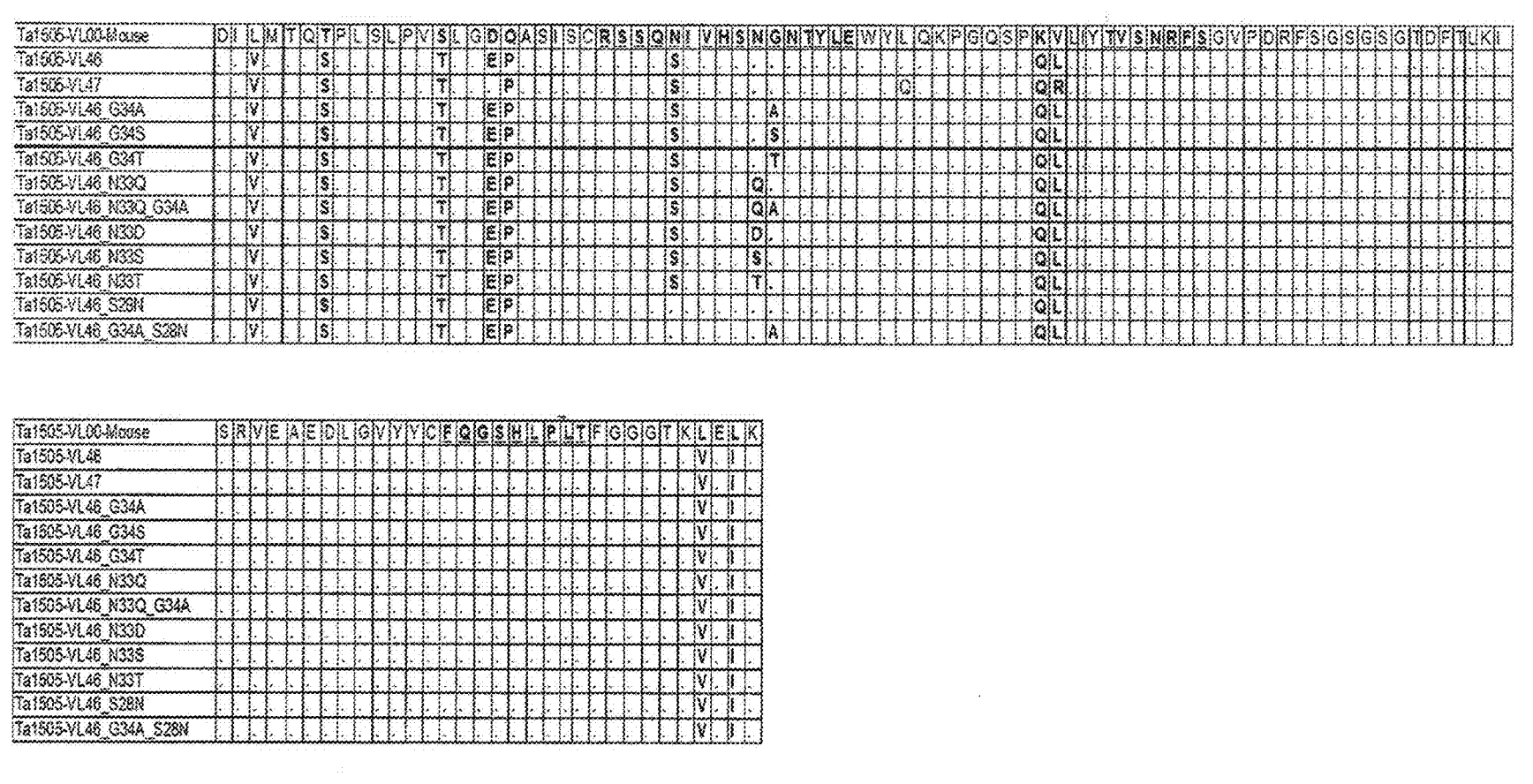
Figure 7B:
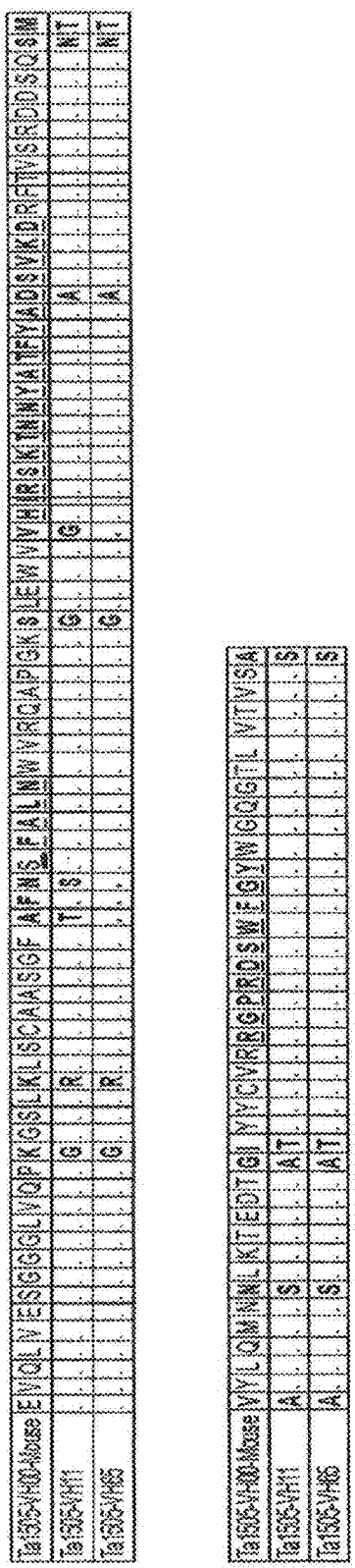

FIG. 7A and FIG. 7B show alignment of amino acid sequences of the light chain variable region (FIG. 7A) and the heavy chain variable region (FIG. 7B) of representative humanized antibody variants with the parent mouse antibody.

FIG. 8A-FIG. 8D demonstrate that the parent mouse antibody (FIGS. 8A and 8B) and the chimeric antibody (FIGS. 8C and 8D) bind to a phosphorylated peptide (FIGS. 8A and 8C) but not to the non-phosphorylated counterpart (FIGS. 8B and 8D).

Figure 9A:
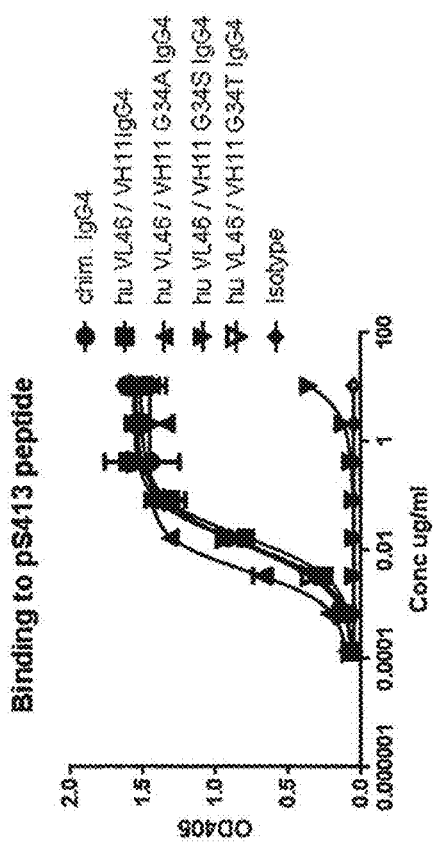
Figure 9B:
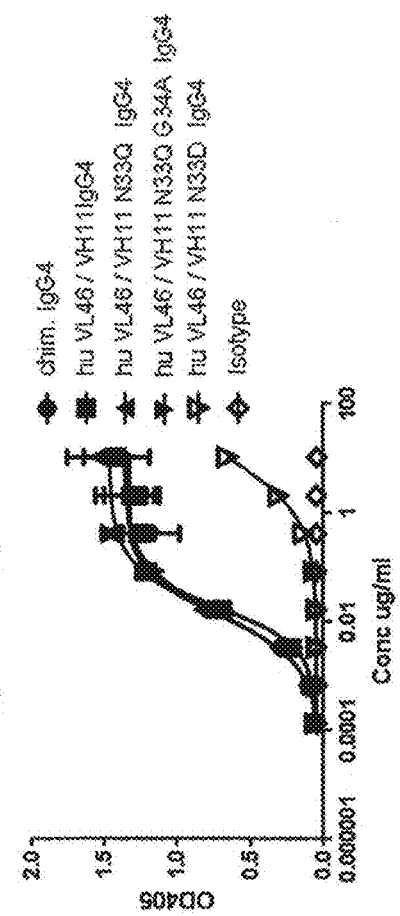
Figure 9C:
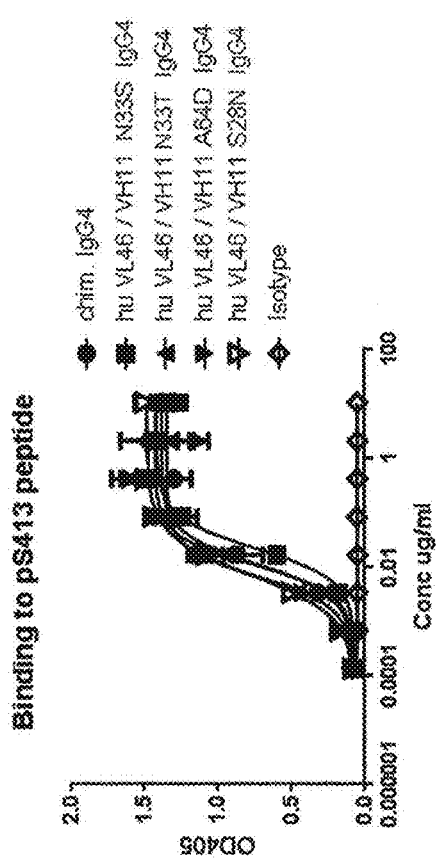

FIG. 9A-FIG. 9C show the binding of representative humanized antibody variants to pS413 peptide.

FIG. 10A-FIG. 10E show comparable binding characteristics of the parent mouse antibody (FIG. 10A), the chimeric antibody (FIG. 10B), and selected humanized antibody variants (FIG. 10C-10E) to the S413-phosphorylated Tau protein in brain homogenates from Alzheimer's disease patients.

FIG. 11A-FIG. 11E show the variable heavy and variable light regions of some of the anti-pSer413 tau protein humanized antibodies of the invention.

FIG. 12A-FIG. 12C show a number of different human IgG constant domains that find use in combinations of the variable heavy and variable light chains of anti-pSer413 tau antibodies. "Human_IgG1_" is the constant domain (CH1-hinge-CH2-CH3) of human wild type IgG1. "Human_IgG1_L234A_L235A" is the constant domain (CH1-hinge-CH2-CH3) of human wild type IgG1 with two amino acid substitutions, L234A and L235A (sometimes referred to as "LALA" mutations) that reduce/ablate effector function. "Human_IgG1_L234A_L235A_D265S" is the constant domain (CH1-hinge-CH2-CH3) of human wild type IgG_1 with three amino acid substitutions, L234A, L235A and D265S that reduce/ablate effector function. "Human_IgG1_YTE_" or "Human IgG1_YTE (M252Y_S254T_T256E)" is the constant domain (CH1-hinge-CH2-CH3) of human wild type IgG1 with three amino acid substitutions, M252Y, S254T, T256E that increase half life of the antibody in serum. "Human_IgG1_N297A_" is the constant domain (CH1-hinge-CH2-CH3) of human wild type IgG1 with the amino acid substitution N297A, which eliminates a glycosylation site and reduces/ablates effector function. "Human_IgG1_N297Q_" is the constant domain (CH1-hinge-CH2-CH3) of human wild type IgG1 with the amino acid substitution N297Q, which eliminates a glycosylation site and reduces/ablates effector function. "_Human_IgG2" is the constant domain (CH1-hinge-CH2-CH3) of human wild type IgG2. "_Human_IgG4" is the constant domain (CH1-hinge-CH2-CH3) of human wild type IgG4. "Human_IgG4_S228P_" is the constant domain (CH1-hinge-CH2-CH3) of human wild type IgG4 with an amino acid substitution S228P to prevent arm switching FIG. 13A-FIG. 13E show full length heavy chains for the H11 and H65 variable regions in conjunction with the backbones of FIG. 12A-FIG. 12C. A "slash" ("/") indicates the junction of the variable and constant domains, and the CDRs are underlined.

FIG. 14A-FIG. 14D show the full length light chains for 12 different variable light domains with either the human kappa or lambda light constant domains. A "slash" ("/") indicates the junction of the variable and constant domains, and the CDRs are underlined.

FIG. 15 depicts a matrix of possible combinations of heavy and light chains of the invention. An "A" in the box indicates that the heavy constant domain "Human_IgG1_" is used. A "B" in the box indicates that the heavy constant domain "Human_IgG1_L234A_L235A" is used. A "C" in the box indicates that the heavy constant domain "Human_IgG1_ _L234A_L235A_D265S" is used. A "D" in the box means that the heavy constant domain "Human_IgG1_YTE_" is used. An "E" in the box means that the heavy constant domain "Human_IgG1_N297A_" is used. An "F" in the box means that the heavy constant domain "Human_IgG1_N297Q_" is used. A "G" in the box means that the heavy constant domain "_Human_IgG2" is used. An "H" in the box means that the heavy constant domain "_Human_IgG4" is used. An "I" in the box means that the heavy constant domain "Human_IgG4_S228P_" is used. A "J" in the box means that a human IgG1 constant domain with from 1, 2, 3, 4, 5, 6, 7, 8, 9 or 10 amino acid substitutions is used.

VII. DETAILED DESCRIPTION

A. Overview

The present disclosure provides antibodies that include an antigen binding portion that specifically binds to Tau protein that is phosphorylated at serine residue 413 (pSer413-Tau). Also provided are nucleic acids encoding the proteins, and cells that include such nucleic acids. In some embodiments, the methods and compositions provided are used in the treatment of tauopathies (e.g., Alzheimer's disease).

The MAPT gene encoding tau has been identified as consisting of 13 exons disposed on the genome, which can be expressed as multiple different protein isoforms via alternative splicing (see Arai, supra). The tau protein comprises an N-terminal acidic domain containing 0-2 repetitive sequences (N) of 29 amino acids depending on alternative splicing of exon 2 and exon 3 (N0-N2), an intermediate domain rich in proline, and a C-terminal microtubule-binding domain (encoded by exons 9 to 12) containing 3 (3R) or 4 (4R) repetitive sequences (R) that contribute to microtubule binding (Burns, supra and Arai, supra). Therefore, human tau has six representative isoforms: 3R0N (352 amino acids), 3R1N (381 amino acids), 3R2N (410 amino acids), 4R0N (383 amino acids), 4R1N (412 amino acids), and 4R2N (441 amino acids), depending on the number of 29 amino acid repetitive sequences (N) and microtubule-binding repetitive sequences (R) that it contains. Of these isoforms, only 3R0N is present in the embryonic brain, whereas all six isoforms are present in the adult human brain, with 4R being most abundant (Burns, supra). The difference between the 3R and 4R isoforms results from whether exon 10 is removed via alternative splicing (3R) or present (4R). In order to unambiguously identify the position of an amino acid residue in any of these tau isoforms, the amino acid numbers (1 to 441) of the longest isoform, i.e., 4R2N (defined in SEQ ID NO:1), are used as a reference. For example, "Ser413" refers to the serine residue at the 413th amino acid position in 4R2N (defined in SEQ ID NO:1), which corresponds to the serine at the 384th in 4R1N (defined in SEQ ID NO:2), the 355th in 4R0N (defined in SEQ ID NO:3), the 382nd in 3R2N (defined in SEQ ID NO:4), the 353rd in 3R1N (defined in SEQ ID NO:5), and the 324th in 3R0N (defined in SEQ ID NO:6).

Tau has a phosphorylated amino acid residue at the position corresponding to the serine residue at position 413 (Ser413, when phosphorylated it is referred to herein as "pSer413") of the amino acid sequence defined in SEQ ID NO:1 (and thus the tau protein phosphorylated at Ser413 is "pSer413 tau" or "pSer413-tau") which is a site specifically phosphorylated in AD. As previously shown in WO 2013/180238, administration of antibodies that participate in specific antigen-antibody reactions with PSer413-tau to transgenic mice which develop cognitive function impairment while maturing, resulted in restoration of cognitive functions to almost the same level as that of the control group. Interestingly, administration of similar concentration of a monoclonal antibody against a tau protein having a phosphorylated amino acid residue at the position corresponding to Ser396 of the amino acid sequence defined in SEQ ID NO:1, which has a stronger affinity to an equivalent antigen than the above antibody, did not result in sufficient improvement in cognitive functions. Since there was no specific information about a region including the amino acid residue at the position corresponding to Ser413 of the amino acid sequence defined in SEQ ID NO:1 in relation to the structure and functions of tau, it was a totally unexpected result that the antibody that binds with this region had such a strong effect of improving cognitive function.

Accordingly, the present invention is directed to humanized and optimized anti-pSer413 tau antibodies useful as a therapeutic or prophylactic agent for treating cognitive disorders such as tauopathy in a human subject.

The humanized anti-phosphorylated tau antibody according to the present invention exhibits high binding affinity to phosphorylated tau while having significantly reduced antigenicity to the human body, and can effectively be used as a therapeutic or prophylactic agent for cognitive disorders such as tauopathy in a human subject. Additionally, amino acid modifications within the CDRs as compared to the murine CDRs reduce deamidation leading to increased stability; see Examples 8, 9 and 10.

B. Definitions

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

By "ablation" herein is meant a decrease or removal of activity. Thus for example, "ablating FcγR binding" means the Fc region amino acid variant has less than 50% starting binding as compared to an Fc region not containing the specific variant, with less than 70-80-90-95-98% loss of activity being preferred, and in general, with the activity being below the level of detectable binding in a Biacore assay.

By "ADCC" or "antibody dependent cell-mediated cytotoxicity" as used herein is meant the cell-mediated reaction wherein nonspecific cytotoxic cells that express FcγRs recognize bound antibody on a target cell and subsequently cause lysis of the target cell. ADCC is correlated with binding to FcγRIIIa; increased binding to FcγRIIIa leads to an increase in ADCC activity. As is discussed herein, many embodiments of the invention ablate ADCC activity entirely.

By "ADCP" or antibody dependent cell-mediated phagocytosis as used herein is meant the cell-mediated reaction wherein nonspecific cytotoxic cells that express FcγRs recognize bound antibody on a target cell and subsequently cause phagocytosis of the target cell.

By "antigen binding domain" or "ABD" herein is meant a set of six Complementary Determining Regions (CDRs) that, when present as part of a polypeptide sequence, specifically binds a target antigen as discussed herein. Thus, an "antigen binding domain" binds a target antigen as outlined herein. As is known in the art, these CDRs are generally present as a first set of variable heavy CDRs (vhCDRs or $V_H$CDRs or CDR-HC) and a second set of variable light CDRs (vlCDRs or $V_L$CDRs or CDR-LC), each comprising three CDRs: vhCDR1, vhCDR2, vhCDR3 for the heavy chain and vlCDR1, vlCDR2 and vlCDR3 for the light chain. The CDRs are present in the variable heavy and variable light domains, respectively, and together form an Fv region. Thus, in some cases, the six CDRs of the antigen binding domain are contributed by a variable heavy and variable light chain. In a "Fab" format, the set of 6 CDRs are contributed by two different polypeptide sequences, the variable heavy domain (vh or $V_H$; containing the vhCDR1, vhCDR2 and vhCDR3) and the variable light domain (vl or $V_L$; containing the vlCDR1, vlCDR2 and vlCDR3), with the C-terminus of the vh domain being attached to the N-terminus of the CH1 domain of the heavy chain and the C-terminus of the vl domain being attached to the N-terminus of the constant light domain (and thus forming the light chain). In a scFv format, the vh and vl domains are covalently attached, generally through the use of a linker as outlined herein, into a single polypeptide sequence, which can be either (starting from the N-terminus) vh-linker-vl or vl-linker-vh, with the former being generally preferred (including optional domain linkers on each side, depending on the format used. As is understood in the art, the CDRs are separated by framework regions in each of the variable heavy and variable light domains: for the light variable domain, these are FR1-vlCDR1-FR2-vlCDR2-FR3-vlCDR3-FR4, and for the heavy variable domain, these are FR1-vhCDR1-FR2-vhCDR2-FR3-vhCDR3-FR4, with the framework regions showing high identity to human germline sequences. Antigen binding domains of the invention include, Fab, Fv and scFv.

By "modification" herein is meant an amino acid substitution, insertion, and/or deletion in a polypeptide sequence or an alteration to a moiety chemically linked to a protein. For example, a modification may be an altered carbohydrate or PEG structure attached to a protein. By "amino acid modification" herein is meant an amino acid substitution, insertion, and/or deletion in a polypeptide sequence. For clarity, unless otherwise noted, the amino acid modification is always to an amino acid coded for by DNA, e.g. the 20 amino acids that have codons in DNA and RNA.

By "amino acid substitution" or "substitution" herein is meant the replacement of an amino acid at a particular position in a parent polypeptide sequence with a different amino acid. In particular, in some embodiments, the substitution is to an amino acid that is not naturally occurring at the particular position, either not naturally occurring within the organism or in any organism. For example, the substitution M252Y refers to a variant polypeptide, in this case an Fc variant, in which the methionine at position 252 is replaced with tyrosine. For clarity, a protein which has been engineered to change the nucleic acid coding sequence but not change the starting amino acid (for example exchanging CGG (encoding arginine) to CGA (still encoding arginine) to increase host organism expression levels) is not an "amino acid substitution"; that is, despite the creation of a new gene encoding the same protein, if the protein has the same amino acid at the particular position that it started with, it is not an amino acid substitution.

By "variant protein" or "protein variant", or "variant" as used herein is meant a protein that differs from that of a parent protein by virtue of at least one amino acid modification. Protein variant may refer to the protein itself, a composition comprising the protein, or the amino sequence that encodes it. Preferably, the protein variant has at least one amino acid modification compared to the parent protein, e.g., from about one to about seventy amino acid modifications, and preferably from about one to about five amino acid modifications compared to the parent. As described below, in some embodiments the parent polypeptide, for example an Fc parent polypeptide, is a human wild type sequence, such as the Fc region from IgG1, IgG2, IgG3 or IgG4. The protein variant sequence herein will preferably possess at least about 80% identity with a parent protein sequence, and most preferably at least about 90% identity, more preferably at least about 95%-98%-99% identity. Variant protein can refer to the variant protein itself, compositions comprising the protein variant, or the DNA sequence that encodes it.

Accordingly, by "antibody variant" or "variant antibody" as used herein is meant an antibody that differs from a parent antibody by virtue of at least one amino acid modification, "IgG variant" or "variant IgG" as used herein is meant an antibody that differs from a parent IgG (again, in many cases, from a human IgG sequence) by virtue of at least one amino acid modification, and "immunoglobulin variant" or "variant immunoglobulin" as used herein is meant an immunoglobulin sequence that differs from that of a parent immunoglobulin sequence by virtue of at least one amino acid modification. "Fc variant" or "variant Fc" as used herein is meant a protein comprising an amino acid modification in an Fc domain. The Fc variants of the present invention are defined according to the amino acid modifications that compose them. Thus, for example M252Y or 252Y is an Fc variant with the substitution tyrosine at position 252 relative to the parent Fc polypeptide, wherein the numbering is according to the EU index. Likewise, M252Y/S254T/T256E defines an Fc variant with the substitutions M252Y, S254T and T256E relative to the parent Fc polypeptide. The identity of the WT amino acid may be unspecified, in which case the aforementioned variant is referred to as 252Y/254T/256E. It is noted that the order in which substitutions are provided is arbitrary, that is to say that, for example, 252Y/254T/256E is the same Fc variant as 254T/252Y/256E, and so on. For all positions discussed in the present invention that relate to antibodies, unless otherwise noted, amino acid position numbering is according to Kabat for the variable domain numbering and is according to the EU index for the constant domains, including the Fc domain. The EU index or EU index as in Kabat or EU numbering scheme refers to the numbering of the EU antibody (Edelman et al., 1969, Proc Natl Acad Sci USA 63:78-85, hereby entirely incorporated by reference.) The modification can be an addition, deletion, or substitution. Substitutions can include naturally occurring amino acids and, in some cases, synthetic amino acids.

As used herein, "protein" herein is meant at least two covalently attached amino acids, which includes proteins, polypeptides, oligopeptides and peptides. The peptidyl group may comprise naturally occurring amino acids and peptide bonds.

By "Fab" or "Fab region" as used herein is meant the polypeptide that comprises the VH, CH1, VL, and CL immunoglobulin domains. Fab may refer to this region in isolation, or this region in the context of a full length antibody, antibody fragment or Fab fusion protein.

By "Fv" or "Fv fragment" or "Fv region" as used herein is meant a polypeptide that comprises the VL and VH domains of a single antigen binding domain (ABD). As will be appreciated by those in the art, these generally are made up of two chains, or can be combined (generally with a linker as discussed herein) to form a scFv.

By "amino acid" and "amino acid identity" as used herein is meant one of the 20 naturally occurring amino acids that are coded for by DNA and RNA.

By "effector function" as used herein is meant a biochemical event that results from the interaction of an antibody Fc region with an Fc receptor or ligand. Effector functions include but are not limited to ADCC, ADCP, and CDC.

By "Fc gamma receptor", "FcγR" or "FcgammaR" as used herein is meant any member of the family of proteins that bind the IgG antibody Fc region and is encoded by an FcγR gene. In humans this family includes but is not limited to FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIb-NA1 and FcγRIIb-NA2) (Jefferis et al., 2002, Immunol Lett 82:57-65, entirely incorporated by reference), as well as any undiscovered human FcγRs or FcγR isoforms or allotypes. In some cases, as outlined herein, binding to one or more of the FcγR receptors is reduced or ablated. For example, reducing binding to FcγRIIIa reduces ADCC, and in some cases, reducing binding to FcγRIIIa and FcγRIIb is desired.

By "FcRn" or "neonatal Fc Receptor" as used herein is meant a protein that binds the IgG antibody Fc region and is encoded at least in part by an FcRn gene. The FcRn may be from any organism, including but not limited to humans, mice, rats, rabbits, and monkeys. As is known in the art, the functional FcRn protein comprises two polypeptides, often referred to as the heavy chain and light chain. The light chain is beta-2-microglobulin and the heavy chain is encoded by the FcRn gene. Unless otherwise noted herein, FcRn or an FcRn protein refers to the complex of FcRn heavy chain with beta-2-microglobulin.

By "parent polypeptide" as used herein is meant a starting polypeptide that is subsequently modified to generate a variant. The parent polypeptide may be a naturally occurring polypeptide, or a variant or engineered version of a naturally occurring polypeptide. Parent polypeptide may refer to the polypeptide itself, compositions that comprise the parent polypeptide, or the amino acid sequence that encodes it. Accordingly, by "parent immunoglobulin" as used herein is meant an unmodified immunoglobulin polypeptide that is modified to generate a variant, and by "parent antibody" as used herein is meant an unmodified antibody that is modified to generate a variant antibody. It should be noted that "parent antibody" includes known commercial, recombinantly produced antibodies as outlined below.

By "heavy constant region" herein is meant the CH1-hinge-CH2-CH3 portion of an antibody, generally from human IgG1, IgG2 or IgG4.

By "target antigen" as used herein is meant the molecule that is bound specifically by the variable region of a given antibody. In the present case, the target antigen is a tau protein that is phosphorylated at position Ser413 ("pSer413-tau").

By "target cell" as used herein is meant a cell that expresses a target antigen.

By "variable region" as used herein is meant the region of an immunoglobulin that comprises one or more Ig domains substantially encoded by any of the V.kappa., V.lamda., and/or VH genes that make up the kappa, lambda, and heavy chain immunoglobulin genetic loci respectively.

By "wild type or WT" herein is meant an amino acid sequence or a nucleotide sequence that is found in nature, including allelic variations. A WT protein has an amino acid sequence or a nucleotide sequence that has not been intentionally modified.

The term "tau protein" used herein means any one of six isoforms of human tau protein having the amino acid sequences define in SEQ ID NOS:1 to 6, i.e., 4R2N (defined in SEQ ID NO:1), 4R1N (defined in SEQ ID NO:2), 4R0N (defined in SEQ ID NO:3), 3R2N (defined in SEQ ID NO:4), 3R1N (defined in SEQ ID NO:5), and 3R0N (defined in SEQ ID NO:6), as well as gene variants thereof. As explained in the BACKGROUND OF THE INVENTION section above, more than 40 mutations have been implicated with FTDP-17, which is a familial neurodegenerative disease relating to cognitive disorders. However, the sites of mutations in a tau protein should not be limited to those implicated with FTDP-17. The number of amino acid mutations introduced into the amino acid sequences of SEQ ID NOS:1 to 6 should not be limited, but may be 1 to 50, particularly 1 to 30, more particularly 1 to 10. However, the amino acid residue corresponding to the amino acid sequence defined in the serine residue at position 413 of SEQ ID NO:1 (Ser413) should preferably be conserved. The tau protein according to the present invention also encompasses proteins having similarities or identities of 80% or more to the amino acid sequence of human tau protein defined in SEQ ID NO:1 in accordance with the BLAST method (with default conditions of PBLAST provided by NCBI) and their isoforms. Such tau proteins include tau derived from non-human species such as chimpanzees, macaques, horses, pigs, dogs, mice, rabbits, and rats. It is possible to produce a therapeutic or prophylactic agent targeted to tau derived from such a non-human animal for the purpose of improving the cognitive function of the target animal.

The term "tau peptide" used herein means a peptide including a part of the amino acid sequence of a tau protein. The position and length of the tau peptide's amino acid sequence derived from a tau protein should not be limited, but should preferably contain, e.g., a series of at least three consecutive amino acids, particularly at least five consecutive amino acids, more particularly at least eight consecutive amino acids, derived from the amino acid residues corresponding to amino acid numbers 410 to 421 of SEQ ID NO:1, at least including the amino acid corresponding to Ser413. The length of the tau peptide should also not be limited, but should preferably have an amino acid length of four or more, particularly six or more, more particularly eight or more.

The term "tau" used herein means a tau protein or a tau peptide collectively.

The term "anti-pSer413 tau protein" means an antibody as described herein that preferentially binds to a tau protein that is phosphorylated at the serine at position 413 as compared to the binding of a tau protein is not phosphorylated at the serine at position 413. The tau protein phosphorylated at Ser413 can be human and/or murine.

By "position" as used herein is meant a location in the sequence of a protein. Positions may be numbered sequentially, or according to an established format, for example the EU index for antibody numbering.

By "residue" as used herein is meant a position in a protein and its associated amino acid identity. For example, Asparagine 297 (also referred to as Asn297 or N297) is a residue at position 297 in the human antibody IgG1.

In the context of the present invention, the position of an amino acid residue in a tau protein or a tau peptide is indicated by an amino acid number, which is identified based on the amino acid sequence defined in SEQ ID NO:1 for clarification. For example, the amino acid residue corresponding to Ser413 of SEQ ID NO:1 means the serine residue at position 413 of SEQ ID NO:1 (4R2N), position 384 of SEQ ID NO:2 (4R1N), position 355 of SEQ ID NO:3 (4R0N), position 382 of SEQ ID NO:4 (3R2N), position 353 of SEQ ID NO:5 (3R1N), or position 324 of SEQ ID NO:6 (3R0N). Correspondence of the positions of amino acid residues between tau isoforms is shown in Table 1 below.

TABLE 1

Isoforms of human tau protein

| Amino acid residue | Isoform | | | | | |
| | 4R2N | 4R1N | 4R0N | 3R2N | 3R1N | 3R0N |
| | Sequence | | | | | |
| | SEQ ID NO: 1 | SEQ ID NO: 2 | SEQ ID NO: 3 | SEQ ID NO: 4 | SEQ ID NO: 5 | SEQ ID NO: 6 |
| | Amino acid number | | | | | |
| Asn | 410 | 381 | 352 | 379 | 350 | 321 |
| Val | 411 | 382 | 353 | 380 | 351 | 322 |
| Ser | 412 | 383 | 354 | 381 | 352 | 323 |
| Ser | 413 | 384 | 355 | 382 | 353 | 324 |
| Thr | 414 | 385 | 356 | 383 | 354 | 325 |
| Gly | 415 | 386 | 357 | 384 | 355 | 326 |
| Ser | 416 | 387 | 358 | 385 | 356 | 327 |
| Ile | 417 | 388 | 359 | 386 | 357 | 328 |
| Asp | 418 | 389 | 360 | 387 | 358 | 329 |
| Met | 419 | 390 | 361 | 388 | 359 | 330 |
| Val | 420 | 391 | 362 | 389 | 360 | 331 |
| Asp | 421 | 392 | 363 | 390 | 361 | 332 |

While Table 1 shows the positions of amino acid residues of these isoforms corresponding to positions 410 to 421 of the amino acid sequence defined in SEQ ID NO:1, correspondence of the positions of amino acid residues in other regions can easily be recognized based on, e.g., FIGS. 1A and 1B. A person skilled in the art would be able to determine corresponding positions of amino acids in isoforms or homologues using pairwise sequence alignment such as Needleman-Wunsch method or Smith-Waterman method, or multiple sequence alignment such as ClustalW method or PRRP method. As an example of analysis of corresponding positions, FIGS. 1A and 1B show an alignment of the amino acid sequences of the six human isoforms (indicated with one letter code) based on ClustalW. These figures indicate that the structure surrounding the amino acid residue corresponding to Ser413 of the amino acid sequence defined in SEQ ID NO:1 is conserved among the six isoforms.

The antibodies of the present invention are generally isolated or recombinant. "Isolated," when used to describe the various polypeptides disclosed herein, means a polypeptide that has been identified and separated and/or recovered from a cell or cell culture from which it was expressed. Ordinarily, an isolated polypeptide will be prepared by at least one purification step. An "isolated antibody," refers to an antibody which is substantially free of other antibodies having different antigenic specificities. "Recombinant" means the antibodies are generated using recombinant nucleic acid techniques in exogeneous host cells.

"Percent (%) amino acid sequence identity" with respect to a protein sequence is defined as the percentage of amino acid residues in a candidate sequence that are identical with the amino acid residues in the specific (parental) sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. One particular program is the ALIGN-2 program outlined at paragraphs [0279]to [0280] of US Pub. No. 20160244525, hereby incorporated by reference. Another approximate alignment for nucleic acid sequences is provided by the local homology algorithm of Smith and Waterman, *Advances in Applied Mathematics*, 2:482-489 (1981). This algorithm can be applied to amino acid sequences by using the scoring matrix developed by Dayhoff, *Atlas of Protein Sequences and Structure*, M. O. Dayhoff ed., 5 suppl. 3:353-358, National Biomedical Research Foundation, Washington, D.C., USA, and normalized by Gribskov, *Nucl. Acids Res.* 14(6):6745-6763 (1986).

An example of an implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). Another method of establishing percent identity in the context of the present invention is to use the MPSRCH package of programs copyrighted by the University of Edinburgh, developed by John F. Collins and Shane S. Sturrok, and distributed by Intelli- Genetics, Inc. (Mountain View, Calif.). From this suite of packages, the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the internet address located by placing http:// in front of blast.ncbi.nlm.nih.gov/Blast.cgi.

The degree of identity between an amino acid sequence of the present invention ("invention sequence") and the parental amino acid sequence is calculated as the number of exact matches in an alignment of the two sequences, divided by the length of the "invention sequence," or the length of the parental sequence, whichever is the shortest. The result is expressed in percent identity.

In some embodiments, two or more amino acid sequences are at least 50%, 60%, 70%, 80%, or 90% identical. In some embodiments, two or more amino acid sequences are at least 95%, 97%, 98%, 99%, or even 100% identical.

"Specific binding" or "specifically binds to" or is "specific for" a particular antigen or an epitope means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target.

The term "$K_{assoc}$" or "$K_a$", as used herein, is intended to refer to the association rate of a particular antibody-antigen interaction, whereas the term "$K_{dis}$" or "$K_a$," as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. In some embodiments, the method for determining the $K_D$ of an antibody is by using surface plasmon resonance, for example, by using a biosensor system such as a BIACORE® system. In certain embodiments, the $K_D$ value is measured with a phosphorylated Tau protein. In some embodiments, the $K_D$ value is measured with a phosphorylated peptide. In some embodiments, the $K_D$ value is measured with the antigen (e.g., the phosphorylated Tau protein or the phosphorylated peptide) immobilized. In other embodiments, the $K_D$ value is measured with the antibody (e.g., parent mouse antibody, chimeric antibody, or humanized antibody variants) immobilized. In yet other embodiments, the $K_D$ value is measured with a phosphorylated Tau protein as the analyte. In still other embodiments, the KD value is measured with a phosphorylated peptide as the analyte. In certain embodiments, the KD value is measured in a bivalent binding mode. In other embodiments, the KD value is measured in a monovalent binding mode.

A "disease" includes a state of health of an animal, including a human, wherein the animal cannot maintain homeostasis, and wherein if the disease is not ameliorated then the animal's health continues to deteriorate.

In contrast, a "disorder" in an animal, including a human, includes a state of health in which the animal is able to maintain homeostasis, but in which the animal's state of health is less favorable than it would be in the absence of the disorder. Left untreated, a disorder does not necessarily cause a further decrease in the animal's state of health.

The terms "treatment", "treating", "treat", and the like, refer to obtaining a desired pharmacologic and/or physiologic effect. The effect may be prophylactic in terms of completely or partially preventing a disease or symptom thereof or reducing the likelihood of a disease or symptom thereof and/or may be therapeutic in terms of a partial or complete cure for a disease and/or adverse effect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development or progression; and (c) relieving the disease, i.e., causing regression of the disease and/or relieving one or more disease symptoms. "Treatment" is also meant to encompass delivery of an agent in order to provide for a pharmacologic effect, even in the absence of a disease or condition. For example, "treatment" encompasses delivery of a composition that can elicit an immune response or confer immunity in the absence of a disease condition, e.g., in the case of a vaccine.

As used herein, the term "mammal" refers to any mammal, including, but not limited to, mammals of the order Rodentia, such as mice and hamsters, and mammals of the order Logomorpha, such as rabbits. In some embodiments, the mammals are from the order Carnivora, including felines (cats) and canines (dogs). In some embodiments, the mammals are from the order Artiodactyla, including bovines (cows) and swines (pigs) or of the order Perssodactyla, including Equines (horses). It is most preferred that the mammals are of the order Primates, Ceboids, or Simoids (monkeys) or of the order Anthropoids (humans and apes). In some embodiments, the mammal is a human.

The term "regression," as well as words stemming therefrom, as used herein, does not necessarily imply 100% or complete regression. Rather, there are varying degrees of regression of which one of ordinary skill in the art recognizes as having a potential benefit or therapeutic effect. In this respect, the disclosed methods can provide any amount of any level of regression of a tauopathy in a mammal. Furthermore, the regression provided by the inventive method can include regression of one or more conditions or symptoms of the disease, e.g., a tauopathy. Also, for purposes herein, "regression" can encompass delaying the onset of the disease, delaying the onset of a symptom, and/or delaying the onset of a condition thereof. With respect to progressive diseases and disorders, "regression" can encompass slowing the progression of the disease or disorder, slowing the progression of a symptom of the disease or disorder, and/or slowing the progression of a condition thereof.

An "effective amount" or "therapeutically effective amount" of a composition includes that amount of the composition which is sufficient to provide a beneficial effect to the subject to which the composition is administered. An "effective amount" of a delivery vehicle includes that amount sufficient to effectively bind or deliver a composition.

By "individual" or "host" or "subject" or "patient" is meant any mammalian subject for whom diagnosis, treatment, or therapy is desired, particularly humans. Other subjects may include cattle, dogs, cats, guinea pigs, rabbits, rats, mice, horses, and so on.

The term "in combination with" as used herein refers to uses where, for example, a first therapy is administered during the entire course of administration of a second therapy; where the first therapy is administered for a period of time that is overlapping with the administration of the second therapy, e.g. where administration of the first therapy begins before the administration of the second therapy and the administration of the first therapy ends before the administration of the second therapy ends; where the administration of the second therapy begins before the administration of the first therapy and the administration of the second therapy ends before the administration of the first therapy ends; where the administration of the first therapy begins before administration of the second therapy begins and the administration of the second therapy ends before the administration of the first therapy ends; where the administration of the second therapy begins before administration of the first therapy begins and the administration of the first therapy ends before the administration of the second therapy ends. As such, "in combination" can also refer to regimen involving administration of two or more therapies. "In combination with" as used herein also refers to administration of two or more therapies which may be administered in the same or different formulations, by the same or different routes, and in the same or different dosage form type.

"Encoding" includes the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if, for example, transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

The term "nucleic acid" includes RNA or DNA molecules having more than one nucleotide in any form including single-stranded, double-stranded, oligonucleotide or polynucleotide. The term "nucleotide sequence" includes the ordering of nucleotides in an oligonucleotide or polynucleotide in a single-stranded form of nucleic acid.

By "nucleic acid construct" it is meant a nucleic acid sequence that has been constructed to comprise one or more functional units not found together in nature. Examples include circular, linear, double-stranded, extrachromosomal DNA molecules (plasmids), cosmids (plasmids containing COS sequences from lambda phage), viral genomes including non-native nucleic acid sequences, and the like.

The term "operably linked" as used herein includes a polynucleotide in functional relationship with a second polynucleotide, e.g. a single-stranded or double-stranded nucleic acid moiety comprising the two polynucleotides arranged within the nucleic acid moiety in such a manner that at least one of the two polynucleotides is able to exert a physiological effect by which it is characterized, upon the other. By way of example, a promoter operably linked to the coding region of a gene is able to promote transcription of the coding region. The order specified when indicating operably linkage is not important. For example, the phrases: "the promoter is operably linked to the nucleotide sequence" and "the nucleotide sequence is operably linked to the promoter" are used interchangeably herein and are considered equivalent. In some cases, when the nucleic acid encoding the desired protein further comprises a promoter/regulatory sequence, the promoter/regulatory sequence is positioned at the 5' end of the desired protein coding sequence such that it drives expression of the desired protein in a cell.

The terms "oligonucleotide," "polynucleotide," and "nucleic acid molecule", used interchangeably herein, refer to a polymeric forms of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups.

The term "recombinant," as applied to a polynucleotide means the polynucleotide is the product of various combinations of cloning, restriction or ligation steps, and other procedures resulting in a construct distinct and/or different from a polynucleotide found in nature. The terms respectively include replicates of the original polynucleotide construct and progeny of the original virus construct.

The term "promoter" as used herein includes a DNA sequence operably linked to a nucleic acid sequence to be transcribed such as a nucleic acid sequence encoding a desired molecule. A promoter is generally positioned upstream of a nucleic acid sequence to be transcribed and provides a site for specific binding by RNA polymerase and other transcription factors.

A "vector" is capable of transferring gene sequences to target-cells. Typically, "vector construct," "expression vector," and "gene transfer vector," mean any nucleic acid construct capable of directing the expression of a gene of interest and which can transfer gene sequences to target-cells, which can be accomplished by genomic integration of all or a portion of the vector, or transient or inheritable maintenance of the vector as an extrachromosomal element. Thus, the term includes cloning, and expression vehicles, as well as integrating vectors.

The term "regulatory element" as used herein includes a nucleotide sequence which controls some aspect of the expression of nucleic acid sequences. Examples of regulatory elements illustratively include an enhancer, an internal ribosome entry site (IRES), an intron, an origin of replication, a polyadenylation signal (pA), a promoter, an enhancer, a transcription termination sequence, and an upstream regulatory domain, which contribute to the replication, transcription, and/or post-transcriptional processing of a nucleic acid sequence. In cases, regulatory elements can also include cis-regulatory DNA elements as well as transposable elements (TEs). Those of ordinary skill in the art are capable of selecting and using these and other regulatory elements in an expression construct with no more than routine experimentation. Expression constructs can be generated using a genetic recombinant approach or synthetically using well-known methodology.

A "control element" or "control sequence" is a nucleotide sequence involved in an interaction of molecules contributing to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter.

The statement that an amino acid residue is "phosphorylated" used herein means that a phosphate group is ester-linked to the side chain of the amino acid residue. Typical amino acid residues that may be phosphorylated include serine (Ser), threonine (Thr), and tyrosine (Tyr).

VIII. ANTIBODIES

The present invention is directed to antibodies and antigen binding fragments that bind human tau protein that has been phosphorylated at position 413.

Traditional antibody structural units typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). Human light chains are classified as kappa and lambda light chains. The present invention is directed to antibodies that generally are based on the IgG class, which has several subclasses, including, but not limited to IgG1, IgG2, IgG3, and IgG4. In general, IgG1, IgG2 and IgG4 are used more frequently than IgG3. It should be noted that IgG1 has different allotypes with polymorphisms at 356 (D or E) and 358 (L or M). The sequences depicted herein use the 356D/358L allotype, however the other allotype is included herein. That is, any sequence inclusive of an IgG1 Fc domain included herein can have 356E/358M replacing the 356D/358L allotype.

As will be appreciated by those in the art, the exact numbering and placement of the CDRs can be different among different numbering systems. However, it should be understood that the disclosure of a variable heavy and/or variable light sequence includes the disclosure of the associated (inherent) CDRs. Accordingly, the disclosure of each variable heavy region is a disclosure of the vhCDRs (e.g. vhCDR1, vhCDR2 and vhCDR3) and the disclosure of each variable light region is a disclosure of the vlCDRs (e.g. vlCDR1, vlCDR2 and vlCDR3).

Methods for identifying the sequence of each of CDR-H1, CDR-H2, CDR-H3, CDR-L1, CDR-L2, and CDR-L3 of an antibody include: Kabat method (Kabat et al., The Journal of Immunology, 1991, Vol. 147, No. 5, pp.1709-1719) and Chothia method (Al-Lazikani et al., Journal of Molecular Biology, 1997, Vol. 273, No. 4, pp.927-948). These methods are within the technical common knowledge to persons skilled in the art, the summaries thereof being available, e.g., on the website of Dr. Andrew C. R. Martin's Group (http://www.bioinf.org.uk/abs/).

A useful comparison of CDR numbering is as below, see Lafranc et al., Dev. Comp. Immunol. 27(1):55-77 (2003):

TABLE 1

|  | Kabat + Chothia | IMGT | Rabat | AbM | Chothia | Contact |
|---|---|---|---|---|---|---|
| vhCDR1 | 26-35 | 27-38 | 31-35 | 26-35 | 26-32 | 30-35 |
| vhCDR2 | 50-65 | 56-65 | 50-65 | 50-58 | 52-56 | 47-58 |
| vhCDR3 | 95-102 | 105-117 | 95-102 | 95-102 | 95-102 | 93-101 |
| vlCDR1 | 24-34 | 27-38 | 24-34 | 24-34 | 24-34 | 30-36 |
| vlCDR2 | 50-56 | 56-65 | 50-56 | 50-56 | 50-56 | 46-55 |
| vlCDR3 | 89-97 | 105-117 | 89-97 | 89-97 | 89-97 | 89-96 |

Throughout the present specification, the Kabat numbering system is generally used when referring to a residue in the variable domain (approximately, residues 1-107 of the light chain variable region and residues 1-113 of the heavy chain variable region) and the EU numbering system for constant regions such as Fc regions (e.g, Kabat et al., supra (1991)).

The present invention provides a number of different CDR sets. In this case, a "full CDR set" comprises the three variable light and three variable heavy CDRs, e.g. a vlCDR1, vlCDR2, vlCDR3, vhCDR1, vhCDR2 and vhCDR3. These can be part of a larger variable light or variable heavy domain, respectfully. In addition, as more fully outlined herein, the variable heavy and variable light domains can be on separate polypeptide chains, when a heavy and light chain is used (for example when Fabs are used), or on a single polypeptide chain in the case of scFv sequences.

The CDRs contribute to the formation of the antigen-binding, or more specifically, epitope binding site of antibodies. "Epitope" refers to a determinant that interacts with a specific antigen binding site in the variable region of an antibody molecule known as a paratope. Epitopes are groupings of molecules such as amino acids or sugar side chains and usually have specific structural characteristics, as well as specific charge characteristics. A single antigen may have more than one epitope.

In the present case, the epitope comprises not only the amino acid residues directly involved in the binding of the antibodies of the invention but also the phosphorylation at Ser413.

The carboxy-terminal portion of each chain defines a constant region primarily responsible for effector function. Kabat et al. collected numerous primary sequences of the variable regions of heavy chains and light chains. Based on the degree of conservation of the sequences, they classified individual primary sequences into the CDR and the framework and made a list thereof (see SEQUENCES OF IMMUNOLOGICAL INTEREST, 5th edition, NIH publication, No. 91-3242, E. A. Kabat et al., entirely incorporated by reference).

In the IgG subclass of immunoglobulins, there are several immunoglobulin domains in the heavy chain. By "immunoglobulin (Ig) domain" herein is meant a region of an immunoglobulin having a distinct tertiary structure. Of interest in the present invention are the heavy chain domains, including, the constant heavy (CH) domains and the hinge domains. In the context of IgG antibodies, the IgG isotypes each have three CH regions. Accordingly, "CH" domains in the context of IgG are as follows: "CH1" refers to positions 118-220 according to the EU index as in Kabat. "CH2" refers to positions 237-340 according to the EU index as in Kabat, and "CH3" refers to positions 341-447 according to the EU index as in Kabat.

Another type of Ig domain of the heavy chain is the hinge region. By "hinge" or "hinge region" or "antibody hinge region" or "immunoglobulin hinge region" herein is meant the flexible polypeptide comprising the amino acids between the first and second constant domains of an antibody. Structurally, the IgG CH1 domain ends at EU position 220, and the IgG CH2 domain begins at residue EU position 237. Thus for IgG the antibody hinge is herein defined to include positions 221 (D221 in IgG1) to 236 (G236 in IgG1), wherein the numbering is according to the EU index as in Kabat. In some embodiments, for example in the context of an Fc region, the lower hinge is included, with the "lower hinge" generally referring to positions 226 or 230. As noted herein, pI variants can be made in the hinge region as well.

The light chain generally comprises two domains, the variable light domain (containing the light chain CDRs and together with the variable heavy domains forming the Fv region), and a constant light chain region (often referred to as CL or Cκ).

Another region of interest for additional substitutions, outlined below, is the Fc region.

Thus, the present invention provides different antibody domains. As described herein and known in the art, the antibodies of the invention comprise different domains within the heavy and light chains, which can be overlapping as well. These domains include, but are not limited to, the Fc domain, the CH1 domain, the CH2 domain, the CH3 domain, the hinge domain, the heavy constant domain (CH1-hinge-Fc domain or CH1-hinge-CH2-CH3), the variable heavy domain, the variable light domain, the light constant domain, Fab domains and scFv domains.

Thus, the "Fc domain" includes the —CH2-CH3 domain, and optionally a hinge domain. The heavy chain comprises a variable heavy domain and a constant domain, which includes a CH1-hinge-Fc domain comprising a CH2-CH3. The light chain comprises a variable light chain and the light constant domain. A scFv comprises a variable heavy chain, an scFv linker, and a variable light domain. Some embodiments of the invention comprise at least one scFv domain, which, while not naturally occurring, generally includes a variable heavy domain and a variable light domain, linked together by a scFv linker. As outlined herein, while the scFv domain is generally from N- to C-terminus oriented as vh-scFv linker-vl, this can be reversed for any of the scFv domains (or those constructed using vh and vl sequences from Fabs), to vl-scFv linker-vh.

As shown herein, there are a number of suitable scFv linkers that can be used, including traditional peptide bonds, generated by recombinant techniques. The linker peptide may predominantly include the following amino acid residues: Gly, Ser, Ala, or Thr. The linker peptide should have a length that is adequate to link two molecules in such a way that they assume the correct conformation relative to one another so that they retain the desired activity. In one embodiment, the linker is from about 1 to 50 amino acids in length, preferably about 1 to 30 amino acids in length. In one embodiment, linkers of 1 to 20 amino acids in length may be used, with from about 5 to about 10 amino acids finding use in some embodiments. Useful linkers include glycine-serine polymers, including for example (GS)n, (GSGGS)n, (GGGGS)n, and (GGGS)n, where n is an integer of at least one (and generally from 3 to 4), glycine-alanine polymers, alanine-serine polymers, and other flexible linkers. Alternatively, a variety of nonproteinaceous polymers, including but not limited to polyethylene glycol (PEG), polypropylene glycol, polyoxyalkylenes, or copolymers of polyethylene glycol and polypropylene glycol, may find use as linkers, that is may find use as linkers.

Other linker sequences may include any sequence of any length of CL/CH1 domain but not all residues of CL/CH1 domain; for example the first 5-12 amino acid residues of the CL/CH1 domains. Linkers can be derived from immunoglobulin light chain, for example Cκ or Cλ. Linkers can be derived from immunoglobulin heavy chains of any isotype, including for example Cγ1, Cγ2, Cγ3, C±4, Cα1, Cα2, Cδ, Cε, and Cμ. Linker sequences may also be derived from other proteins such as Ig-like proteins (e.g. TCR, FcR, KIR), hinge region-derived sequences, and other natural sequences from other proteins.

In some embodiments, the linker is a "domain linker", used to link any two domains as outlined herein together. While any suitable linker can be used, many embodiments utilize a glycine-serine polymer, including for example (GS)n, (GSGGS)n, (GGGGS)n, and (GGGS)n, where n is an integer of at least one (and generally from 3 to 4 to 5) as well as any peptide sequence that allows for recombinant attachment of the two domains with sufficient length and flexibility to allow each domain to retain its biological function.

A. Chimeric and Humanized Antibodies

In some embodiments, the antibodies herein can be derived from a mixture from different species, e.g. a chimeric antibody and/or a humanized antibody. In general, both "chimeric antibodies" and "humanized antibodies" refer to antibodies that combine regions from more than one species. For example, "chimeric antibodies" traditionally comprise variable region(s) from a mouse (or rat, in some cases) and the constant region(s) from a human. "Humanized antibodies" generally refer to non-human antibodies that have had the variable-domain framework regions swapped for sequences found in human antibodies. Generally, in a humanized antibody, the entire antibody, except the CDRs, is encoded by a polynucleotide of human origin or is identical to such an antibody except within its CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones, 1986, Nature 321: 522-525, Verhoeyen et al., 1988, Science 239:1534-1536, all entirely incorporated by reference. "Backmutation" of selected acceptor framework residues to the corresponding donor residues is often required to regain affinity that is lost in the initial grafted construct (U.S. Pat. Nos. 5,530,101; 5,585,089; 5,693,761; 5,693,762; 6,180,370; 5,859,205; 5,821,337; 6,054,297; 6,407,213, all entirely incorporated by reference). The humanized antibody optimally also will comprise at least a portion of an immunoglobulin constant region, typically that of a human immunoglobulin, and thus will typically comprise a human Fc region. Humanized antibodies can also be generated using mice with a genetically engineered immune system. Roque et al., 2004, Biotechnol. Prog. 20:639-654, entirely incorporated by reference. A variety of techniques and methods for humanizing and reshaping non-human antibodies are well known in the art (See Tsurushita & Vasquez, 2004, Humanization of Monoclonal Antibodies, Molecular Biology of B Cells, 533-545, Elsevier Science (USA), and references cited therein, all entirely incorporated by reference). Humanization methods include but are not limited to methods described in Jones et al., 1986, Nature 321:522-525; Riechmann et al.,1988; Nature 332:323-329; Verhoeyen et al., 1988, Science, 239:1534-1536; Queen et al., 1989, Proc Natl Acad Sci, USA 86:10029-33; He et al., 1998, J. Immunol. 160: 1029-1035; Carter et al., 1992, Proc Natl Acad Sci USA 89:4285-9, Presta et al., 1997, Cancer Res. 57(20):4593-9; Gorman et al., 1991, Proc. Natl. Acad. Sci. USA 88:4181-4185; O'Connor et al., 1998, Protein Eng 11:321-8, all entirely incorporated by reference. Humanization or other methods of reducing the immunogenicity of nonhuman antibody variable regions may include resurfacing methods, as described for example in Roguska et al., 1994, Proc. Natl. Acad. Sci. USA 91:969-973, entirely incorporated by reference.

In certain embodiments, the antibodies of the invention comprise a heavy chain variable region from a particular germline heavy chain immunoglobulin gene and/or a light chain variable region from a particular germline light chain immunoglobulin gene. For example, such antibodies may comprise or consist of a human antibody comprising heavy or light chain variable regions that are "the product of" or "derived from" a particular germline sequence. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally-occurring somatic mutations or intentional introduction of site-directed mutation. However, a humanized antibody typically is at least 80% identical in amino acids sequence to an amino acid sequence encoded by a human germline immunoglobulin gene and contains amino acid residues that identify the antibody as being derived from human sequences when compared to the germline immunoglobulin amino acid sequences of other species (e.g., murine germline sequences). In certain cases, a humanized antibody may be at least 95, 96, 97, 98 or 99%, or even at least 96%, 97%, 98%, or 99% identical in amino acid sequence to the amino acid sequence encoded by the germline immunoglobulin gene. Typically, a humanized antibody derived from a particular human germline sequence will display no more than 10-20 amino acid differences from the amino acid sequence encoded by the human germline immunoglobulin gene. In certain cases, the humanized antibody may display no more than 5, or even no more than 4, 3, 2, or 1 amino acid difference from the amino acid sequence encoded by the germline immunoglobulin gene.

In one embodiment, the parent antibody has been affinity matured, as is known in the art. Structure-based methods may be employed for humanization and affinity maturation, for example as described in U.S. Pat. No. 7,657,380. Selection based methods may be employed to humanize and/or affinity mature antibody variable regions, including but not limited to methods described in Wu et al., 1999, J. Mol. Biol. 294:151-162; Baca et al., 1997, J. Biol. Chem. 272(16): 10678-10684; Rosok et al., 1996, J. Biol. Chem. 271(37): 22611-22618; Rader et al., 1998, Proc. Natl. Acad. Sci. USA 95: 8910-8915; Krauss et al., 2003, Protein Engineering 16(10):753-759, all entirely incorporated by reference. Other humanization methods may involve the grafting of only parts of the CDRs, including but not limited to methods described in Tan et al., 2002, J. Immunol. 169:1119-1125; De Pascalis et al., 2002, J. Immunol. 169:3076-3084, all entirely incorporated by reference.

The term "antibody" is used in the broadest sense and includes, for example, an intact immunoglobulin or an antigen binding portion. Antigen binding portions may be produced by recombinant DNA techniques or by enzymatic or chemical cleavage of intact antibodies. Thus the term antibody includes traditional tetrameric antibodies of two heavy chains and two light chains, as well as antigen binding fragments such as Fv, Fab and scFvs. In some cases, the invention provides bispecific antibodies that include at least one antigen binding domain as outlined herein.

The humanized anti-phosphorylated tau antibody according to the present invention should preferably exhibit improved plasma kinetics. The improvement in plasma kinetics of a humanized antibody herein means that a parameter representing the kinetics of the humanized antibody in plasma is altered in comparison to a non-humanized antibody corresponding to the humanized antibody. Examples of parameters representing plasma kinetics include: plasma half-life, average retention time in plasma, and plasma clearance. Such a parameter being "altered" means that the parameter is increased or decreased. The non-humanized antibody "corresponding" to the humanized antibody means a non-humanized antibody used as a basis for producing the humanized antibody, e.g., a mouse antibody or a chimeric antibody.

The term "chimeric antibody" refers to an antibody that contains one or more regions from one antibody and one or more regions from one or more other antibodies. A "CDR grafted antibody" is an antibody comprising one or more CDRs derived from an antibody of a particular species or isotype and the framework of another antibody of the same or different species or isotype.

IX. COMPOSITIONS

The present invention provides a number of different antigen binding domains (generally incorporated into antibodies) that bind to human tau protein that is phosphorylated at Ser413 (pSer413), in an "antigen-antibody reaction".

The "antigen-antibody reaction" is measured by the affinity of an antibody to a phosphorylated Tau protein or a phosphorylated Tau peptide, i.e., equilibrium dissociation constant ($K_D$). In certain embodiments, the $K_D$ value is measured with a phosphorylated Tau protein. In some embodiments, the $K_D$ value is measured with a phosphorylated Tau peptide. In one embodiment, the phosphorylated Tau peptide is phosphorylated at only one residue (e.g., SEQ ID NO:75). In another embodiment, the phosphorylated peptide is phosphorylated at multiple residues (e.g., SEQ ID NO:76 or SEQ ID NO:78). In some embodiments, the $K_D$ value is measured with the antigen (e.g., the phosphorylated Tau protein or the phosphorylated Tau peptide) immobilized, in which cases the affinity measurement includes an avidity component, i.e., in a bivalent binding mode. In other embodiments, the $K_D$ value is measured with the antibody (e.g., the mouse parent antibody, the chimeric antibody, or the humanized antibody variants) immobilized, in which case the affinity measurement does not include an avidity component, i.e., in a monovalent binding mode. In yet other embodiments, the $K_D$ value is measured with the antibody immobilized and with the phosphorylated Tau protein as the analyte. In still other embodiments, the $K_D$ value is measured with the antibody immobilized and with the phosphorylated peptide as the analyte. In certain embodiments, the $K_D$ value is measured in a bivalent binding mode. In other embodiments, the $K_D$ value is measured in a monovalent binding mode.

Thus, in certain embodiments, the $K_D$ value is $5 \times 10^{-8}$ M or less; in some embodiments, the $K_D$ value is $5 \times 10^{-9}$ M or less; in other embodiments, the $K_D$ value is $5\times10^{-10}$M or less; in yet other embodiments, the $K_D$ value is $1.86\times10^{-8}$M or less; in still other embodiments, the $K_D$ value is $2\times10^{-9}$M or less; in yet still other embodiments, the $K_D$ value is $2\times10^{-10}$M or less. In a specific embodiment, the antibody disclosed herein binds to a phosphorylated Tau protein or a phosphorylated Tau peptide with a $K_D$ of $5\times10^{-8}$M or less, measured with the antibody immobilized and the phosphorylated tau protein or phosphorylated tau peptide as an analyte. In another specific embodiment, the antibody disclosed herein binds to a phosphorylated Tau protein or a phosphorylated Tau peptide with a $K_D$ of $5\times10^{-9}$M or less, measured with the phosphorylated Tau protein or the phosphorylated Tau peptide immobilized and the antibody as an analyte. In yet another specific embodiment, the antibody disclosed herein binds to a phosphorylated Tau protein or a phosphorylated Tau peptide with a $K_D$ of $2\times10^{-9}$M or less, measured with the phosphorylated Tau protein or the phosphorylated Tau peptide immobilized and the antibody as an analyte. In one another specific embodiment, the antibody disclosed herein binds to a phosphorylated Tau protein or a phosphorylated Tau peptide with a $K_D$ of $5\times10^{-10}$M or less, measured with the phosphorylated Tau protein or the phosphorylated Tau peptide immobilized and the antibody as an analyte. In another specific embodiment, the antibody disclosed herein binds to a phosphorylated Tau protein or a phosphorylated Tau peptide with a $K_D$ of $2\times10^{-10}$M or less, measured with the phosphorylated Tau protein or the phosphorylated Tau peptide immobilized and the antibody as an analyte.

Additionally, as outlined herein, the antibodies of the invention preferentially bind to tau peptides or proteins that are phosphorylated at position S413 over proteins or peptides that do not contain a phosphate at position 413.

The humanized anti-phosphorylated tau antibody according to the present invention is an antibody which can cause an antigen-antibody reaction with the phosphorylated tau protein or phosphorylated tau peptide according to the present invention.

Phosphorylated tau proteins and tau peptides with which the humanized anti-phosphorylated tau antibody according to the present invention can cause antigen-antibody reaction are those that phosphorylated at an amino acid residue which is phosphorylated specifically in neurodegenerative diseases such as AD. Specifically, such tau proteins and tau peptides are phosphorylated at least at the serine residue at position 413 of the amino acid sequence defined in SEQ ID NO:1 (Ser413), and also may be phosphorylated at one or more of the amino acid residues corresponding to amino acid numbers 410 to 421, i.e., one or more of the amino acid residues corresponding to the serine residue at position 412 (Ser412), the threonine residue at position 414 (Thr414), and the serine residue at position 416 (Ser416) of the amino acid sequence defined in SEQ ID NO:1. Typical such phosphorylated peptides include, although not limited to: pSer412/pSer413(Cys-), which has the amino acid sequence defined in SEQ ID NO:7; pSer413(Cys-), which has the amino acid sequence defined in SEQ ID NO:8, and pSer409/pSer412/pSer413(Cys-), which has the amino acid sequence defined in SEQ ID NO:9.

The phosphorylated tau peptide according to the present invention can be used in the production of the humanized anti-phosphorylated tau antibody according to the present invention, or as an antigen for studying reactivity.

The phosphorylated tau peptide according to the present invention can be produced by a person skilled in the art by using appropriate synthesis methods or genetic engineering methods. Examples of methods for producing the phosphorylated peptide via synthesis include Boc method (Wakamiya T., Chemistry Letters, Vol. 22, p.1401, 1993), Fmoc method (Perich, J. W., International Journal of Peptide and Protein Research, Vol. 40, pp.134-140, 1992), and JP3587390B and WO2013/180238, although a person skilled in the art can employ any other methods as appropriate. Examples of methods for producing the phosphorylated peptide via genetic engineering includes a method in which a genetic material (DNA or RNA) having a nucleic acid sequence encoding a peptide to be produced or a precursor thereof is prepared and, after optional steps such as introduction into an expression vector and addition of a promoter sequence, introduced into a suitable host for expression or subjected to a cell-free protein synthesis system. In this case, the peptide can be phosphorylated at a desired site by causing phosphorylation reaction in the host by means of enzymes such as kinases, which may be either inherent to the host or caused to express via genetic engineering, or by recovering the target peptide from the host and then causing phosphorylation reaction using enzymes such as kinases. In the latter case, phosphorylation reaction can be caused in vitro by subjecting the target peptide to an enzyme which is known to play a role in phosphorylation reaction of tau, such as glycogen synthase kinase 3 (GSK3) or cyclin-dependent protein kinase 5 (CDK5). From among the peptides phosphorylated in the host or in vitro in accordance with the above methods, peptides phosphorylated at a desired amino acid residue can be recovered by, e.g., selecting ones which specifically bound to the anti-phosphorylated tau antibody mentioned above via antibody-antigen reaction.

The phosphorylated tau peptide according to the present invention can be modified at its N-terminal sequence and/or C-terminal sequence with a substance having other functions suitable for desired purposes. For example, the phosphorylated tau peptide according to the present invention may be added at its N-terminal and/or C-terminal with, e.g., methionine residue, acetyl group or pyroglutamic acid, or modified at its N-terminal and/or C-terminal with, e.g., fluorescent material. Alternatively, the N-terminal and/or C-terminal of the phosphorylated tau peptide according to the present invention may be modified with, e.g., a peptide or a protein. Examples of peptides usable for such a modification include suitable tag sequences (typically histidine tag or FLAG tag), peptides having amino acid sequences which can be recognized by a T-cell receptor (TCR) or a major histocompatibility complex (MHC), proteins derived from viruses or bacteria or peptides having sequences derived from such proteins. In addition, the phosphorylated tau peptide according to the present invention includes ones having at least one which amino acid residue other than the N-terminal and C-terminal residues modified with any other compound or peptide. A person skilled in the art would be able to carry out such a modification to a phosphorylated tau peptide using any known methods, such as the ones described in Hermanson et al., "Bioconjugate Techniques", (US), Academic Press, 1996.

A person skilled in the art would be able to carry out measurement of an antigen-antibody reaction by selecting an appropriate binding assay in a system of a solid phase or liquid phase. Examples of such assays include, although not limited to: enzyme-linked immunosorbent assay (ELISA), enzyme immunoassay (EIA), surface plasmon resonance (SPR), fluorescence resonance energy transfer (FRET), and luminescence resonance energy transfer (LRET). Measurement of antigen-antibody binding affinity can be carried out by, e.g., labelling an antibody and/or an antigen with, e.g., an enzyme, a fluorescent material, a luminescent material, or radioisotope, and detecting the antigen-antibody reaction using a method suitable for measuring the physical and/or chemical properties characteristic to the label used.

The humanized anti-phosphorylated tau antibody according to the present invention should preferably have an improved selective binding affinity to a phosphorylated tau protein or tau peptide over its binding affinity to a non-phosphorylated tau protein or tau peptide. The improvement in the selective binding affinity of an antibody to a phosphorylated tau protein or tau peptide in this context means that the ratio of the antibody's binding affinity to the phosphorylated tau protein or tau peptide to its binding affinity to the corresponding non-phosphorylated tau protein or tau peptide is increased. Such selective binding affinity can be analyzed by, e.g., using a plate on which the phosphorylated tau protein or tau peptide has been immobilized and a plate on which the corresponding non-phosphorylated tau protein or tau peptide has been immobilized, measuring the antibody's binding affinity to each of these proteins or peptides by means of, e.g., ELISA (e.g., as an absorbance OD value of emission wavelength), and dividing the value of the binding affinity (e.g., absorbance OD value) obtained for phosphorylated tau protein or tau peptide by the value obtained for the corresponding non-phosphorylated tau protein or tau peptide. Specific conditions for ELISA may be those described in the Examples section below.

The humanized anti-phosphorylated tau antibody according to the present invention should preferably have a ratio of the selective binding affinity to the phosphorylated tau protein or tau peptide to the binding affinity for the non-phosphorylated tau protein or tau peptide of at least about 40 or more, particularly at least about 50 or more, more particularly at least about 60 or more, provided that the selective binding affinity is obtained in accordance with the method described in Example 2, below. In one embodiment, the ratio is calculated by comparing the binding affinity of the anti-pSer413 tau antibodies to a phosphorylated peptide such as SEQ ID NO:8 to the binding affinity to the non-phosphorylated peptide of SEQ ID NO:69.

The humanized anti-phosphorylated tau antibody according to the present invention should preferably exhibit an improved ability to enter the brain when administered into the blood. The improvement in the ability of an antibody to enter the brain when administered into the blood in this context means that when the antibody is administered into the blood of a human or any other mammal (e.g., a mouse or a rat), the ratio of the antibody concentration in the brain to the antibody concentration in the plasma is increased. An antibody's ability to enter the brain can be analyzed, e.g., by administering the antibody to an animal (e.g., a mouse or a rat) via blood and, after a predetermined period (e.g., one week), collecting the blood and preparing brain homogenate, measuring the antibody concentration in each of the obtained plasma sample and the obtained brain homogenate sample using a known method (e.g., Sandwich ELISA using an anti-human polyclonal antibody), and dividing the antibody concentration in the brain by the antibody concentration in the plasma. Specific conditions for ELISA may be those described in the Examples section below. It is known that the concentration of an antibody entering the brain is generally about 0.1 to 0.3% of that in the plasma.

The humanized anti-phosphorylated tau antibody according to the present invention should preferably have a ratio of the antibody concentration in the brain to the antibody concentration in the plasma of 0.30% or more, particularly 0.35% or more, more particularly 0.40% or more, even more particularly 0.45% or more, provided that the ratio is obtained in accordance with the method described in the "[7] Example 7: Analysis of intracerebral migration" section of the Examples below.

A. Antigen Binding Domains of the Invention

The invention provides antigen binding domains that bind to human pSer413 tau protein preferentially over binding to tau proteins that are not phosphorylated at Ser413 as described herein.

In one embodiment, the invention provides antigen binding domains that comprise a vlCDR1 having SEQ ID NO:91, a vlCDR2 having SEQ ID NO:82; a vlCDR3 having SEQ ID NO:83; a vhCDR1 having SEQ ID NO:86; a vhCDR2 having SEQ ID NO:115; and a vhCDR3 having SEQ ID NO:88.

In one embodiment, the invention provides antigen binding domains that comprise a vlCDR1 having SEQ ID NO:92, a vlCDR2 having SEQ ID NO:82; a vlCDR3 having SEQ ID NO:83; a vhCDR1 having SEQ ID NO:86; a vhCDR2 having SEQ ID NO:115; and a vhCDR3 having SEQ ID NO:88.

In one embodiment, the invention provides antigen binding domains that comprise a vlCDR1 having SEQ ID NO:93, a vlCDR2 having SEQ ID NO:82; a vlCDR3 having SEQ ID NO:83; a vhCDR1 having SEQ ID NO:86; a vhCDR2 having SEQ ID NO:115; and a vhCDR3 having SEQ ID NO:88.

In one embodiment, the invention provides antigen binding domains that comprise a vlCDR1 having SEQ ID NO:94, a vlCDR2 having SEQ ID NO:82; a vlCDR3 having SEQ ID NO:83; a vhCDR1 having SEQ ID NO:86; a vhCDR2 having SEQ ID NO:115; and a vhCDR3 having SEQ ID NO:88.

In one embodiment, the invention provides antigen binding domains that comprise a vlCDR1 having SEQ ID NO:95, a vlCDR2 having SEQ ID NO:82; a vlCDR3 having SEQ ID NO:83; a vhCDR1 having SEQ ID NO:86; a vhCDR2 having SEQ ID NO:115; and a vhCDR3 having SEQ ID NO:88.

In one embodiment, the invention provides antigen binding domains that comprise a vlCDR1 having SEQ ID NO:96, a vlCDR2 having SEQ ID NO:82; a vlCDR3 having SEQ ID NO:83; a vhCDR1 having SEQ ID NO:86; a vhCDR2 having SEQ ID NO:115; and a vhCDR3 having SEQ ID NO:88.

In one embodiment, the invention provides antigen binding domains that comprise a vlCDR1 having SEQ ID NO:97, a vlCDR2 having SEQ ID NO:82; a vlCDR3 having SEQ ID NO:83; a vhCDR1 having SEQ ID NO:86; a vhCDR2 having SEQ ID NO:115; and a vhCDR3 having SEQ ID NO:88.

In one embodiment, the invention provides antigen binding domains that comprise a vlCDR1 having SEQ ID NO:98, a vlCDR2 having SEQ ID NO:82; a vlCDR3 having SEQ ID NO:83; a vhCDR1 having SEQ ID NO:86; a vhCDR2 having SEQ ID NO:115; and a vhCDR3 having SEQ ID NO:88.

In one embodiment, the invention provides antigen binding domains that comprise a vlCDR1 having SEQ ID NO:99, a vlCDR2 having SEQ ID NO:82; a vlCDR3 having SEQ ID NO:83; a vhCDR1 having SEQ ID NO:86; a vhCDR2 having SEQ ID NO:115; and a vhCDR3 having SEQ ID NO:88.

In one embodiment, the invention provides antigen binding domains that comprise a vlCDR1 having SEQ ID NO:100, a vlCDR2 having SEQ ID NO:82; a vlCDR3 having SEQ ID NO:83; a vhCDR1 having SEQ ID NO:86; a vhCDR2 having SEQ ID NO:115; and a vhCDR3 having SEQ ID NO:88.

In one embodiment, the invention provides antigen binding domains that comprise a vlCDR1 having SEQ ID NO:101, a vlCDR2 having SEQ ID NO:82; a vlCDR3 having SEQ ID NO:83; a vhCDR1 having SEQ ID NO:86; a vhCDR2 having SEQ ID NO:115; and a vhCDR3 having SEQ ID NO:88.

In one embodiment, the invention provides antigen binding domains that comprise a vlCDR1 having SEQ ID NO:102, a vlCDR2 having SEQ ID NO:82; a vlCDR3 having SEQ ID NO:83; a vhCDR1 having SEQ ID NO:86; a vhCDR2 having SEQ ID NO:115; and a vhCDR3 having SEQ ID NO:88.

The invention provides antigen binding domains to human pSer413 tau protein. As shown in the examples, a number of humanized variable heavy and variable light domains are provided, which can be combined in any combination, and can be added to human IgG constant domains in any combination.

In one embodiment, the variable light domain Ta1505-VL46 (SEQ ID NO:84) is combined with the variable heavy domain Ta1505-VH11 (SEQ ID NO:116) to form an Fv domain that binds pSer413 tau. In this embodiment, the human heavy constant domain is selected from SEQ ID NO:s118, 119, 120, 121, 122, 123, 124, 125 and 126 and the human light kappa constant domain, SEQ ID NO:52.

In one embodiment, the variable light domain Ta1505-VL46 (SEQ ID NO:84) is combined with the variable heavy domain Ta1505-VH65 (SEQ ID NO:117). In this embodiment, the human heavy constant domain is selected from SEQ ID NO:s118, 119, 120, 121, 122, 123, 124, 125 and 126 and the human light kappa constant domain, SEQ ID NO:52.

In one embodiment, the variable light domain Ta1505-VL47 (SEQ ID NO:104) is combined with the variable heavy domain Ta1505-VH11 (SEQ ID NO:116). In this embodiment, the human heavy constant domain is selected from SEQ ID NO:s118, 119, 120, 121, 122, 123, 124, 125 and 126 and the human light kappa constant domain, SEQ ID NO:52.

In one embodiment, the variable light domain Ta1505-VL47 (SEQ ID NO:104) is combined with the variable heavy domain Ta1505-VH65 (SEQ ID NO:117). In this embodiment, the human heavy constant domain is selected from SEQ ID NO:s118, 119, 120, 121, 122, 123, 124, 125 and 126 and the human light kappa constant domain, SEQ ID NO:52.

In one embodiment, the variable light domain Ta1505-VL46_G34A (SEQ ID NO:105) is combined with the variable heavy domain Ta1505-VH11 (SEQ ID NO:116). In this embodiment, the human heavy constant domain is selected from SEQ ID NO:s118, 119, 120, 121, 122, 123, 124, 125 and 126 and the human light kappa constant domain, SEQ ID NO:52.

In one embodiment, the variable light domain Ta1505-VL46_G34A (SEQ ID NO:105) is combined with the variable heavy domain Ta1505-VH65 (SEQ ID NO:117). In this embodiment, the human heavy constant domain is selected from SEQ ID NO:s118, 119, 120, 121, 122, 123, 124, 125 and 126 and the human light kappa constant domain, SEQ ID NO:52.

In one embodiment, the variable light domain Ta1505-VL46_G34S (SEQ ID NO:106) is combined with the variable heavy domain Ta1505-VH11 (SEQ ID N0116). In this embodiment, the human heavy constant domain is selected from SEQ ID NO:s118, 119, 120, 121, 122, 123, 124, 125 and 126 and the human light kappa constant domain, SEQ ID NO:52.

In one embodiment, the variable light domain Ta1505-VL46_G34S (SEQ ID NO:106) is combined with the variable heavy domain Ta1505-VH65 (SEQ ID NO:117). In this embodiment, the human heavy constant domain is selected from SEQ ID NO:s118, 119, 120, 121, 122, 123, 124, 125 and 126 and the human light kappa constant domain, SEQ ID NO:52.

In one embodiment, the variable light domain Ta1505-VL46_G34T (SEQ ID NO:107) is combined with the variable heavy domain Ta1505-VH11 (SEQ ID NO:116). In this embodiment, the human heavy constant domain is selected from SEQ ID NO:s118, 119, 120, 121, 122, 123, 124, 125 and 126 and the human light kappa constant domain, SEQ ID NO:52.

In one embodiment, the variable light domain Ta1505-VL46_G34T (SEQ ID NO:107) is combined with the variable heavy domain Ta1505-VH65 (SEQ ID NO:117). In this embodiment, the human heavy constant domain is selected from SEQ ID NO:s118, 119, 120, 121, 122, 123, 124, 125 and 126 and the human light kappa constant domain, SEQ ID NO:52.

In one embodiment, the variable light domain Ta1505-VL46_N33Q (SEQ ID NO:108) is combined with the variable heavy domain Ta1505-VH11 (SEQ ID NO:116). In this embodiment, the human heavy constant domain is selected from SEQ ID NO:s118, 119, 120, 121, 122, 123, 124, 125 and 126 and the human light kappa constant domain, SEQ ID NO:52.

In one embodiment, the variable light domain Ta1505-VL46_N33Q (SEQ ID NO:108) is combined with the variable heavy domain Ta1505-VH65 (SEQ ID NO:117). In this embodiment, the human heavy constant domain is selected from SEQ ID NO:s118, 119, 120, 121, 122, 123, 124, 125 and 126 and the human light kappa constant domain, SEQ ID NO:52.

In one embodiment, the variable light domain Ta1505-VL46_N33Q_G34A (SEQ ID NO:109) is combined with the variable heavy domain Ta1505-VH11 (SEQ ID NO:116). In this embodiment, the human heavy constant domain is selected from SEQ ID NO:s118, 119, 120, 121, 122, 123, 124, 125 and 126 and the human light kappa constant domain, SEQ ID NO:52.

In one embodiment, the variable light domain Ta1505-VL46_N33Q_G34A (SEQ ID NO:109) is combined with the variable heavy domain Ta1505-VH65 (SEQ ID NO:117). In this embodiment, the human heavy constant domain is selected from SEQ ID NO:s118, 119, 120, 121, 122, 123, 124, 125 and 126 and the human light kappa constant domain, SEQ ID NO:52.

In one embodiment, the variable light domain Ta1505-VL46_N33D (SEQ ID NO:110) is combined with the variable heavy domain Ta1505-VH11 (SEQ ID NO:116). In this embodiment, the human heavy constant domain is selected from SEQ ID NO:s118, 119, 120, 121, 122, 123, 124, 125 and 126 and the human light kappa constant domain, SEQ ID NO:52.

In one embodiment, the variable light domain Ta1505-VL46_N33D (SEQ ID NO:110) is combined with the variable heavy domain Ta1505-VH65 (SEQ ID NO:117). In this embodiment, the human heavy constant domain is selected from SEQ ID NO:s118, 119, 120, 121, 122, 123, 124, 125 and 126 and the human light kappa constant domain, SEQ ID NO:52.

In one embodiment, the variable light domain Ta1505-VL46_N33S (SEQ ID NO:111) is combined with the variable heavy domain Ta1505-VH11 (SEQ ID NO:116). In this embodiment, the human heavy constant domain is selected from SEQ ID NO:s118, 119, 120, 121, 122, 123, 124, 125 and 126 and the human light kappa constant domain, SEQ ID NO:52.

In one embodiment, the variable light domain Ta1505-VL46_N33S (SEQ ID NO:111) is combined with the variable heavy domain Ta1505-VH65 (SEQ ID NO:117). In this embodiment, the human heavy constant domain is selected from SEQ ID NO:s118, 119, 120, 121, 122, 123, 124, 125 and 126 and the human light kappa constant domain, SEQ ID NO:52.

In one embodiment, the variable light domain Ta1505-VL46_N33T (SEQ ID NO:112) is combined with the variable heavy domain Ta1505-VH11 (SEQ ID NO:116). In this embodiment, the human heavy constant domain is selected from SEQ ID NO:s118, 119, 120, 121, 122, 123, 124, 125 and 126 and the human light kappa constant domain, SEQ ID NO:52.

In one embodiment, the variable light domain Ta1505-VL46_N33T (SEQ ID NO:112) is combined with the variable heavy domain Ta1505-VH65 (SEQ ID NO:117). In this embodiment, the human heavy constant domain is selected from SEQ ID NO:s118, 119, 120, 121, 122, 123, 124, 125 and 126 and the human light kappa constant domain, SEQ ID NO:52.

In one embodiment, the variable light domain Ta1505-VL46_S28N (SEQ ID NO:113) is combined with the variable heavy domain Ta1505-VH11 (SEQ ID NO:116). In this embodiment, the human heavy constant domain is selected from SEQ ID NO:s118, 119, 120, 121, 122, 123, 124, 125 and 126 and the human light kappa constant domain, SEQ ID NO:52.

In one embodiment, the variable light domain Ta1505-VL46_S28N (SEQ ID NO:113) is combined with the variable heavy domain Ta1505-VH65 (SEQ ID NO:117). In this embodiment, the human heavy constant domain is selected from SEQ ID NO:s118, 119, 120, 121, 122, 123, 124, 125 and 126 and the human light kappa constant domain, SEQ ID NO:52.

In one embodiment, the variable light domain Ta1505-VL46_G34A_S28N (SEQ ID NO:114) is combined with the variable heavy domain Ta1505-VH11 (SEQ ID NO:116). In this embodiment, the human heavy constant domain is selected from SEQ ID NO:s118, 119, 120, 121, 122, 123, 124, 125 and 126 and the human light kappa constant domain, SEQ ID NO:52.

In one embodiment, the variable light domain Ta1505-VL46_G34A_S28N (SEQ ID NO:114) is combined with the variable heavy domain Ta1505-VH65 (SEQ ID NO:117). In this embodiment, the human heavy constant domain is selected from SEQ ID NO:s118, 119, 120, 121, 122, 123, 124, 125 and 126 and the human light kappa constant domain, SEQ ID NO:52.

The humanized anti-phosphorylated tau antibody according to the present invention should also preferably have a heavy chain variable region and a light chain variable region having specific amino acid sequences, specifically as mentioned below.

As a heavy chain variable region, the antibody of the present invention should preferably include an amino acid sequence having 80% or more, particularly 85% or more, more particularly 90% or more, even more particularly 95% or more, still even more particularly 100%, identity with a sequence selected from sequence VH11 (defined in SEQ ID NO:18), sequence VH12 (defined in SEQ ID NO:20), sequence VH47 (defined in SEQ ID NO:22), sequence VH61 (defined in SEQ ID NO:24), sequence VH62 (defined in SEQ ID NO:26), sequence VH64 (defined in SEQ ID NO:28), and sequence VH65 (defined in SEQ ID NO:30). In one embodiment, an antibody of the present invention could include, as a heavy chain variable region, the amino acid sequence of sequence VH65, or an amino acid sequence derived from sequence VH65 by one or more substitutions selected from the group consisting of: substitution of Ala at position 28 (Kabat No. H28) with Thr; substitution of Asn at position 30 (Kabat No. H30) with Ser; substitution of Val at position 49 (Kabat No. H49) with Gly; substitution of Ala at position 64 (Kabat No. H61) with Asp; and substitution of Gln at position 78 (Kabat No. H75) with Lys.

As a light chain variable region, the antibody of the present invention should preferably include an amino acid sequence having 80% or more, particularly 85% or more, more particularly 90% or more, even more particularly 95% or more, still even more particularly 100%, identity with a sequence selected from sequence VL15 (defined in SEQ ID NO:32), sequence VL36 (defined in SEQ ID NO:34), sequence VL46 (defined in SEQ ID NO:36), sequence VL47 (defined in SEQ ID NO:38), sequence VL48 (defined in SEQ ID NO:40), and sequence VL50 (defined in SEQ ID NO:42). In one embodiment, an antibody of the present invention could include, as a light chain variable region, the amino acid sequence of sequence VL47, or an amino acid sequence derived from sequence VL47 by one or more substitutions selected from the group consisting of: substitution of Asp at position 17 (Kabat No. L17) with Glu; substitution of Ser at position 28 (Kabat No. L27A) with Asn; substitution of Gln at position 42 (Kabat No. L37) with Leu; substitution of Gln at position 50 (Kabat No. L45) with Arg; and substitution of Arg at position 51 (Kabat No. L46) with Leu.

In another embodiment, the humanized anti-phosphorylated tau antibody according to the present invention could include any combination selected from:

(1) sequence VH11 (SEQ ID NO:116) as a heavy chain variable region and sequence VL15 (SEQ ID NO:32) as a light chain variable region;

(2) sequence VH11 (SEQ ID NO:116) as a heavy chain variable region and sequence VL36 (SEQ ID NO:34) as a light chain variable region;

(3) sequence VH11 (SEQ ID NO:116) as a heavy chain variable region and sequence VL46 (SEQ ID NO:36) as a light chain variable region;

(4) sequence VH11 (SEQ ID NO:116) as a heavy chain variable region and sequence VL47 (SEQ ID NO:38) as a light chain variable region;

(5) sequence VH11 (SEQ ID NO:116) as a heavy chain variable region and sequence VL48 (SEQ ID NO:40) as a light chain variable region;

(6) sequence VH11 (SEQ ID NO:116) as a heavy chain variable region and sequence VL50 (SEQ ID NO:42) as a light chain variable region;

(7) sequence VH12 (SEQ ID NO:20) as a heavy chain variable region and sequence VL48 (SEQ ID NO:40) as a light chain variable region;

(8) sequence VH47 (SEQ ID NO:22) as a heavy chain variable region and sequence VL48 (SEQ ID NO:40_) as a light chain variable region;

(9) sequence VH61 (SEQ ID NO:24) as a heavy chain variable region and sequence VL48 (SEQ ID NO:40) as a light chain variable region;

(10) sequence VH62 (SEQ ID NO:26) as a heavy chain variable region and sequence VL48 (SEQ ID NO:40) as a light chain variable region;

(11) sequence VH64 (SEQ ID NO:28) as a heavy chain variable region and sequence VL47 (SEQ ID NO:38) as a light chain variable region;

(12) sequence VH64 (SEQ ID NO:28) as a heavy chain variable region and sequence VL48 (SEQ ID NO:40) as a light chain variable region;

(13) sequence VH65 (SEQ ID NO:117) as a heavy chain variable region and sequence VL47 (SEQ ID NO:37) as a light chain variable region;

By selecting amino acid sequences of CDRs and/or variable regions of a heavy chain and a light chain from those mentioned above and combining them with amino acid sequences of framework regions and/or constant regions of a heavy chain and a light chain of a human antibody as appropriate, a person skilled in the art will be able to design a humanized anti-phosphorylated tau antibody according to the present invention. Amino acid sequences of framework regions and/or constant regions of a heavy chain and a light chain of a human antibody can be selected from, e.g., those of human IgG, IgA, IgM, IgE, and IgD subtypes or variants thereof.

B. Specific Anti-pSer413 tau Antibodies

The invention provides a number of specific antibodies comprising a pair of sequences, a heavy chain and a light chain as follows:

mAb-aPT1: LC SEQ ID NO:184 and HC SEQ ID NO:144
mAb-aPT2: LC SEQ ID NO:184 and HC SEQ ID NO:145
mAb-aPT3: LC SEQ ID NO:184 and HC SEQ ID NO:146
mAb-aPT4: LC SEQ ID NO:184 and HC SEQ ID NO:147
mAb-aPT5: LC SEQ ID NO:184 and HC SEQ ID NO:148
mAb-aPT6: LC SEQ ID NO:184 and HC SEQ ID NO:149
mAb-aPT7: LC SEQ ID NO:184 and HC SEQ ID NO:150
mAb-aPT8: LC SEQ ID NO:184 and HC SEQ ID NO:151
mAb-aPT9: LC SEQ ID NO:184 and HC SEQ ID NO:152
mAb-aPT10: LC SEQ ID NO:184 and HC SEQ ID NO:153
mAb-aPT11: LC SEQ ID NO:184 and HC SEQ ID NO:154
mAb-aPT12: LC SEQ ID NO:184 and HC SEQ ID NO:155
mAb-aPT13: LC SEQ ID NO:184 and HC SEQ ID NO:156
mAb-aPT14: LC SEQ ID NO:184 and HC SEQ ID NO:157
mAb-aPT15: LC SEQ ID NO:184 and HC SEQ ID NO:158
mAb-aPT16: LC SEQ ID NO:184 and HC SEQ ID NO:159
mAb-aPT17: LC SEQ ID NO:184 and HC SEQ ID NO:160
mAb-aPT18: LC SEQ ID NO:184 and HC SEQ ID NO:161
mAb-aPT19: LC SEQ ID NO:185 and HC SEQ ID NO:144
mAb-aPT20: LC SEQ ID NO:185 and HC SEQ ID NO:145
mAb-aPT21: LC SEQ ID NO:185 and HC SEQ ID NO:146
mAb-aPT22: LC SEQ ID NO:185 and HC SEQ ID NO:147
mAb-aPT23: LC SEQ ID NO:185 and HC SEQ ID NO:148
mAb-aPT24: LC SEQ ID NO:185 and HC SEQ ID NO:149
mAb-aPT25: LC SEQ ID NO:185 and HC SEQ ID NO:150
mAb-aPT26: LC SEQ ID NO:185 and HC SEQ ID NO:151
mAb-aPT27: LC SEQ ID NO:185 and HC SEQ ID NO:152
mAb-aPT28: LC SEQ ID NO:185 and HC SEQ ID NO:153
mAb-aPT29: LC SEQ ID NO:185 and HC SEQ ID NO:154
mAb-aPT30: LC SEQ ID NO:185 and HC SEQ ID NO:155
mAb-aPT31: LC SEQ ID NO:185 and HC SEQ ID NO:156
mAb-aPT32: LC SEQ ID NO:185 and HC SEQ ID NO:157
mAb-aPT33: LC SEQ ID NO:185 and HC SEQ ID NO:158
mAb-aPT34: LC SEQ ID NO:185 and HC SEQ ID NO:159
mAb-aPT35: LC SEQ ID NO:185 and HC SEQ ID NO:160
mAb-aPT36: LC SEQ ID NO:185 and HC SEQ ID NO:161

C. Antibodies that Compete for Binding

In addition to the antigen binding domains and antibodies containing them that bind to human tau protein that is phosphorylated at position 413 (pSer413), the invention provides antibodies that compete for binding with the recited antibodies herein.

A humanized antibody which causes competitive binding to pSer413 tau with the humanized anti-phosphorylated tau antibody according to the present invention is also included in the scope of the present invention. The term "competitive binding" used herein means that when there are two or more monoclonal antibodies together with an antigen, the binding of one of the antibodies to the antigen is inhibited by the binding of the other antibody to the antigen. The competitive binding can usually be measured by, e.g., adding, to a constant amount (concentration) of a monoclonal antibody, another monoclonal antibody with varying the amount (concentration) thereof, and determining the amount (concentration) of the latter monoclonal antibody at which the binding amount of the former monoclonal antibody, existing in the constant amount, is decreased. The degree of inhibition thereof can be expressed in the unit of IC50 or Ki. The humanized antibody which causes competitive binding with the humanized anti-phosphorylated tau antibody according to the present invention means an antibody having a IC50 of 1 µM or less, particularly 100 nM or less, more particularly 10 nM or less when measuring an antigen-antibody binding using the humanized anti-phosphorylated tau antibody according to the present invention at 10 nM.

Competitive binding studies can be done as is known in the art, generally using SPR/Biacore® or Octet® binding assays, as well as ELISA and cell based assays.

In some embodiments, the variable heavy and variable light domains of the competitive binding antibodies have at least 85%, 90%, 95%, 98% or 99% identity to at least one of the variable regions outlined herein, and in the constant domains, have at least 99 or 100% identity to a human IgG sequence outlined in FIG. 13.

D. Amino Acid Substitutions

In addition to the sequences outlined herein, the invention provides antigen binding domains and antibodies containing them that can have one or more amino acid substitutions as compared to the parent, starting sequence.

Thus for example, for all of the variable heavy and light domains listed herein, further variants can be made. As outlined herein, in some embodiments the set of 6 CDRs can have from 0, 1, 2, 3, 4 or 5 amino acid modifications (with amino acid substitutions finding particular use). In these embodiments, generally a single CDR has no more than 1 or 2 amino acid substitutions, and the mutated sequences retain binding to pSer413 tau protein. However, when amino acid variants are made to the CDRs of the sequences outlined herein, the resulting CDRs are not to the murine CDRs outlined in PCT/JP13/65090 and shown in SEQ ID NOs:81, 82 and 83 (variable light CDRs) and SEQ ID NOs:86, 87 and 88 (variable heavy CDRs).

In some cases, changes in the framework region(s) of the variable heavy and/or light domains can be made. In this embodiment, preferred variants in the framework regions (e.g. excluding the CDRs) retain at least about 80, 85, 90 or 95% identity to a human germline sequence. Thus, for example, the identical CDRs as described herein can be combined with different framework sequences from human germline sequences, as long as the framework regions retain at least 80, 85, 90 or 95% identity to a human germline sequence.

In some embodiments, for the humanized light chains outlined herein, the closest human light chain germline is IGKV2-30 that has an 81% identity to the sequences herein. Thus additional variants can be made in light framework regions as long as the identity is at least 80%, 85%, 90% or 95% identity to IGKV2-30.

For the humanized heavy chains herein, the closest human germline for heavy chain is IGHV3-73 that has an 85% identity to the sequences herein. Thus additional variants can be made in light framework regions as long as the identity is at least 80%, 85%, 90% or 95% identity to IGHV3-73.

Alternatively, the CDRs can have amino acid modifications (e.g. from 1, 2, 3, 4 or 5 amino acid modifications in the set of CDRs (that is, the CDRs can be modified as long as the total number of changes in the set of 6 CDRs is less than 6 amino acid modifications, with any combination of CDRs being changed; e.g. there may be one change in vlCDR1, two in vhCDR2, none in vhCDR3, etc.)), as well as having framework region changes, as long as the framework regions retain at least 80, 85 or 90% identity to a human germline sequence, and the resulting CDRs are not to the murine CDRs outlined in PCT/JP13/65090 and shown in SEQ ID NOs:81, 82 and 83 (variable light CDRs) and SEQ ID NOs:86, 87 and 88 (variable heavy CDRs).

In general, the percentage identity for comparison between anti-pSer413 tau antibodies is at least 75%, at least 80%, at least 90%, with at least about 95, 96, 97, 98 or 99% percent identity being preferred. The percentage identity may be along the whole amino acid sequence, for example the entire heavy or light chain or along a portion of the chains. For example, included within the definition of the anti-pSer413 tau antibodies of the invention are those that share identity along the entire variable region (for example, where the identity is 95 or 98% identical along the variable regions), or along the entire constant region.

X. NUCLEIC ACIDS OF THE INVENTION

Nucleic acid compositions encoding the anti-pSer413 tau antibodies of the invention are also provided, as well as expression vectors containing the nucleic acids and host cells transformed with the nucleic acid and/or expression vector compositions. As will be appreciated by those in the art, the protein sequences depicted herein can be encoded by any number of possible nucleic acid sequences, due to the degeneracy of the genetic code.

Thus, the invention further provides nucleic acid compositions encoding the antigen binding domains and antibodies containing them. As will be appreciated by those in the art, in the case of antigen binding domains, the nucleic acid compositions generally include a first nucleic acid encoding the variable heavy domain and a second nucleic acid encoding the variable light domain. In the case of scFvs, a single nucleic acid encoding the variable heavy and variable light domain, separated by a proteinaceous linker, can be made. In the case of traditional antibodies, the nucleic acid compositions generally include a first nucleic acid encoding the heavy chain and a second nucleic acid encoding the light chain, which will, upon expression in a cell, spontaneously assemble into the "traditional" tetrameric format of two heavy chains and two light chains.

As is known in the art, the nucleic acids encoding the components of the invention can be incorporated into expression vectors as is known in the art, and depending on the host cells, used to produce the heterodimeric antibodies of the invention. As will be appreciated by those in the art, these two nucleic acids can be incorporated into a single expression vector or into two different expression vectors. Generally, the nucleic acids are operably linked to any number of regulatory elements (promoters, origin of replication, selectable markers, ribosomal binding sites, inducers, etc.). The expression vectors can be extra-chromosomal or integrating vectors.

The nucleic acids and/or expression vectors of the invention are then transformed into any number of different types of host cells as is well known in the art, including mammalian, bacterial, yeast, insect and/or fungal cells, with mammalian cells (e.g. CHO cells), finding use in many embodiments.

The antibodies of the invention are made by culturing host cells comprising the expression vector(s) as is well known in the art. Once produced, traditional antibody purification steps are done.

XI. BIOLOGICAL AND BIOCHEMICAL ASSAYS

The anti-pSer413 tau antibodies of the invention can be assayed for efficacy in several ways. As a preliminary matter, the antibodies can be tested for binding to human tau protein or peptides that are phosphorylated at position S413 using techniques known in the art such as ELISA techniques (see for example Example 2(1)), Octet, Biacore or FACS, where binding to phosphorylated peptides (e.g. SEQ ID NO:8) is compared to binding to non-phosphorylated peptides (e.g. SEQ ID NO:69) as outlined herein.

In some embodiments, the binding efficacies of the antibodies disclosed herein are measured by Biacore assay. In certain embodiments, the $K_D$ value is measured with a phosphorylated Tau protein. In some embodiments, the $K_D$ value is measured with a phosphorylated Tau peptide. In one embodiment, the phosphorylated Tau peptide is phosphorylated at only one residue (e.g., SEQ ID NO:75). In another embodiment, the phosphorylated peptide is phosphorylated at multiple residues (e.g., SEQ ID NO:76 or SEQ ID NO:78). In some embodiments, the $K_D$ value is measured with the antigen (e.g., the phosphorylated Tau protein or the phosphorylated Tau peptide) immobilized, in which cases the affinity measurement includes an avidity component, i.e., in a bivalent binding mode. In other embodiments, the $K_D$ value is measured with the antibody (e.g., the mouse parent antibody, the chimeric antibody, or the humanized antibody variants) immobilized, in which case the affinity measurement does not include an avidity component, i.e., in a monovalent binding mode. In yet other embodiments, the $K_D$ value is measured with the antibody immobilized and with the phosphorylated Tau protein as the analyte. In still other embodiments, the $K_D$ value is measured with the antibody immobilized and with the phosphorylated peptide as the analyte. In certain embodiments, the $K_D$ value is measured in a bivalent binding mode. In other embodiments, the $K_D$ value is measured in a monovalent binding mode.

In addition, the anti-pSer413 tau antibodies of the invention can also be assayed for binding affinities in human AD brain homogenates, as well as assayed in neutralization studies of AD-derived au seeds in a HEC293 Tau P301L aggregation assay, and/or in AD-derived tau seeding and spreading models using human iPSC neurons in microfluidic chambers.

Additionally, the anti-pSer413 tau antibodies of the invention can also be used in immunohistochemical assays of AD patient brain samples Additionally, the anti-pSer413 tau antibodies of the invention can be assayed for efficacy in animal models of cognitive disorders including Alzheimer's Disease (AD). Animals for research on therapeutic or prophylactic agents for cognitive disorders of the invention include animal models for cognitive disorders, specifically animal models of tauopathies. Animal models for tauopathies are animals expressing normal-type or mutant tau in the brain, and particularly animal models exhibiting impairment in cognitive function. Such animals expressing normal-type or mutant tau in the brain can be prepared by genetic engineering, a typical example being transgenic mice (Tg mice). Animal models such as Tg mice that express mutant tau are useful as models of genetic familial tauopathies, but for examination of the effect of a therapeutic agent or prophylactic agent for sporadic tauopathies that constitute the majority of cases among humans, preferably an effect is exhibited in Tg mice expressing normal-type tau. Most suitable as Tg mice expressing normal-type tau are mice prepared in the production examples of the present invention, but there may also be used the Tg mice reported by Kambe et al. (Neurobiology of Disease, Vol. 42, P.404-414, 2011) and Kimura et al. (The EMBO J. vol. 26. P.5143-5152, 2007), both of which are incorporated herein by reference in their entirety and specifically for the creation and use of transgenic mice. However, although cognitive function impairment is seen in the mice of Kambe et al. and Kimura et al., it appears after 14 months of age and 20 months of age, respectively, and therefore the onset is well into senescence and aging effects may also be contributing factors, while the effects and labor of long-term breeding are also issues.

The preferred method of examining the effect of a therapeutic agent or prophylactic agent for cognitive disorders according to the invention in an animal model is a method of testing cognitive function, such as a memory learning test. Such a method may be a Morris water maze test, a step-through learning test or a novel object recognition test, but preferably it is a combination of behavioral measurement tests such as an Open Field Test, in order to take into account the conditions of behavior quantity and animal anxiety.

As methods for examining the effect of a therapeutic agent or prophylactic agent for cognitive disorders according to the invention, it is possible to use methods of examining the levels of tau protein or phosphorylated tau in brain tissue, during administration to an animal model of the cognitive disorder. In AD and other neurodegenerative diseases, expression levels of tau protein or increased abnormal phosphorylated tau are associated with pathology (Khalid Iqbal et al., Curr. Alzheimer Res., Vol. 7, p654-664, 2010). It is also well known that reducing tau expression and abnormal phosphorylated tau levels in some pathological model animals leads to improvement in cognitive function and motor function (K. Santa Cruz et al., Science, 30, Vol. 9, p.476-481, 2005; Sylvie Le Corre et al., Proc. Nat. Acad. Sci. USA, Vol. 103, p.9673-9678, 2006). As a method of examining changes in tau protein or phosphorylated tau, this can be accomplished by a method such as Western blotting using a brain tissue homogenate, as described in the examples, but a person skilled in the art can select another appropriate method such as ELISA (Xiyun Chai et al., J. Biol. Chem., Vol. 286, p.34457-34467, 2011) or an immunohistochemical method (David J. Irwin et al., BRAIN, Vol. 135, p.807-818, 2012).

XII. FORMULATIONS

Formulations of the antibodies used in accordance with the present invention are prepared for storage by mixing an antibody having the desired degree of purity with optional pharmaceutically acceptable carriers, excipients or stabilizers (as generally outlined in Remington's Pharmaceutical Sciences 16th edition, Osol, A. Ed. [1980]), in the form of lyophilized formulations or aqueous solutions.

The therapeutic or prophylactic agent for cognitive disorders according to the present invention may be formulated in the form of a pharmaceutical composition containing, in addition to the humanized anti-phosphorylated tau antibody according to the present invention, a pharmaceutically acceptable carrier and/or other excipients. Formulation using a pharmaceutically acceptable carrier and/or other excipients can be carried out using the method described in, e.g., University of the Sciences in Philadelphia, "Remington: The Science and Practice of Pharmacy, 20th EDITION", Lippincott Williams & Wilkins, 2000. Such a therapeutic or prophylactic agent may be provided as a liquid formulation prepared by dissolving, suspending, or emulsifying the ingredients into sterile aqueous medium or oily medium, or as a lyophilized formulation thereof. A medium or solvent for preparing such a formulation may be an aqueous medium, examples of which include distilled water for injection and physiological saline solution, which may optionally be used with addition of an osmoregulating agent (e.g., D-glucose, D-sorbitol, D-mannitol, and sodium chloride), and/or in combination with a suitable dissolving aid such as an alcohol (e.g., ethanol), a polyalcohol (e.g., propylene glycol or polyethylene glycol), or a nonionic surfactant (e.g., polysorbate 80 or polyoxyethylene hydrogenated castor oil 50). Such a formulation can also be prepared with an oily medium or solvent, examples of which include sesame oil and soybean oil, which can optionally be used in combination with a dissolving aid such as benzyl benzoate and benzyl alcohol. Such liquid drugs may often be prepared using appropriate additives such as buffering agents (e.g., phosphate buffering agents and acetate buffering agents), soothing agents (e.g., benzalkonium chloride and procaine hydrochloride), stabilizers (e.g., human serum albumin and polyethylene glycol), preservatives (e.g., ascorbic acid, erythorbic acid, and their salts), coloring agents (e.g., copper chlorophyll (β-carotene, Red #2 and Blue #1), antiseptic agents (e.g., paraoxybenzoic acid esters, phenol, benzethonium chloride and benzalkonium chloride), thickeners (e.g., hydroxypropyl cellulose, carboxymethyl cellulose, and their salts), stabilizers (e.g., human serum albumin mannitol and sorbitol), and odor correctives (e.g., menthol and citrus aromas). Different forms of therapeutic or prophylactic agents include solid formulations such as powders, tablets, granules, capsules, pills, suppositories, and lozenges. For a solid formulation to be administered in oral form, there may be used additives such as excipients (e.g., crystalline cellulose, lactose and starch), lubricants (e.g., magnesium stearate and talc), binders (hydroxypropyl cellulose, hydroxypropyl methyl cellulose, macrogol and the like), and disintegrators (e.g., starch and carboxymethyl cellulose calcium). If necessary, additives such as antiseptic agents (e.g., benzyl alcohol, chlorobutanol, methyl paraoxybenzoate and propyl paraoxybenzoate), antioxidants, coloring agents, sweeteners and the like may be used. Other alternative forms include therapeutic agents or prophylactic agent for application onto mucous membranes, such formulations often containing additives such as pressure-sensitive adhesives, pressure-sensitive enhancers, viscosity regulators, thickening agents and the like (e.g., mucin, agar, gelatin, pectin, carrageenan, sodium alginate, locust bean gum, xanthan gum, tragacanth gum, gum arabic, chitosan, pullulan, waxy starch, sucralfate, cellulose and its derivatives (such as hydroxypropyl methyl cellulose), polyglycerol fatty acid esters, acrylic acid-alkyl (meth)acrylate copolymers, or their salts and polyglycerol fatty acid esters), primarily for the purpose of imparting mucosal adsorption or retention properties. However, the form, solvent and additives for the therapeutic agent or prophylactic agent to be administered to the body are not limited to these, and appropriately selection may be made by a person skilled in the art.

The therapeutic or prophylactic agent for cognitive disorders according to the present invention may contain, in addition to the humanized anti-phosphorylated tau antibody according to the present invention, other known drugs having the effect of treating or preventing cognitive disorders, and in particular drugs having the effect of inhibiting the progression of cognitive disorders. Alternatively, the therapeutic or prophylactic agent for cognitive disorders according to the present invention containing the humanized anti-phosphorylated tau antibody according to the present invention may be combined with another therapeutic or prophylactic agent containing a known drug having the effect of treating or preventing cognitive disorders, and in particular a drug having the effect of inhibiting the progression of cognitive disorders, to be made in the form of a kit. Ingredients having the effects of inhibiting the progression of cognitive disorders include, but not limited to, Donepezil, Galantamine, Memantine, and Rivastigmine. The dosage of the ingredient having the effect of inhibiting the progression of cognitive disorders and the dosage of the therapeutic or prophylactic agent containing the ingredient having the effect of inhibiting the progression of cognitive disorders may be within the scope of dosages used for normal therapy, but can be increased or decreased depending on the conditions.

While the present inventors indicated experiment results, in WO2013/180238A (Patent Document 4), which demonstrate that the antibody exhibits a drug effect by acting on the brain through the blood-brain barrier even when administered peripherally by intraperitoneal administration, it is also possible to prepare a formulation that efficiently supplies the humanized anti-phosphorylated tau antibody according to the present invention, which is contained in the therapeutic or prophylactic agent for cognitive disorders according to the present invention, to the brain tissue. Such formulations are also encompassed by the therapeutic or prophylactic agent for cognitive disorders according to the invention. Methods for efficiently supplying antibodies or peptides to brain tissue through the blood-brain barrier are known, such as methods of adding targeting substances or methods of encapsulating in liposomes or nanoparticles. Substances to be used for targeting include those that undergo total or partial change in charge characteristics by binding with antibody, or peptides, proteins or other compounds having a property of binding with a specific receptor or transporter. Examples of peptides, proteins or other compounds having a property of binding with a specific receptor or membrane protein include ligands that bind to receptor ligands or membrane proteins, and their analogs, and antibodies, agonist compounds/antagonist compounds/allosteric modulators that bind to receptor ligands or membrane proteins, and their analog compounds. Examples of receptor ligands or membrane proteins as targets for a peptide, protein or other compound having the property of binding to a specific receptor or transporter include transferrin receptor (TfR), insulin receptor (IR), insulin-like growth factor receptor (IGFR), LDL receptor-related protein (LRP) and diphtheria toxin receptor (HB-EGF), with no particular limitation to these (Angela R. Jones et al., Pharm. Res., 2007, Vol. 24, No. 9, pp.1759-1771). A substance for targeting may be chemically added to the antibody to be used for the therapeutic or prophylactic agent for cognitive disorders according to the invention, the method being one that can be appropriately carried out by a person skilled in the art with reference to a known method such as described in, for example, Hermanson et al., Bioconjugate techniques, USA, Academic Press, 1996. The substance for targeting may also be bound to liposomes or nanoparticles encapsulating the antibody or peptide (Sonu Bhaskar et al., Particle and Fibre Toxicology, 2010, 7:3). In addition, when the substance for targeting is a peptide or protein, it can be produced as an appropriate fusion protein by a person skilled in the art using genetic engineering techniques, either by producing a fusion peptide by peptide chemical synthesis, or by combining a nucleic acid comprising a nucleotide sequence coding for the amino acid sequence of the peptide or protein with a nucleic acid comprising a nucleotide sequence coding for the amino acid sequence for the antibody or peptide to be used.

The therapeutic or prophylactic agent according to the present invention may be administered to a patient in need thereof orally or parenterally, for the purpose of improving symptoms. For oral administration, a dosage form such as granules, powder, tablets, capsules, liquid drug, syrup, emulsion, suspending agent or elixir may be selected. For parenteral administration, a transnasal agent may be prepared, and a liquid drug, suspension or solid formulation may be selected. An injection may be prepared as a different form of parenteral administration, the injection being selected as subcutaneous injection, intravenous injection, infusion, intramuscular injection, intracerebroventricular injection or intraperitoneal injection. Other formulations used for parenteral administration include suppositories, sublingual agents, percutaneous agents and transmucosal administration agents other than transnasal agents. In addition, intravascular local administration is possible by a mode of addition or coating onto a stent or intravascular obturator.

The dose for an agent for treatment or prevention according to the invention will differ depending on the patient age, gender, body weight and symptoms, the therapeutic effect, the method of administration, the treatment time, or the types of active ingredients in the medical composition, but normally it may be administered in the range of 0.1 mg to 1 g and preferably in the range of 0.5 mg to 200 mg of active compound per administration for adults. However, since the dose will vary depending on a variety of conditions, lower doses than those mentioned above may be sufficient, or doses exceeding these ranges may be necessary. The agent for treatment or prevention according to the invention can exhibit an effect within a short administration period.

XIII. ADMINISTRATION OF ANTIBODIES

Once made, the antibodies of the invention find use in the treatment of cognitive disorders such as tauopathies. As discussed herein, the intracellular accumulation of tau protein has been demonstrated in a variety of neuropathological conditions. The diseases caused by such intracellular accumulation of tau are collectively referred to as "tauopathies" (see Arai, supra, hereby incorporated by reference in its entirety and for the disorders outlined therein). Tauopathies include neurodegenerative diseases such as Alzheimer's disease (AD), corticobasal degeneration (CBD) or corticobasal syndrome (CBS), progressive supranuclear palsy, Pick's disease, argyrophilic grain dementia (argyrophilic grain disease), multiple system tauopathy with dementia (MSTD), chromosome 17-linked frontotemporal dementia with Parkinsonism (FTDP-17), neurofibrillary tangle dementia, diffuse neurofibrillaty tangles with calcification (DNTC), white matter tauopathy with globular glial inclusions (WMT-GGI), frontotemporal lobar degeneration with tau-positive inclusions (FTLD-tau). Tauopathies also include non-neurodegenerative diseases including: infectious diseases such as Economo's encephalitis sequela and subacute sclerosing panencephalitis; and trauma-induced conditions such as boxer's encephalopathy.

The cognitive disorders are defined as a type of intellectual impairment which involves a state where once developed or acquired intellectual function has declined ("New Psychiatry (Nankodo's Essential Well-Advanced Series)" (Japanese book), edited by Kunitoshi Kamijima and Shinichi Niwa, Nankodo Co., Ltd., 2008, pp.69-70), but are deemed in a broad sense to be diseases exhibiting intellectual impairment and/or memory impairment. In the diagnosis of neurodegenerative diseases such as AD, whether the condition is "neurodegenerative" is determined by, e.g., analyzing as to whether neurofibrillary tangle (NFT) exists via histological analysis after death, while physicians diagnose cognitive disorders, especially as neurodegenerative diseases, by using various means, e.g. neuropsychological examinations via inquiries such as Hasegawa's dementia scale for revised (HDS-R) and mini-mental state examination (MMSE); neuropsychological examinations via observations such as clinical dementia rating (CDR) or functional assessment staging (FAST); biochemical examinations based on, e.g., increase in the levels of tau and phosphorylated tau or increase in the level of Aβ in cerebrospinal fluid; and image inspection based on information obtained via, e.g., head CT, head MRI, SPECT, or PET. The therapeutic or prophylactic agent for cognitive disorders according to the present invention is administered to a patient whom a physician has diagnosed as suffering from a cognitive disorder, and has the effect of improving the condition of the patient compared to the state before administration, controlling the progression of the condition via administration, or maintaining the condition at, or recovering the condition to, the state before administration, based on at least one of the diagnosis indexes for neurodegenerative disease The therapeutic or prophylactic agent for cognitive disorders according to the present invention may also have the effect of improving cognitive function, or inhibiting a decline in cognitive function, or maintaining cognitive function, in a human or non-human animal. Examples of such non-human animals should preferably be those expressing tau having high homology with human tau, and include, although not limited to: chimpanzee, macaque, horse, pig, dog, mouse, rabbit, rat, and cat.

XIV. EXAMPLES

A. Example 1

Production of Antibody

1. Mouse Antibody (Parent Antibody)

Mouse antibody Ta1505 was used as a parent antibody of a chimeric antibody and a humanized antibody. The details of mouse antibody Ta1505 are described in the examples of International Publication No. WO2013/180238A. The amino acid sequence of the light chain (L chain) of mouse antibody Ta1505 is defined in SEQ ID NO: 44, and the nucleotide sequence encoding it is defined in SEQ ID NO: 45. The amino acid sequence of the heavy chain (H chain) of mouse antibody Ta1505 is defined in SEQ ID NO: 46, and the nucleotide sequence encoding it is defined in SEQ ID NO: 47.

2. Chimeric Antibody

The chimeric antibody was produced by combining the variable regions of the light chain (L chain) and the heavy chain (H chain) of mouse antibody Ta1505 with, respectively, the constant regions of the L chain and the H chain of human immunoglobulin (Ig) G1(κ). The amino acid sequence of the light chain (L chain) of the chimeric antibody is defined in SEQ ID NO: 48, and the nucleotide sequence encoding it is defined in SEQ ID NO: 49. The amino acid sequence of the heavy chain (H chain) of the chimeric antibody is defined in SEQ ID NO: 50, and the nucleotide sequence encoding it is defined in SEQ ID NO: 51. Throughout the specification, this chimeric antibody is referred to as "the chimeric antibody" or "chimeric antibody Ta1505".

3. Humanized Antibody a. Design of VL and VH

Primary sequences having high homology were selected from the human germline, and humanization was carried out by complementarity determining region (CDR) grafting to design a variety of humanized antibodies.

In detail, human frameworks having high homology were selected from a database; the CDR region of mouse antibody Ta1505 was inserted into each of the frameworks; and amino acid substitutions were carried out for, e.g., reducing immunogenicity while maintaining the activity. Amino acid sequences of various light-chain variable regions (VLs) and heavy-chain variable regions (VHs) were thereby designed. The SEQ ID Numbers of the amino acid sequences of VLs and the SEQ ID Numbers of the nucleotide sequences of genes encoding them are shown in Table 2A, and the SEQ ID Numbers of the amino acid sequences of VHs and the nucleotide sequences of genes encoding them are shown in Table 2B. The alignments of the amino acid sequences of VLs and VHs are shown in FIG. 2A and FIG. 2B, respectively.

TABLE 2A

Light-chain variable region (VL)

| Code name | Amino acid sequence | Nucleotide sequence |
|---|---|---|
| VL15 | SEQ ID NO: 32 | SEQ ID NO: 33 |
| VL36 | SEQ ID NO: 34 | SEQ ID NO: 35 |
| VL46 | SEQ ID NO: 36 | SEQ ID NO: 37 |
| VL47 | SEQ ID NO: 38 | SEQ ID NO: 39 |
| VL48 | SEQ ID NO: 40 | SEQ ID NO: 41 |
| VL50 | SEQ ID NO: 42 | SEQ ID NO: 43 |

TABLE 2B

Heavy-chain variable region (VH)

| Code name | Amino acid sequence | Nucleotide sequence |
|---|---|---|
| VH11 | SEQ ID NO: 18 | SEQ ID NO: 19 |
| VH12 | SEQ ID NO: 20 | SEQ ID NO: 21 |
| VH47 | SEQ ID NO: 22 | SEQ ID NO: 23 |
| VH61 | SEQ ID NO: 24 | SEQ ID NO: 25 |
| VH62 | SEQ ID NO: 26 | SEQ ID NO: 27 |
| VH64 | SEQ ID NO: 28 | SEQ ID NO: 29 |
| VH65 | SEQ ID NO: 30 | SEQ ID NO: 31 | b. Selection of Combination of VL and VH Based on Immunogenicity Score

The VLs and VHs designed by the above-described procedure were combined arbitrarily, and the immunogenicity score (DRB1 score) of each combination was calculated by in vitro assay software Epibase (Lonza). The combinations of VL and VH to be used in the subsequent experiments were selected from the combinations showing low immunogenicity with immunogenicity scores equal to or lower than a predetermined value (DRB1 score: 1500). The selected combinations of VL and VH are shown in Table 3A, and the immunogenicity scores (DRB1 scores) of these combinations are shown in Table 3B.

TABLE 3A

Selected combinations of VL and VH

| | | Heavy chain variable region (VH) | | | | | | |
|---|---|---|---|---|---|---|---|---|
| | | H11 | H12 | H47 | H61 | H62 | H64 | H65 |
| Light chain variable region (VL) | L15 | L15H11 | | | | | | |
| | L36 | L36H11 | | | | | | |
| | L46 | L46H11 | | | | | | |
| | L47 | L47H11 | | | | | L47H64 | L47H65 |
| | L48 | L48H11 | L48H12 | L48H47 | L48H61 | L48H62 | L48H64 | |
| | L50 | L50H11 | | | | | | |

TABLE 3B

Immunogenicity score (DRB1 score)

| | | Heavy chain variable region (VH) | | | | | | |
|---|---|---|---|---|---|---|---|---|
| | | H11 | H12 | H47 | H61 | H62 | H64 | H65 |
| Light chain variable region (VL) | L15 | 1495 | | | | | | |
| | L36 | 1437 | | | | | | |
| | L46 | 1463 | | | | | | |
| | L47 | 1333 | | | | | 1382 | 1426 |
| | L48 | 1417 | 1352 | 1433 | 1383 | 1433 | 1466 | |
| | L50 | 1475 | | | | | | | c. Expression Culture and Purification of Humanized Antibody

For each combination of VL and VH selected by the above-described procedure, genes encoding the amino acid sequences of the VL and the VH were prepared. The VL gene was fused in-frame to a human immunoglobulin kappa L-chain constant region (CL) gene (the amino acid sequence and the nucleotide sequence thereof are defined in SEQ ID NO: 52 and SEQ ID NO: 53, respectively), and the VH gene was fused in-frame to a human immunoglobulin gamma-1 H-chain constant region (CH) gene (the amino acid sequence and the nucleotide sequence thereof are defined in SEQ ID NO: 54 and SEQ ID NO: 55, respectively), such that no mutation or defect should occur at each binding site. The 5'-ends of the VL gene and the VH gene were fused in-frame to, respectively, a signal sequence derived from the human immunoglobulin kappa L-chain gene (the amino acid sequence and the nucleotide sequence thereof are defined in SEQ ID NO: 56 and SEQ ID NO: 57, respectively) and a signal sequence derived from the human immunoglobulin gamma-1 H-chain gene (the amino acid sequence and the nucleotide sequence thereof are defined in SEQ ID NO: 58 and SEQ ID NO: 59, respectively), such that no mutation or defect should occur at each binding site.

The nucleic acid constructs encoding, respectively, the signal sequence-fused L and H chains designed by the above-described procedure were each incorporated into an expression vector for animal cell expression, and then cultured using ExpiCHO (manufactured by Thermo Fisher Scientific K.K.) according to the standard protocol to express antibodies. Each culture was clarified by centrifugation, and the resultant culture supernatant was applied to a protein A affinity column to purify the humanized antibody. The fraction eluted with an acidic solution having a pH of 2.8 to 3.5 was rapidly neutralized, concentrated, and applied to a gel filtration column to remove aggregate. The buffer was changed to phosphate buffered saline (PBS) to collect the main fraction, which was diluted with a solvent into an appropriate concentration and then used in the following tests.

In the following descriptions, each humanized antibody produced by the above-described procedure may be abbreviated using a combination of the code names of its VL and VH. For example, a humanized antibody produced using L15 as the VL and H11 as the VH is referred to as L15H11.

In the following tests, 3% BSA/PBS was used as a solvent for adjusting the concentration of an antibody, without otherwise specified.

B. Example 2

ELISA Analysis of Antigen Peptide Binding Affinity

1. ELISA Analysis of Binding Affinity to Antigen Peptide

Some of the humanized antibodies having combinations of VL and VH shown in Table 3A were analyzed for the binding affinity to an antigen peptide by enzyme-linked immunosorbent assay (ELISA).

A non-phosphorylated tau peptide PD17(Ser413) and a phosphorylated tau peptide PD17P(pSer413), in which Ser413 was phosphorylated, were each diluted with cooled PBS to 1 µg/mL, and the resultant solutions were each dispensed to a plate at 50 µL/well and allowed to stand at 4° C. overnight. The solution was removed, and a blocking buffer (3% bovine serum albumin (BSA)-PBS) was then dispensed at 270 µL/well, and the plate was allowed to stand at 4° C. overnight. After the solution was removed, an antibody solution was diluted in a stepwise fashion with 3% BSA-PBS was then added to the plate at 50 µL/well to allow a reaction at room temperature for 90 minutes. The amino acid sequences of non-phosphorylated tau peptide PD17 (Ser413) and phosphorylated tau peptide PD17P(pSer413) are defined in SEQ ID NO: 60 and SEQ ID NO: 8, respectively.

Each well was washed with Tris-buffered saline with Tween 20 (TBS-T), which contains 0.05% of Tween 20. A goat anti-human IgG-alkaline phosphatase label (manufactured by Sigma-Aldrich Co. LLC.) diluted by 2000-fold with a dilution buffer (3% BSA-PBS) was added to the plate at 50 µL/well to allow a reaction at room temperature for 60 minutes. After washing with TBS-T, a chromogenic solution (1 mg/mL p-nitrophenylphosphate (pNPP) solution) was added to the plate at 100 µL/well for color development for 40 minutes. The absorbance (optical density (OD) value) was measured at a wavelength of 405 nm.

The reactivity was evaluated by determining the ratio of the OD value of each antibody to the OD value of 0.25 nM chimeric antibody, and rating the resultant ratio on the following three-point scale:

+: sufficient reactivity (0.6≤OD ratio),
±: very slight reactivity (0.15<OD ratio<0.6), and
−: no reactivity (OD ratio≤0.15).

Table 4A shows the evaluation results of the reactivity of the antibodies with phosphorylated tau peptide PD17P. Table 4B shows the evaluation results of the reactivity of the antibodies with non-phosphorylated tau peptide PD17. Compared to the chimeric antibody, all the humanized antibodies exhibited higher reactivity with phosphorylated tau peptide PD17P, but lower reactivity with non-phosphorylated tau peptide PD17. These results demonstrate that the humanized antibodies have selective reactivity with the phosphorylated tau peptide.

TABLE 4A

ELISA analysis of reactivity with phosphorylated peptide PD17P

| | | Heavy chain variable region (VH) | | | | | |
|---|---|---|---|---|---|---|---|
| | | VH11 | VH12 | VH47 | VH61 | VH62 | VH64 | VH65 |
| Light chain variable region (VL) | VL15 | + | | | | | | |
| | VL36 | + | | | | | | |
| | VL46 | + | | | | | | |
| | VL47 | | | | | | | + |
| | VL48 | + | + | + | + | + | + | |
| | VL50 | + | | | | | | |

TABLE 4B

ELISA analysis of reactivity with non-phosphorylated peptide PD17

| | | Heavy chain variable region (VH) | | | | | |
|---|---|---|---|---|---|---|---|
| | | VH11 | VH12 | VH47 | H61 | VH62 | VH64 | VH65 |
| Light chain variable region (VL) | VL15 | − | | | | | | |
| | VL36 | − | | | | | | |
| | VL46 | − | | | | | | |
| | VL47 | | | | | | | − |
| | VL48 | − | − | − | − | − | − | |
| | VL50 | − | | | | | | |

2. ELISA Analysis of Selective Binding Affinity to Phosphorylated Tau Peptide Some of the humanized antibodies having combinations of VL and VH shown in Table 3A were analyzed for the selective binding affinity of the anti-tau humanized antibodies to a phosphorylated tau peptide by enzyme-linked immunosorbent assay (ELISA), using chimeric antibody Ta1505 as a reference antibody.

A solution containing 1 µg/mL of non-phosphorylated peptide PD17 or phosphorylated peptide PD17P was dispensed to a plate at 50 µL/well, and allowed to stand at 4° C. overnight. After the solution was removed, a blocking buffer (3% bovine serum albumin (BSA)-PBS) was dispensed at 270 µL/well, and the plate was allowed to stand at 4° C. overnight, to thereby produce plates in which non-phosphorylated peptide PD17 or phosphorylated peptide PD17P was immobilized on each well.

A series of five concentrations of each antibody were prepared by 4-fold serial dilution, starting from an initial concentration of 0.6 µg/mL (4 nM). Each solution was added to a well of the plates at 50 µL/well to allow a reaction at room temperature for one hour. After washing process, a goat anti-human IgG-alkaline phosphatase label (manufactured by Sigma-Aldrich Co. LLC.) was diluted by 2000-fold, and then added to each well at 50 µL/well to further allow a reaction for one hour.

After washing process, 1 mg/mL p-nitrophenylphosphate (pNPP) solution was added to each well at 100 µL/well to allow a reaction for 20 minutes. The absorbance (OD) was measured at a wavelength of 405 nm.

The data of the absorbance OD at the respective concentrations of each prepared antibody were analyzed with SoftMax Pro software Ver.6.5 (Molecular Devices Corporation) to determine the following numeric values A to D, which were assigned to the four parameter logistic regression curve shown below:

$$y = D + \frac{A - D}{1 + \left(\frac{x}{C}\right)^B} \quad \text{(Equation I)}$$

where x represents the concentration of the antibody, and
y represents the absorbance (OD value).

The absorbance OD value of the non-phosphorylated peptide PD17 at a concentration of 1 nM was input to the expression to calculate the concentration x of each antibody corresponding to the OD value. Since the concentration of PD17 was 1 nM, the scale factor of the binding affinity to phosphorylated tau peptide PD17P based on the binding affinity to PD17 for each peptide was calculated by 1/x, and used as an indicator of selective binding affinity to a phosphorylated tau peptide.

Figure 3:
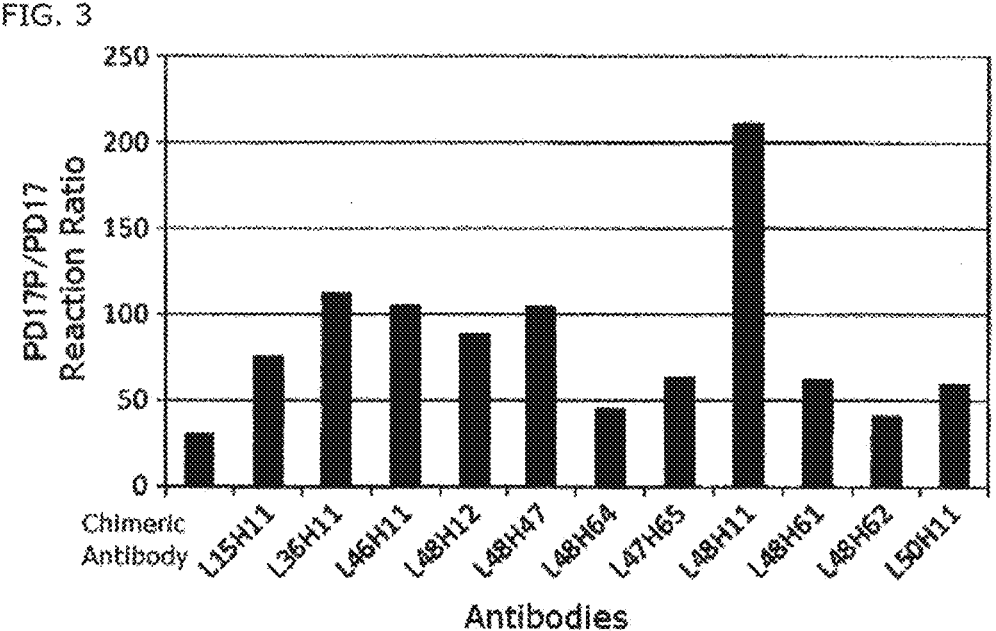
FIG. 3 illustrates the selective binding affinity of several anti-pS413-Tau antibodies for phosphorylated peptide PD17P, relative to non-phosphorylated peptide PD17, in accordance with some embodiments of the disclosure.

The results are shown in the graph of FIG. 3. The binding affinity of chimeric antibody Ta1505 to phosphorylated tau peptide PD17P was 30 times as strong as that to non-phosphorylated peptide PD17. In contrast, the selective binding affinity in humanized antibodies exhibited high selectivity with a scale factor of 40 to 210 times. The results demonstrate that the humanized antibodies have specific binding affinity to the phosphorylated peptide.

3. ELISA Analysis of Selective Binding Affinity to Ser413 Phosphorylation Site Using Phosphorylated Tau Peptide The humanized antibodies having combinations of VL and VH shown in Table 3A were each analyzed for its ability to selectively bind to the Ser413 phosphorylation site among the main phosphorylation sites of the protein, by means of ELISA using a variety of phosphorylated peptides.

Twelve phosphorylated peptides were used as shown in Table 5. The column named "Epitope" indicates the phosphorylated site(s) of 4R2N-type tau protein (for example, "p546" in Peptide No. 1 indicates that the site of Ser46 is phosphorylated epitope, and descriptions of multiple epitopes indicate that one peptide has two or three phosphorylated sites), with the exception that Peptide No. 12 has an epitope including Ser413 site but is not phosphorylated (PD17).

TABLE 5

Peptide for analysis of specific binding to tau protein Ser413 phosphorylation site

| Peptide No. | Epitope | Amino acid sequence (one-letter code) | SEQ ID NO: |
|---|---|---|---|
| 1 | pS46 | H-GLKE(pS)PLQT-OH | 61 |
| 2 | pS199 | H-SGYS(pS)PGSPGC-OH | 62 |
| 3 | pS202 | H-SSPG(pS)PGTPC-OH | 63 |
| 4 | pT212/ pS214 | H-GCGSPGTPGSRSR(pT)P(pS) LPTPPTREPK-OH | 64 |
| 5 | pT217 | H-GC-GSRSRTPSLP(pT) PPTREPKKVAVV-OH | 65 |
| 6 | pT231 | H-KVAVVR(pT)PPKSPS-OH | 66 |
| 7 | pS396/ pS400/ pS404 | H-GC-RENAKAKTDHGAEIVYK(pS) PVV(pS)GDT(pS)PRHL-OH | 67 |
| 8 | pS412 | H-NV(pS)STGSC-OH | 68 |
| 9 | pS412/ pS413 | H-PRHLSNV(pS)(pS)TGSIDMVD-OH | 7 |
| 10 | pS413 | H-PRHLSNVS(pS)TGSIDMVD-OH (PD17P) | 8 |
| 11 | pS409/ pS412/ pS413 | H-PRHL(pS)NV(pS)(pS)TGSIDMVD-OH | 9 |
| 12 | S413 | H-PRHLSNVSSTGSIDMVD-OH (PD17) | 69 |

The twelve peptides shown in Table 5, i.e., Peptides Nos. 1 to 12, or conjugates of these peptides with bovine serum albumin (BSA) or keyhole limpet hemocyanin (KLH), were each diluted with PBS cooled to 4° C. to 1 µg/mL, and the resultant solution was dispensed to a plate at 50 µL/well and allowed to stand at 4° C. overnight. The solution was removed, and a blocking buffer (3% BSA-PBS) was then dispensed at 270 µL/well, and the plate was allowed to stand at 4° C. overnight. After the solution was removed, the purified antibody was diluted with 3% BSA-PBS to 150 ng/mL, and then added to the plate at 50 µL/well to allow a reaction at room temperature for 90 minutes. Each well was washed with Tris-buffered saline (TBS-T) containing 0.05% Tween 20. A goat anti-human IgG (H+L)-alkaline phosphatase label (manufactured by Sigma-Aldrich Co. LLC.) diluted by 2000-fold with a dilution buffer (3% BSA-PBS) was added to the plate at 50 µL/well to allow a reaction at room temperature for 60 minutes. After washing with TBS-T, a chromogenic solution (1 mg/mL pNPP solution) was added to the plate at 100 µL/well for color development for 40 minutes. The absorbance (OD value) was measured at a measurement wavelength of 405 nm and a reference wavelength of 550 nm.

The reactivity was evaluated on the following three-point scale:

+: sufficient reactivity (1.0≤OD value),
±: very slight reactivity (0.5≤OD value<1.0), and
−: no reactivity (OD value<0.5).

The results are shown in Table 6. All the humanized antibodies showed strong binding affinity to only Peptide No. 9 (pSer412/pSer413: PRHLSNV(pS)(pS)TGSIDMVD), Peptide No. 10 (pSer413: PRHLSNVS(pS)TGSIDMVD), and Peptide No. 11 (pSer409/pSer412/pSer413: PRHL(pS) NV(pS)(pS)TGSIDMVD), but did not bind to the other peptides, of which the site corresponding to Ser413 of tau protein was not phosphorylated. The pattern and the strength of the binding were substantially the same as those of the chimera (chimeric antibody Ta1505). These results indicate that the humanized antibodies have binding affinity specific to tau protein having a phosphorylated Ser413 site.

TABLE 6

Results of ELISA analysis of reactivity with various phosphorylated tau peptides

| Antibody | Peptide No. in Table 5 | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Chimera | − | − | − | − | − | − | − | − | + | + | + | − |
| L15H11 | − | − | − | − | − | − | − | − | + | + | + | − |
| L36H11 | − | − | − | − | − | − | − | − | + | + | + | − |
| L46H11 | − | − | − | − | − | − | − | − | + | + | + | − |
| L47H11 | − | − | − | − | − | − | − | − | + | + | + | − |
| L48H11 | − | − | − | − | − | − | − | − | + | + | + | − |
| L50H11 | − | − | − | − | − | − | − | − | + | + | + | − |
| L48H12 | − | − | − | − | − | − | − | − | + | + | + | − |
| L48H47 | − | − | − | − | − | − | − | − | + | + | + | − |
| L48H61 | − | − | − | − | − | − | − | − | + | + | + | − |
| L48H62 | − | − | − | − | − | − | − | − | + | + | + | − |
| L47H64 | − | − | − | − | − | − | − | − | + | + | + | − |
| L48H64 | − | − | − | − | − | − | − | − | + | + | + | − |
| L47H65 | − | − | − | − | − | − | − | − | + | + | + | − |

C. Example 3

ELISA Analysis of Binding Affinity to Antigen Protein

Some of the humanized antibodies having combinations of VL and VH shown in Table 3A were analyzed for the binding affinity to an antigen protein by ELISA.

In order to prepare a phosphorylated tau protein pTau, tau protein 4R2N was expressed in insect cells using a baculovirus system. In addition, in order to prepare a hyperphosphorylated tau protein hpTau, a recombinant baculovirus capable of simultaneously expressing a tau protein and GSK3β was produced.

In the production of a recombinant baculovirus, pFastBac1 and pFastBac Dual vectors were used. For the phosphorylated tau protein pTau, a cDNA encoding tau protein 4R2N having a His-tagged C-terminal was inserted into pFastBac1. For the hyperphosphorylated tau protein hpTau, a cDNA encoding tau protein 4R2N having a His-tagged C-terminal and a cDNA encoding GSK3β were inserted into pFastBac Dual. The amino acid sequence and the nucleotide sequence of His-tagged tau protein 4R2N are defined in SEQ ID NOs: 70 and 71, respectively. The amino acid sequence and the nucleotide sequence of GSK3β are defined in SEQ ID NOs: 72 and 73, respectively.

The resultant vectors were each introduced into cell line Sf9 by lipofection, and the cells were cultured to prepare recombinant baculoviruses. The resultant recombinant baculoviruses were then used to infect cell line Sf9 or Tn5, to thereby express the phosphorylated tau protein (pTau) and the hyperphosphorylated tau protein (hpTau).

The cells expressing the desired protein were collected, and subjected to sonication and centrifugation to obtain a cell lysate, which was then applied to a Ni-NTA column to purify the tau protein. The concentration of the purified tau protein was determined by bicinchoninic acid (BCA) assay, using bovine serum albumin (BSA) as a standard sample.

The resultant hyperphosphorylated tau protein (hpTau) and phosphorylated tau protein (pTau) were diluted with cooled PBS to 1 μg/mL, and the diluted solutions were dispensed to a plate at 50 μL/well and allowed to stand at 4° C. overnight. After the solutions were removed, a blocking buffer (3% BSA-PBS) was then dispensed at 270 μL/well, and the plate was allowed to stand at 4° C. overnight. After removal of the buffer solution, a series of antibody solutions prepared via serial dilution with 3% BSA-PBS was added to the plate at 50 μL/well to allow a reaction at room temperature for 90 minutes.

The wells were then washed with Tris-buffered saline (TBS-T) containing 0.05% Tween 20. A goat anti-human IgG-alkaline phosphatase label (manufactured by Sigma-Aldrich Co. LLC.) diluted by 2000-fold with a dilution buffer (3% BSA-PBS) was added to the plate at 50 μL/well to allow a reaction at room temperature for 60 minutes. After washing with TBS-T, a chromogenic solution (1 mg/mL pNPP solution) was added to the plate at 100 μL/well for color development for 40 minutes. The absorbance (OD value) was measured at a wavelength of 405 nm.

The reactivity was evaluated by determining the ratio of the OD value of each antibody to the OD value of 0.25 nM chimeric antibody, and rating the resultant ratio on the following three-point scale:
+: sufficient reactivity (0.6≤OD ratio),
±: very slight reactivity (0.15<OD ratio<0.6), and
−: no reactivity (OD ratio≤0.15).

Table 7A shows the results of the evaluated reactivity of the humanized antibodies with hyperphosphorylated tau protein hpTau. Table 7B shows the results of the evaluated reactivity of the humanized antibodies with phosphorylated tau protein pTau. The results demonstrate that all the humanized antibodies have high reactivity with both hyperphosphorylated tau protein hpTau and phosphorylated tau protein pTau, compared to that of the chimeric antibody.

TABLE 7A

Result of ELISA analysis of reactivity with hyperphosphorylated tau protein hpTau

| | VH11 | VH12 | VH47 | VH61 | VH62 | VH64 | VH65 |
|---|---|---|---|---|---|---|---|
| VL15 | + | | | | | | |
| VL36 | + | | | | | | |
| VL46 | + | | | | | | |
| VL47 | | | | | | | + |
| VL48 | + | + | + | + | + | + | |
| VL50 | + | | | | | | |

TABLE 7B

Result of ELISA analysis of reactivity with phosphorylated tau protein pTau

| | VH11 | VH12 | VH47 | VH61 | VH62 | VH64 | VH65 |
|---|---|---|---|---|---|---|---|
| VL15 | + | | | | | | |
| VL36 | + | | | | | | |
| VL46 | + | | | | | | |
| VL47 | | | | | | | + |
| VL48 | + | ± | + | + | + | + | |
| VL50 | + | | | | | | |

D. Example 4

Analysis of Binding Affinity by SPR

Some of the humanized antibodies having combinations of VL and VH shown in Table 3A were subjected to binding affinity analysis by surface plasmon resonance (SPR) using chimeric antibody Ta1505 as a reference antibody.

The hyperphosphorylated tau protein 4R2N (hpTau: see Example 3) was used as an antigen protein, and a non-phosphorylated tau protein produced by *Escherichia coli* (Tau: His-tagged non-phosphorylated tau protein 4R0N: ATGen Co. Ltd., Cat. No. ATGP0795) was used as a negative control. Antigen peptides used were a monophosphorylated tau peptide (1× P), in which only Ser413 was phosphorylated, and a triphosphorylated tau peptide (3× P), in which Ser409 and Ser412 were further phosphorylated in addition to Ser413. The amino acid sequences of these peptides are shown in Table 8. A negative control peptide used was a non-phosphorylated tau peptide (Non P), whose amino acid sequence is also shown in Table 8. The amino acid sequence of the His-tagged non-phosphorylated tau protein 4R0N is defined in SEQ ID NO: 74. The amino acid sequences of the monophosphorylated tau peptide 1× P, the triphosphorylated tau peptide 3× P, and the non-phosphorylated tau peptide Non P are defined in SEQ ID NOs: 75, 76, and 77, respectively.

TABLE 8

Antigen peptide used in SPR

| Code name | Amino acid sequence (one-letter code) | SEQ ID NO: |
|---|---|---|
| 1×P | TSPRHLSNVS(pS)TGSIDMVDSPC | 75 |
| 3×P | TSPRHL(pS)NV(pS)(pS)TGSIDMVDSPC | 76 |
| Non P | TSPRHLSNVSSTGSIDMVDSPC | 77 |

The binding affinities of the hyperphosphorylated tau protein 4R2N (hpTau), non-phosphorylated tau protein 4R0N, monophosphorylated tau peptide 1× P, triphosphorylated tau peptide 3× P, and non-phosphorylated tau peptide Non P with each antibody were measured with an SPR system Biacore T200 (GE Healthcare Japan), in accordance with the instruction manual for evaluation attached to the system.

The binding affinity was measured by a method including: preparing an NTA sensor chip (including a carboxymethyl dextran layer to which nitrilotriacetic acid (NTA) was already immobilized: code No. BR-1005-32); immobilizing each of the above-mentioned peptides fused with His-tag and each of the antigen peptides shown in Table 8 on the sensor chip by covalent bonds through an amine coupling reaction using an amine coupling kit (GE Healthcare Japan, code No. BR-1006-33); and measuring the binding kinetics of antibodies to the immobilized proteins and peptides.

The His-tagged hpTau or Tau proteins were each immobilized on a sensor chip using an HBS-N buffer (code No. BR-1003-69) as the immobilization reaction solution and allowing a nickel chloride solution to react with the NTA sensor chip for bonding Ni to NTA. Subsequently, the sensor chip was activated with a mixed solution of N-ethyl-N'-(3-dimethylaminopropyl)-carbodiimide hydrochloride (1-ethyl-3-(3-dimethylaminopropyl)carbodiimide hydrochloride: EDC) and N-hydroxysuccinimide (NETS). A solution of each of the His-tagged proteins, adjusted to a concentration of 100 to 500 ng/mL with a 4-(2-hydroxyethyl)-1-piperazineethanesulfonic acid (HEPES) buffer (0.01 M HEPES, 150 mM KCl, 2 mM DTT, 1 mM EDTA, pH 7.2), was applied to the sensor chip, whereby the protein was immobilized on the sensor chip through covalent bonds with the Ni-NTA. The remaining active NHS was blocked with ethanolamine, and Ni ions were removed with an EDTA solution (Ni-affinity amine coupling: see International Publication No. WO2005/022156). The antigen peptides (1× P, 3× P, and Non P) were each immobilized on a sensor chip by activating the NTA sensor chip with a mixed solution of N-ethyl-N'-(3-dimethylaminopropyl)-carbodiimide (EDC) hydrochloride and N-hydroxysuccinimide (NHS), and then applying a solution of the antigen peptide diluted with a 10 mM sodium acetate buffer (pH: 4 to 4.5) to 1 to 10 μM to the sensor chip, whereby the peptide was covalently bound to the sensor chip. The remaining active NHS was blocked with ethanolamine. Thus, sensor chips immobilized respectively with the proteins and peptides mentioned above were produced.

A CAPS buffer (pH 10.5) was applied to these sensor chips at 37° C. to stabilize the protein- or peptide-immobilized surfaces of the sensor chips. A solution of each antibody, prepared with a HEPES buffer (pH 7.2) as a specific binding reaction solution, was applied to the sensor chip surface at concentrations ranging from 0.2 to 1 nM (around the estimated binding dissociation constant [KD]) for 150 seconds (uniform in the same evaluation) for a reaction, and the binding kinetics were measured. The resultant data were analyzed using Biacore analysis software (Biacore T200 Evaluation Software, Version 3.0).

The binding kinetics of each antibody was corrected by subtracting the binding kinetics of the non-phosphorylated protein 4R0N to the sensor chip as a negative control from the binding kinetics of the antigen protein 4R2N (hpTau) to the sensor chip. The binding kinetics of each antigen peptide was corrected by subtracting the binding kinetics of the non-phosphorylated peptide Non P to the sensor chip as a negative control from the binding kinetics of each of the antigen peptides 1×P and 3×P. No binding of each antibody to the non-phosphorylated tau protein 4R0N or the non-phosphorylated peptide Non P was observed within the range of sample concentrations subjected to measurement.

Table 9A shows the binding activities of humanized antibodies to the phosphorylated tau protein 4R2N (hpTau). Table 9B shows the results of binding activities of humanized antibodies to the monophosphorylated tau peptide 1×P and the triphosphorylated tau peptide 3×P. The results demonstrate that each humanized antibody exhibited high binding activity to all of the hyperphosphorylated tau protein hpTau, monophosphorylated tau peptide 1×P, and triphosphorylated tau peptide 3×P.

TABLE 9A

Binding activity of humanized antibodies to phosphorylated tau protein (hpTau) (1:1 binding model)

| Sample | hpTau KD(M) |
|---|---|
| Chimera | 1.70E−10 |
| L15H11 | 1.50E−10 |
| L36H11 | 1.40E−10 |
| L46H11 | 1.30E−10 |
| L47H11 | 1.80E−10 |
| L48H12 | 1.60E−10 |
| L48H47 | 1.40E−10 |
| L48H64 | 1.00E−10 |
| L47H65 | 1.50E−10 |
| L48H11 | 1.40E−10 |
| L48H61 | 1.70E−10 |
| L48H62 | 1.30E−10 |
| L50H11 | 1.50E−10 |

TABLE 9B

Binding activity of humanized antibodies to phosphorylated peptides (1 × P, 3 × P) (1:1 binding model)

| Sample | 1 × P KD(M) | 3 × p KD(M) |
|---|---|---|
| Chimera | 4.60E−11 | 2.20E−11 |
| L15H11 | 3.90E−11 | 1.90E−11 |
| L36H11 | 4.70E−11 | 1.90E−11 |
| L46H11 | 4.80E−11 | 1.70E−11 |
| L47H11 | 6.20E−11 | 2.20E−11 |
| L48H12 | 6.50E−11 | 2.70E−11 |
| L48H47 | 5.80E−11 | 2.20E−11 |
| L48H64 | 5.00E−11 | 1.50E−11 |
| L47H65 | 5.40E−11 | 1.90E−11 |
| L48H11 | 6.00E−11 | 2.00E−11 |
| L48H61 | 1.80E−10 | 2.40E−11 |
| L48H62 | 5.20E−11 | 2.00E−11 |
| L50H11 | 4.80E−11 | 1.90E−11 |

E. Example 5

Binding Affinity Analysis of pSer413-Tau in AD Patient Brain Homogenate

Among the humanized antibodies having combinations of VL and VH shown in Table 3A, L15H11, L46H11, and L47H65 were evaluated for binding affinity to Ser413 phosphorylated tau protein (pSer413-Tau) derived from an Alzheimer's disease (AD) patient clinical sample in a liquid phase, using a mouse antibody Ta1505 and a chimeric antibody as reference antibodies.

The humanized antibodies, mouse antibody, and chimeric antibody were each biotinylated using N-hydroxysuccinimide-LC-biotin (NHS-LC-biotin) (Thermo Fisher Scientific K.K.), followed by dialysis with PBS.

Frozen hippocampus tissue (160 mg) from the brain of an AD patient at Braak stage V/VI was added to 0.8 mL of TBS-I (Tris-buffered saline, protease inhibitor cocktail, phosphatase inhibitor cocktail) and sonicated in iced water. The sonicated solution was centrifuged at 3000×g at 4° C. for 10 minutes, and the supernatant was collected and further ultracentrifuged at 100000×g at 4° C. for 15 minutes to obtain a brain homogenate. Innotest pTau (pT181) kit (Fijirebio Inc.) was used as an ELISA system of Ser413 phosphorylated tau protein (pSer413-Tau), but the biotinylated antibody included in the kit (labelled as CONJ1) was replaced with the biotinylated antibodies produced above.

Each of the biotinylated antibodies produced above was made into a solution at a concentration of 0.1 nM, and added to an HT7 antibody immobilized MT plate (included in the kit), along with a 1000-fold dilution of the brain homogenate. The resultant sample was mixed and incubated at 4° C. overnight. On the following day, the plate was washed, and an HRP-labeled streptavidin (included in the kit as CONJ2) was added to the plate, followed by incubation for one hour. After washing, a color reagent TMB was added, followed by incubation under light-shielding at room temperature for 30 minutes. The reaction was then stopped with a reaction terminator solution (included in the kit as STOP solution), and absorbance at a wavelength of 450 nm was measured.

Figure 4:
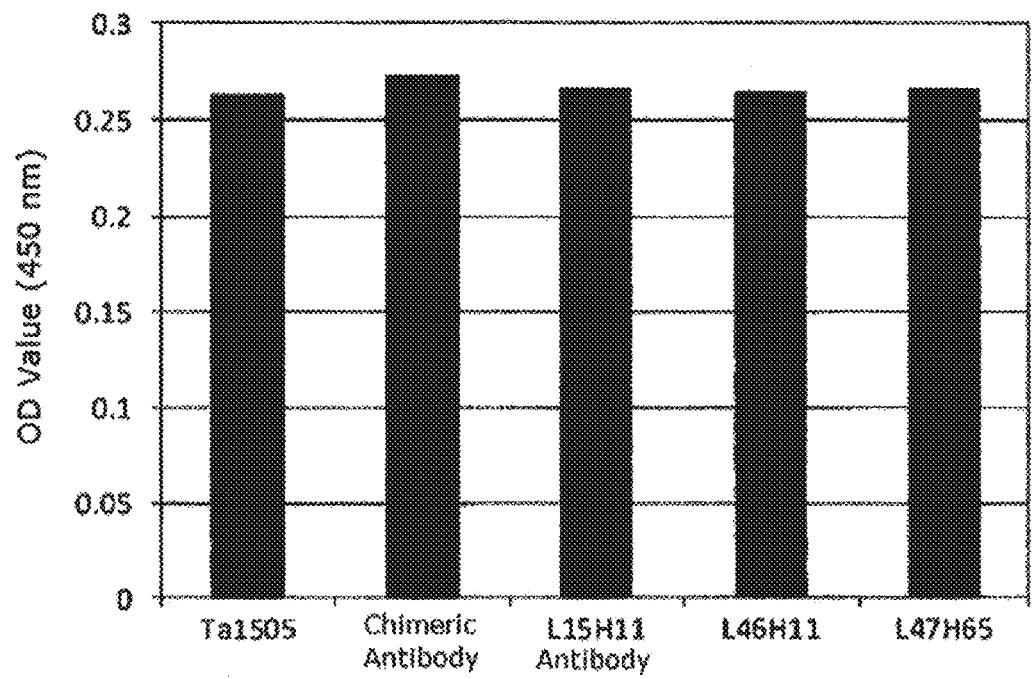
FIG. 4 illustrates the binding affinity of several anti-pS413-Tau antibodies for phosphorylated Tau in brain homogenate from an Alzheimer's patient, in accordance with some embodiments of the disclosure.

The results are shown in FIG. 4. As shown in the graph of FIG. 4, humanized antibodies L15H11, L46H11, and L47H65 all exhibited high binding affinity to the Ser413 phosphorylated tau protein (pSer413-Tau) derived from the AD patient clinical sample.

F. Example 6

Test for Kinetics in Blood

Five initial humanized antibody variants were tested for pharmacokinetics in normal mice, in comparison with a commercially available antibody Herceptin (Genentech, south San Francisco, Calif.) and the chimeric Ta1505 antibody. The light chain and heavy chain of each humanized antibody variant is summarized in Table 10 below.

TABLE 10

Light Chain and Heavy Chain of Some Initial Humanized Antibody Variants

| Antibody | LC | HC |
|---|---|---|
| Variant 2 | L1 (SEQ ID NO: 130) | H2 (SEQ ID NO: 134) |
| Variant 5 | L2 (SEQ ID NO: 131) | H1 (SEQ ID NO: 133) |
| Variant 6 | L2 (SEQ ID NO: 131) | H2 (SEQ ID NO: 134) |
| Variant 9 | L3 (SEQ ID NO: 132) | H1 (SEQ ID NO: 133) |
| Variant 10 | L3 (SEQ ID NO: 132) | H2 (SEQ ID NO: 134) |

The antibodies were intraperitoneally injected at a dose of 10 mg/kg to 11-week-old male C57BL/6J mice (Charles River Laboratories Japan, Inc.). Plasma was obtained from the blood collected 1, 3, 8, 24, and 72 hours post dose. The sample size was 2 animals per antibody.

Sandwich ELISA with anti-human IgG polyclonal antibodies was used to determine plasma antibody concentrations. A calibration curve was plotted by serial dilution of each antibody with mouse plasma.

Plasma was diluted by a factor of 1,000 and the antibody concentration was measured.

A 1 μg/mL PBS solution of goat anti-human IgG (Fc) polyclonal antibodies was pipetted into a 96-well plate (MaxSorp (NUNC)) and allowed to stand at 4° C. overnight. Then, blocking was accomplished with 3% BSA/PBS to prepare a plate with immobilized goat anti-human IgG (Fc) polyclonal antibodies. Mouse plasma was used to serially dilute the antibodies and obtain the standard substance. The plasma and standard substance were diluted with 3% BSA/PBS and pipetted into the plate with immobilized goat anti-human IgG (Fc) polyclonal antibodies at 50 μL/well. The mixtures were allowed to react at room temperature for 1.5 hours, and the plate was then washed with TBS-T (TBS, 0.05% Tween 20). Then, a solution prepared by diluting alkaline phosphatase-labeled anti-human IgG (H+L) polyclonal antibodies (Southern Biotech, Cat #2087-04) by a factor of 2000 with 3% BSA/PBS was pipetted at 50 μL/well, and the reaction was allowed to proceed for 1 hour at room temperature. Next, the plate was washed with TBS-T, the coloring reagent was added at 100 μL/well, and the plate was incubated for 1 hour at room temperature. Thereafter, a plate reader was used to measure absorbance at 405 nm and 550 nm.

A calibration curve was plotted with standard substance and used to calculate plasma antibody concentrations. The results are shown in FIG. 5A.

The initial humanized variants tested (Variant 2, 5, 6, 9, and 10) showed a rapid decrease of plasma concentration at 8 hours after administration, compared to the level of Herceptin and the chimeric antibody, which stayed high and stable up to 3 days after injection. These initial humanized antibodies presented a shorter half-life and poor PK profile in comparison with the chimeric antibody, which is likely attributable to the high pI values of these variants. Further improvement was required to reach the PK of the chimeric antibody.

Among the humanized antibodies having combinations of VL and VH shown in Table 3A, L15H11, L46H11, and L47H65 were subjected to a test for kinetics in blood. The reference antibodies used were chimeric antibody Ta1505 and known humanized antibodies used in clinical trial studies for AD treatment, which were produced by recombinant expression based on the amino acid sequence information disclosed in patent information or database information. Specifically, the database of the international ImMunoGeneTics information system (registered trademark) (IMGT) (http://www.imgt.org) was referred to for Solanezumab (anti-A□ antibody, Eli Lilly and Company); the amino acid sequence of VH2Vk3 disclosed in WO2014/200921 A1 was used for IPN007 (anti-Tau N-terminal antibody, Bristol-Myers Squibb iPierian); and the amino acid sequence of VH32VL21 disclosed in WO2015/091656A1 was used for MAb3221 (anti-Tau-pS422 antibody, Roche Diagnostics K.K.).

Each of the antibodies was intraperitoneally administered to 11-week old male C57BL/6J mice (Charles River Laboratories Japan, Inc.) at a concentration of 10 mg/kg each. Blood was drawn at 1, 3, 8, and 24 hours, and subsequently on the 3rd and 7th day after the administration to collect plasma. Each antibody was tested in triplicate (N=3).

The concentration of the antibody in plasma was measured by sandwich ELISA using an anti-human polyclonal antibody. Specifically, a PBS solution containing 1 pg/mL goat anti-human IgG (Fc) polyclonal antibody (Southern Biotech) was added to a 96-well plate (Max Sorp (NUNC)) for immobilization at 4° C. overnight, followed by blocking with 3% BSA-PBS to thereby produce a goat anti-human IgG (Fc) polyclonal antibody-immobilized plate.

Separately, a series of standard antibody samples of known concentrations were prepared by serial dilution of each antibody with plasma taken from a mouse to which the antibody was not administered, and measured for preparation of a calibration curve.

The plasma samples and the standard samples to be measured were each diluted by 10000-fold, and added to a goat anti-human IgG (Fc) polyclonal antibody-immobilized plate at 50 μL/well for reaction at room temperature for one hour and 30 minutes, and the plate was then washed with TBS-T (Tris-buffered saline, 0.05% Tween 20). Subsequently, a solution of alkaline phosphatase-labeled anti-human IgG (H+L) polyclonal antibody (Southern Biotech) diluted by 2000-fold with 3% BSA-PBS was added to the plate at 50 μL/well to allow a reaction at room temperature for one hour. After washing with TBS-T, a chromogenic solution (1 mg/mL pNPP solution) was added to the plate at 100 μL/well, followed by incubation at room temperature for one hour. The absorbance was then measured with a plate reader at a measurement wavelength of 405 nm and a reference wavelength of 550 nm. A calibration curve was prepared based on the measurement results of the standard samples, and the antibody concentration in each plasma sample was calculated using the calibration curve.

FIG. 5B is a graph showing changes in concentrations of antibodies in plasma over time. As obvious from the graph, humanized antibodies L15H11 (LC SEQ ID NO:32 HC SEQ ID NO:18), L46H11 (LC SEQ ID NO:36, HC SEQ ID NO:18), and L47H65 (LC SEQ ID NO:38, HC SEQ ID NO:30) (all using human IgG1 (SEQ ID NO:135) and human kappa (SEQ ID NO:79) showed substantially the same kinetics in blood as that of chimeric antibody Ta1505. The kinetics of these humanized antibodies L15H11, L46H11, and L47H65 in blood were comparable to those of known humanized antibodies IPN007 and MAb3221, and significantly superior to those of known humanized antibody Solanezumab.

G. Example 7

Analysis of Intracerebral Migration

A study was conducted to analyze the brain concentration of the humanized variants with improved plasma pharmacokinetics.

Blood was collected from the mice injected with the parent mouse antibody, the chimeric antibody, or the humanized antibody variants (L15H11, L36H11, L46H11, L48H12, L48H47, L48H64, L47H65, or L48H11) 1 week after injection of the antibodies. Next, the animals were anesthetized with a 3-anesthetic cocktail, laparotomized, and exsanguinated via the abdominal aorta. Then, brain tissue was collected. This collected brain tissue was divided into left and right hemispheres, frozen on dry ice/ethanol, and stored at −80° C. Each frozen hemisphere was weighed and transferred to a 2 mL tube. Then, 0.8 mL of TBS-I (Tris Buffered Saline, protease inhibitor cocktail and phosphatase inhibitor cocktail) was added, and the mixture was sonicated in ice water. The sonicated mixture was centrifuged at 3000×g and 4° C. for 10 minutes, and the supernatant was collected. The supernatant was further centrifuged at 100,000×g and 4° C. for 15 minutes to obtain a brain homogenate.

A 10 μg/mL PBS solution of goat anti-human IgG (Fc) polyclonal antibodies was pipetted into a 96-well plate (MaxSorp (NUNC)) and allowed to stand at 4° C. overnight. Then, blocking was accomplished with 3% BSA/PBS to prepare a plate with immobilized goat anti-human IgG (Fc) polyclonal antibodies. Brain homogenate obtained from mice not injected with antibodies was used to serially dilute the antibodies and to obtain the standard sub stance.

The brain homogenates and standard substance were diluted by a factor of 10 and pipetted into the plate with immobilized goat anti-human IgG (Fc) polyclonal antibodies at 50 μL/well. The mixtures were allowed to react at room temperature for 2 hours, and the plate was then washed with TBS-T (TBS, 0.025% Tween 20). Then, a solution prepared by diluting alkaline phosphatase-labeled anti-human IgG (H+L) polyclonal antibodies (Sigma, Cat #SAB3701337-1MG) by a factor of 2000 with 3% BSA/PBS was pipetted at 50 μL/well, and the reaction was allowed to proceed for 1 hour at room temperature. Next, the plate was washed with TBS-T, the coloring reagent pNPP (Sigma, Cat #P7998) was added at 100 μL/well, and the plate was incubated for 1 hour at room temperature. Thereafter, a plate reader was used to measure absorbance at 405 nm and 550 nm.

A calibration curve was plotted with standard substance and used to calculate the antibody concentrations in the brain homogenate. The antibody concentration per brain weight (whole brain volume) was determined and the ratio to the plasma concentration was calculated.

FIG. 6A demonstrates that the humanized antibody variants with good pharmacokinetics (e.g., L15H11, L46H11, and L47H65 according to FIG. 5B) had improved concentration in the brain.

Intracerebral migration of each of the humanized antibodies L15H11, L46H11, and L47H65 was analyzed, using chimeric antibody Ta1505 and known humanized antibodies Solanezumab, IPN007, and MAb3221, which were used in clinical trial studies for AD treatment, as reference antibodies.

One week after the administration of each antibody in Example 6, blood was drawn from mice, which were then subjected to laparotomy under anesthesia by three types of mixed anesthetic agents. After death from exsanguination from the abdominal vena cava, the brain tissue was collected. The collected brain tissue was divided into right and left hemispheres, which were frozen in dry ice ethanol and stored at −80° C. Each of the frozen hemispheres was weighed and transferred to a 2-mL tube, to which 0.8 mL of TBS-I (Tris-buffered saline, protease inhibitor cocktail, and phosphatase inhibitor cocktail) was added. Each hemisphere was then sonicated in iced water. The sonicated solution was centrifuged at 3000×g at 4° C. for 10 minutes, and the supernatant was collected and further ultracentrifuged at 100000×g at 4° C. for 15 minutes to obtain a brain homogenate.

The antibody level in the brain homogenate was measured by antigen ELISA using an anti-human polyclonal antibody. Specifically, a PBS solution containing 10 µg/mL of goat anti-human IgG Fc was added to a 96-well plate (Max Sorp (NUNC)) for immobilization at 4° C. overnight, followed by blocking with 3% BSA-PBS to thereby produce an immobilized plate.

Separately, a series of antibody standard samples of known concentrations were prepared by serial dilution of each antibody with a brain homogenate taken from a mouse to which the antibody was not administered, and measured for preparation of a calibration curve.

The brain homogenates and the standard samples to be measured were each diluted by 10-fold with 0.1% skimmed milk-3% BSA-PBS, and added to the PD17(P)-immobilized plate at 50 µL/well for reaction at room temperature for 2 hours. The plate was then washed with TBS-T (TBS, 0.05% Tween 20). Subsequently, a solution of alkaline phosphatase-labeled anti-human IgG (H+L) polyclonal antibody (Sigma-Aldrich Co. LLC., Cat No. SAB3701337: 1 mg) diluted by 2000-fold with 0.1% skimmed milk-3% BSA-PBS was added to the plate at 50 µL/well to allow a reaction at room temperature for one hour. After washing of the plate with TBS-T, pNPP (Sigma-Aldrich Co. LLC., Cat No. P7998: 100 mL) was added as a chromogenic substrate at 100 µL/well, followed by incubation at room temperature for one hour. The absorbance was then measured with a plate reader at a measurement wavelength of 405 nm and a reference wavelength of 550 nm. A calibration curve was prepared based on the measurement results of the standard samples, and the antibody level in each brain homogenate sample was determined using the calibration curve, and evaluated as the antibody level in the brain.

In addition, the antibody level in plasma was determined using blood collected before the laparotomy in the same manner as in Example 6, and the ratio of the antibody level in the brain to that in the plasma was calculated.

FIG. 6B is a graph showing the ratio of the level of each antibody in the brain to the level of the corresponding antibody in the plasma. The ratios of the antibody concentrations in the brain to the antibody concentrations in the plasma of humanized antibodies L15H11, L46H11, and L47H65 were high compared to those of chimeric antibody Ta1505 and known humanized antibodies IPN007, MAb3221, and Solanezumab. The results indicate that these humanized antibodies have high migration to the brain.

Example 8

Further Development of Selective Humanized Antibodies

Further mutations were introduced to the CDR1 sequence of VL46 to remove a deamidation hotspot and/or to revert the CDR sequence to the parent mouse sequence. Table 11 summarizes the mutations introduced to VL46 CDR1.

TABLE 11

| Mutations Introduced in VL46 CDR1 | |
|---|---|
| Mutation | Purpose |
| VL46_G34A (SEQ ID NO: 105) | Remove deamidation |
| VL46_G34S (SEQ ID NO: 106) | Remove deamidation |
| VL46_G34T (SEQ ID NO: 107) | Remove deamidation |
| VL46_N33Q (SEQ ID NO: 108) | Remove deamidation |
| VL46_N33Q_G34A (SEQ ID NO: 109) | Remove deamidation |
| VL46_N33D (SEQ ID NO: 110) | Mimic full deamidation |
| VL46_N33S (SEQ ID NO: 111) | Remove deamidation |
| VL46_N33T (SEQ ID NO: 112) | Remove deamidation |
| VL46_S28N (SEQ ID NO: 113) | Revert LC CDR1 to mouse |
| VL46_G34A_S28N (SEQ ID NO: 114) | Remove deamidation and revert LC CDR1 to mouse |

In addition, different IgG isotypes including IgG1 and IgG4 with S228P mutation were tested in the newly generated humanized antibody variants. Table 12 summarizes the light chain and the heavy chain of the newly generated humanized antibody variants along with the parent mouse antibody and the chimeric antibody.

TABLE 12

| Light Chain and Heavy Chain of Specific Antibodies | |
|---|---|
| Mouse × [MAPT_H] mAb (Ta1505) IgG2a/Kappa (HY) | ms IgG2a |
| Mouse Human Chimera × [MAPT_H] mAb (Ta1505) IgG1/Kappa (CX) | chim. IgG1 |
| Mouse Human Chimera × [MAPT_H] mAb (Ta1505) IgG4S228P/Kappa (CX) | chim. IgG4 |
| Humanized × [MAPT_H] mAb (Ta1505 VL46/VH11) IgG1/Kappa (CX) | hu VL46/VH11 IgG1 |
| Humanized × [MAPT_H] mAb (Ta1505VL46/VH11) IgG4S228P/Kappa (CX) | hu VL46/VH11 IgG4 |
| Humanized × [MAPT_H] mAb (Ta1505-VL46_G34A/VH11) IgG1/Kappa (CX) | hu VL46/VH11 G34A IgG1 |
| Humanized × [MAPT_H] mAb (Ta1505-VL46_G34A/VH11) IgG4 S228P/Kappa (CX) | hu VL46/VH11 G34A IgG4 |
| Humanized × [MAPT_H] mAb (Ta1505-VL46_G34S/VH11) IgG4 S228P/Kappa (CX) | hu VL46/VH11 G34S IgG4 |
| Humanized × [MAPT_H] mAb (Ta1505-VL46_G34T/VH11) IgG4 S228P/Kappa (CX) | hu VL46/VH11 G34T IgG4 |
| Humanized × [MAPT_H] mAb (Ta1505-VL46_N33Q/VH11) IgG4 S228P/Kappa (CX) | hu VL46/VH11 N33Q IgG4 |
| Humanized × [MAPT_H] mAb (Ta1505-VL46_N33Q_G34A/VH11) IgG4S228P/Kappa (CX) | hu VL46/VH11 N33Q G34A IgG4 |
| Humanized × [MAPT_H] mAb (Ta1505-VL46_N33D/VH11) IgG4 S228P/Kappa (CX) | hu VL46/VH11 N33D IgG4 |
| Humanized × [MAPT_H] mAb (Ta1505-VL46_N33S/VH11) IgG4 S228P/Kappa (CX) | hu VL46/VH11 N33S IgG4 |

TABLE 12-continued

Light Chain and Heavy Chain of Specific Antibodies

| | |
|---|---|
| Humanized x [MAPT_H] mAb (Ta1505-VL46_N33T/VH11) IgG4 S228P/Kappa (CX) | hu VL46/VH11 N33T IgG4 |
| Humanized x [MAPT_H] mAb (Ta1505-VL46/VH11A64D) IgG4 S228P/Kappa (CX) | hu VL46/VH11 A64D IgG4 |
| Humanized x [MAPT_H] mAb (Ta1505-VL46S28N/VH11) IgG4 S228P/Kappa (CX) | hu VL46/VH11 S28N IgG4 |
| Humanized x [MAPT_H] mAb (Ta1505 VL47/VH65) IgG1/Kappa (CX) | hu VL47/VH65 IgG1 |
| Humanized x [MAPT_H] mAb (Ta1505-VL46_G34A_S28N/VH11) IgG1/Kappa (CX) | hu VL46/VH11 G34A S28N IgG1 |
| Humanized x [MAPT_H] mAb (Ta1505-VL46 G34A S28N/VH11) IgG4 S228P/Kappa (CX) | hu VL46/VH11 G34A S28N IgG4 |

H. Example 9

Biacore™ Binding Analysis of the Newly Generated Humanized Antibody Variants Binding affinities of the newly generated humanized antibody variants were measured using Biacore™ T200 and 4000 biosensors (GE Healthcare, Chicago, Ill.). The following running buffer: 10 mM HEPES (GE Healthcare, BR100671), 150 mM NaCl (GE Healthcare, BR100671), 0.05% v/v Surfactant P20 (GE Healthcare, BR100671), 2 mM DTT (Sigma, 10708984001, St. Louis, Mo.), and 1 mM EDTA (GE Healthcare, 28995043), was used for immobilization, sample dilution and data collection unless otherwise noted below.

Protein immobilized refers to the recombinant human phosphorylated Tau protein immobilized on the chip; 1× P peptide immobilized refers to the phosphorylated peptide (TSPRHLSNVS(pS)TGSIDMVDSPC, SEQ ID NO:75) immobilized on the chip. Both of these methods have an avidity component to the affinity measurement. 4× P peptide analyte has the antibody captured on the chip and the 4× phosphorylated peptide (GAEIVYK(pS)PVVSGDT(pS)PRHLSNVS(pS)TGSIDMVD(pS)PQLAT-LADEVSASLAK QGL, SEQ ID NO:78) in solution.

Antibody binding to immobilized, phosphorylated Tau protein was measured using Series S Sensor Chips NTA (GE Healthcare, BR100034). The running buffer for the immobilization was 10 mM HEPES, 150 mM NaCl$_2$, 0.05% v/v Surfactant P20, pH 7.4 (GE Healthcare, BR100671) and the flow rate was 10 μL/minute. 350 mM EDTA was injected for 1 minute to clean the chip, followed by a 2 minute injection of 0.5 mM NiCl$_2$ (GE Healthcare, NTA Reagent Kit) to prepare the chip to capture his-tagged protein. The chip was activated according to the manufacturer's instructions using an amine coupling kit (GE Healthcare, BR100633), then 300 nM phosphorylated Tau protein (80AWB) was injected until the desired amount of protein had been immobilized. The chip was blocked with ethanolamine from the amine coupling kit. Each experiment used multiple levels of immobilized phosphorylated Tau protein. The lowest level varied from 54 resonance units (RU) to 452 RU, and the highest level varied from 463 RU to 1020 RU. To measure the affinity of Ta1505 antibody binding to the immobilized phosphorylated Tau protein, a 5-membered, 3-fold dilution series of each antibody was prepared, resulting in concentrations of 0.37 nM to 30 nM. Each concentration and several buffer blanks were injected for 3 minutes at a flowrate of 45 μl/minute. The dissociation of the antibody was monitored for 15 minutes, then the surface was regenerated with a 30 second to 1 minute injection of 100 mM CAPS (Sigma, C6070), 1 M KCl (Sigma, P9541), 1 mM EDTA, 2 mM DTT, pH 10.5.

Antibody binding to immobilized, phosphorylated Tau peptide was measured using a Series S Sensor Chip CM3 (GE Healthcare, BR100536). The chip was activated using an amine coupling kit, then 30 μg/mL phosphorylated Tau peptide (SEQ ID NO:75) in 10 mM sodium acetate, pH 5.0 was injected until 51 RU had been immobilized. The chip was blocked with ethanolamine. A negative control reference surface was prepared similarly, using non-phosphorylated Tau peptide (TSPRHLSNVSSTGSIDMVDSPC, SEQ ID NO:77). To measure the affinity of Ta1505 antibody binding to the immobilized phosphorylated Tau peptide, a 5-membered, 3-fold dilution series of each antibody was prepared, resulting in concentrations of 0.37 nM to 30 nM. Each concentration and several buffer blanks were injected for 3 minutes at a flowrate of 45 μL/minute. The dissociation of the antibody was monitored for 15 minutes. The surface was regenerated with a 30 second injection of 100 mM hydrochloric acid (Fisher Scientific, SA56-1, Waltham, Mass.).

Phosphorylated Tau peptide binding to immobilized antibody was measured using Series S Sensor Chips CM5 (GE Healthcare, 29149603). The chip was activated using an amine coupling kit, then 1 to 3 μg/ml antibody in 10 mM sodium acetate, pH 5.0 (Ge Healthcare, BR100351) was injected until 280 to 9100 RU of antibody had been immobilized. The chip was blocked with ethanolamine. To measure the affinity of phosphorylated Tau peptide (SEQ ID NO:78) binding to the immobilized Ta1505 antibodies, a 6-membered 2.5-fold dilution series of the peptide was prepared, resulting in concentrations of 5.1 nM to 500 nM. Samples and several buffer blanks were injected at 30 to 50 μL/minute for 3 minutes, and dissociation was monitored for 15 minutes. The surface was regenerated with a 30 second injection of 20 mM sodium acetate, pH 4.5, either unadjusted, or with the pH adjusted to 3.5 with hydrochloric acid.

The data were processed and fit using Biacore™ T200 Evaluation Software version 2.0 or Biacore™ 4000 Evaluation Software version 1.1 (GE Healthcare). The data were "double referenced" by subtracting the response from a negative control flowcell and subtracting the response from a buffer injection or the average response from two buffer injections. The data were then fit with the "1:1 Binding" model to determine the association rate constant, $k_a$ ($M^{-1}s^{-1}$, where "M" equals molar and "s" equals seconds) and the dissociation rate constant, $k_d$ ($s^{-1}$). These rate constants were used to calculate the equilibrium dissociation constant, $K_D$ (M)=$k_d/k_a$. Table 13 summarizes the $K_D$ values of the newly generated humanized antibody variants in comparison with those of the parent mouse antibody and the chimeric antibody.

TABLE 13

Kd (nM) Values of Antibodies to Phosphorylated Tau Protein or Peptide

| | Protein Immobilized | 1 × P peptide immobilized | 4 × P peptide analyte |
|---|---|---|---|
| ms IgG2a | 0.43 | 0.03 | 17.5 |
| chim. IgG1 | 0.46 | 0.04 | 27.2 |
| chim. IgG4 | 0.58 | 0.06 | 28.5 |
| hu VL46 (SEQ ID NO: 163)/ VH11 IgG1 (SEQ ID NO: 144) | 0.46 | 0.06 | 24.3 |
| hu VL46 (SEQ ID NO: 163)/ VH11 IgG4 (SEQ ID NO: 152) | 0.70 | 0.09 | 39.3 |
| hu VL46 G34A (SEQ ID NO: 166)/ VH11 IgG1 (SEQ ID NO: 144) | 0.28 | ND | ND |
| hu VL46 G34A (SEQ ID NO: 166)/ VH11 IgG4 (SEQ ID NO: 151) | 0.52 | 0.09 | 36.2 |
| hu VL46 G34S (SEQ ID NO: 168)/ VH11 IgG4 (SEQ ID NO: 151) | NB | NB | ND |
| hu VL46 G34T (SEQ ID NO: 170)/ VH11 IgG4 (SEQ ID NO: 151) | 0.75 | 0.13 | ND |
| hu VL46 N33Q (SEQ ID NO: 172)/ VH11 IgG4 (SEQ ID NO: 151) | 1.27 | 0.14 | ND |
| hu VL46 N33Q G34A (SEQ ID NO: 174)/VH11 IgG4 (SEQ ID N0: 151) | 3.40 | 0.31 | ND |
| hu VL46 (SEQ ID NO: 163)/ VH11 IgG4 (SEQ ID N0: 151) | NB | 1.78 | ND |
| hu VL46 N33S (SEQ ID NO: 178)/ VH11 IgG4 (SEQ ID NO: 151) | 2.31 | 0.29 | ND |
| hu VL46 N33T (SEQ ID NO: 180)/ VH11 IgG4 (SEQ ID NO: 151) | 1.31 | 0.18 | ND |
| hu VL46 A64D/VH11 IgG4 (SEQ ID NO: 151) | 0.77 | 0.16 | ND |
| hu VL46 S28N (SEQ ID NO: 183)/VH11 IgG4 (SEQ ID NO: 151) | 0.42 | 0.10 | 32.5 |
| hu VL47 (SEQ ID NO: 164)/ VH65 IgG1 (SEQ ID NO: 153) | 0.45 | 0.06 | ND |
| hu VL46 G34A S28N (SEQ ID NO: 184)/VH11 IgG1 (SEQ ID NO: 144) | 0.43 | ND | ND |
| hu VL46 G34A S28N (SEQ ID NO: 184)/ VH11 IgG4 (SEQ ID NO: 151) | 0.80 | ND | ND |

I. Example 10

ELISA Binding Analysis of the Parent Mouse Antibody, the Chimeric Antibody, and Some Humanized Antibody Variants Binding of the parent mouse antibody, the chimeric antibody, and the newly generated humanized antibody variants to a phosphorylated peptide (PRHLSNVS(pS)TGSIDMVD, SEQ ID NO:79) and the corresponding non-phosphorylated peptide (PRHLSNVSTGSIDMVD, SEQ ID NO:80) was analyzed by ELISA.

Fifty microliters of 1 µg/ml phosphorylated or non-phosphorylated peptide in PBS were added to each well of ELISA plates and the plates were incubated at 4° C. overnight. On the next day, the plates were washed 3 times and blocked with 200 µL of superblock at 4° C. overnight. On the third day, the plates were washed 3 times. Then 50 µL of antibodies in 1:3 serial dilution in the ELISA buffer, starting at 10 µg/mL, were added to each well of the plate, incubated at room temperature for 1 hour, then washed 3 times. Fifty microliters of 1:3000 dilution of goat anti-mouse-HRP (Southern Biotech, 1030-05) were added for measuring the parent mouse antibody. Fifty microliters of 1:3000 dilution of goat anti-human-HRP (Jackson Immunologics, 109-036-098) were added for measuring the chimeric antibody and humanized antibodies. The ELISA plates were incubated at room temperature for 45 minutes, washed 3 times, then developed with ABTS at room temperature for 5 minutes. Thereafter, a plate reader was used to measure absorbance at 405 nm.

FIGS. 8A and 8B show that the parent antibody generated by hybridoma or recombinant method bound to the phosphorylated peptide (FIG. 8A) but not the non-phosphorylated peptide (FIG. 8B). Similarly, the chimeric antibodies (with either IgG1 or IgG4 backbone) bound to the phosphorylated peptide (FIG. 8C) but not the non-phosphorylated peptide (FIG. 8D).

FIGS. 9A-9C demonstrate that most of the newly generated humanized antibody variants bound to the phosphorylated peptide with affinity comparable to the chimeric IgG4 antibody whereas a few variants lost binding affinity to the phosphorylated peptide. Particularly, in FIG. 9B, the huVL46/VH11_N33D_IgG4 variant, which mimics full deamidation of amino acid N33 to D, had vastly reduced binding to the phosphorylated peptide, suggesting that the fully deamidated antibody would lose its binding affinity to the phosphorylated Tau protein dramatically. Thus, reduction of deamidation at N33 in the humanized antibody variants is imperative.

XV. Example 11

Antigen Binding Analysis of the Newly Generated Humanized Antibody Variants in Brain Homogenates of Alzheimer's Disease Patients The parent mouse antibody, the chimeric antibody, and selected humanized antibody variants were evaluated for their binding potency to Ser413 phosphorylated Tau protein (pSer413-Tau) derived from an Alzheimer's disease (AD) patient clinical samples in a liquid phase.

As described in FIGS. 10A-10E, antibody occupancy on pSer413-Tau was determined by the difference between total and free antigen binding detected using mouse biotinylated-Ta1505 IgG2a antibody after incubation of the AD brain samples with increasing concentration of control human IgG (Sigma, Cat #12511) and selected antibody variants, respectively.

The detection with the same mouse biotinylated-Ta1505 IgG2a antibody allows a direct comparison of binding potency between the antibodies variants. Mouse Ta1505 IgG2a antibody was biotinylated using N-hydroxysuccinimide-LC-biotin (NHS-LC-biotin) (Thermo Fisher Scientific K.K.), followed by dialysis with PBS.

Frozen pre-frontal cortex tissue (100 mg) from the brain of an AD patient was added to 1 mL of TBS-I (Tris-buffered saline, Cat #BP2471-1, Thermo Fisher Scientific) containing a protease and phosphatase inhibitor cocktail (Thermo Fisher Scientific, Cat #1861281) and lysed on iced water using Qiagen Tissue Lyzer II. The homogenized sample was centrifuged at 27,000g (TLA-55 rotor) at 4° C. for 20 minutes in Beckman Coulter Optima Max-XP Ultracentrifuge, and the supernatant was collected and further centrifuged at 150,000×g (TLA-55 rotor) at 4° C. for 20 minutes in Beckman Coulter Optima Max-XP Ultracentrifuge to obtain a pellet called P2 fraction. The P2 fraction was re-suspended in homogenization buffer TBS-I by sonication. Protein concentration of the P2 fraction was determined using Pierce™ BCA Protein Assay Kit (Thermo Fisher Scientific, Cat #23225) per manufacturer's instructions. Protein concentration was adjusted to 4 µg/mL.

INNOTEST® pTau (pT181) kit (Fijirebio Inc., Cat #81581) was used as an ELISA system for Ser413 phosphorylated Tau protein (pSer413-Tau), but the biotinylated antibody included in the kit (labelled as CONJ1) was replaced with the biotinylated mouse Ta1505 IgG2a antibody as produced above.

The parent mouse antibody, the chimeric antibody, the humanized antibody variants, or the control human IgG were diluted to 200 nM from stocks in sample diluent buffer (provided by INNOTEST® kit). Antibody solutions were then serially diluted and incubated with AD brain P2 fractions previously diluted at 1/1000 in assay plate for 4 hours at room temperature. The antibody-antigen mixture was then added to an HT7 antibody immobilized MT plate (included in the kit), along with diluted biotinylated antibody mouse Ta1505 IgG2a (1/10 in CONJ DIL 1, provided by INNOTEST® kit). The resultant sample was mixed and incubated at 4° C. overnight. On the following day, the plate was washed, and an HRP-labeled streptavidin (included in the kit as CONJ2) was added to the plate, followed by incubation for one hour. After washing, a color reagent TMB was added, followed by incubation under light-shielding at room temperature for 30 minutes. The reaction was then stopped with a reaction terminator solution (included in the kit as STOP solution), and absorbance at a wavelength of 450 nm was measured.

Non-linear analysis of the concentration-response curve illustrated in FIGS. 10A-10E allows determination of the concentration of each antibody required for the 50% occupancy of Tau pSer413 in AD brain homogenates, as well as the percentage of maximum occupancy level for each antibody. FIGS. 10A-10E demonstrate comparable binding characteristics, including in vitro level of occupancy and maximum binding of pSer413 Tau antigen, for the parent mouse antibody, the chimeric antibody, and selected humanized antibody variants in brain homogenates of AD patients.

XVI. Example 12

Stability and Purity Analysis of the Newly Generated Humanized Antibody Variants Stability of various antibodies was determined by measuring the melting temperature (Tm1) and aggregation temperature (Tagg) via nano-DSF. Purity of each antibody was measured by SEC and non-reduced capillary SDS (NR-cSDS).

Determination of Tm and Tagg: Tm and Tagg was determined by nano-DSF using a Prometheus NT.48 Differential Scanning Fluorimeter (Nanotemper Technologies) controlled by PR.ThermControl v2.0.4 software. Excitation power was 40% and temperature was increased from 20° C. to 95° C. at a rate of 1° C./min. Tm and Tagg were automatically measured. Samples were prepared by diluting to 1 mg/mL in 20 mM sodium acetate, pH 5.5, buffer and drawn by capillary action into a Prometheus glass capillary (PR-L002).

Determination of purity by SEC: SEC was carried out on an ACQUITY UPLC H-Class system. Column used was an ACQUITY UPLC Protein BEH SEC column (Part No. 186005225, 1.7 µm, 200A, 4.6 mm×150 mm) from Waters (Milford, Mass.). Column temperature was 25° C. and 10 µL sample at 1 mg/mL was injected using a system flow rate of 0.5 mL/min. Mobile phase was 100 mM sodium phosphate, 200 mM sodium chloride, and 0.02% sodium azide, pH 7.0. Data were quantified at both 214 and 280 nm and analyzed using Empower 3 software. A BEH200 SEC Protein Standard Mix (Part No. 186006518) from Waters (Milford, Mass.) was injected at 10 µg and USP Resolution, Theoretical Plates, and Tailing were measured.

Determination of purity by NR-cSDS: To assess purity by NR-cSDS, 5 µL of each sample at 1 mg/mL was mixed in a 96 well plate with 35 µL of loading buffer (HT Protein Express Sample Buffer (Perkin Elmer)) containing 50 mM iodoacetamide. The plate was incubated at 70° C. for 20 minutes and 75 µL of water was added to each well. Each sample was analyzed on a LabChip GXII System (Perkin Elmer) using an HT Protein Express Chip (Perkin Elmer). Electropherograms were collected by measuring the fluorescence of the sample over time, and integrated using the LabChip GX software V4.1.1619.0 SP1 (Perkin Elmer).

Table 14 summarizes the stability and purity of the tested antibodies.

TABLE 14

Stability and Purity of Various Antibodies

| | Stability | | Purity | |
|---|---|---|---|---|
| | Tm1 | Tagg | % SEC purity | %NR-cSDS Purity |
| ms IgG2a | 65.0 | ND | 99.1 | 100 |
| chim. IgG1 | ND | ND | 96.2 | ND |
| chim. IgG4 | ND | ND | 95.3 | ND |
| hu VL46/VH11 IgG1 | 68.5 | 69.5 | 99.0 | 100 |
| hu VL46/VH11 IgG4 (ref) | 66.8 | 66.0 | 98.4 | 100 |
| hu VL46/VH11 G34A IgG1 | 65.9 | 66.2 | 100 | 100 |
| hu VL46/VH11 G34A IgG4 | 64.0 | 63.8 | 100 | 98.0 |
| hu VL46/VH11 G34A IgG4 | 65.3 | 66.6 | 100 | 100 |
| hu VL46/VH11 G34S IgG4 | ND | ND | ND | 100.0 |
| hu VL46/VH11 G34T IgG4 | 65.8 | 66.5 | ND | 99.3 |
| hu VL46/VH11 N33Q IgG4 | 65.2 | 67.1 | 99.6 | 100 |
| hu VL46/VH11 N33Q G34A IgG4 | ND | ND | ND | 100 |
| hu VL46/VH11 N33D IgG4 | ND | ND | ND | 100 |
| hu VL46/VH11 N33S IgG4 | ND | ND | ND | 99.8 |
| hu VL46/VH11 N33T IgG4 | ND | ND | ND | 100 |
| hu VL46/VH11 A64D IgG4 | ND | ND | ND | 100 |
| hu VL46/VH11 S28N IgG4 | 68.1 | 67.8 | 99.6 | 100 |
| hu VL47/VH65 IgG1 | 59.6 | 60.2 | 99.9 | 100 |
| hu VL46/VH11 G34A S28N IgG1 | 65.5 | 66.7 | 100 | 97.0 |
| hu VL46/VH11 G34A S28N IgG4 | 63.8 | 65.0 | 100 | 97.0 |

All of the newly generated humanized antibody variants maintained or improved stability and purity compared to the parent mouse antibody or the chimeric antibodies. One of the original humanized variant huVL47/VH65_IgG1 stood out as having reduced stability as measured by Tm1/Tagg.

XVII. Example 13

Deamidation Analysis of the Newly Generated Humanized Antibody Variants

Deamidation level of amino acid N33 in the light chain CDR1 of various antibodies were determined. Stress conditions, such as 50° C. or pH 10 incubation, were tested. A 4° C. incubation was performed as a control.

4° C. and 50° C. incubation: Samples formulated in 20 mM sodium acetate, pH 5.5, at 2 mg/ml were held at 50° C. in a temperature controlled stability chamber for one week. Samples were held at 4° C. for the 4° C. control for comparison purposes.

pH 10 incubation: Samples formulated in 20 mM sodium acetate, pH 5.5, at 2 mg/mL were adjusted to pH 10 using 0.5 M NaOH and held at 25° C. for one week in a temperature controlled stability chamber. Afterwards, samples were then exchanged into 20 mM sodium acetate, pH 5.5, buffer using Zeba Spin desalting columns (7K MWCO, Thermo Fisher 2 mL, 89890).

Deamidation Analysis by Peptide Mapping: For peptide mapping by mass spectrometry, 100 μg of each sample was denatured with 30 μL of 8 M guanidine/1 M Tris hydrochloride solution (15:1), reduced with 2 μL of 1 M DTT for 30 minutes at 60° C. and alkylated with 5 μL of 1 M iodoacetamide for 45 minutes in dark. Before digestion, samples were buffer exchanged into 50 mM ammonium bicarbonate using 7 kilo Dalton molecular weight cut off ZEBA cartridges. Samples were split into different tubes and digested in parallel with 2 μg of trypsin and chymotrypsin for 2 hours at 37° C. Digestion was quenched by the addition of 3 μL of 5 M hydrochloride to each sample. 2 μL of sample was injected on the Peptide BEH-C18—1×50 mm Waters UPLC column (Part #186005592) maintained at 40° C. Data were acquired in a Dionex/QE plus MS using a linear gradient over 50 min from 2% to 36% acetonitrile in 0.1% formic acid. Samples were analyzed using PEAKS DB (Bioinformatics Solutions Inc.) for database searching as well as PepFinder (Thermo Fisher Scientific) and manual verification for the percent change assessment. Table 15 summarizes deamidation percentage of amino acid N33 in the light chain CDR1 of the tested antibodies.

TABLE 15

Deamidation Percentage of N33 in Light Chain CDR1 under Various Conditions

| | 4° C. control | 50° C. | pH 10 |
|---|---|---|---|
| ms IgG2a | 41.1 | 36.9 | 31.7 |
| hu VL46/VH11 IgG1 | 33.0 | 33.9 | 31.8 |
| hu VL46/VH11 IgG4 | 32.0 | 31.0 | 37.9 |
| hu VL46/VH11 G34A IgG4 | <1% | ND | <1% |
| hu VL46/VH11 G34T IgG4 | <1% | ND | <1% |
| hu VL46/VH11 N33Q IgG4 | <1% | ND | <1% |
| hu VL46/VH11 G34A S28N IgG1 | <1% | 1.2 | 1% |
| hu VL46/VH11 G34A S28N IgG4 | <1% | 2.1 | 1% |

Compared to the parent mouse antibody and the original humanized variant (VL46/VH11) IgG1 or IgG4 antibody, the newly generated humanized antibody variants exhibited significant reduction in the deamidation level of N33 in the light chain CDR1.

What is claimed is:

1. An anti-pSer413 tau antibody or antigen binding fragment thereof comprising:
    (A) a heavy chain variable domain comprising:
        a vhCDR1 comprising an amino acid sequence of SEQ ID NO:86;
        a vhCDR2 comprising an amino acid sequence of SEQ ID NO:115; and
        a vhCDR3 comprising an amino acid sequence of SEQ ID NO:88; and
    (B) a light chain variable domain comprising a set of vlCDRs selected from the group consisting of:
        (i) a vlCDR1 comprising an amino acid sequence of SEQ ID NO:91;
            a vlCDR2 comprising an amino acid sequence of SEQ ID NO:82; and
            a vlCDR3 comprising an amino acid sequence of SEQ ID NO:83;
        (ii) a vlCDR1 comprising an amino acid sequence of SEQ ID NO:92;
            a vlCDR2 comprising an amino acid sequence of SEQ ID NO:82; and
            a vlCDR3 comprising an amino acid sequence of SEQ ID NO:83;
        (iii) a vlCDR1 comprising an amino acid sequence of SEQ ID NO:93;
            a vlCDR2 comprising an amino acid sequence of SEQ ID NO:82; and
            a vlCDR3 comprising an amino acid sequence of SEQ ID NO:83;
        (vi) a vlCDR1 comprising an amino acid sequence of SEQ ID NO:94;
            a vlCDR2 comprising an amino acid sequence of SEQ ID NO:82; and
            a vlCDR3 comprising an amino acid sequence of SEQ ID NO:83;
        (v) a vlCDR1 comprising an amino acid sequence of SEQ ID NO:95;
            a vlCDR2 comprising an amino acid sequence of SEQ ID NO:82; and
            a vlCDR3 comprising an amino acid sequence of SEQ ID NO:83;
        (vi) a vlCDR1 comprising an amino acid sequence of SEQ ID NO:96;
            a vlCDR2 comprising an amino acid sequence of SEQ ID NO:82; and
            a vlCDR3 comprising an amino acid sequence of SEQ ID NO:83;
        (vii) a vlCDR1 comprising an amino acid sequence of SEQ ID NO:97;
            a vlCDR2 comprising an amino acid sequence of SEQ ID NO:82; and
            a vlCDR3 comprising an amino acid sequence of SEQ ID NO:83;
        (viii) a vlCDR1 comprising an amino acid sequence of SEQ ID NO:98;
            a vlCDR2 comprising an amino acid sequence of SEQ ID NO:82; and
            a vlCDR3 comprising an amino acid sequence of SEQ ID NO:83;
        (xi) a vlCDR1 comprising an amino acid sequence of SEQ ID NO:99;
            a vlCDR2 comprising an amino acid sequence of SEQ ID NO:82; and
            a vlCDR3 comprising an amino acid sequence of SEQ ID NO:83;
        (x) a vlCDR1 comprising an amino acid sequence of SEQ ID NO:100;
            a vlCDR2 comprising an amino acid sequence of SEQ ID NO:82; and
            a vlCDR3 comprising an amino acid sequence of SEQ ID NO:83;
        (xi) a vlCDR1 comprising an amino acid sequence of SEQ ID NO:101;
            a vlCDR2 comprising an amino acid sequence of SEQ ID NO:82; and
            a vlCDR3 comprising an amino acid sequence of SEQ ID NO:83; and
        (xii) a vlCDR1 comprising an amino acid sequence of SEQ ID NO:102;
            a vlCDR2 comprising an amino acid sequence of SEQ ID NO:82; and
            a vlCDR3 comprising an amino acid sequence of SEQ ID NO:83.

2. The anti-pSer413 tau antibody or antigen binding fragment thereof of claim 1, wherein the ratio of said antibody's binding affinity to a phosphorylated peptide of SEQ ID NO:8 to said antibody's binding affinity to a non-phosphorylated peptide of SEQ ID NO:69 is at least about 40 to 1.

3. A method of treating a tauopathy in a subject, comprising administering to the subject the anti-pSer413 tau antibody or antigen binding fragment thereof of claim 1.

4. The method of claim 3, wherein the tauopathy is selected from a group consisting of Alzheimer's disease, corticobasal degeneration, progressive supranuclear palsy, Pick's disease, argyrophilic grain dementia (argyrophilic grain disease), multiple system tauopathy with presenile dementia (MSTD), frontotemporal dementia and parkinsonism linked to chromosome 17 (FTDP-17), dementia with neurofibrillary tangles, diffuse neurofibrillary tangle with calcification (DNTC), white matter tauopathy with globular glial inclusions (WMT-GGI), frontotemporal lobar degeneration with tau pathology (FTLD-tau), Economo's encephalitis sequela, subacute sclerosing panencephalitis, and boxer's encephalopathy.

5. An anti-pSer413 tau antibody or antigen binding fragment thereof comprising:
    (A) a heavy chain variable domain comprising a vhCDR1 comprising an amino acid sequence of SEQ ID NO:86;
        a vhCDR2 comprising an amino acid sequence of SEQ ID NO:115; a vhCDR3 comprising an amino acid sequence of SEQ ID NO:88; and
(B) a light chain variable domain comprising a vlCDR1 comprising an amino acid sequence of SEQ ID NO:102; a vlCDR2 comprising an amino acid sequence of SEQ ID NO:82; and a vlCDR3 comprising an amino acid sequence of SEQ ID NO:83.

6. The anti-pSer413 tau antibody or antigen binding fragment thereof of claim 5, wherein the ratio of said antibody's binding affinity to a phosphorylated peptide of SEQ ID NO:8 to said antibody's binding affinity to a non-phosphorylated peptide of SEQ ID NO:69 is at least about 40 to 1.

7. A method of treating a tauopathy in a subject, comprising administering to the subject the anti-pSer413 tau antibody or antigen binding fragment thereof of claim 5.

8. The method of claim 7, wherein the tauopathy is selected from a group consisting of Alzheimer's disease, corticobasal degeneration, progressive supranuclear palsy, Pick's disease, argyrophilic grain dementia (argyrophilic grain disease), multiple system tauopathy with presenile dementia (MSTD), frontotemporal dementia and parkinsonism linked to chromosome 17 (FTDP-17), dementia with neurofibrillary tangles, diffuse neurofibrillary tangle with calcification (DNTC), white matter tauopathy with globular glial inclusions (WMT-GGI), frontotemporal lobar degeneration with tau pathology (FTLD-tau), Economo's encephalitis sequela, subacute sclerosing panencephalitis, and boxer's encephalopathy.

9. A humanized antibody, or antigen binding fragment thereof, which causes an antigen-antibody reaction with a tau protein or a tau peptide phosphorylated at least on an amino acid residue corresponding to Ser413 of SEQ ID NO: 1, comprising:
(A) a heavy chain variable domain comprising:
a vhCDR1 comprising an amino acid sequence of SEQ ID NO:86;
a vhCDR2 comprising an amino acid sequence of SEQ ID NO:115; and
a vhCDR3 comprising an amino acid sequence of SEQ ID NO:88; and
(B) a light chain variable domain comprising a set of vlCDRs selected from the group consisting of:
(i) a vlCDR1 comprising an amino acid sequence of SEQ ID NO:91;
a vlCDR2 comprising an amino acid sequence of SEQ ID NO:82; and
a vlCDR3 comprising an amino acid sequence of SEQ ID NO:83;
(ii) a vlCDR1 comprising an amino acid sequence of SEQ ID NO:92;
a vlCDR2 comprising an amino acid sequence of SEQ ID NO:82; and
a vlCDR3 comprising an amino acid sequence of SEQ ID NO:83;
(iii) a vlCDR1 comprising an amino acid sequence of SEQ ID NO:93;
a vlCDR2 comprising an amino acid sequence of SEQ ID NO:82; and
a vlCDR3 comprising an amino acid sequence of SEQ ID NO:83;
(vi) a vlCDR1 comprising an amino acid sequence of SEQ ID NO:94;
a vlCDR2 comprising an amino acid sequence of SEQ ID NO:82; and
a vlCDR3 comprising an amino acid sequence of SEQ ID NO:83;
(v) a vlCDR1 comprising an amino acid sequence of SEQ ID NO:95;
a vlCDR2 comprising an amino acid sequence of SEQ ID NO:82; and
a vlCDR3 comprising an amino acid sequence of SEQ ID NO:83;
(vi) a vlCDR1 comprising an amino acid sequence of SEQ ID NO:96;
a vlCDR2 comprising an amino acid sequence of SEQ ID NO:82; and
a vlCDR3 comprising an amino acid sequence of SEQ ID NO:83;
(vii) a vlCDR1 comprising an amino acid sequence of SEQ ID NO:97;
a vlCDR2 comprising an amino acid sequence of SEQ ID NO:82; and
a vlCDR3 comprising an amino acid sequence of SEQ ID NO:83;
(viii) a vlCDR1 comprising an amino acid sequence of SEQ ID NO:98;
a vlCDR2 comprising an amino acid sequence of SEQ ID NO:82; and
a vlCDR3 comprising an amino acid sequence of SEQ ID NO:83;
(xi) a vlCDR1 comprising an amino acid sequence of SEQ ID NO:99;
a vlCDR2 comprising an amino acid sequence of SEQ ID NO:82; and
a vlCDR3 comprising an amino acid sequence of SEQ ID NO:83;
(x) a vlCDR1 comprising an amino acid sequence of SEQ ID NO:100;
a vlCDR2 comprising an amino acid sequence of SEQ ID NO:82; and
a vlCDR3 comprising an amino acid sequence of SEQ ID NO:83;
(xi) a vlCDR1 comprising an amino acid sequence of SEQ ID NO:101;
a vlCDR2 comprising an amino acid sequence of SEQ ID NO:82; and
a vlCDR3 comprising an amino acid sequence of SEQ ID NO:83; and
(xii) a vlCDR1 comprising an amino acid sequence of SEQ ID NO:102;
a vlCDR2 comprising an amino acid sequence of SEQ ID NO:82; and
a vlCDR3 comprising an amino acid sequence of SEQ ID NO:83.

10. The humanized antibody or antigen binding fragment thereof of claim 9, wherein the ratio of said antibody's binding affinity to a phosphorylated peptide of SEQ ID NO:8 to said antibody's binding affinity to a non-phosphorylated peptide of SEQ ID NO:69 is at least about 40 to 1.

11. A method of treating a tauopathy in a subject, comprising administering to the subject the humanized antibody or antigen binding fragment thereof of claim 9.

12. The method of claim 11, wherein the tauopathy is selected from a group consisting of Alzheimer's disease, corticobasal degeneration, progressive supranuclear palsy, Pick's disease, argyrophilic grain dementia (argyrophilic grain disease), multiple system tauopathy with presenile dementia (MSTD), frontotemporal dementia and parkinsonism linked to chromosome 17 (FTDP-17), dementia with neurofibrillary tangles, diffuse neurofibrillary tangle with calcification (DNTC), white matter tauopathy with globular glial inclusions (WMT-GGI), frontotemporal lobar degeneration with tau pathology (FTLD-tau), Economo's encephalitis sequela, subacute sclerosing panencephalitis, and boxer's encephalopathy.

13. A humanized antibody or antigen binding fragment thereof, which causes an antigen-antibody reaction with a tau protein or a tau peptide phosphorylated at least on an amino acid residue corresponding to Ser413 of SEQ ID NO: 1, comprising:
  (A) a heavy chain variable domain comprising a vhCDR1 comprising an amino acid sequence of 1M (SEQ ID NO: 10); a vhCDR2 comprising an amino acid sequence of 2H1 (SEQ ID NO: 12) or an amino acid sequence differs from sequence 2H1 (SEQ ID NO: 12) in that Ala at position 15 is substituted with Asp; a vhCDR3 comprising an amino acid sequence of 3M (SEQ ID NO: 13); and
  (B) a light chain variable domain comprising a vlCDR1 comprising an amino acid sequence of 4L1 (SEQ ID NO: 14) or an amino acid sequence differs from sequence 4L1 (SEQ ID NO: 14) in that Ser at position 5 is substituted with Asn; a vlCDR2 comprising an amino acid sequence of 5M (SEQ ID NO: 16); and a vlCDR3 comprising an amino acid sequence of 6M (SEQ ID NO: 17).

14. The humanized antibody or or antigen binding fragment thereof of claim 13, comprising:
  (A) a vhCDR1 comprising an amino acid sequence of 1M (SEQ ID NO: 10);
    a vhCDR2 comprising an amino acid sequence of 2H1 (SEQ ID NO: 12);
    a vhCDR3 comprising an amino acid sequence of 3M (SEQ ID NO: 13);
    a vlCDR1 comprising an amino acid sequence of 4L1 (SEQ ID NO: 14);
    a vlCDR2 comprising an amino acid sequence of 5M (SEQ ID NO: 16); and
    a vlCDR3 comprising an amino acid sequence of 6M (SEQ ID NO: 17), or
  (B) a vhCDR1 comprising an amino acid sequence of 1M (SEQ ID NO: 10);
    a vhCDR2 comprising an amino acid sequence of 2H1 (SEQ ID NO: 12);
    a vhCDR3 comprising an amino acid sequence of 3M (SEQ ID NO: 13);
    a vlCDR1 comprising an amino acid sequence of 4M (SEQ ID NO: 15);
    a vlCDR2 comprising an amino acid sequence of 5M (SEQ ID NO: 16); and
    a vlCDR3 comprising an amino acid sequence of 6M (SEQ ID NO: 17), or
  (C) a vhCDR1 comprising an amino acid sequence of 1M (SEQ ID NO: 10);
    a vhCDR2 comprising an amino acid sequence of 2M (SEQ ID NO: 11);
    a vhCDR3 comprising an amino acid sequence of 3M (SEQ ID NO: 13);
    a vlCDR1 comprising an amino acid sequence of 4M (SEQ ID NO: 15);
    a vlCDR2 comprising an amino acid sequence of 5M (SEQ ID NO: 16); and
    a vlCDR3 comprising an amino acid sequence of 6M (SEQ ID NO: 17).

15. The humanized antibody or antigen binding fragment thereof of claim 13, wherein the ratio of said antibody's binding affinity to a phosphorylated peptide of SEQ ID NO:8 to said antibody's binding affinity to a non-phosphorylated peptide of SEQ ID NO:69 is at least about 40 to 1.

16. A method of treating a tauopathy in a subject, comprising administering to the subject the humanized antibody or antigen binding fragment thereof of claim 13.

17. The method of claim 16, wherein the tauopathy is selected from a group consisting of Alzheimer's disease, corticobasal degeneration, progressive supranuclear palsy, Pick's disease, argyrophilic grain dementia (argyrophilic grain disease), multiple system tauopathy with presenile dementia (MSTD), frontotemporal dementia and parkinsonism linked to chromosome 17 (FTDP-17), dementia with neurofibrillary tangles, diffuse neurofibrillary tangle with calcification (DNTC), white matter tauopathy with globular glial inclusions (WMT-GGI), frontotemporal lobar degeneration with tau pathology (FTLD-tau), Economo's encephalitis sequela, subacute sclerosing panencephalitis, and boxer's encephalopathy.

* * * * *